US008247401B2

(12) United States Patent
Burgey et al.

(10) Patent No.: US 8,247,401 B2
(45) Date of Patent: Aug. 21, 2012

(54) P2X₃ RECEPTOR ANTAGONISTS FOR TREATMENT OF PAIN

(75) Inventors: Christopher S. Burgey, Philadelphia, PA (US); Diem Nguyen, Eagleville, PA (US); Zhengwu Deng, Harleysville, PA (US); Daniel V. Paone, Lansdale, PA (US); Craig M. Potteiger, Reading, PA (US); Joseph P. Vacca, Telford, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 39 days.

(21) Appl. No.: 12/740,105

(22) PCT Filed: Oct. 29, 2008

(86) PCT No.: PCT/US2008/012270
§ 371 (c)(1),
(2), (4) Date: Apr. 27, 2010

(87) PCT Pub. No.: WO2009/058298
PCT Pub. Date: May 7, 2009

(65) Prior Publication Data
US 2010/0266714 A1    Oct. 21, 2010

Related U.S. Application Data

(60) Provisional application No. 61/001,376, filed on Oct. 31, 2007, provisional application No. 61/132,194, filed on Jun. 16, 2008.

(51) Int. Cl.
| | |
|---|---|
| *A61K 31/397* | (2006.01) |
| *A61K 31/5377* | (2006.01) |
| *A61K 31/538* | (2006.01) |
| *A61K 31/506* | (2006.01) |
| *A61K 31/425* | (2006.01) |
| *A61K 31/44* | (2006.01) |
| *A61K 31/4427* | (2006.01) |
| *A61K 31/445* | (2006.01) |
| *A61K 31/495* | (2006.01) |
| *A61K 31/42* | (2006.01) |
| *A61K 31/4245* | (2006.01) |
| *A61K 31/4155* | (2006.01) |
| *A61K 31/4192* | (2006.01) |
| *A61K 31/4196* | (2006.01) |
| *C07D 265/28* | (2006.01) |
| *C07D 413/00* | (2006.01) |
| *C07D 401/00* | (2006.01) |
| *C07D 471/00* | (2006.01) |
| *C07D 491/00* | (2006.01) |

(52) U.S. Cl. ............ 514/210.01; 514/230.5; 514/231.5; 514/248; 514/252.2; 514/256; 514/366; 514/279; 514/332; 514/336; 514/315; 514/364; 514/365; 514/374; 514/383; 514/406; 544/105; 544/111; 544/124; 544/333; 544/336; 544/350; 544/358; 546/112; 546/184; 546/255; 546/268.1; 548/131; 548/143; 548/152; 548/202; 548/235; 548/255; 548/262.2; 548/373.1; 548/950

(58) Field of Classification Search ............ 514/210.01, 514/230.5, 231.5, 248, 252.2, 256, 366, 279, 514/332, 336, 315, 364, 365, 374, 383, 406; 544/105, 111, 124, 333, 336, 350, 358; 546/112, 546/184, 255, 268.1; 548/131, 143, 152, 548/202, 235, 255, 262.2, 373.1, 950
See application file for complete search history.

(56) References Cited

U.S. PATENT DOCUMENTS

| | | | | |
|---|---|---|---|---|
| 4,916,145 | A | | 4/1990 | Tilley et al. |
| 7,786,110 | B2 | * | 8/2010 | Dillon et al. ............... 514/227.8 |
| 2004/0029920 | A1 | | 2/2004 | Kuduk et al. |
| 2007/0037974 | A1 | | 2/2007 | Brotherton-Pleiss et al. |
| 2007/0219239 | A1 | | 9/2007 | Mjalli et al. |
| 2008/0004442 | A1 | | 1/2008 | Dillon et al. |
| 2009/0326220 | A1 | * | 12/2009 | Dillon et al. ................. 544/58.2 |

FOREIGN PATENT DOCUMENTS

| | | | | |
|---|---|---|---|---|
| GB | 2003068773 | * | 8/2003 | ................... 546/200 |
| US | 2002022584 | * | 3/2002 | ................... 546/200 |
| WO | WO0112627 A1 | | 2/2001 | |
| WO | WO0212210 | | 2/2002 | |
| WO | WO2005073193 | | 8/2005 | |
| WO | WO2006119504 | | 11/2006 | |
| WO | WO2007/010553 | | 1/2007 | |
| WO | WO2007001973 | | 1/2007 | |
| WO | WO2007020194 | | 2/2007 | |
| WO | WO2007041087 | | 4/2007 | |

OTHER PUBLICATIONS

G. Burnstock et al., "Physiological and Pathological Roles of Purines: An Update", Drug Development Research, vol. 28, pp. 195-206, 1993.
S. Valera et al., "A New Class of Ligand-Gated Ion Channel Defined by P2X Recepotr for Extracellular ATP", Nature, vol. 371, pp. 516-519, 1994.
A. J. Brake et al., "New Structural Motif for Ligand-Gated Ion Channels Defined by an Ionotropic ATP Receptor", Nature, vol. 371, pp. 519-523, 1994.
C. Lewis et al., "Coexpression of P2X2 and P2X3 Receptor Subunits can Account for ATP-Gated Currents in Sensory Neurons", Nature, vol. 377, pp. 432-435, 1995.
C. Chen et al., "A P2X Purinoceptor Expressed by a Subset of Sensory Neurons", Nature, vol. 377, pp. 428-431, 1995.

(Continued)

*Primary Examiner* — Rebecca Anderson
*Assistant Examiner* — Samantha Shterengarts
(74) *Attorney, Agent, or Firm* — Sylvia A. Ayler; Gerard M. Devlin

(57) ABSTRACT

The subject invention relates to novel P2X₃ receptor antagonists that play a critical role in treating disease states associated with pain, in particular peripheral pain, inflammatory pain, or tissue injury pain that can be treated using a P2X₃ receptor subunit modulator.

19 Claims, No Drawings

OTHER PUBLICATIONS

G. Buell et al., "P2X Receptors: An Emerging Channel Family", E. J. of Neuroscience, vol. 8, pp. 2221-2238, 1996.
P. Seguela et al., "A Novel Neuronal P2X ATP Receptor Ion Channel with Widespread Distribution in the Brain", J. of Neuroscience, vol. 16, pp. 448-455, 1996.
X. Bo et al., A P2X Purinoceptor cDNA Conferring a Novel Pharmacological Profile, FEBS Letters, vol. 375, pp. 129-133, 1995.
F. Soto et al., "P2X4: An ATP-Activated Ionotropic Receptor Cloned from Rat Brain", Proc. Natl. Acad. Sci, vol. 93, pp. 3684-3688, 1996.
C. Z. Wang et al., "Cloning and Pharmacological Characterization of a Fourth P2X Receptor Subtype Widely Expressed in Brain and Peripheral Tissues Including Various Endocrine Tissues", Biochemical and Biophyscial Research Communications, vol. 220, pp. 196-202, 1996.
G. Collo et al., "Cloning of P2X5 and P2X6 Receptors and Distribution and Properties of an Extended Family of ATP-Gated Ion Channels", J. of Neuroscience, vol. 16, pp. 2495-2507, 1996.
M. Garcia-Guzman et al., "Molecular Cloning and Functional Expression of a Novel Rat Heart P2X Purinoceptor", FEBS Letters, vol. 388, pp. 123-127, 1996.
F. Soto et al., "Cloning and Tissue Distribution of a Novel P2X Receptor from Rat Brain", Biochemical and Biophysical Research Communications, vol. 223, pp. 456-460, 1996.
A. Surprenant et al., "The Cytolytic P2Z Receptor for Extracellular ATP Identified as a P2X Receptor (P2X7)", Science, vol. 272, pp. 735-737, 1996.
G. Buell et al., "An Antagonist-Insensitive P2X Receptor Expressed in Epithelia and Brain", EMBO, vol. 15, pp. 55-62, 1996.
G. E. Torres et al., "Co-Expression of P2X1 and P 2X5 Receptor Subunits Reveals a Novel ATP-Gated Ion Channel", Molecular Pharmacology,vol. 54, pp. 989-993, 1998.
Y. Yiangou et al., "ATP-Gated Ion Channel P2X3 is Increased in Human Inflammatory Bowel Disease", Neurokastroenterol Mot, pp. 365-369, 2001.
X. Bian et al., "Peristalsis is Impaired in the Small Intestine of Mice Lacking the P2X3 Subunit", J. Physiol., vol. 551, pp. 309-322, 2003.
G. Wynn et al., "Purinergic Component of Mechanosensory Transduction is Increased in a Rat Model of Colitis", Am. J. Physiol. Gastrintest Liver Physiol, vol. 287, pp. G647-G657, 2004.
I. Brouns et al., "Am J. Respir Cell Mol Biol.," Intraepithelial Vagal Sensory Nerve Terminals in Rat Pulmonary Neuroepithelial Bodies Express P2X3 Receptors, vol. 23, pp. 54-60, 2000.
W. Rong et al., "Pivotal Role of Nucleotide P2X2 Receptor Subunit of the ATP-Gated Ion Channel Mediating Ventilatory Responses to Hypoxia", J. of Neuroscience, vol. 23, pp. 11315-11321, 2003.

V. Ralevic et al., "Receptors for Purines and Pyrimidines", Pharmacological Reviews, vol. 50, pp. 416-492, 1998.
G. Burnstock., "Purinergic Nerves", Pharmacological Reviews, vol. 24, pp. 509-581, 1972.
P.A. Bland-Ward et al., "Acute Nociception Mediated by Hindpaw P2X Receptor Activation in the Rat", British J. of Pharmacology, vol. 122, pp. 365-371, 1997.
S. G. Hamilton et al., "The Effects of Inflammation and Inflammatory Mediators on Nociceptive Behaviour Induced by ATP Analogues in the Rat", B. J. of Pharmacology, vol. 126, pp. 326-332.
B. Driessen et al., "Antinociceptive Effect of Intrathecally Administered P2-Purinoceptor Antagonists in Rats", vol. 666, pp. 182-188, 1994.
M. Tsuda et al., "In Vivo Pathway of Thermal Hyperalgesia by Intrathecal Administration of alpha,Beta-Methylene ATP in Mouse Spinal Cord: Involvement of the Glutamate-NMDA Receptor System", B. J. of Pharmacology, vol. 127, pp. 449-456, 1999.
M. Tsuda et al., "Evidence for the Involvement of Spinal Endogenous ATP and P2Z Receptors in Nociceptive Responses Caused by Formalin and Capsaicin in Mice", B. J. of Pharmacology, vol. 128, pp. 1497-1504, 1999.
Y. Chen et al., "Ectopic Purinergic Sensitivity Develops at Sites of Chronic Nerve Constriction Injury in Rat", NeuroReport, vol. 10, pp. 2779-2782, 1999.
L. Vulchanova et al., "Immunohistochemical Study of the P2X2 and P2X3 Receptor Subunits in Rat and Monkey Sensory Neurons and Their Central Terminals", Neuropharmacology, vol. 36, pp. 1229-1242, 1997.
G. Burnstock, "Release of Vasoactive Substances from Endothelial Cells by Shear Stress and Purinergic Mechanosensory Transduction", J. Anatomy, vol. 194, pp. 335-342, 1999.
D. R. Ferguson et al., "ATP is Released from Rabbit Urinary Bladder Epithelial Cells by Hydrostatic Pressure Changes—A Possible Sensory Mechanism?", J. of Physiology, vol. 505, pp. 503-511, 1997.
S. Namasivayam et al., "Purinergic Sensory neurotransmission in the Urinary Bladder: An in Vitro Study in the Rat", BJU International, vol. 84, pp. 854-860, 1999.
Y. Zhong et al., "Pharmacological Molecular Characterization of P2X Receptors in Rat Pelvic Ganglion Neurons", B. J. of Pharmacology, vol. 125, pp. 771-781, 1998.
G. Burnstock, "A Basis for Distinguishing Two Types of Purinergic Receptor", Cell Membrane Receptors for Drugs and Hormones: A Multidisciplinary Approach, edited by R.W. Straub and L. Bolis, Raven Press, NY, pp. 107-118, 1978.
K. T. Le et al., "Central P2X4 and P2X6 Channel Subunits Coassemble into a Novel Heteromeric ATP Receptor", J. of Neuroscience, vol. 18, pp. 7152-7159, 1998.

* cited by examiner

P2X₃ RECEPTOR ANTAGONISTS FOR TREATMENT OF PAIN

CROSS REFERENCE TO RELATED APPLICATIONS

This application is the National Stage of International Application No. PCT/US2008/011270 filed on Oct. 29, 2008, which claims the benefit under 35 U.S.C. 119(e) of U.S. Provisional Applications No. 61/001,376 filed Oct. 31, 2007 and 61/132,194 filed Jun. 16, 2008.

FIELD OF THE INVENTION

The invention relates generally to compounds which act as modulators, e.g., antagonists of the P2X$_3$ receptor, compositions and therapeutic uses thereof.

BACKGROUND OF THE INVENTION

Purines, acting via an extracellular purinoreceptor, have been implicated as having a variety of physiological and pathological roles. (See, Burnstock (1993) Drug Dev. Res. 28:195-206.) Purinoreceptors (P2) have been generally categorized as either metabotropic nucleotide receptors or ionotropic receptors for extracellular nucleotides. Metabotropic nucleotide receptors (usually designated P2Y or P2Y$_{(n)}$, where "n" is a subscript integer indicating subtype) are believed to differ from ionotropic receptors (usually designated P2X or P2X$_n$) in that they are based on a different fundamental means of transmembrane signal transduction: P2Y receptors operate through a G protein-coupled system, while P2X receptors are ligand-gated ion channels.

At least seven P2X receptors, and the cDNA sequences encoding them, have been identified to date. P2X$_1$ cDNA was cloned from the smooth muscle of the rat vas deferens (Valera et al. (1994) Nature 371:516-519) and P2X$_2$ cDNA was cloned from PC12 cells (Brake et al. (1994) Nature 371:519-523). Five other P2X receptors have been found in cDNA libraries by virtue of their sequence similarity to P2X$_1$ and P2X$_2$-P2X$_3$: Lewis et al. (1995) Nature 377:432-435, Chen et al. (1995) Nature 377:428-431; P2X$_4$: Buell et al. (1996) EMBO J. 15:55-62, Seguela et al. (1996) J. Neurosci. 16:448-455, Bo et al. (1995) FEBS Lett. 375:129-133, Soto et al. (1996) Proc. Natl. Acad. Sci. USA 93:3684-3688, Wang et al. (1996) Biochem. Biophys. Res. Commun. 220:196-202; P2X$_5$: Collo et al. (1996) J. Neurosci. 16:2495-2507, Garcia-Guzman et al. (1996) FEBS Lett. 388:123-127; P2X$_6$: Collo et al. (1996), supra, Soto et al. (1996) Biochem. Biophys. Res. Commun. 223:456-460; P2X$_7$: Surprenant et al. (1996) Science 272:735-738). For a comparison of the amino acid sequences of rat P2X receptor see Buell et al. (1996) Eur. J. Neurosci. 8:2221-2228.

Purinergic receptors, in particular, P2X receptors, are known to function as homomultimeric cation-permeable ion channels and, in some cases, as heteromeric channels consisting of two different P2X receptor subtypes (Lewis et al., Nature 377:432-435 (1995); Le et al., J. Neurosci. 18:7152-7159 (1998); Tones et al., Mol. Pharmacol. 54:989-993 (1998)). The P2X$_2$ and P2X$_3$ subunits form functional channels when expressed alone, and can also form a functional heteromultimeric channel that has properties similar to currents seen in native sensory channels when co-expressed. At least one pair of P2X receptor subtypes, P2X$_2$ and P2X$_3$, functions as a heteromeric channel in rat nodose ganglion neurons where it exhibits distinct pharmacological and electrophysiological properties (Lewis et al., supra (1995)).

Native P2X receptors are known to form rapidly activated, nonselective cationic channels upon activation by ATP. The channels formed by P2X receptors generally have high Ca$^{2+}$ permeability (P$_{(Ca)}$/P$_{(Na)}$). With respect to individual receptors, the P2X$_3$ purinergic receptor is a ligand-gated cation channel that is selectively permeable to small cations. Known ligands for P2X receptors include natural nucleotides, for example, ATP, UTP, UDP, or synthetic nucleotides, for example 2-methylthioATP. ATP, in addition to its function as an intracellular energy donor, is now recognized as an important neurotransmitter or cotransmitter, in both the central and peripheral nervous system (Ralevic, V., et al., Pharmacol. Rev., 50:413-492 (1998)). It is released from a variety of cell types, including nerve fibers, upon stimulation and produces diverse effects on many tissues by activation of specific membrane receptors including purinoreceptors (P2 receptor) (See Burnstock, G., Pharmacol. Rev., 24:509-581 (1972); Burnstock, G., Cell Membrane Receptor for Drugs and Hormones: A Multidisciplinary Approach, edited by R. W. Straub and L. Bolid. New York: Raven, 1978, p. 107-118). With respect to the P2X purinergic receptor, data suggest that ATP is capable of activating P2X$_3$ homomeric receptors and P2X$_2$/P2X$_3$ heteromeric receptors where it functions as an excitatory neurotransmitter in the spinal cord dorsal horn and in primary afferents from sensory ganglia. In vitro, co-expression of P2X$_2$ and P2X$_3$ receptor subunits is necessary to produce ATP-gated currents with the properties seen in some sensory neurons. See, Lewis, et al. (1995) Nature 377:432-435.

ATP, and to a lesser extent, adenosine, can stimulate sensory nerve endings resulting in intense pain and a pronounced increase in sensory nerve discharge. According to available data, ATP released from damaged cells can evoke pain by activating P2X$_3$ homomeric receptors, or P2X$_2$/P2X$_3$ heteromeric receptors expressed on nociceptive nerve endings of sensory nerves. This is consistent with reports of the induction of pain by intradermally applied ATP in the human blister-base model; the identification of P2X$_3$ containing receptor on nociceptive neurons in the tooth pulp; and with reports that P2X antagonists are analgesic in animal models. To date, research data suggests that the mechanism whereby ATP-induced activation of the P2X purinergic receptors on dorsal root ganglion nerve terminals in the spinal cord and on neurons in the brain results in pain sensation is by the stimulation of the release of glutamate, a key neurotransmitter involved in nociceptive signaling.

It has also been recently demonstrated that P2X$_3$ receptor gene disruption results in a diminished sensitivity to noxious chemical stimuli and reduced pain. The nociceptive effects of exogenously administered ATP and P2X containing receptor agonists have also been demonstrated in laboratory animals. See Bland-Ward et al., Dr. J. Pharmacol. 122:366-371 (1997); Hamilton et al., Br. J. Phamacol. 126:326-332 (1999). The peripheral nociceptive actions of P2X activation and stimulation of spinal P2X containing receptor also contribute to nociception as indicated by the ability of intrathecally (i.t.) administered P2 receptor agonists to increase sensitivity to acute and persistent noxious stimuli in rodents. See Driessen et al., Brain Res. 666:182-188 (1994); Tsuda et al., Br. J. Pharmacol. 127:449-4S6 (1999); Tsuda et al., Br. J. Pharmacol. 128:1497-1504 (1999). A selective P2 receptor-mediated increase in ectopic neuronal excitability that is localized to damaged sensory afferents has also been recently reported in rats following chronic constriction nerve injury. See Chen et al., NeuroReport 10:2779-2782 (1999). This role in pain transmission is consistent with the observation that the rat P2X$_3$ receptor expression is found primarily in a subset of neurons of the sensory ganglia, which are involved in pain transmission. See Chen et al., Nature 377:428-430 (1995); Vulchanova et al., Neuropharmacol. 36:1229-1242 (1997). See also US20080004442, US200700409609, WO2007041087, WO2006119504, WO200112627, WO2007001973 and WO2007010553.

Taken together, the functional and immunohistochemical localization of P2X$_3$ containing receptors (P2X$_3$ and/or P2X$_{2/3}$) on sensory nerves indicates that these P2X receptors may have a primary role in mediating the nociceptive effects of ATP. Thus, compounds which block or inhibit activation of P2X$_3$ receptors serve to block the pain stimulus. More, receptor antagonists to compounds which normally activate the P2X$_3$ receptor and/or P2X$_2$/P2X$_3$ heteromeric channels, such as ATP, could successfully block the transmission of pain. Indeed, modulators of P2X receptors, e.g., P2X$_3$ receptor may find use as analgesics.

Additionally, compounds that block or inhibit activation of P2X$_3$ receptors also serve to treat genitourinary, gastrointestinal and respiratory diseases, conditions and disorders or receptor antagonists to compounds which normally activate the P2X$_3$ receptor and/or P2X$_2$/P2X$_3$ heteromeric channels, such as ATP are useful for treatment of genitourinary, gastrointestinal and respiratory diseases, conditions and disorders.

Burnstock (1999) *J. Anatomy* 194:335-342; and Ferguson et al. (1997) *J. Physiol.* 505:503-511 disclose that P2X receptor subunits have been found on afferents in rodent and human bladder urothelium. There data suggests that ATP may be released from epithelial/endothelial cells of the urinary bladder or other hollow organs as a result of distention. ATP released in this manner may serve a role in conveying information to sensory neurons located in subepithelial components, e.g., suburothelial lamina propria (Namasibayam, et al. (1999) *BJU Intl.* 84:854-860). P2X receptors have been studied in a number of neurons including sensory, sympathetic, parasympathetic, mesenteric, and central neurons (Zhong, et al. (1998) *Br. J. Pharmacol.* 125:771-781). These studies indicate that purinergic receptors play a role in affterent neurotransmission from the bladder, and that modulators of P2X receptors are potentially useful in the treatment of bladder disorders and other genitourinary diseases or conditions.

P2X$_3$ receptors have been shown to be expressed in human colon, and are expressed at higher levels in inflamed colon, than in normal colon (Y. Yiangou et al, *Neurokastroenterol Mot* (2001) 13:365-69). P2X$_3$ receptors have also been implicated in detection of distension or intraluminal pressure in the intestine and initiation of reflex contractions (X. Bian et al. *J. Physiol* (2003) 551.1:309-22), and have linked this to coilitis (G. Wynn et al., *Am J. Physiol Gastrointest Liver Physiol* (2004) 287:G647-57).

P2X$_3$ receptors also have been shown to be expressed in pulmonary neuroepithelial bodies (NEBs), implicating the receptor in pain transmission in the lung (Inge Brouns et al., *Am J. Respir Cell Mol Biol* (2000) 23:52061). Additionally, P2X$_2$ and P2X$_3$ receptors have been implicated in pO$_2$ detection in pulmonary NEBs (W. Rong et al., *J. Neurosci* (2003) 23(36):11315-21).

However, the utility of available purinergic ligands to evaluate the role of individual P2 receptor subtypes in mammalian physiology has been complicated by the susceptibility of P2 receptor agonists to undergo enzymatic degradation. As well, the study of the role of an individual P2X receptor is hampered by the lack of receptor subtype-specific agonists and antagonists.

Consequently, the state of the art begs an inquiry into methods and/or compounds which will provide the ability to regulate or control the P2X receptors, for example, P2X$_3$, because control of such receptors will provide the ability to minimize pain in patients in need of such treatment. In addition, for both research and therapeutic purposes there is a need in the art for specific agonists and antagonists for each P2X receptor subtype and, in particular, agents that will be effective in vivo, as well as for methods for identifying purinoreceptor-specific agonist and antagonist compounds.

The present invention aims to overcome some of the aforementioned drawbacks by providing novel P2X$_3$ receptor antagonists that play a critical role in treating disease states associated with pain, in particular peripheral pain, inflammatory pain, or tissue injury pain that can be treated using a P2X$_3$ receptor subunit modulator.

SUMMARY OF THE INVENTION

The present invention relates to a novel P2X$_3$ type receptor antagonists of structural formula I:

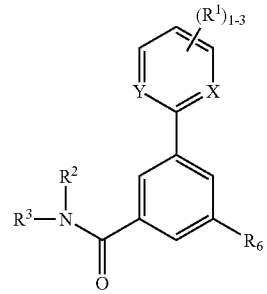

or pharmaceutically acceptable salts and individual enantiomers and diastereomers thereof wherein:
X and Y independently represent N, or CR$^1$;
R$^6$ represents hydrogen, OH, (CH$_2$)$_n$CF$_3$, SO$_{0-2}$R$^2$, N(R$^2$)$_2$, C(R$^2$)$_2$OR$^2$, C$_{1-6}$ alkyl, C$_{2-6}$ alkenyl, C$_{2-6}$ alkynyl, C$_{3-10}$ cycloalkyl, (CH$_2$)$_n$C$_{6-10}$ aryl, (CH$_2$)$_n$C$_{5-10}$ heterocyclyl, said alkyl, alkenyl, alkynyl, aryl and heterocyclyl optionally substituted with 1 to 3 groups of R$^a$, provided said heterocyclyl is not oxazolyl, isoxazolyl, dihydro-isoxazolyl, or oxadiazolyl;
R$^1$ represents H, C$_{1-6}$ alkyl, halogen, (CH$_2$)$_n$CF$_3$, C$_{3-10}$ cycloalkyl, C(R$^2$)$_2$OH, —O—, CN, (CH$_2$)$_n$OR$^2$, (CH$_2$)$_n$C$_{5-10}$ heterocyclyl, (CH$_2$)$_n$C$_{6-10}$ aryl, or C$_{1-6}$ alkoxy; said alkyl, cycloalkyl, heterocyclyl and aryl optionally substituted with 1 to 3 groups of C$_{1-6}$ alkyl, halogen, hydroxyl, (CH$_2$)$_n$CF$_3$, or CN;
R$^2$ represents H, C$_{1-6}$ alkyl, CF$_3$, CHF$_2$, CH$_2$F, OH;
R$^3$ represents —CR$^2$R$^4$R$^5$, —(C(R$^2$)$_2$)$_n$C$_{3-10}$ cycloalkyl, —(C(R$^2$)$_2$)$_n$C$_{5-10}$ heterocycle, said cycloalkyl and heterocyclyl optionally substituted with 1 to 3 groups of R$^a$;
or R$^2$ and R$^3$ can be combined with the nitrogen to which they are attached to form a C$_{5-10}$ heterocyclyl optionally substituted with 1 to 3 groups of R$^a$;
R$^4$ and R$^5$ independently represent H, (CH$_2$)$_n$OR$^2$, (CH$_2$)$_n$C$_{5-10}$ heterocyclyl, (CH$_2$)$_n$C$_{6-10}$ aryl, C$_{3-10}$ cycloalkyl, C$_{1-6}$ alkoxy, $C_{2-6}$ alkenyl, $C_{2-6}$ alkynyl, $(CH_2)_nCF_3$, $CHF_2$, CN, $C(O)_{1-2}R^2$, or $C_{1-6}$ alkyl; said alkyl, cycloalkyl, heterocyclyl and aryl optionally substituted with 1 to 3 groups of $R^a$;
$R^a$ represents $C_{1-6}$ alkyl, halogen, —$CHF_2$, —$(CH_2)_nCF_3$, —O—, $C_{3-6}$ cycloalkyl, $NR^2C(O)R^2$, $C(O)N(R^2)_2$, $C(R^2)_2OR^2$, $C(O)R^2$, $NO_2$, CN, $N(R^2)_2$, $C(O)OR^2$, $SO_2R^2$, $OR^2$, $(CH_2)_nC_{5-10}$ heterocyclyl, or $(CH_2)_nC_{6-10}$ aryl, said alkyl, heterocyclyl and aryl optionally substituted with 1 to 3 groups of $C_{1-6}$ alkyl, halogen, $OR^2$, $N(R^4)_2$, $C(O)N(R^2)_2$, $(CH_2)_nCF_3$, or CN; and
n represents 0 to 4.

This invention also relates to compositions and methods for using the compounds disclosed herein. These and other embodiments of the present invention will readily occur to those of ordinary skill in the art in view of the disclosure herein.

DETAILED DESCRIPTION OF THE INVENTION

The present invention relates to a novel $P2X_3$ type receptor antagonists of structural formula I that are useful in treating pain and diseases associated with pain.

One embodiment of the present invention is realized when one of X and Y is N and the other is CH and all other variables are as previously described.

Another embodiment of the present invention is realized when X and Y are CH at the same time and all other variables are as previously described.

Another embodiment of the present invention is realized when X is N and Y is CH and all other variables are as previously described.

Still another embodiment of the invention is realized when $R^6$ represents a $C_{1-6}$ alkyl, said alkyl optionally substituted with 1 to 3 groups of $R^a$. A sub-embodiment of this invention is realized when the substituents are selected from the group consisting of $N(R^2)_2$, $CF_3$, OH, $CHF_2$, $CH_3$, phenyl and pyridyl, preferably OH.

Still another embodiment of the invention is realized when $R^6$ represents a $(CH_2)_nC_{6-10}$ aryl, said aryl optionally substituted with 1 to 3 groups of $R^a$. A sub-embodiment of this invention is realized when $R^6$ is phenyl.

Still another embodiment of the invention is realized when $R^6$ represents a $(CH_2)_nC_{5-10}$ heterocyclyl, said heterocyclyl optionally substituted with 1 to 3 groups of $R^a$, provided said heterocyclyl is not oxazolyl, isoxazolyl, dihydro-isoxazolyl, or oxadiazolyl. A sub-embodiment of this invention is realized when $R^6$ is benzimidazolyl, benzisoxazolyl, imidazolidinyl, imidazolinyl, imidazolyl, isoimidazolyl, indazolyl, indolinyl, indolyl, isoindolinyl, naphthyridinyl, oxazinyl, piperidyl, piperidino, piperazinyl, pyridyl, pyrazinyl, pyrazolidinyl, pyrazolyl, pyridazinyl, pyrimidinyl, pyrrolidinyl, pyrrolyl, pyrrollidino, triazolyl (e.g., 1,2,3, triazolyl and 1,2,4 triazolyl), and tetrazolyl. A further sub-embodiment of this invention is realized when $R^6$ is imidazolyl, pyrazolyl, oxazinyl, triazolyl, benzimidazolyl, piperazinyl, morpholinyl, and pyridyl.

Another embodiment of the present invention is realized when $R^3$ is $CR^2R^4R^5$ wherein $R^2$ in $CR^2R^4R^5$ is hydrogen and both of $R^4$ and $R^5$ are $C_{1-6}$ alkyl, said alkyl optionally substituted with 1 to 3 groups of $R^a$, and all other variables are as previously described. A sub-embodiment of this invention is realized when $R^3$ is $C_{1-6}$ alkyl optionally substituted by 1 to 3 groups of $R^a$ Another embodiment of the present invention is realized when $R^3$ is $CR^2R^4R^5$ wherein $R^2$ in $CR^2R^4R^5$ is hydrogen and one of $R^4$ and $R^5$ is optionally substituted $C_{1-6}$ alkyl and the other is $C_{5-10}$ heterocyclyl, said heterocylyl optionally substituted with 1 to 3 groups of $R^a$ and all other variables are as previously described. A sub-embodiment of this invention is realized when the substitution on the heterocyclyl can occur on a carbon and/or nitrogen atom and $R^a$ is selected from the group consisting of $CF_3$, OH, —O—, $C_{1-6}$ alkyl, halo, and $C_{3-10}$ cycloalkyl.

Another embodiment of the present invention is realized when $R^3$ is —$(C(R^2)_2)_nC_{3-10}$ cycloalkyl optionally substituted by 1 to 3 groups of $R^a$, and all other variables are as originally described.

Another embodiment of the present invention is realized when $R^3$ is —$(C(R^2)_2)_nC_{5-10}$ heterocycle optionally substituted by 1 to 3 groups of $R^a$, and all other variables are as originally described. A sub-embodiment of this invention is realized when said heterocyclyl is triazolyl, pyridyl, pyrimidinyl, oxazolyl, pyrazolyl or oxadiazolyl, optionally substituted by 1 to 3 groups of $R^a$. A sub-embodiment of this invention is realized when the substitution on the heterocyclyl can occur on a carbon and/or nitrogen atom and $R^a$ is selected from the group consisting of $CF_3$, OH, —O—, $C_{1-6}$ alkyl, halo, and $C_{3-10}$ cycloalkyl.

Another embodiment of the present invention is realized when $R^3$ is $CR^2R^4R^5$ wherein $R^2$ of $CR^2R^4R^5$ is hydrogen, X and Y are CH or X is N and Y is CH, and $R^6$ is benzimidazolyl, benzisoxazolyl, imidazolidinyl, imidazolinyl, imidazolyl, isoimidazolyl indazolyl, indolinyl, indolyl, isoindolinyl, naphthyridinyl, oxazinyl, piperidyl, piperazinyl, pyridyl, pyrazinyl, pyrazolidinyl, pyrazolyl, pyridazinyl, pyrimidinyl, pyrrolidinyl, pyrrolyl, triazolyl (e.g., 1,2,3, triazolyl and 1,2,4 triazolyl), and tetrazolyl all optionally substituted with 1 to 3 groups of $R^a$. A further sub-embodiment of this invention is realized when $R^6$ is imidazolyl, pyrazolyl, oxazinyl, triazolyl, benzimidazolyl, piperazinyl, morpholinyl, and pyridyl optionally substituted with 1 to 3 groups of $R^a$. A sub-embodiment of this invention is realized when $R^6$ is imidazolyl. Another sub-embodiment of this invention is realized when $R^6$ is triazolyl. Another sub-embodiment of this invention is realized when $R^6$ is oxazinyl. Another sub-embodiment of this invention is realized when $R^6$ is pyrazolyl. Another sub-embodiment of this invention is realized when $R^6$ is pyridyl. Another sub-embodiment of this invention is realized when $R^6$ is morpholinyl. Another sub-embodiment of this invention is realized when $R^6$ is piperizinyl Another sub-embodiment of this invention is realized when the substitution on the heterocylyl can occur on a carbon and/or nitrogen atom and $R^a$ is selected from the group consisting of $CF_3$, OH, —O—, $C_{1-6}$ alkyl, halo, and $C_{3-10}$ cycloalkyl Still another embodiment of the this invention is realized when $R^6$ is imidazolyl, optionally substituted with 1 to 3 groups of $R^a$, one of X and Y is nitrogen and the other is CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is imidazolyl, optionally substituted with 1 to 3 groups of $R^a$, X and Y are CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is triazolyl, optionally substituted with 1 to 3 groups of $R^a$, one of X and Y is nitrogen and the other is CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is triazolyl, optionally substituted with 1 to 3 groups of $R^a$, X and Y are CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is pyrazolyl, optionally substituted with 1 to 3 groups of $R^a$, one of X and Y is nitrogen and the other is CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is pyrazolyl, optionally substituted with 1 to 3 groups of $R^a$, X and Y are CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is oxazinyl, optionally substituted with 1 to 3 groups of $R^a$, one of X and Y is nitrogen and the other is CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is oxazinyl, optionally substituted with 1 to 3 groups of $R^a$, X and Y are CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is morpholinyl, optionally substituted with 1 to 3 groups of $R^a$, one of X and Y is nitrogen and the other is CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is morpholinyl, optionally substituted with 1 to 3 groups of $R^a$, X and Y are CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is piperazinyl, optionally substituted with 1 to 3 groups of $R^a$, one of X and Y is nitrogen and the other is CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is piperazinyl, optionally substituted with 1 to 3 groups of $R^a$, X and Y are CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is pyridyl, optionally substituted with 1 to 3 groups of $R^a$, one of X and Y is nitrogen and the other is CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is pyridyl, optionally substituted with 1 to 3 groups of $R^a$, X and Y are CH, $R^2$ is hydrogen, $R^3$ is $CR^2R^4R^5$, the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$.

Still another embodiment of the this invention is realized when $R^6$ is $C_{1-6}$ alkyl, optionally substituted with 1 to 3 groups of $R^a$, one of X and Y is nitrogen and the other is CH, $R^2$ is hydrogen, $R^3$ is $CR^2R^4R^5$, wherein the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$. A sub-embodiment of this invention is realized when said heterocyclyl is triazolyl, pyridyl, pyrimidinyl, oxazolyl, pyrazolyl or oxadiazolyl, preferably pyridyl, optionally substituted with 1 to 3 groups of $R^a$. Another sub-embodiment of this invention is realized when the substitution on the heterocyclyl can occur on a carbon and/or nitrogen atom and $R^a$ is selected from the group consisting of $CF_3$, OH, —O—, $C_{1-6}$ alkyl, halo, and $C_{3-10}$ cycloalkyl.

Still another embodiment of the this invention is realized when $R^6$ is $C_{1-6}$ alkyl, optionally substituted with 1 to 3 groups of $R^a$, X is nitrogen and Y is CH, $R^2$ is hydrogen, $R^3$ is $CR^2R^4R^5$, wherein the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$. A sub-embodiment of this invention is realized when said heterocyclyl is triazolyl, pyridyl, pyrimidinyl, oxazolyl, pyrazolyl or oxadiazolyl, preferably pyridyl, optionally substituted with 1 to 3 groups of $R^a$. Another sub-embodiment of this invention is realized when the substitution on the heterocyclyl can occur on a carbon and/or nitrogen atom and $R^a$ is selected from the group consisting of $CF_3$, OH, —O—, $C_{1-6}$ alkyl, halo, and $C_{3-10}$ cycloalkyl.

Still another embodiment of the this invention is realized when $R^6$ is $C_{1-6}$ alkyl, optionally substituted with 1 to 3 groups of $R^a$, X and Y are CH, $R^2$ is hydrogen, $R^3$ is $CR^2R^4R^5$, wherein the $R^2$ in $CR^2R^4R^5$ is hydrogen, and one of $R^4$ and $R^5$ is $C_{1-6}$ alkyl and the other is $C_{5-10}$ heterocyclyl, said heterocylyl optionally substituted with 1 to 3 groups of $R^a$. A sub-embodiment of this invention is realized when said heterocyclyl is triazolyl, pyridyl, pyrimidinyl, oxazolyl, pyrazolyl or oxadiazolyl, preferably pyridyl, optionally substituted with 1 to 3 groups of $R^a$. Another sub-embodiment of this invention is realized when the substitution on the heterocyclyl can occur on a carbon and/or nitrogen atom and $R^a$ is selected from the group consisting of $CF_3$, OH, —O—, $C_{1-6}$ alkyl, halo, and $C_{3-10}$ cycloalkyl.

Examples of compounds of this invention are found in Tables 1-7 below:

TABLE 1

| EX | Structure | MS M + H | Stereo-chemistry |
|---|---|---|---|
| 1.1 | 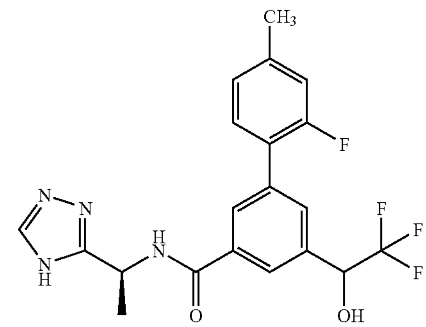 | 423.0 | S, R/S |
| 1.2 | 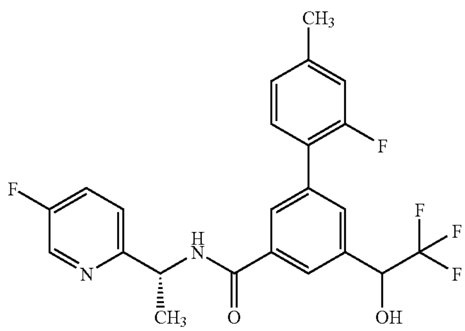 | 451.0 | R, R/S |
| 1.3 | 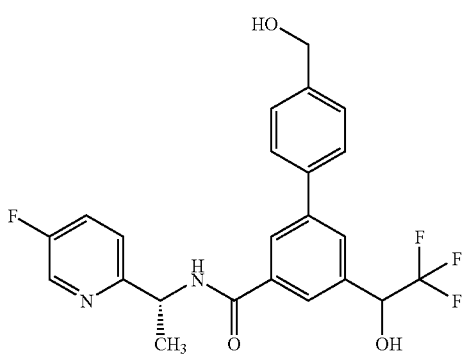 | 449.1 | R, R/S |
| 1.4 | 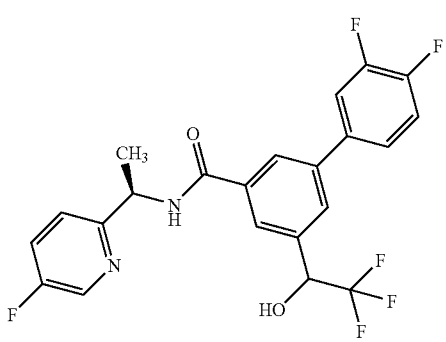 | 455.0 | R, R/S |

TABLE 1-continued

| EX | Structure | MS M + H | Stereo-chemistry |
|---|---|---|---|
| 1.5 | 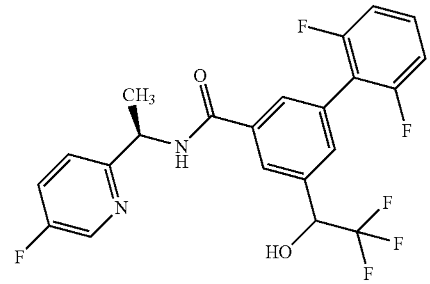 | 455.0 | R, R/S |
| 1.6 | 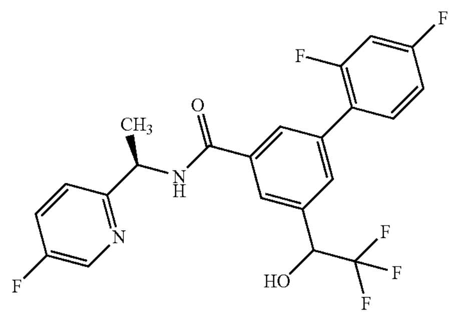 | 455.0 | R, R/S |
| 1.7 | 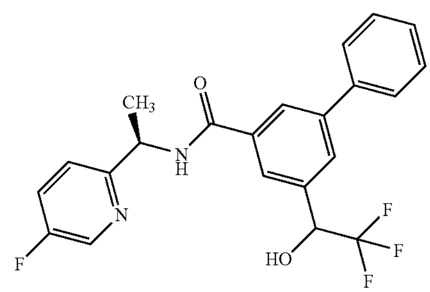 | 419.1 | R, R/S |
| 1.8 | 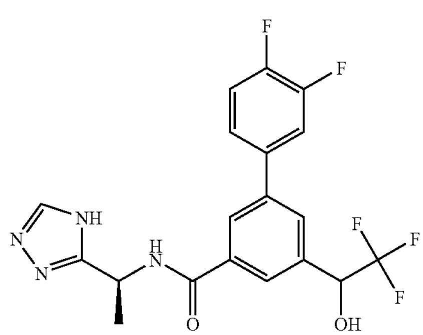 | 427.1 | S, R/S |
| 1.9 | 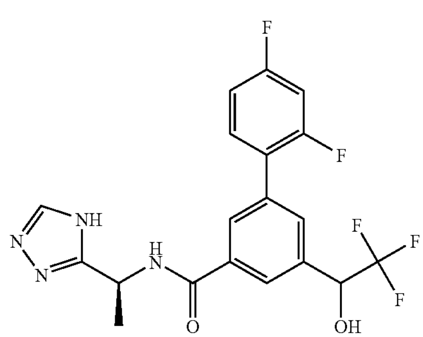 | 427.1 | S, R/S |

TABLE 1-continued

| EX | Structure | MS M + H | Stereo-chemistry |
|---|---|---|---|
| 1.10 | 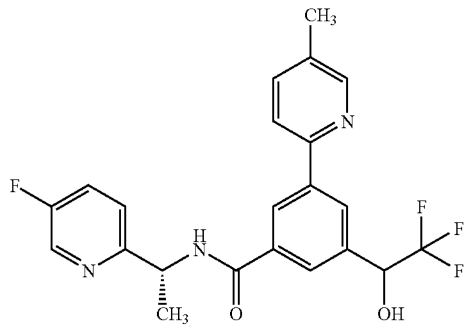 | 434.1484 | R, R/S |
| 1.11 | 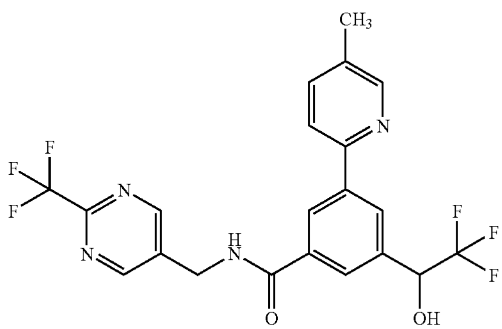 | 471.1 | R/S |
| 1.12 | 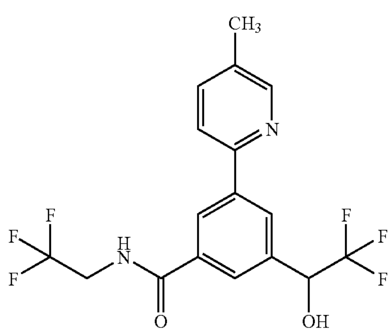 | 393.1 | R/S |
| 1.13 | 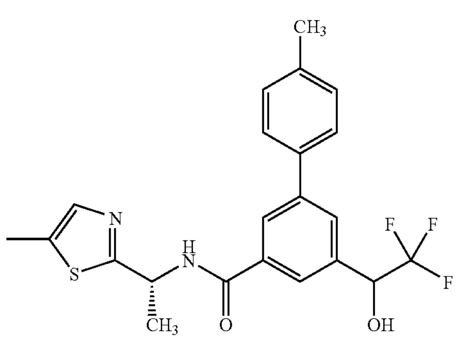 | 435.1 | R, R/S |

TABLE 1-continued

| EX | Structure | MS M + H | Stereo-chemistry |
|---|---|---|---|
| 1.14 | 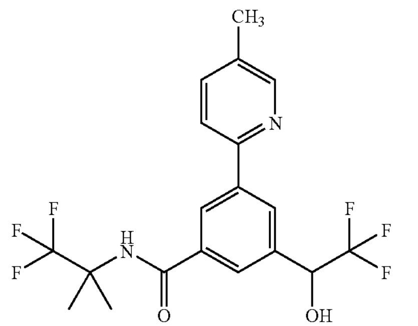 | 420.1 | R/S |
| 1.15 | 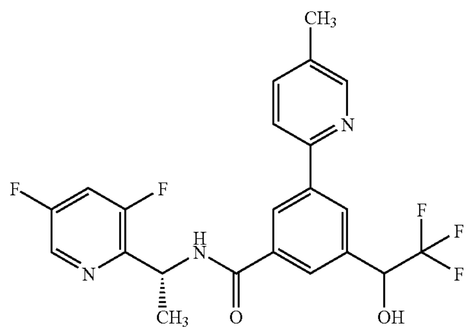 | 452.1 | R, R or S |
| 1.16 | 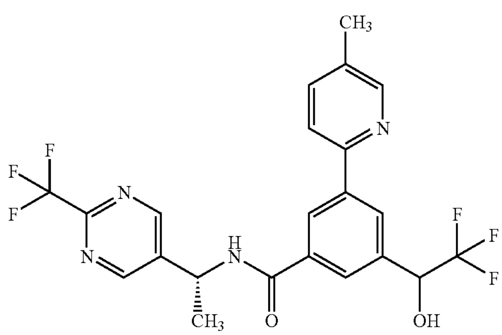 | 485.1 | R, R or S |
| 1.17 | 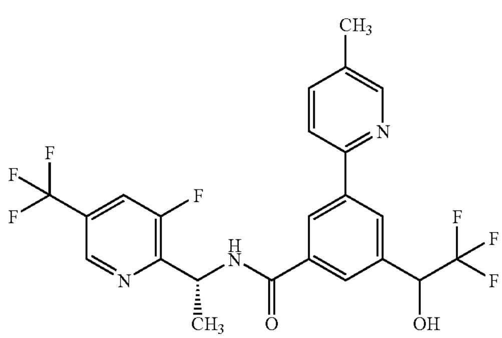 | 502.1 | R, R or S |

TABLE 1-continued

| EX | Structure | MS M + H | Stereo-chemistry |
|---|---|---|---|
| 1.18 | 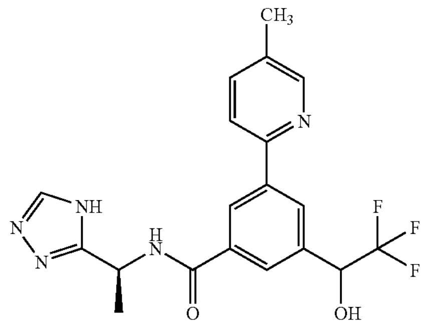 | 406.1 | S, R or S |
| 1.19 | 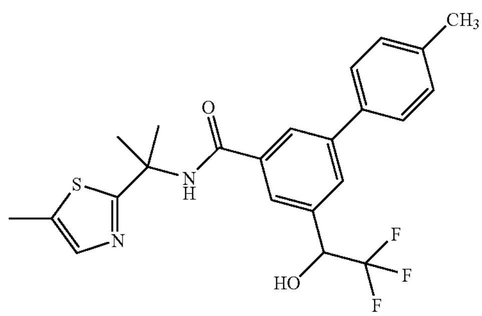 | 449.1 | R/S |
| 1.20 | 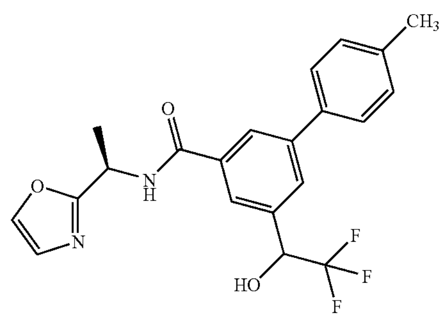 | 405.1 | R/S |
| 1.21 | 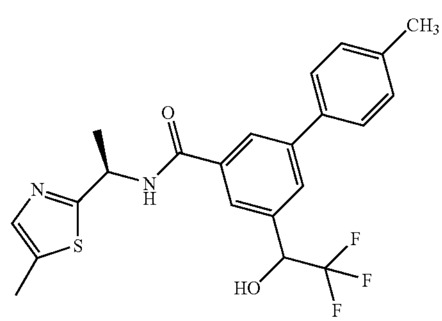 | 435.1 | R, R/S |
| 1.22 | 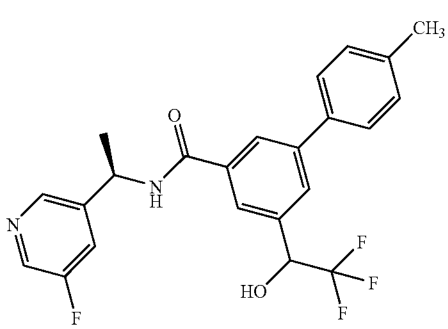 | 433.1 | R, R/S |

TABLE 1-continued
| EX | Structure | MS M + H | Stereo-chemistry |
|---|---|---|---|
| 1.23 | 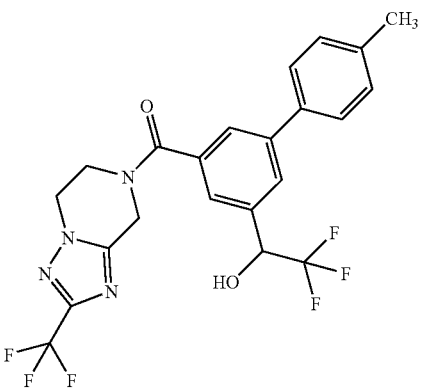 | 485.1 | R/S |
| 1.24 | 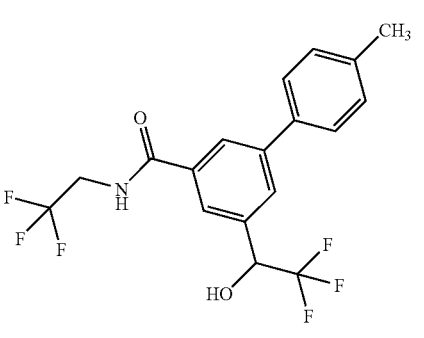 | 392.1079 | R/S |
| 1.25 | 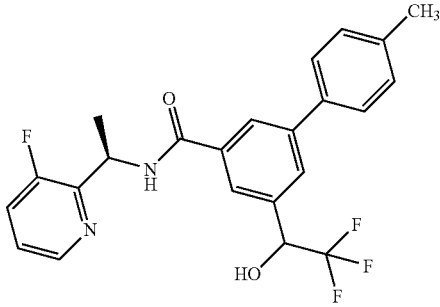 | 433.1 | R, R/S |
| 1.26 | 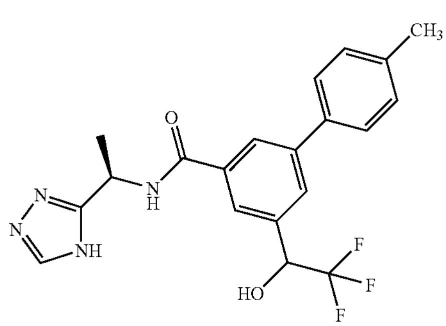 | 405.1 | S, R/S |

TABLE 1-continued

| EX | Structure | MS M + H | Stereo-chemistry |
|---|---|---|---|
| 1.27 | 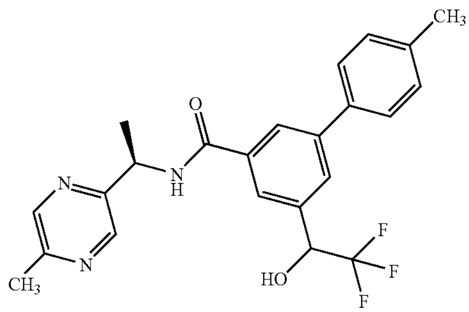 | 430.1 | R, R/S |
| 1.28 | 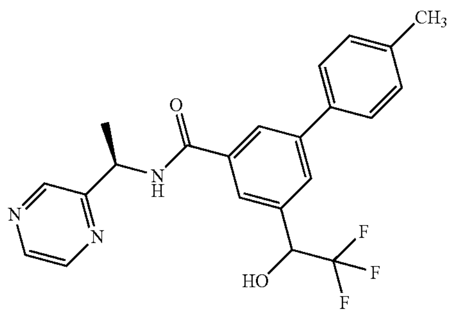 | 416.1 | R, R/S |
| 1.29 | 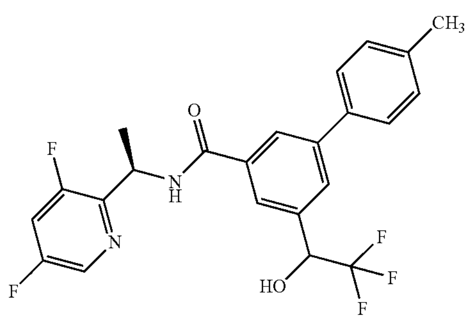 | 451.1 | R, R/S |
| 1.30 | 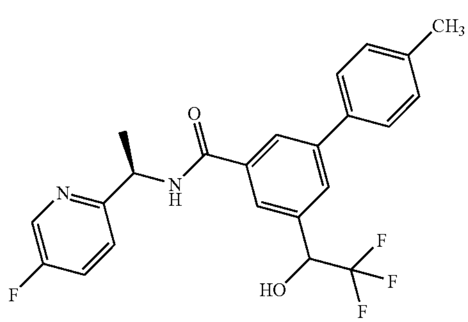 | 433.1 | R, R/S |

TABLE 1-continued

| EX | Structure | MS M + H | Stereo-chemistry |
|---|---|---|---|
| 1.31 | 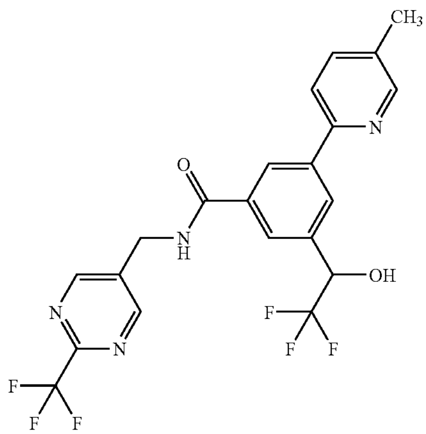 | 471.1 | R/S |
| 1.32 | 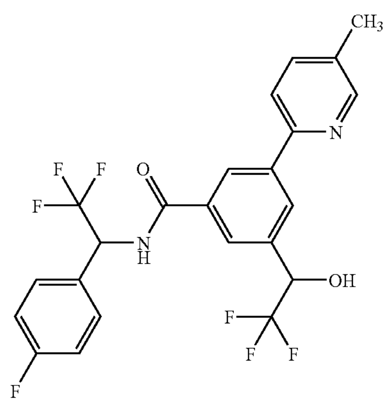 | 487.1 | R/S, R/S |
| 1.33 | 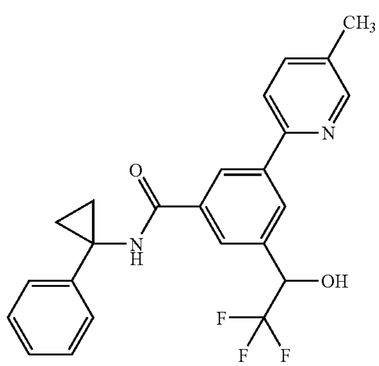 | 427.1 | R/S |
| 1.34 | 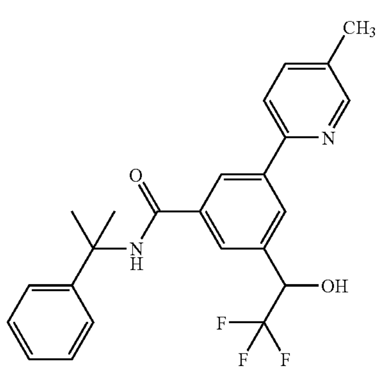 | 429.1 | R/S |

TABLE 1-continued

| EX | Structure | MS M + H | Stereo-chemistry |
|---|---|---|---|
| 1.35 | 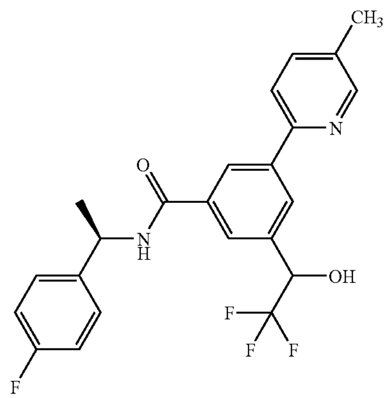 | 433.1 | R, R/S |
| 1.36 | 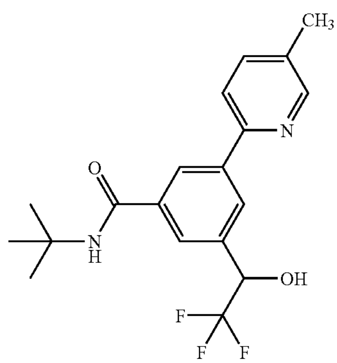 | 367.1 | R/S |
| 1.37 | 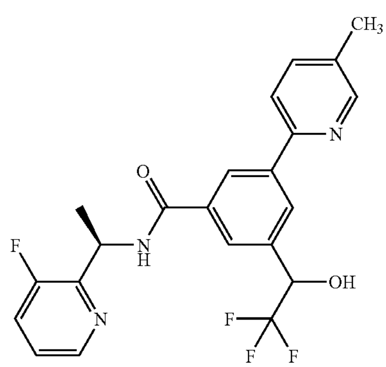 | 434.0 | R, R/S |
| 1.38 | 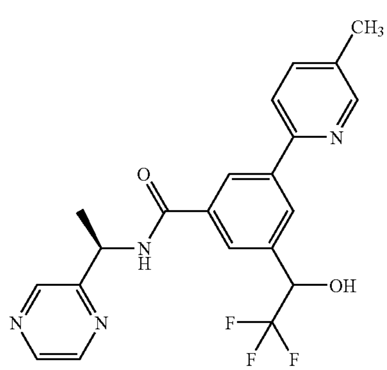 | 417.1 | R, R/S |

TABLE 1-continued

| EX | Structure | MS M + H | Stereo-chemistry |
|---|---|---|---|
| 1.39 | 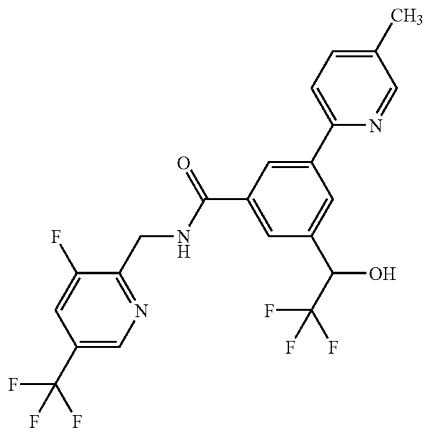 | 488.1 | R/S |
| 1.40 | 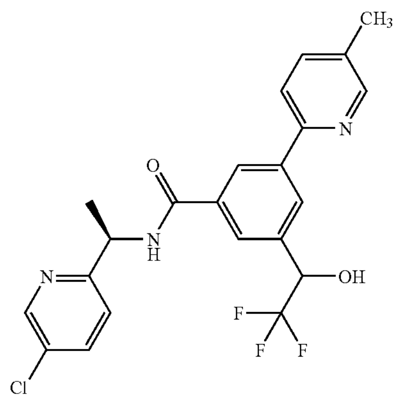 | 450.1 | R, R/S |
| 1.41 | 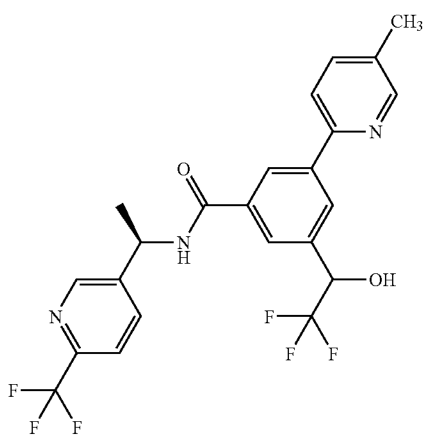 | 484.1 | R, R/S |
| 1.42 | 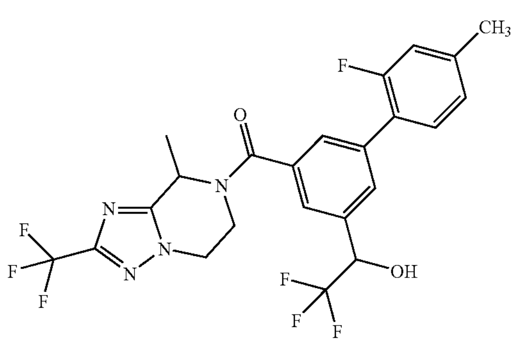 | 516.8 | R/S, R/S |

TABLE 1-continued

| EX | Structure | MS M + H | Stereo-chemistry |
|---|---|---|---|
| 1.43 | 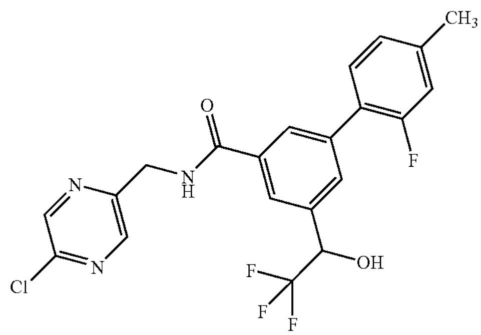 | 454.8 | R/S |
| 1.44 | 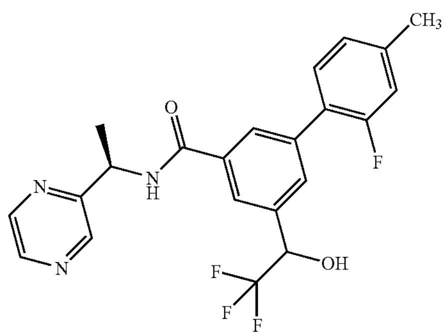 | 434.8 | R, R/S |
| 1.45 | 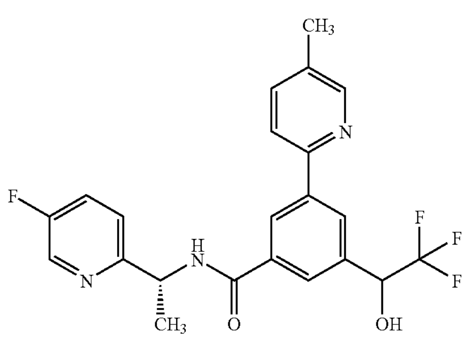 | 434.2 | R, R or S |
| 1.46 | 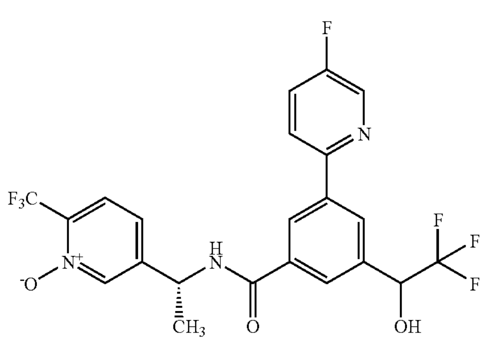 | 504.0 | R, R or S |

TABLE 1-continued

| EX | Structure | MS M + H | Stereo-chemistry |
|---|---|---|---|
| 1.47 | 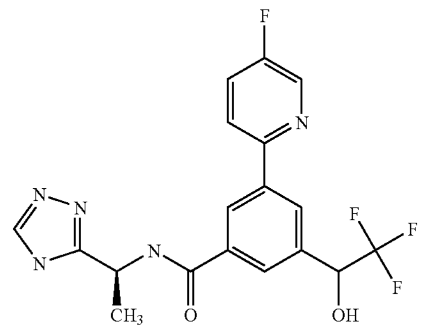 | 410.1 | S, R/S |
| 1.48 | 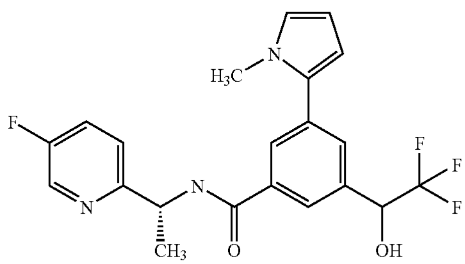 | 422.1 | R, R/S |
| 1.49 | 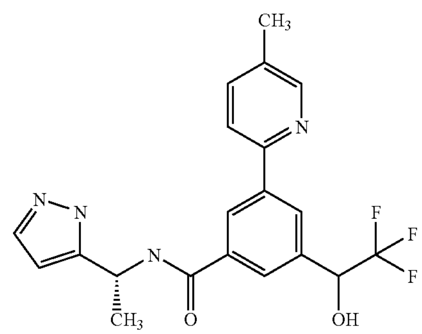 | 405.1 | R, R or S |
| 1.50 | 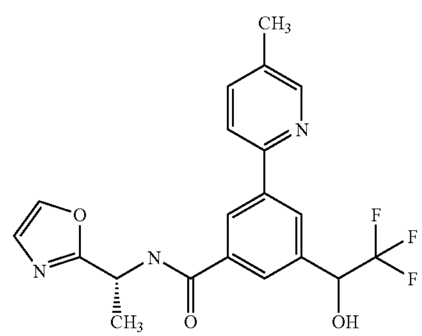 | 406.1 | R, R or S |
| 1.51 | 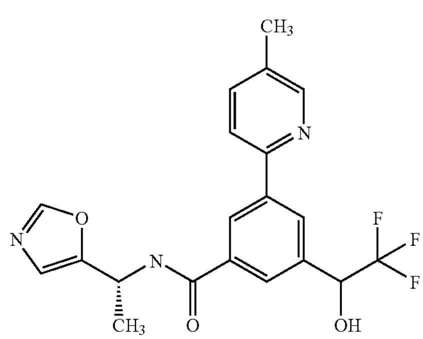 | 406.1 | R, R or S |

TABLE 1-continued

| EX | Structure | MS M + H | Stereo-chemistry |
|---|---|---|---|
| 1.52 | 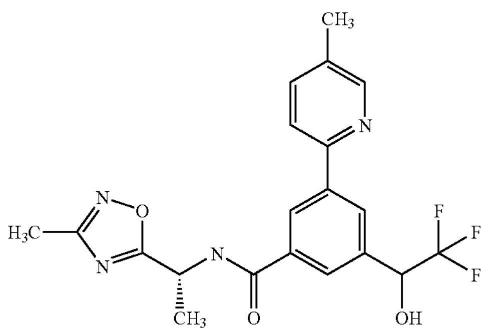 | 421.1 | R, R or S |
| 1.53 | 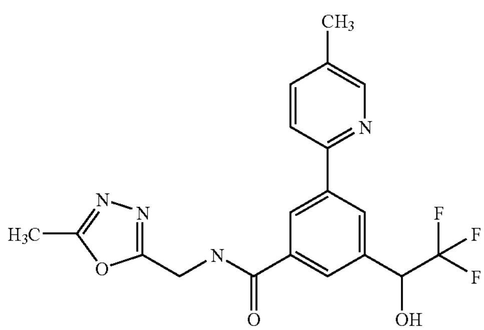 | 407.1 | R or S |
| 1.54 | 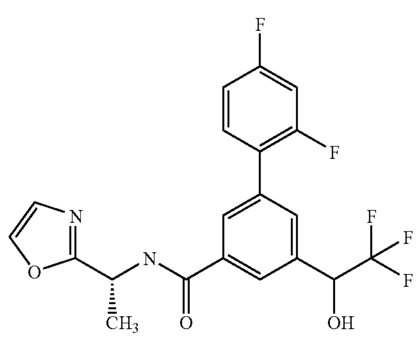 | 427.0 | R, R or S |
| 1.55 | 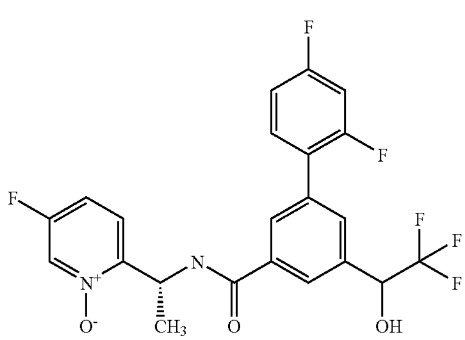 | 471.0 | R, R or S |

TABLE 1-continued

| EX | Structure | MS M + H | Stereo-chemistry |
|---|---|---|---|
| 1.56 | 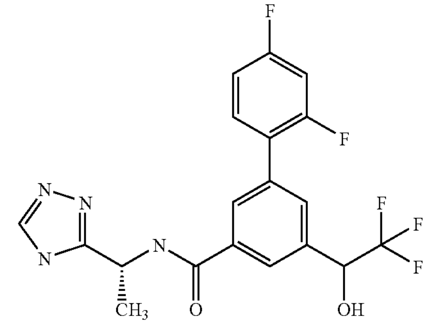 | 426.9 | R, R or S |
| 1.57 | 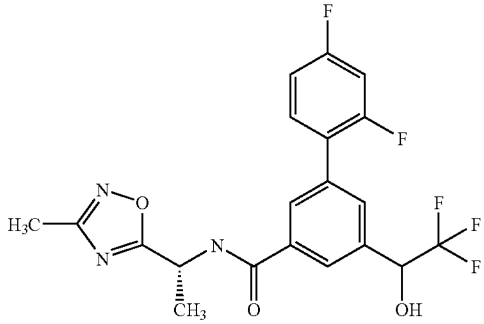 | 442.0 | R, R or S |
| 1.58 | 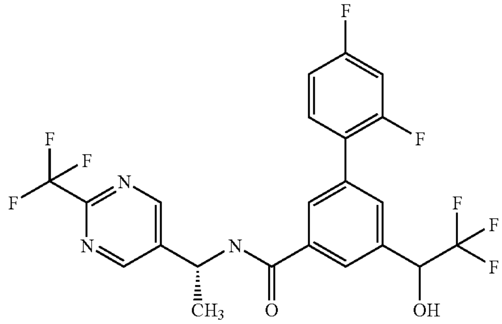 | 506.0 | R, R or S |
| 1.59 | 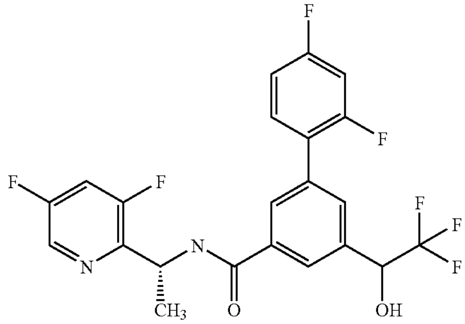 | 473.0 | R, R or S |

TABLE 1-continued

| EX | Structure | MS M + H | Stereo-chemistry |
|---|---|---|---|
| 1.60 | 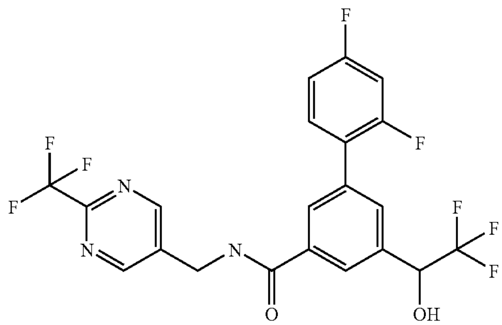 | 492.0 | R or S |
| 1.61 | 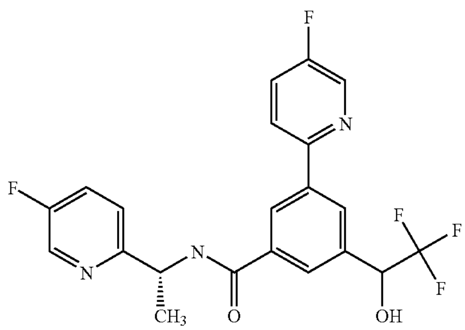 | 438.1 | R, R or S |
| 1.62 | 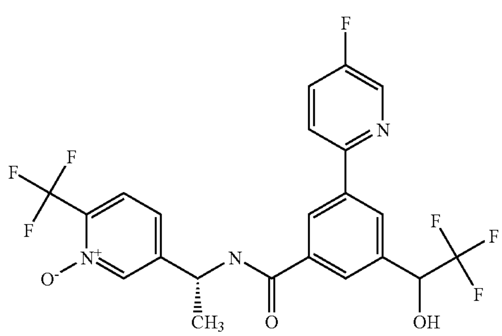 | 504.0 | R, R or S |
| 1.63 | 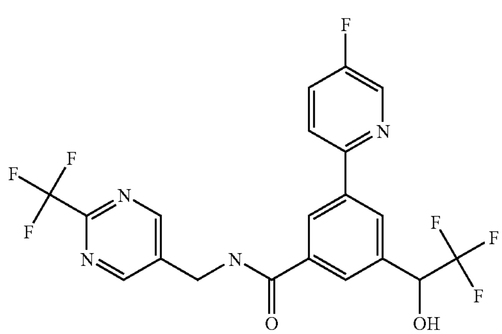 | 475.0 | R or S |

TABLE 1-continued

| EX | Structure | MS M + H | Stereo-chemistry |
|---|---|---|---|
| 1.64 | 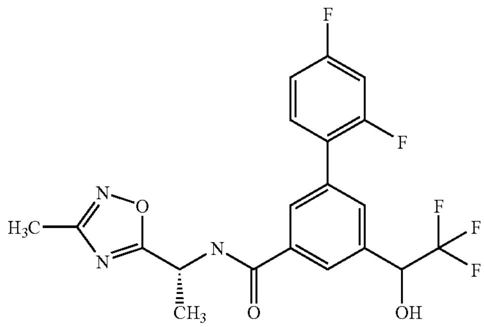 | 442.0 | R, R or S |
| 1.65 | 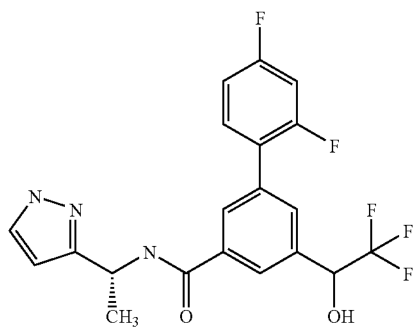 | 426.0 | R, R or S |
| 1.66 | 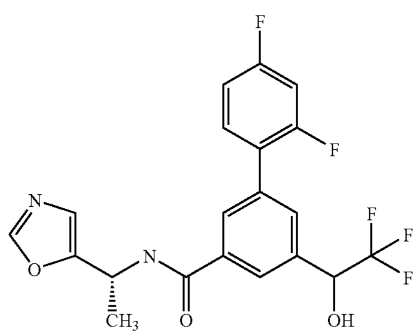 | 427.0 | R, R or S |
| 1.67 | 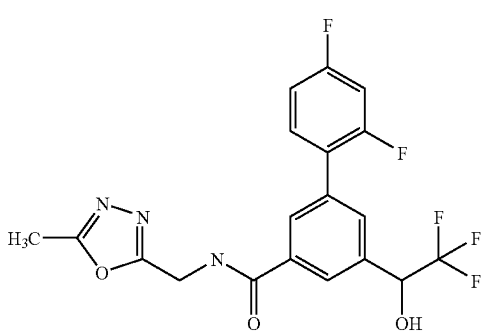 | 428.0 | R or S |

TABLE 1-continued

| EX | Structure | MS M + H | Stereo-chemistry |
|---|---|---|---|
| 1.68 | 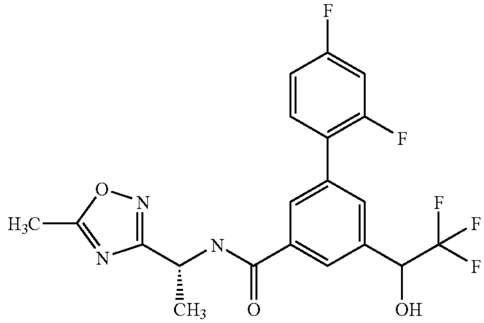 | 442.0 | R, R or S |
| 1.69 | 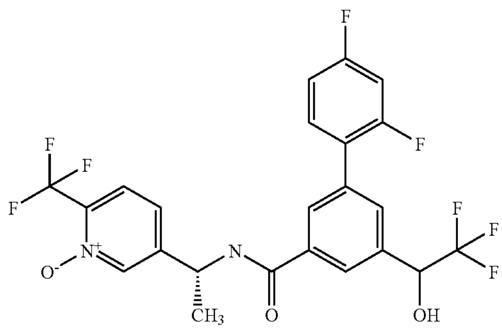 | 520.9 | R, R or S |
| 1.70 | 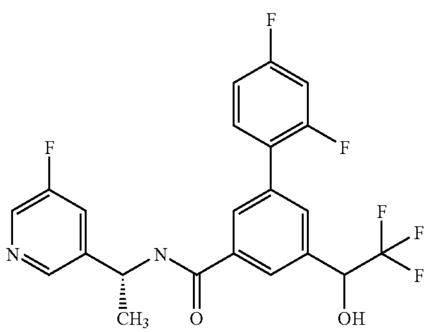 | 455.0 | R, R or S |
| 1.71 | 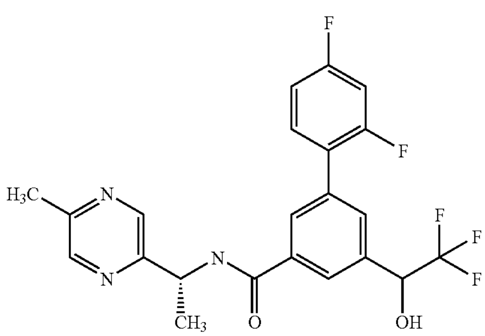 | 452.0 | R, R or S |

TABLE 1-continued

| EX | Structure | MS M + H | Stereo-chemistry |
|---|---|---|---|
| 1.72 | 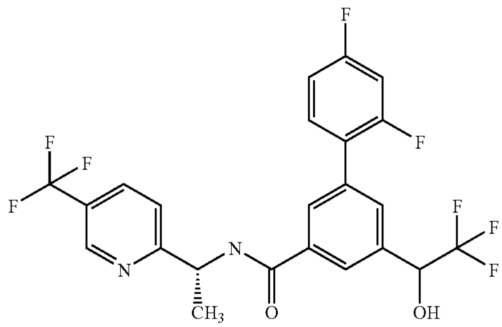 | 505.0 | R, R or S |
| 1.73 | 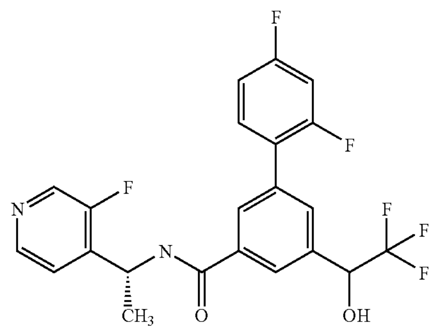 | 455.0 | R, R or S |
| 1.74 | 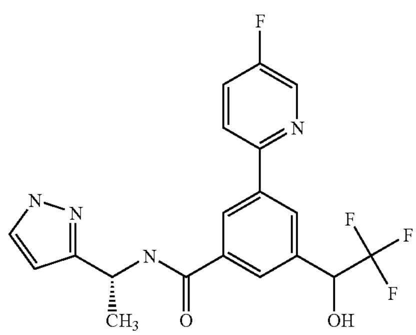 | 409.0 | R, R or S |
| 1.75 | 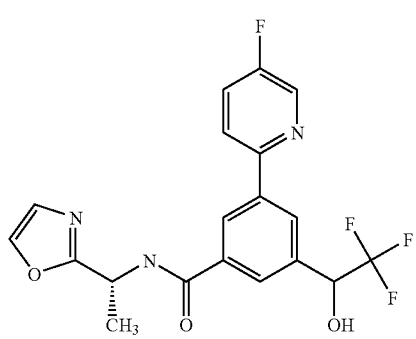 | 410.0 | R, R or S |

TABLE 1-continued

| EX | Structure | MS M + H | Stereo-chemistry |
|---|---|---|---|
| 1.76 | 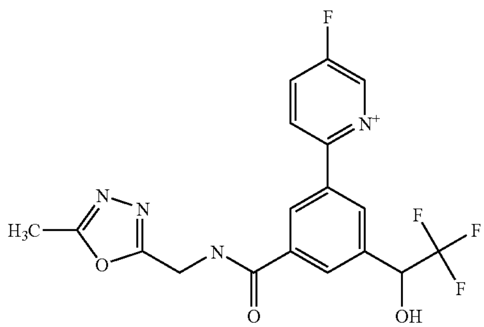 | 411.0 | R or S |
| 1.77 | 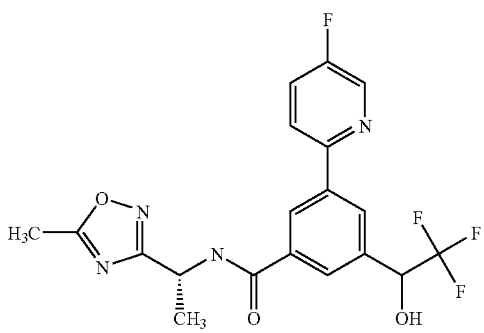 | 425.0 | R, R or S |
| 1.78 | 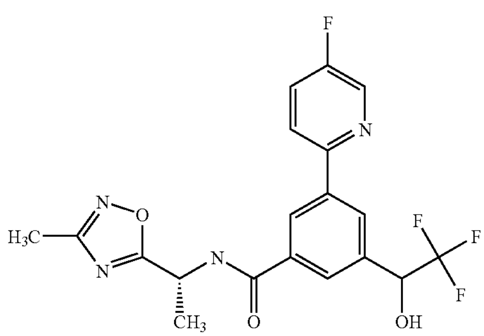 | 425.0 | R, R or S |
| 1.79 | 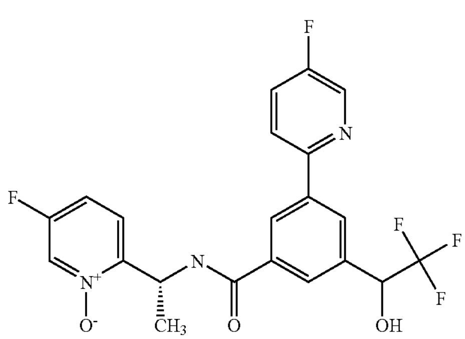 | 453.9 | R, R or S |

TABLE 1-continued

| EX | Structure | MS M + H | Stereo-chemistry |
|---|---|---|---|
| 1.80 | 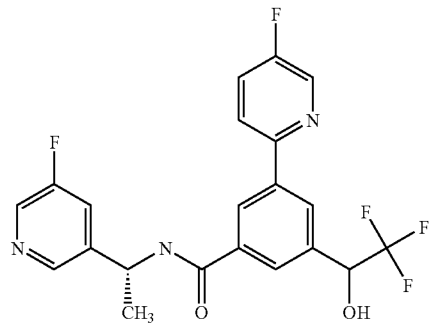 | 438.0 | R, R or S |
| 1.81 | 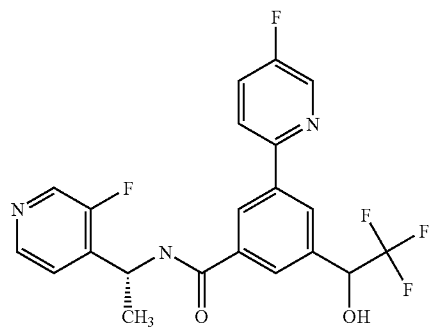 | 438.0 | R, R or S |
| 1.82 | 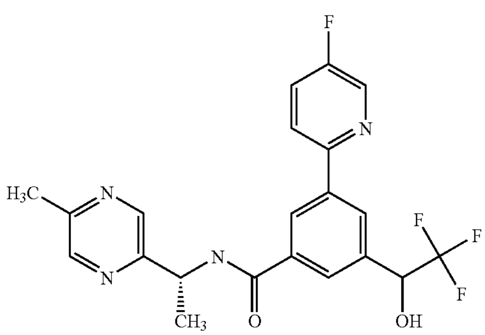 | 435.0 | R, R or S |
| 1.83 | 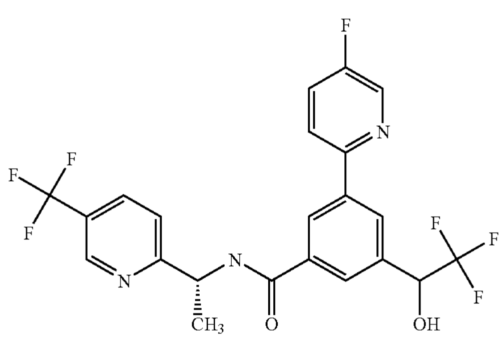 | 487.9 | R, R or S |

TABLE 1-continued

| EX | Structure | MS M + H | Stereo-chemistry |
|---|---|---|---|
| 1.84 | 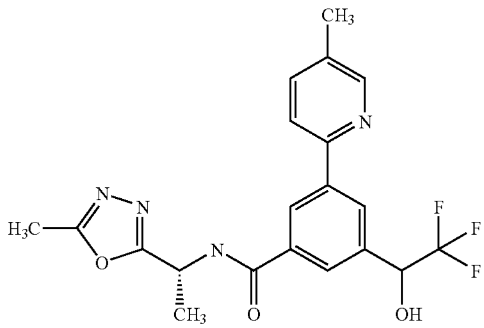 | 421.1 | R, R or S |
| 1.85 | 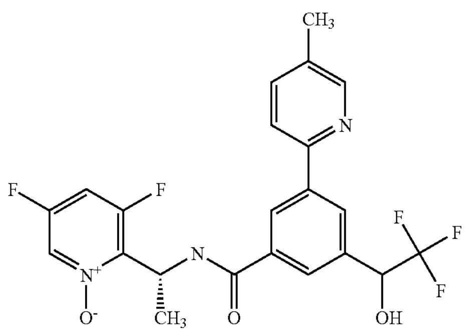 | 468.0 | R, R or S |
| 1.86 | 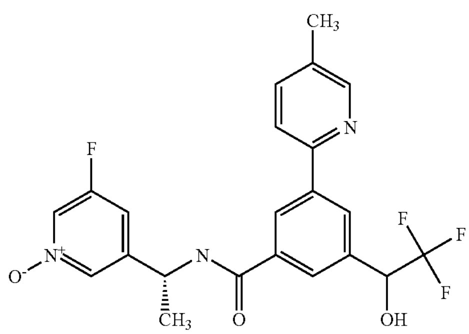 | 450.0 | R, R or S |
| 1.87 | 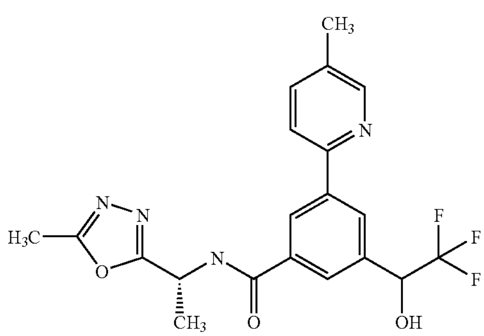 | 421.1 | R, R or S |

TABLE 1-continued

| EX | Structure | MS M + H | Stereo-chemistry |
|---|---|---|---|
| 1.88 | 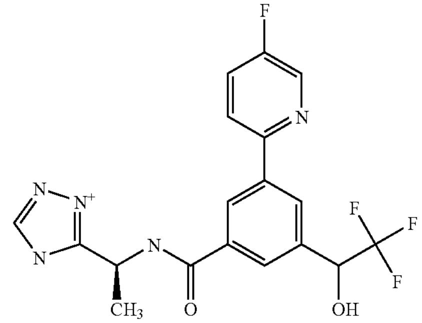 | 410.1 | S, R or S |
| 1.89 | 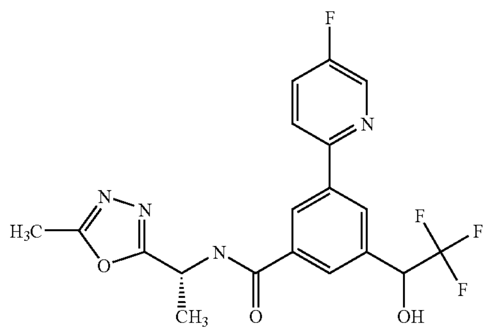 | 425.1 | R, R or S |
| 1.90 | 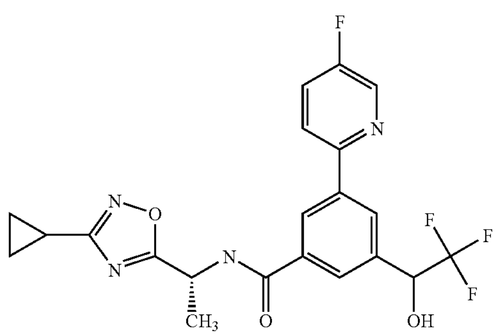 | 451.1 | R, R or S |
| 1.91 | 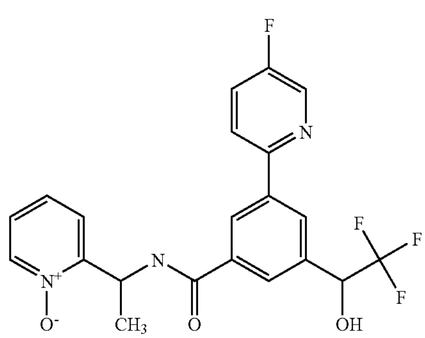 | 436.0 | R/S, R or S |

TABLE 1-continued

| EX | Structure | MS M + H | Stereo-chemistry |
|---|---|---|---|
| 1.92 | 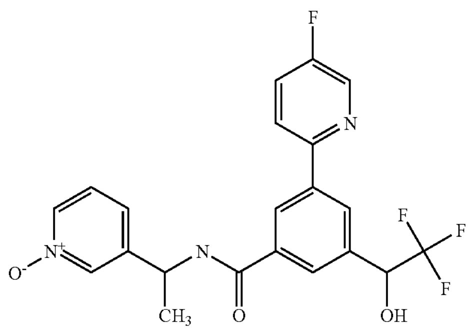 | 436.0 | R/S, R or S |
| 1.93 | 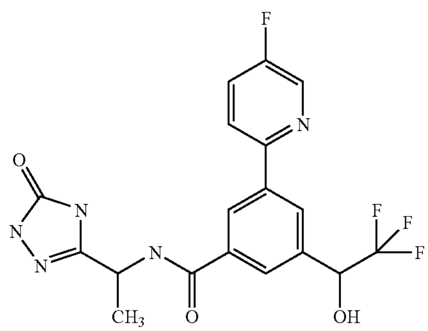 | 426.0 | R/S, R or S |
| 1.94 | 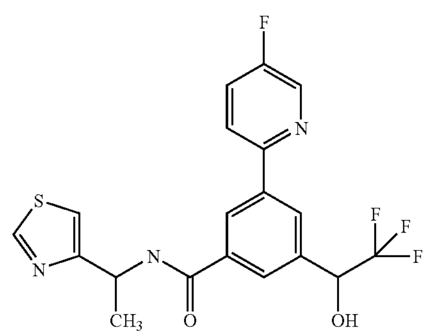 | 426.0 | R/S, R or S |
| 1.95 | 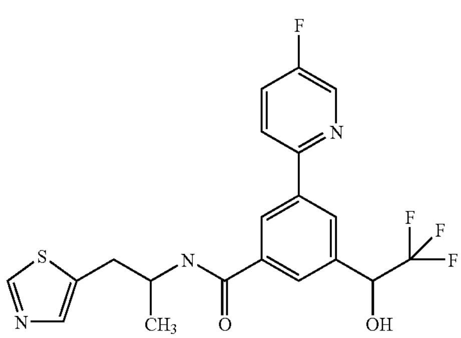 | 440.0 | R/S, R or S |

TABLE 1-continued

| EX | Structure | MS M + H | Stereo-chemistry |
|---|---|---|---|
| 1.96 | 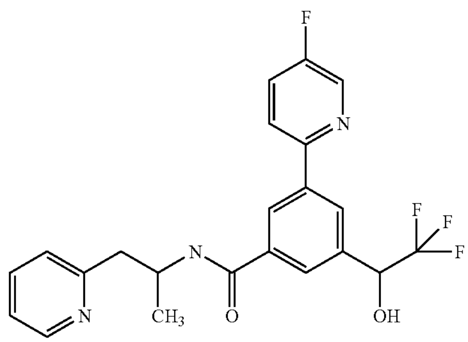 | 434.1 | R/S, R or S |
| 1.97 | 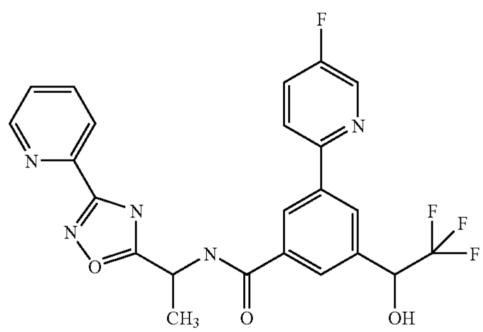 | 488.0 | R/S, R or S |
| 1.98 | 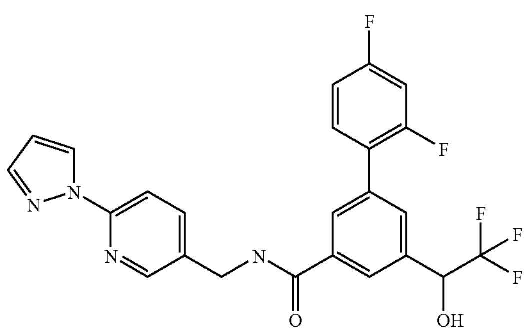 | 489.3 | R or S |
| 1.99 | 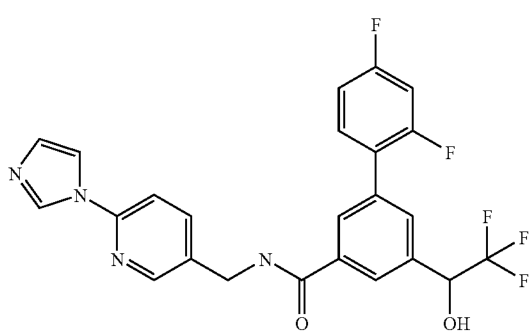 | 489.3 | R or S |

TABLE 1-continued

| EX | Structure | MS M + H | Stereo- chemistry |
|---|---|---|---|
| 1.100 | 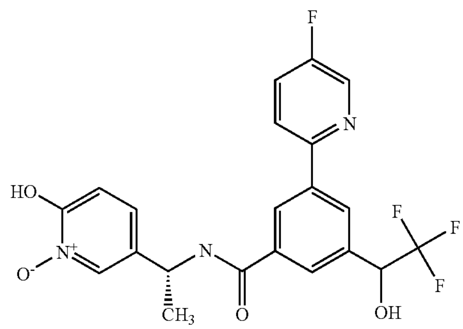 | 452.3 | R, R or S |
| 1.101 | 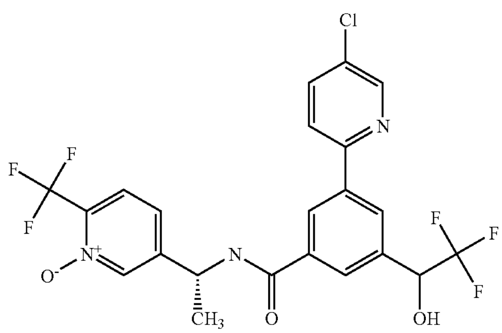 | 520.0 | R, R or S |
| 1.102 | 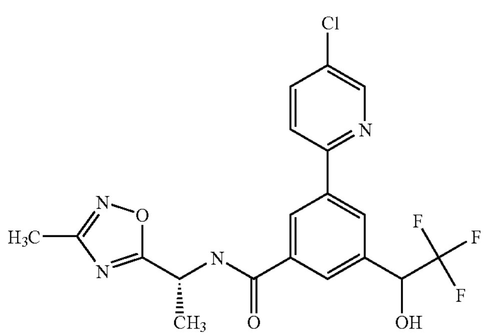 | 441.0 | R, R or S |
| 1.103 | 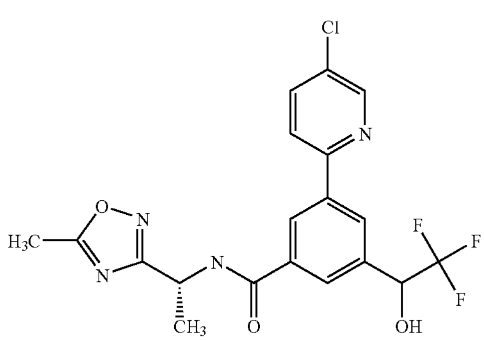 | 440.9 | R, R or S |

TABLE 1-continued

| EX | Structure | MS M + H | Stereo-chemistry |
|---|---|---|---|
| 1.104 | 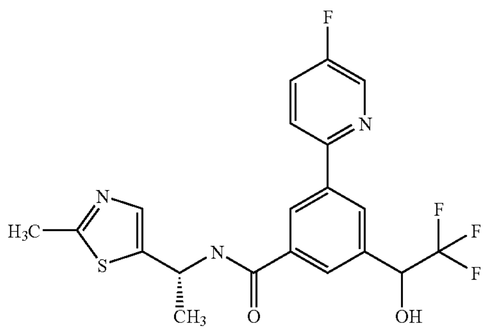 | 440.3 | R, R or S |

TABLE 2

| EX | Structure | MS M + H | Stereo-chemistry |
|---|---|---|---|
| 2.1 | 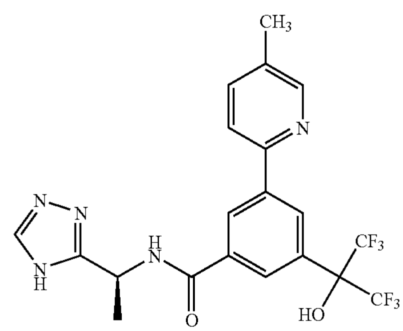 | 474.0 | S |
| 2.2 | 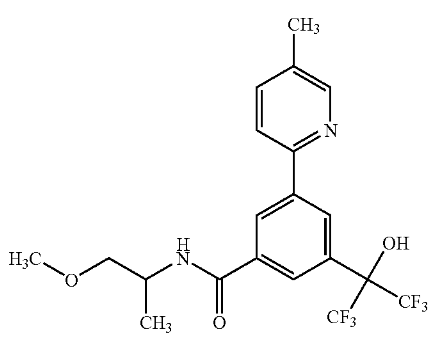 | 451.1 | R/S |
| 2.3 | 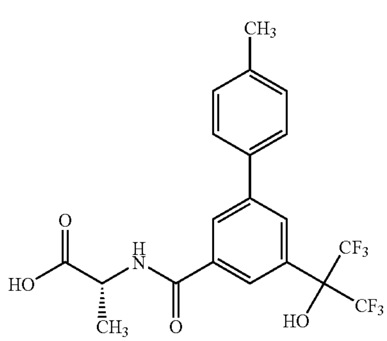 | 450.0 | R |

TABLE 2-continued
| EX | Structure | MS M + H | Stereo-chemistry |
|---|---|---|---|
| 2.4 | 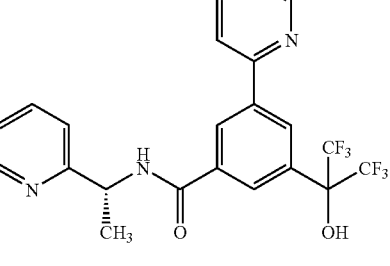 | 502.1 | R |
| 2.5 | 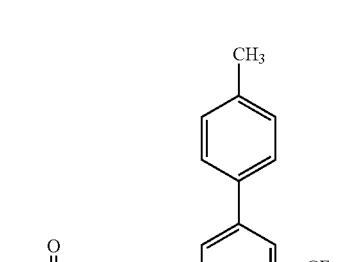 | 464.1 | R |
| 2.6 | 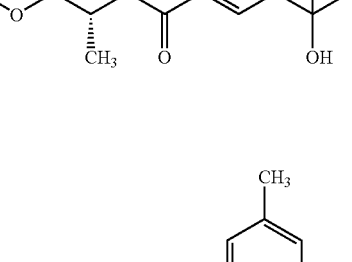 | 568.1 | R |
| 2.7 | 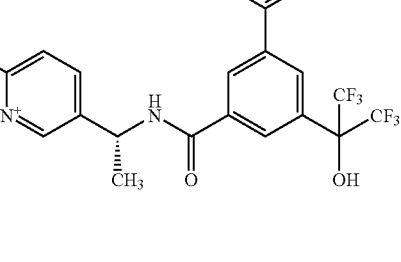 | 567.1 | R |

TABLE 2-continued

| EX | Structure | MS M + H | Stereo-chemistry |
|---|---|---|---|
| 2.8 | 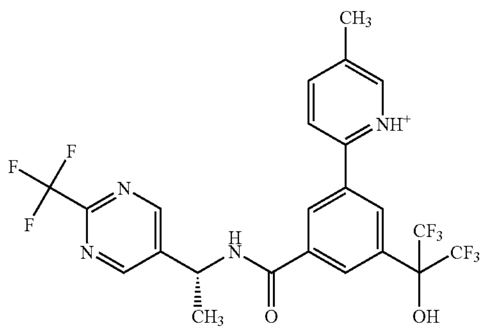 | 553.0 | R |
| 2.9 | 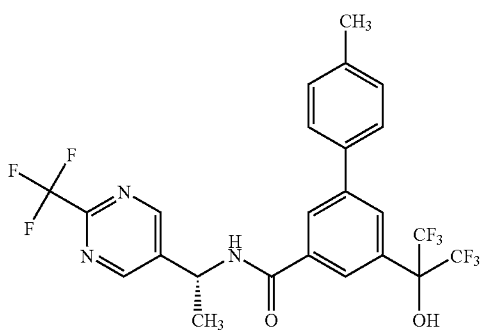 | 552.1314 | R |
| 2.10 | 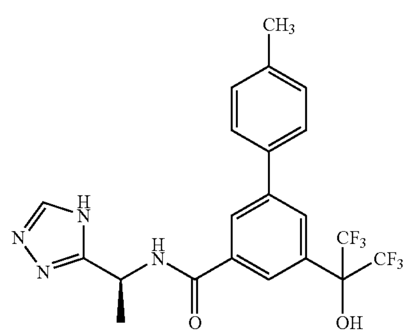 | 473.1 | S |
| 2.11 | 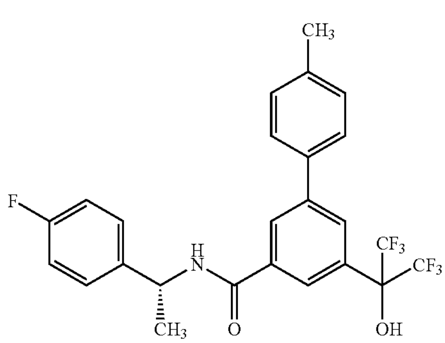 | 500.1 | R |

TABLE 2-continued

| EX | Structure | MS M + H | Stereo-chemistry |
|---|---|---|---|
| 2.12 | 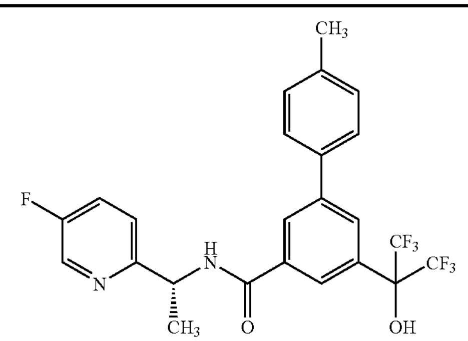 | 501.1 | R |
| 2.13 | 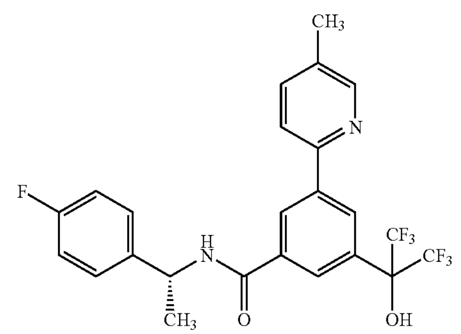 | 501.1408 | R |
| 2.14 | 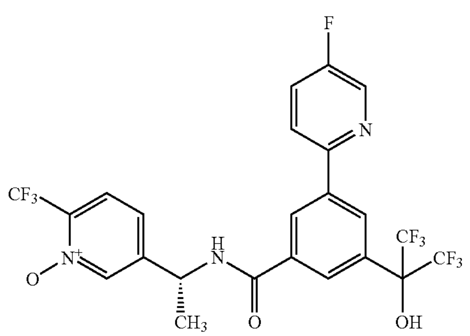 | 572.1 | R |

The following examples in Table 3 were prepared using methods A and B as described in Scheme 4. Compounds in Table 3 having a basic group or acidic group are depicted as the free base acid. Depending on the reaction and purification conditions, various compounds in Table 3 having a basic group were isolated in either the free base form, or as a salt (such as TFA or HCl salt), or in both free base and salt forms.

TABLE 3

| EX | Structure | MS M + H | Method |
|---|---|---|---|
| 3.1 | 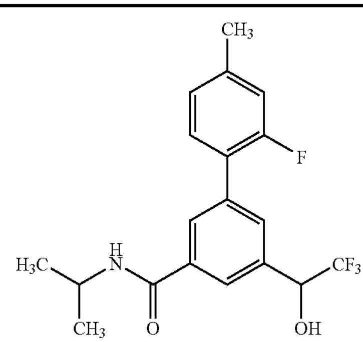 | 316.1 | A |

TABLE 3-continued
| EX | Structure | MS M + H | Method |
|---|---|---|---|
| 3.2 | 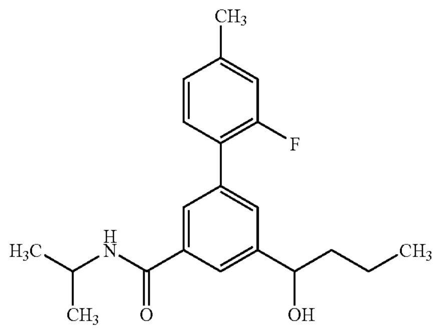 | 344.1 | A |
| 3.3 | 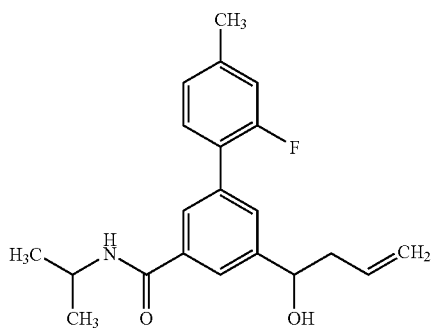 | 342.1 | A |
| 3.4 | 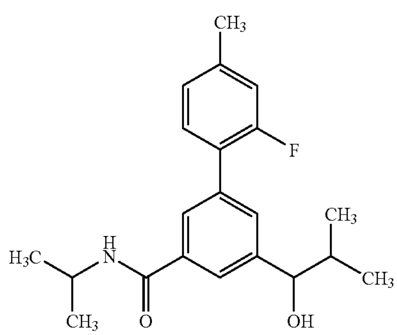 | 344.1 | A |
| 3.5 | 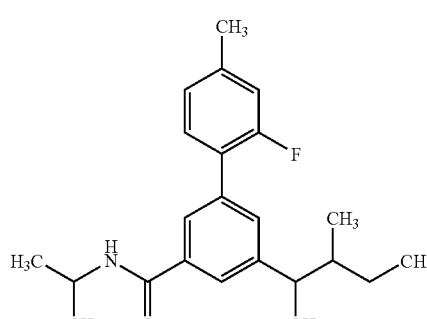 | 358.2 | A |

TABLE 3-continued

| EX | Structure | MS M + H | Method |
|---|---|---|---|
| 3.6 | 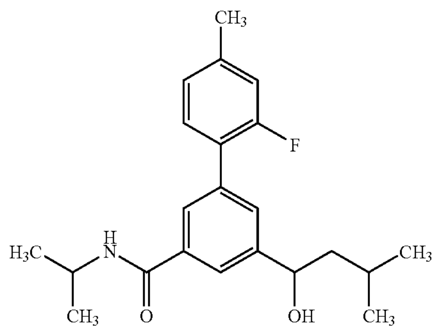 | 358.1 | A |
| 3.7 | 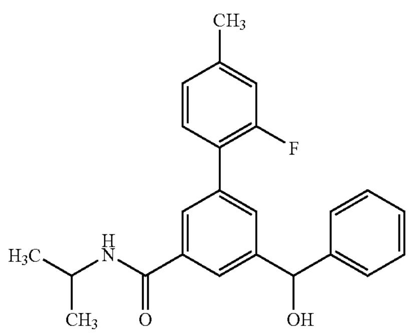 | 378.1856 | A |
| 3.8 | 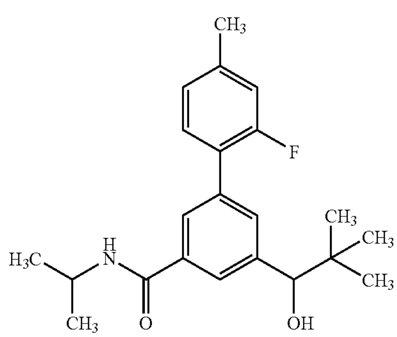 | 358.1 | A |
| 3.9 | 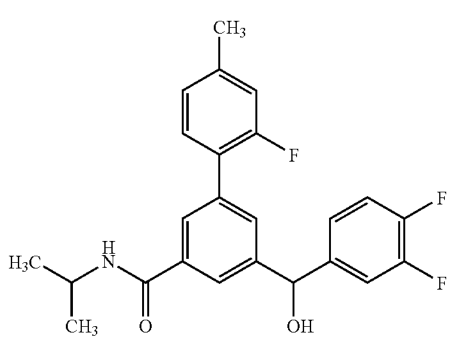 | 414.1 | A |

TABLE 3-continued

| EX | Structure | MS M + H | Method |
|---|---|---|---|
| 3.10 | 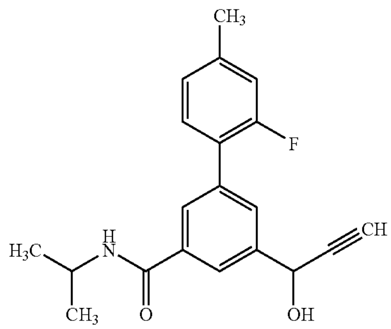 | 326.2 | A |
| 3.11 | 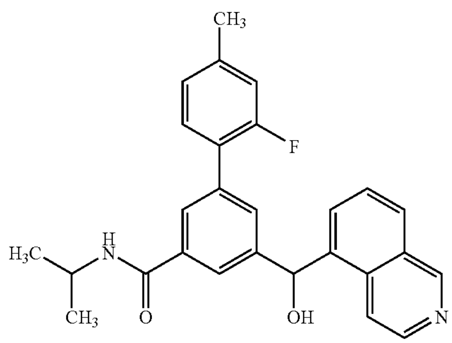 | 429.1 | B |
| 3.12 | 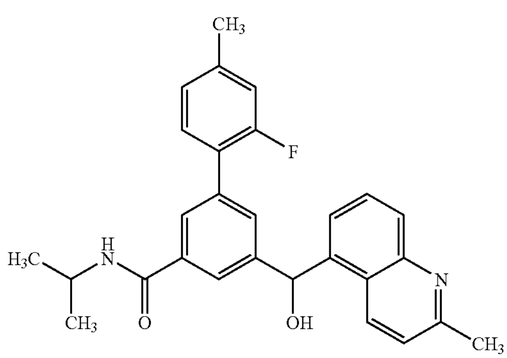 | 443.1 | B |
| 3.13 | 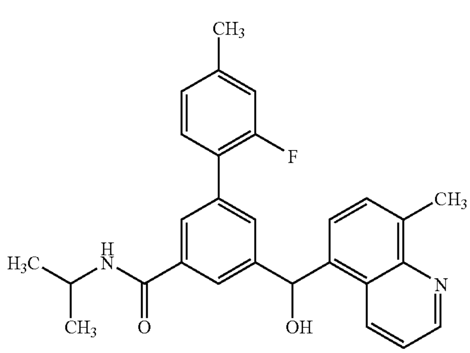 | 443.1 | B |

TABLE 3-continued

| EX | Structure | MS M + H | Method |
|---|---|---|---|
| 3.14 | 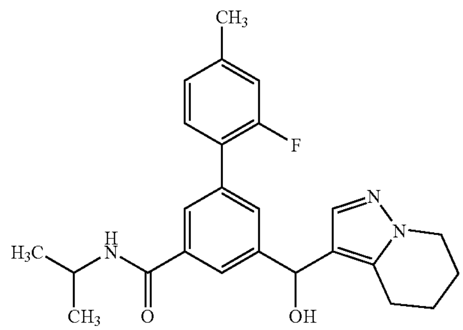 | 422.1 | B |
| 3.15 | 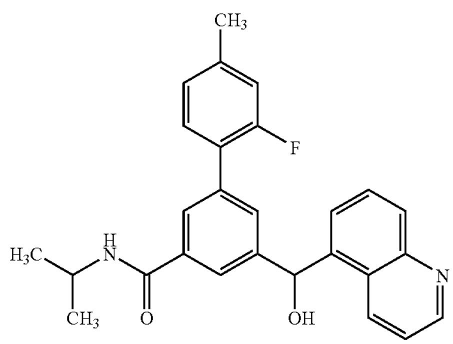 | 429.1 | B |
| 3.16 | 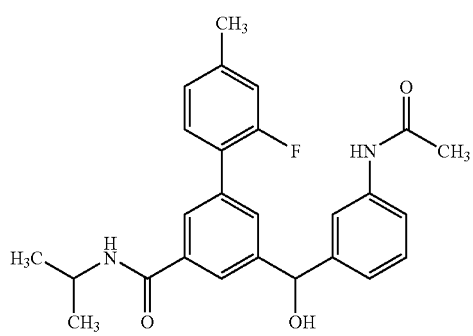 | 435.1 | B |
| 3.17 | 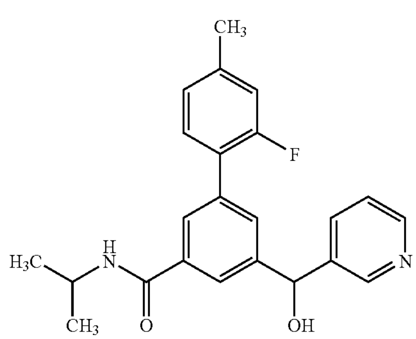 | 379.1 | B |

TABLE 3-continued

| EX | Structure | MS M + H | Method |
|---|---|---|---|
| 3.18 | 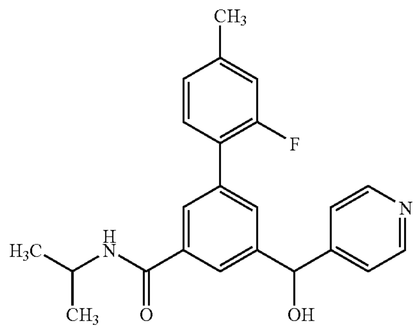 | 379.1 | B |
| 3.19 | 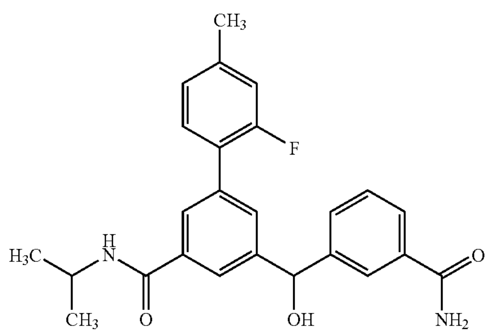 | 421.1 | B |
| 3.20 | 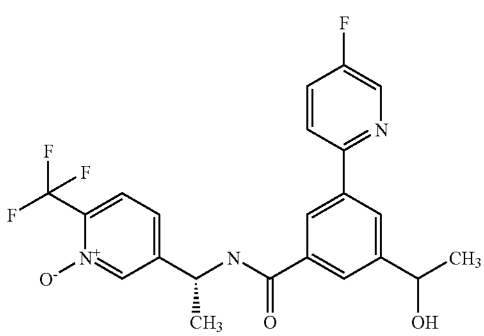 | 450.4 | A |
| 3.21 | 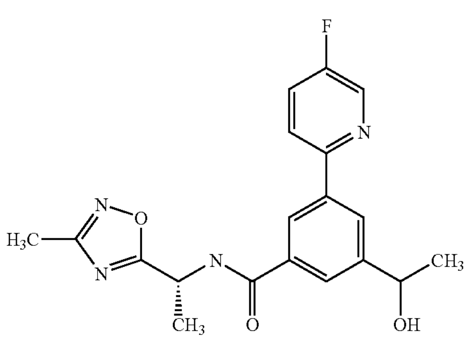 | 371.4 | A |

TABLE 4

| Example | R¹ | R² | R³ | MS (M + 1) |
|---|---|---|---|---|
| 4.1 | 5-fluoropyridin-2-yl (with chiral methyl) | 5-pyridyl | 4-methyl-5-cyclopropyl-4H-1,2,4-triazol-3-yl | 457.2156 |
| 4.2 | 2-(trifluoromethyl)pyrimidin-5-yl (with chiral methyl) | 5-pyridyl | 4-methyl-5-cyclopropyl-4H-1,2,4-triazol-3-yl | 508.2058 |
| 4.3 | 3,5-difluoropyridin-2-yl (with chiral methyl) | 5-pyridyl | 4-methyl-5-cyclopropyl-4H-1,2,4-triazol-3-yl | 475.2067 |
| 4.4 | pyrazin-2-yl (with chiral methyl) | 5-pyridyl | 4-methyl-5-cyclopropyl-4H-1,2,4-triazol-3-yl | 440.2200 |
| 4.5 | 1H-1,2,4-triazol-3-yl (with chiral methyl) | 5-pyridyl | 4-methyl-5-cyclopropyl-4H-1,2,4-triazol-3-yl | 429.2151 |

TABLE 4-continued
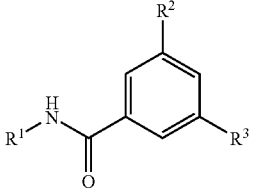
| Example | R¹ | R² | R³ | MS (M + 1) |
|---|---|---|---|---|
| 4.6 | 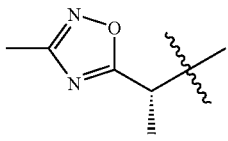 | 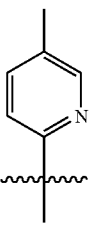 | 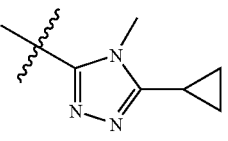 | 444.2138 |
| 4.7 | 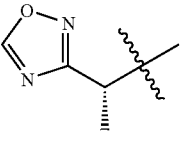 | 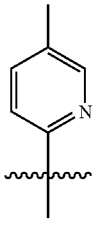 | 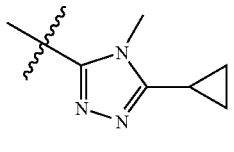 | 430.1992 |
| 4.8 | 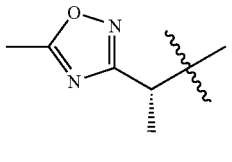 | 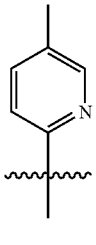 | 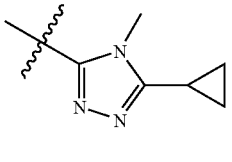 | 444.2138 |
| 4.9 | 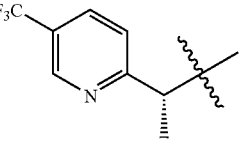 | 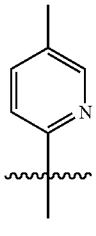 | 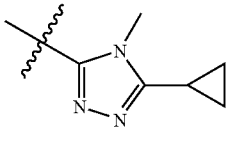 | 507.2122 |
| 4.10 | 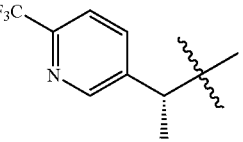 | 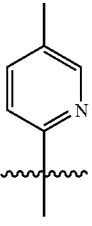 | 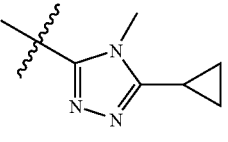 | 507.2107 |

TABLE 4-continued

| Example | R¹ | R² | R³ | MS (M + 1) |
|---|---|---|---|---|
| 4.11 | 3,5-difluoropyridin-2-yl (R-methyl) | 5-pyridyl | 4-methyl-5-(2-hydroxypropan-2-yl)-1,2,4-triazol-3-yl | 493.2141 |
| 4.12 | 2-(trifluoromethyl)pyrimidin-5-yl (R-methyl) | 5-pyridyl | 4,5-dimethyl-1,2,4-triazol-3-yl | 481.1948 |
| 4.13 | 3,5-difluoropyridin-2-yl (R-methyl) | 5-pyridyl | 4-methyl-1,2,4-triazol-3-yl | 435.1745 |
| 4.14 | 5-(trifluoromethyl)pyridin-2-yl (R-methyl) | 5-methylpyridin-2-yl | 4-methyl-1,2,4-triazol-3-yl | 467.1807 |
| 4.15 | 5-fluoropyridin-2-yl (R-methyl) | 5-pyridyl | 4-methyl-1,2,4-triazol-3-yl | 417.1828 |

TABLE 4-continued
| Example | R¹ | R² | R³ | MS (M + 1) |
|---|---|---|---|---|
| 4.16 | 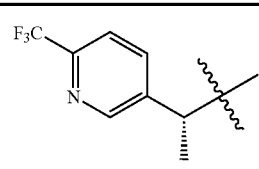 | 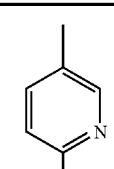 | 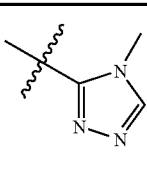 | 467.1790 |
| 4.17 | 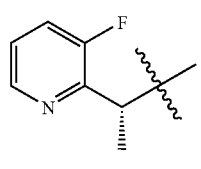 | 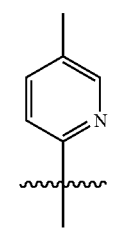 | 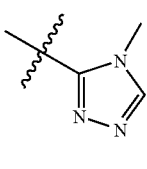 | 417.1832 |
| 4.18 | 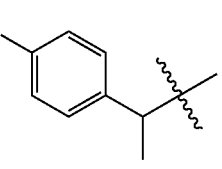 | 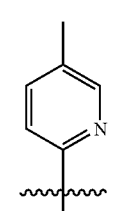 | 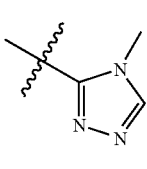 | 416.1865 |
| 4.19 | 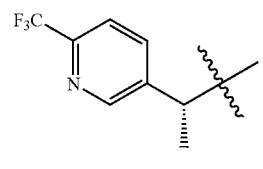 | 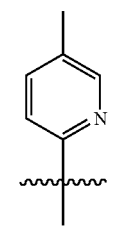 | 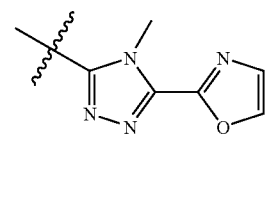 | 534.1852 |
| 4.20 | 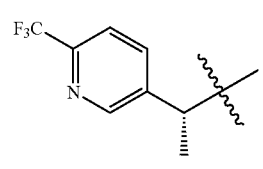 | 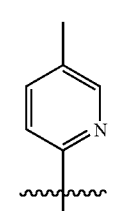 | 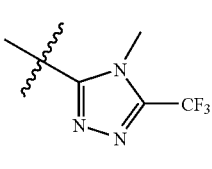 | 535.1679 |

TABLE 4-continued

| Example | R¹ | R² | R³ | MS (M + 1) |
|---|---|---|---|---|
| 4.21 | 3-methyl-1,2,4-oxadiazol-5-yl with chiral methyl | 3-fluorophenyl (para attach) | 4-(2,2,2-trifluoroethyl)-5-cyclopropyl-4H-1,2,4-triazol-3-yl | 529.1955 |
| 4.22 | 3-methyl-1,2,4-oxadiazol-5-yl with chiral methyl | 3-fluorophenyl (para attach) | 4-methyl-5-cyclopropyl-4H-1,2,4-triazol-3-yl | 461.2085 |
| 4.23 | 2-(trifluoromethyl)pyrimidin-5-yl with chiral methyl | 3-fluorophenyl (para attach) | 4-methyl-4H-1,2,4-triazol-3-yl | 471.1549 |
| 4.24 | 3,5-difluoropyridin-2-yl with chiral methyl | 2,4-difluorophenyl | 4-methyl-5-cyclopropyl-4H-1,2,4-triazol-3-yl | 496.1769 |
| 4.25 | 3,5-difluoropyridin-2-yl with chiral methyl | 5-fluoropyridin-2-yl | 4-methyl-5-cyclopropyl-4H-1,2,4-triazol-3-yl | 479.1 |
| 4.26 | 6-(trifluoromethyl)pyridin-3-yl with chiral methyl | 2-fluorophenyl | 4-methyl-5-cyclopropyl-4H-1,2,4-triazol-3-yl | 510.1904 |

TABLE 4-continued
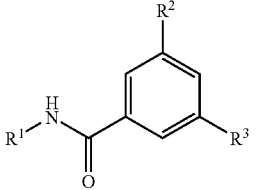
| Example | R¹ | R² | R³ | MS (M + 1) |
|---|---|---|---|---|
| 4.27 | 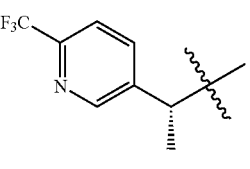 | 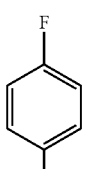 | 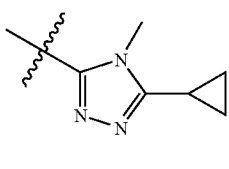 | 510.1901 |
| 4.28 | 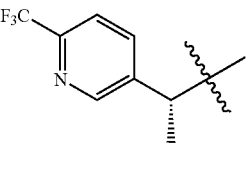 | 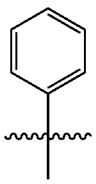 | 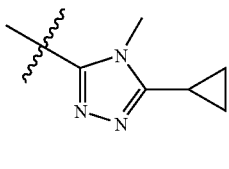 | 492.1999 |
| 4.29 | 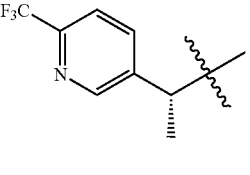 | 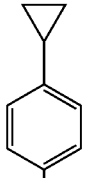 | 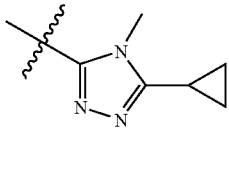 | 532.2326 |
| 4.30 | 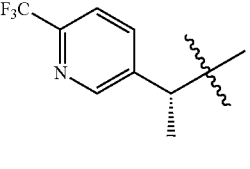 | 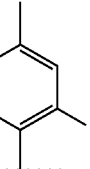 | 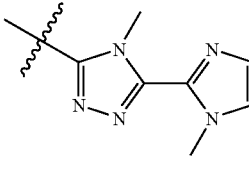 | 564.2127 |
| 4.31 | 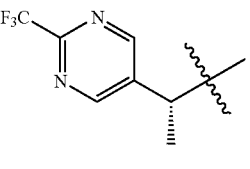 | 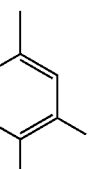 | 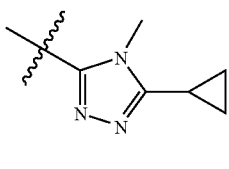 | 525.2 |

TABLE 4-continued
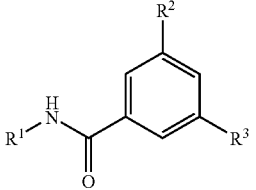
| Example | R¹ | R² | R³ | MS (M + 1) |
|---|---|---|---|---|
| 4.32 | 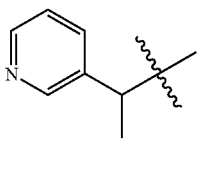 | 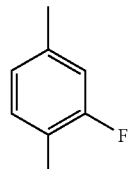 | 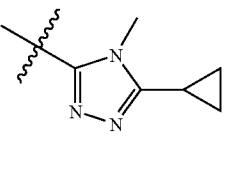 | 456.2185 |
| 4.33 | 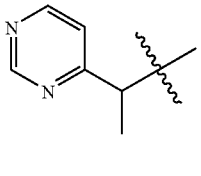 | 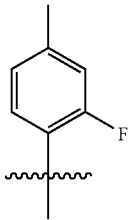 | 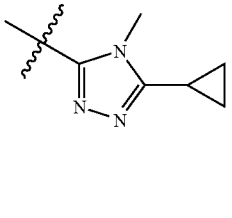 | 457.2146 |
| 4.34 | 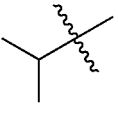 | 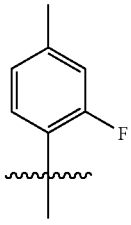 | 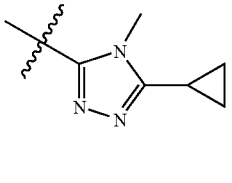 | 393.2087 |
| 4.35 | 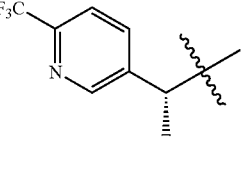 | 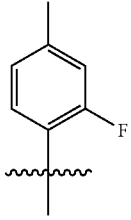 | 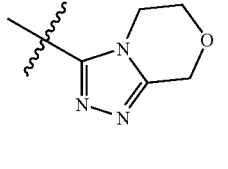 | 526.1866 |
| 4.36 | 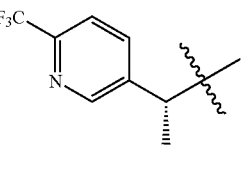 | 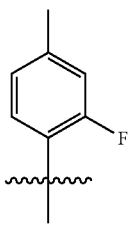 | 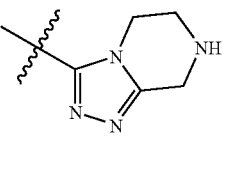 | 525.2038 |

TABLE 4-continued
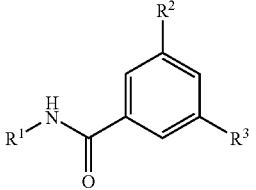
| Example | R¹ | R² | R³ | MS (M + 1) |
|---|---|---|---|---|
| 4.37 | 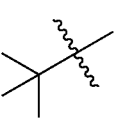 | 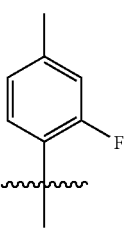 | 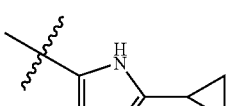 | 393.2083 |
| 4.38 | 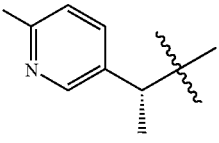 | 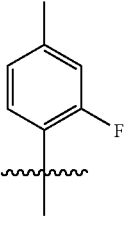 | 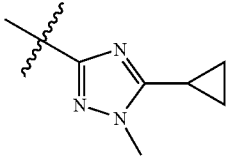 | 524.2097 |
| 4.39 | 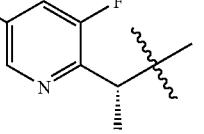 | 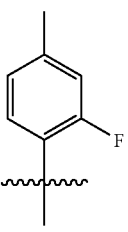 | 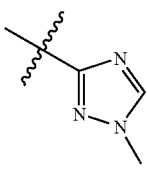 | 452.1693 |
| 4.40 | 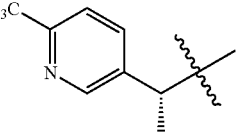 | 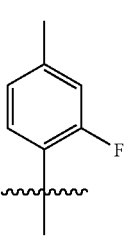 | 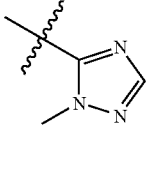 | 484.1762 |
| 4.41 | 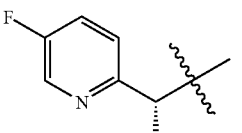 | 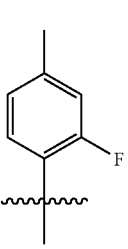 | 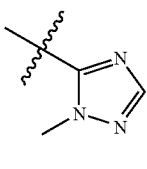 | 434.1796 |

TABLE 4-continued
| Example | R¹ | R² | R³ | MS (M + 1) |
|---|---|---|---|---|
| 4.42 | 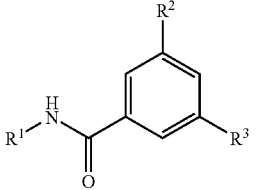 | 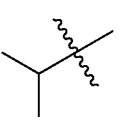 | 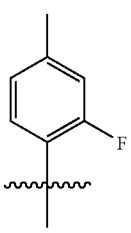 | 421.1666 |
| 4.43 | 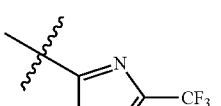 | 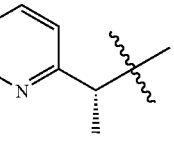 | 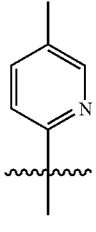 | 457.2155 |
| 4.44 | 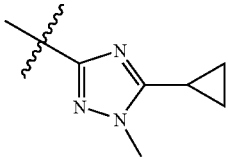 | 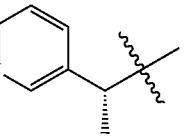 | 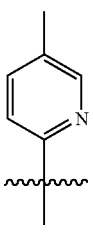 | 467.1 |
| 4.45 | 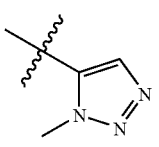 | 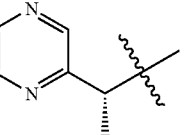 | 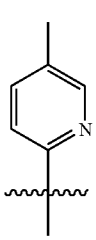 | 468.1754 |
| 4.46 | 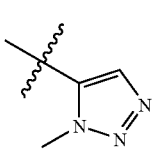 | 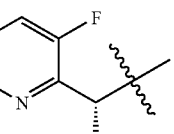 | 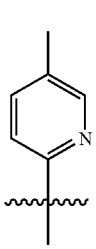 | 435.1739 |

TABLE 4-continued

| Example | R¹ | R² | R³ | MS (M + 1) |
|---|---|---|---|---|
| 4.47 | 6-CF₃-pyridin-3-yl (S)-CH(CH₃)- | 6-pyridin-3-yl (5-methyl) | 1-methyl-1,2,3-triazol-4-yl | 467.1794 |
| 4.48 | 2-CF₃-pyrimidin-5-yl (S)-CH(CH₃)- | 6-pyridin-3-yl (5-methyl) | 1-methyl-1,2,3-triazol-4-yl | 468.1749 |
| 4.49 | 6-CF₃-pyridin-3-yl (S)-CH(CH₃)- | 6-pyridin-3-yl (5-methyl) | 1-methyl-imidazol-2-yl | 466.1849 |
| 4.50 | 6-CF₃-pyridin-3-yl (S)-CH(CH₃)- | 4-methyl-2-fluorophenyl | 1-methyl-imidazol-2-yl | 483.1808 |
| 4.51 | 6-CF₃-pyridin-3-yl (S)-CH(CH₃)- | 6-pyridin-3-yl (5-methyl) | 1-methyl-imidazol-5-yl | 466.1847 |

TABLE 4-continued
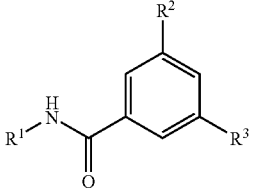
| Example | R¹ | R² | R³ | MS (M + 1) |
|---|---|---|---|---|
| 4.52 | 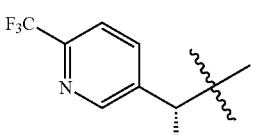 | 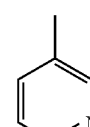 | 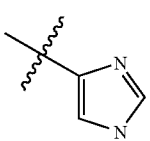 | 466.1838 |
| 4.53 | 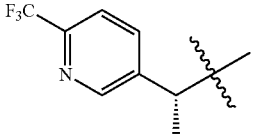 | 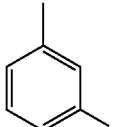 | 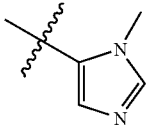 | 483.1803 |
| 4.54 | 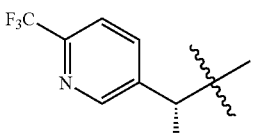 | 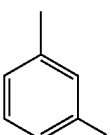 | 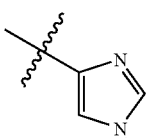 | 483.1793 |
| 4.55 | 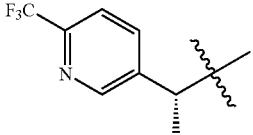 | 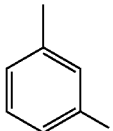 | 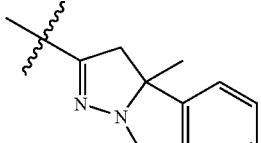 | 575.2441 |
| 4.56 | 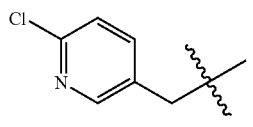 | 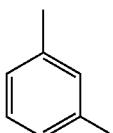 | 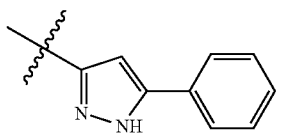 | 497.1558 |

TABLE 4-continued
| Example | R¹ | R² | R³ | MS (M + 1) |
|---|---|---|---|---|
| 4.57 | 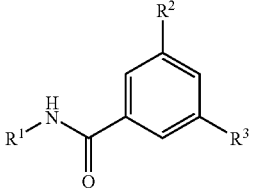 | 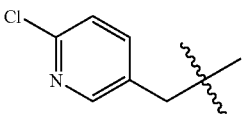 | 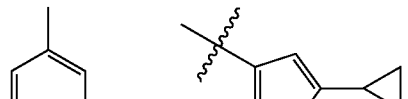 | 475.1691 |
| 4.58 | 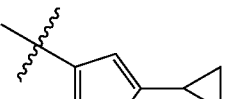 | 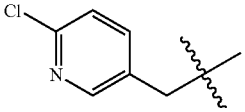 | 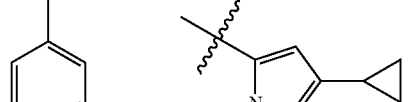 | 475.1698 |
| 4.59 | 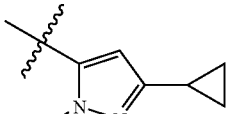 | 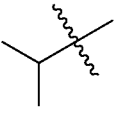 | 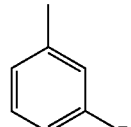 | 352.1826 |
| 4.60 | 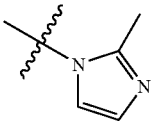 | 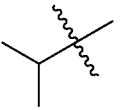 | 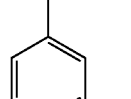 | 352.1824 |
| 4.61 | 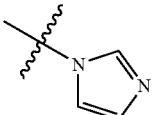 | 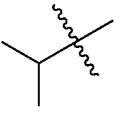 | 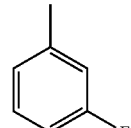 | 391.1169 (M + Na) |

TABLE 4-continued
| Example | R¹ | R² | R³ | MS (M + 1) |
|---|---|---|---|---|
| 4.62 | 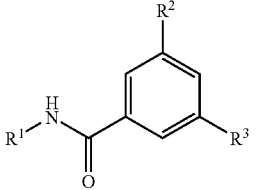 | 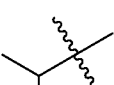 | 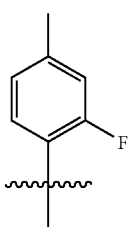 | 384.1729 |
| 4.63 | 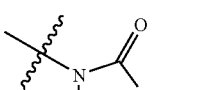 | 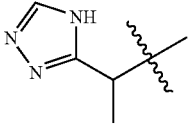 | 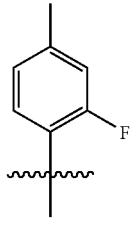 | 458.1746 |
| 4.64 | 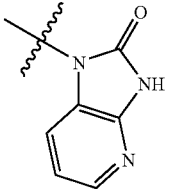 | 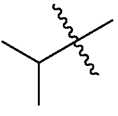 | 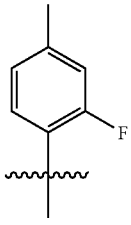 | 404.1761 |
| 4.65 | 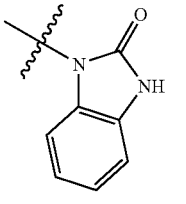 | 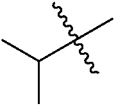 | 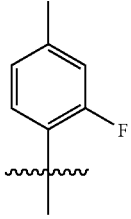 | 445.2023 |
| 4.66 | 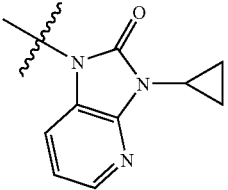 | 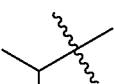 | 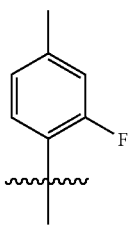 | 433.1933 |

TABLE 4-continued

| Example | R¹ | R² | R³ | MS (M + 1) |
|---|---|---|---|---|
| 4.67 | isopropyl-methyl | 3-fluoro-4-phenyl | 4-phenyl-2-oxopyrrolidin-1-yl | 431.2119 |
| 4.68 | isopropyl-methyl | 3-fluoro-4-phenyl | 3-fluoroazetidin-1-yl | 345.1774 |
| 4.69 | 1-(6-(trifluoromethyl)pyridin-3-yl)ethyl | 3-fluoro-4-phenyl | 3-(trifluoromethyl)-5,6-dihydro-[1,2,4]triazolo[4,3-a]pyrazin-7(8H)-yl | 593.1913 |
| 4.70 | 1-(pyrimidin-4-yl)ethyl | 3-fluoro-4-phenyl | 2-(trifluoromethyl)-5,6-dihydroimidazo[1,2-a]pyrazin-7(8H)-yl | 525.2015 |
| 4.71 | tert-butyl-methyl | 3-fluoro-4-phenyl | 3-benzyl-5,6-dihydroimidazo[1,2-a]pyrazin-7(8H)-yl | 497.2710 |

TABLE 4-continued
| Example | R¹ | R² | R³ | MS (M + 1) |
|---|---|---|---|---|
| 4.72 | 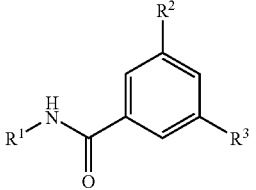 | 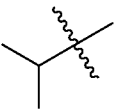 | 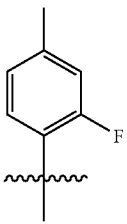 | 476.1903 |
| 4.73 | 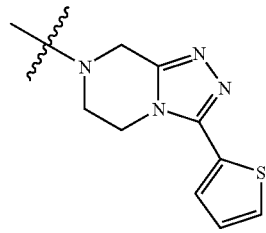 | 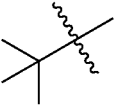 | 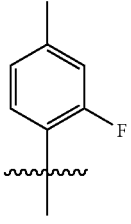 | 487.2110 |
| 4.74 | 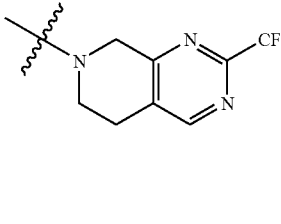 | 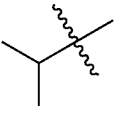 | 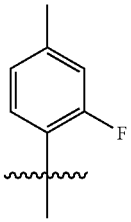 | 431.2255 |
| 4.75 | 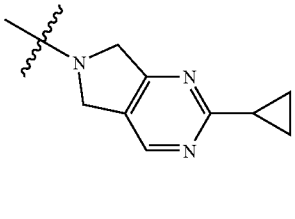 | 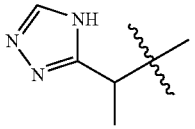 | 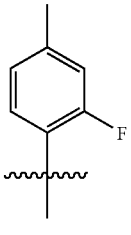 | 340.1579 |
| 4.76 | 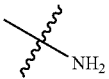 | 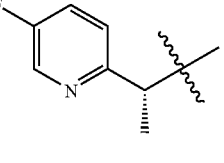 | 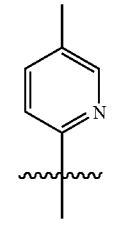 | 421.2043 |

TABLE 4-continued
| Example | R¹ | R² | R³ | MS (M + 1) |
|---|---|---|---|---|
| 4.77 | 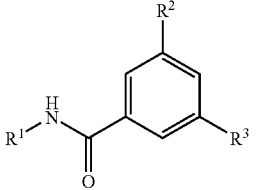 | 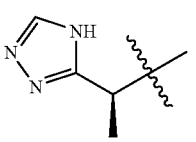 | 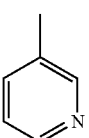 | 379.1879 |
| 4.78 |  |  | 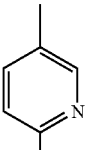 | 407.1885 |
| 4.79 | 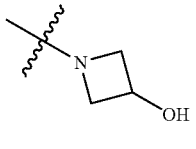 | 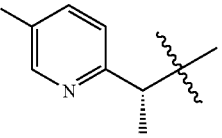 | 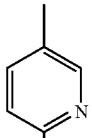 | 503.2081 |
| 4.80 | 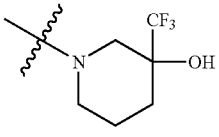 | 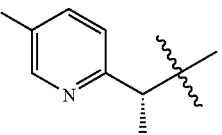 | 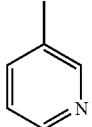 | 449.2363 |
| 4.81 |  |  | 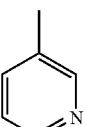 | 449.2345 |

TABLE 4-continued
| Example | R¹ | R² | R³ | MS (M + 1) |
|---|---|---|---|---|
| 4.82 | 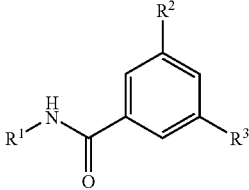 | 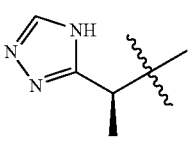 | 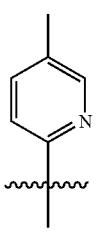 | 421.2359 |
| 4.83 | 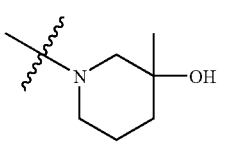 | 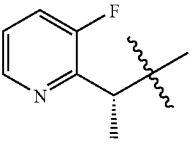 | 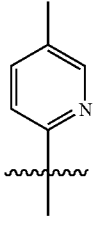 | 419.2250 |
| 4.84 |  |  | 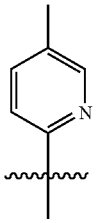 | 391.2257 |
| 4.85 | 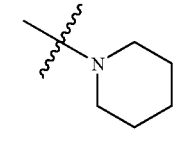 | 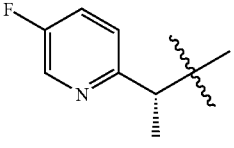 | 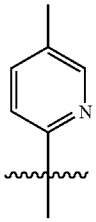 | 419.2259 |
| 4.86 | 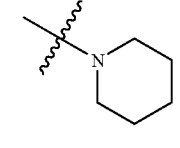 | 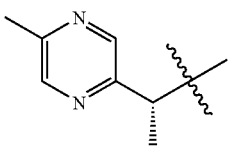 | 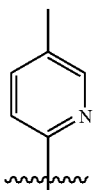 | 508.2738 |

TABLE 4-continued

| Example | R¹ | R² | R³ | MS (M + 1) |
|---|---|---|---|---|
| 4.87 | 5-fluoropyridin-2-yl with (S)-methyl | 5-methylpyridin-2-yl | (R)-3-hydroxypiperidin-1-yl | 435.2205 |
| 4.88 | 5-fluoropyridin-2-yl with (R)-methyl | 5-methylpyridin-2-yl | (R)-3-hydroxypiperidin-1-yl | 435.1 |
| 4.89 | 5-fluoropyridin-2-yl with (S)-methyl | 5-fluoropyridin-2-yl | 3-hydroxy-3-methylpiperidin-1-yl | 453.2091 |
| 4.90 | 4H-1,2,4-triazol-3-yl with (S)-methyl | 2,4-difluorophenyl | 3-hydroxy-3-methylpiperidin-1-yl | 442.2062 |
| 4.91 | pyrazin-2-yl with (S)-methyl | 5-methylpyridin-2-yl | 4-hydroxy-4-methylpiperidin-1-yl | 432.2395 |

TABLE 4-continued

| Example | R¹ | R² | R³ | MS (M + 1) |
|---|---|---|---|---|
| 4.92 | isopropyl | 3-fluorophenyl | 3-hydroxy-3-methylpiperidin-1-yl | 385.2296 |
| 4.93 | (2-(trifluoromethyl)pyrimidin-5-yl)isopropyl | pyridin-2-yl | 4-hydroxy-4-methylpiperidin-1-yl | 486.2107 |
| 4.94 | (3,5-difluoropyridin-2-yl)(methyl)methyl | pyridin-2-yl | piperazin-1-yl | 438.2113 |
| 4.95 | (4H-1,2,4-triazol-3-yl)(methyl)methyl | pyridin-2-yl | piperazin-1-yl | 392.2200 |
| 4.96 | (3-methyl-1,2,4-oxadiazol-5-yl)(methyl)methyl | pyridin-2-yl | piperazin-1-yl | 407.2197 |

TABLE 4-continued

| Example | R¹ | R² | R³ | MS (M + 1) |
|---|---|---|---|---|
| 4.97 | (3-oxo-2,4-dihydro-1,2,4-triazol-5-yl)-isopropyl | 5-pyridin-2-yl | 3-methylpiperazin-1-yl | 436.2449 |
| 4.98 | (5-trifluoromethylpyrazin-2-yl)-isopropyl | 5-pyridin-2-yl | 3-methylpiperazin-1-yl | 499.2417 |
| 4.99 | (2-trifluoromethylpyrimidin-5-yl)-isopropyl | 5-pyridin-2-yl | 3-methylpiperazin-1-yl | 499.2419 |
| 4.100 | (2-trifluoromethylpyrimidin-5-yl)-isopropyl | 4-methyl-2-fluorophenyl | piperazin-1-yl | 488.2079 |
| 4.101 | (4H-1,2,4-triazol-3-yl)-isopropyl | 2-fluorophenyl | piperazin-1-yl | 409.2158 |

TABLE 4-continued

| Example | R¹ | R² | R³ | MS (M + 1) |
|---|---|---|---|---|
| 4.102 | 3-methyl-1,2,4-oxadiazol-5-yl, CH(CH₃)- | 3-F-phenyl (4-linked) | piperazin-1-yl | 424.2143 |
| 4.103 | 3-methyl-1,2,4-oxadiazol-5-yl, CH(CH₃)- | 2,4-diF-phenyl | piperazin-1-yl | 428.1900 |
| 4.104 | 4H-1,2,4-triazol-3-yl, CH(CH₃)- | 2,4-diF-phenyl | piperazin-1-yl | 413.1901 |
| 4.105 | 2-(trifluoromethyl)pyrimidin-5-yl, CH(CH₃)- | 2,4-diF-phenyl | piperazin-1-yl | 492.1833 |
| 4.106 | 4H-1,2,4-triazol-3-yl, CH(CH₃)- | pyridin-2-yl | morpholin-4-yl | 393.2048 |

TABLE 4-continued
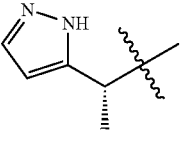
| Example | R¹ | R² | R³ | MS (M + 1) |
|---|---|---|---|---|
| 4.107 | 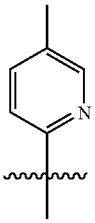 | 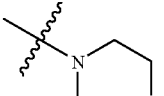 | 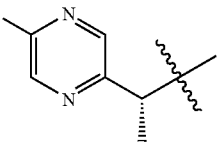 | 392.2087 |
| 4.108 | 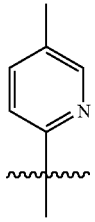 | 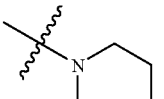 | 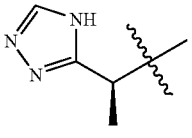 | 472.1961 |
| 4.109 | 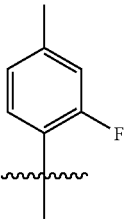 | 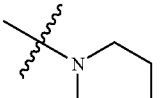 | 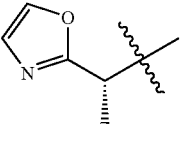 | 410.1990 |
| 4.110 | 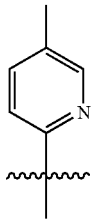 | 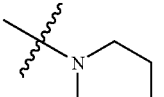 | 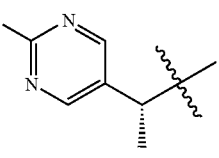 | 393.1923 |
| 4.111 | 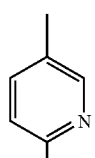 | 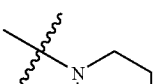 | | 458.1794 |

TABLE 4-continued

| Example | R¹ | R² | R³ | MS (M + 1) |
|---|---|---|---|---|
| 4.112 | 5-fluoropyridin-2-yl CH(CH₃) | 5-pyridyl | morpholine | 421.2035 |
| 4.113 | 3-fluoropyridin-2-yl CH(CH₃) | 5-pyridyl | morpholine | 421.2041 |
| 4.114 | 4H-1,2,4-triazol-3-yl CH(CH₃) | 5-pyridyl | 2,2-dimethylmorpholine | 421.2358 |
| 4.115 | 5-fluoropyridin-2-yl CH(CH₃) | 5-pyridyl | 1-oxa-4-azaspiro[4.5]/cyclopentane-morpholine spiro | 475.2519 |
| 4.116 | 1H-imidazol-5-yl CH(CH₃) | 5-pyridyl | 2-phenylmorpholine | 468.2418 |

TABLE 4-continued

| Example | R¹ | R² | R³ | MS (M + 1) |
|---|---|---|---|---|
| 4.117 | 5-(trifluoromethyl)pyridin-2-yl with CH(CH₃) linker | 5-pyridyl (2-attached) | 2-phenylmorpholin-4-yl | 547.2304 |
| 4.118 | 4H-1,2,4-triazol-3-yl with CH(CH₃) linker | 5-pyridyl (2-attached) | 2-phenylmorpholin-4-yl | 532.1945 |
| 4.119 | 5-oxo-2,5-dihydro-1H-1,2,4-triazol-3-yl with CH(CH₃) linker | 5-pyridyl (2-attached) | 2-phenylmorpholin-4-yl | 485.2327 |
| 4.120 | 3-fluoro-5-(trifluoromethyl)pyridin-2-yl with CH₂ linker | 5-pyridyl (2-attached) | 2-phenylmorpholin-4-yl | 551.2083 |
| 4.121 | 5-methylpyrazin-2-yl with CH(CH₃) linker | 5-pyridyl (2-attached) | 2-phenylmorpholin-4-yl | 494.2579 |

TABLE 4-continued

| Example | R¹ | R² | R³ | MS (M + 1) |
|---|---|---|---|---|
| 4.122 | | | | 480.2408 |
| 4.123 | | | | 515.2257 |
| 4.124 | | | | 548.2255 |
| 4.125 | | | | 479.2442 |
| 4.126 | | | | 499.2709 |

TABLE 4-continued
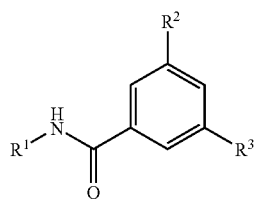
| Example | R¹ | R² | R³ | MS (M + 1) |
|---|---|---|---|---|
| 4.127 | 2-pyridyl-CH2-CH(CH3)- | 5-pyridyl (2-attached) | 2-phenylmorpholin-4-yl | 493.2596 |
| 4.128 | cyclopropyl | 5-pyridyl (2-attached) | 2-phenylmorpholin-4-yl | 414.2183 |
| 4.129 | furan-2-yl-CH2- | 5-pyridyl (2-attached) | 2-phenylmorpholin-4-yl | 454.2131 |
| 4.130 | iPrO-(CH2)3- | 5-pyridyl (2-attached) | 2-phenylmorpholin-4-yl | 474.2748 |
| 4.131 | HO-(CH2)5- | 5-pyridyl (2-attached) | 2-phenylmorpholin-4-yl | 460.2605 |

TABLE 4-continued

| Example | R¹ | R² | R³ | MS (M + 1) |
|---|---|---|---|---|
| 4.132 | (imidazol-1-yl-propyl) | (5-methylpyridin-2-yl) | (2-phenylmorpholin-4-yl) | 482.2571 |
| 4.133 | (1,2,4-triazol-1-yl-isobutyl) | (5-methylpyridin-2-yl) | (2-phenylmorpholin-4-yl) | 483.2504 |
| 4.134 | (pyridin-3-yl) | (5-methylpyridin-2-yl) | (2-phenylmorpholin-4-yl) | 451.2147 |
| 4.135 | (4-methylthiazol-2-yl-isopropyl) | (5-methylpyridin-2-yl) | (2-phenylmorpholin-4-yl) | 499.2183 |
| 4.136 | (2-methylthiazol-4-yl-isopropyl) | (5-methylpyridin-2-yl) | (2-phenylmorpholin-4-yl) | 499.2187 |

TABLE 4-continued
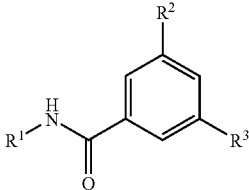
| Example | R¹ | R² | R³ | MS (M + 1) |
|---|---|---|---|---|
| 4.137 | 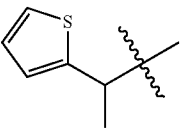 | 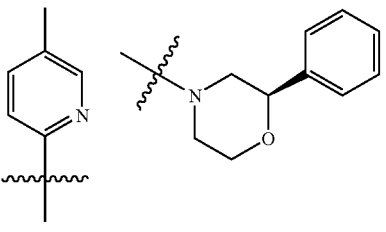 | 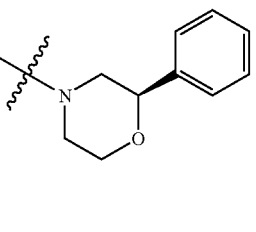 | 484.2080 |
| 4.138 | 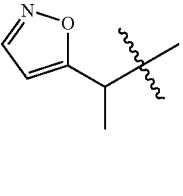 | 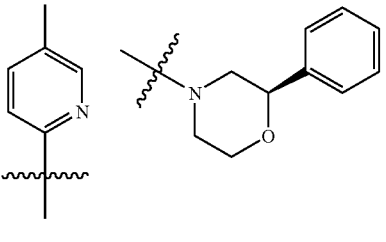 | 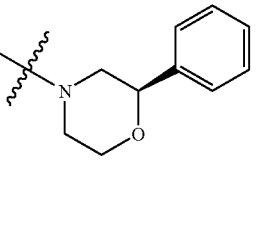 | 469.2252 |
| 4.139 | 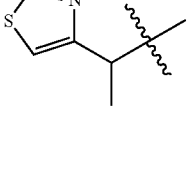 | 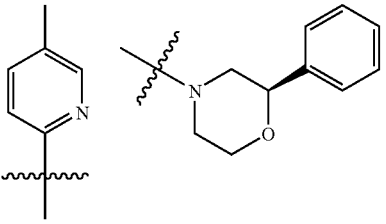 | 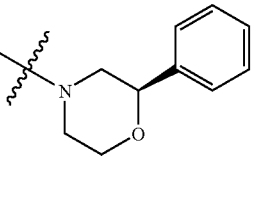 | 485.2026 |
| 4.140 | 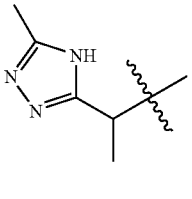 | 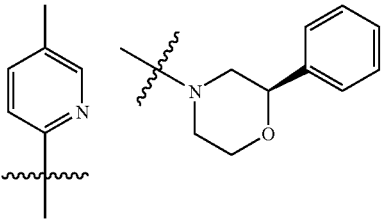 | 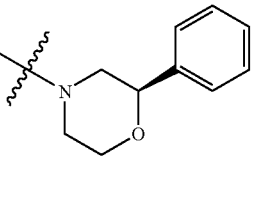 | 483.2522 |
| 4.141 | 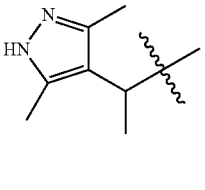 | 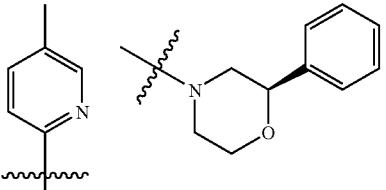 | 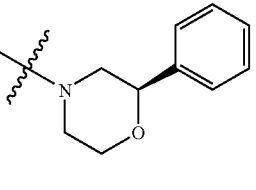 | 496.2723 |

TABLE 4-continued
| Example | R¹ | R² | R³ | MS (M + 1) |
|---|---|---|---|---|
| 4.142 | 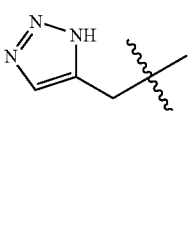 | 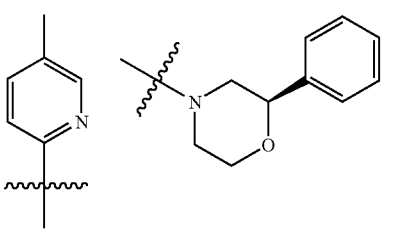 | 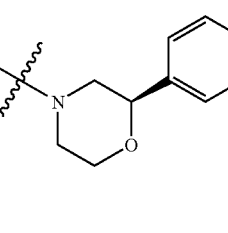 | 455.2212 |
| 4.143 | 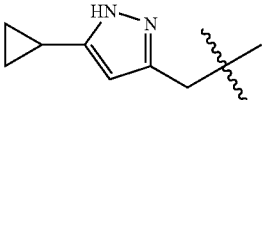 | 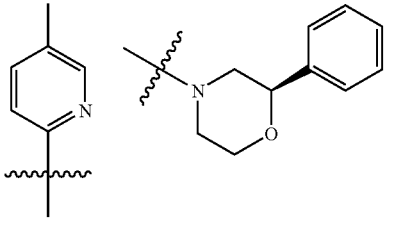 | 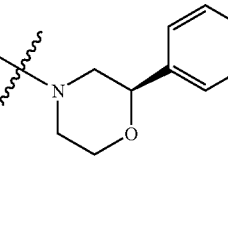 | 494.2570 |
| 4.144 | 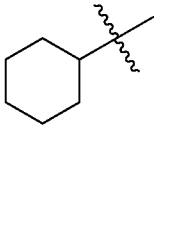 | 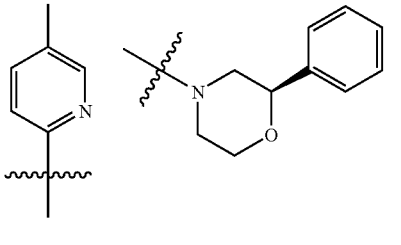 | 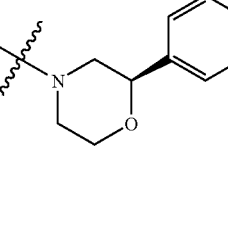 | 456.2669 |
| 4.145 | 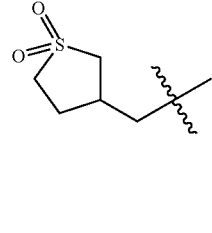 | 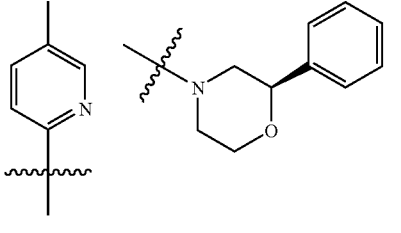 | 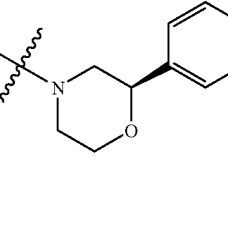 | 506.2109 |
| 4.146 | 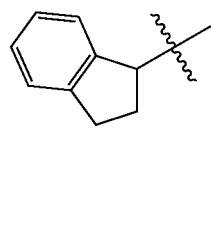 | 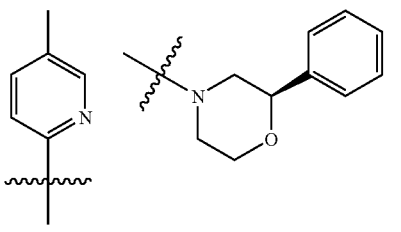 | 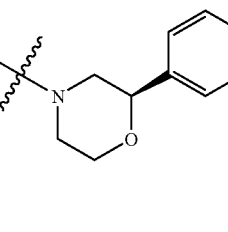 | 490.2487 |

TABLE 4-continued
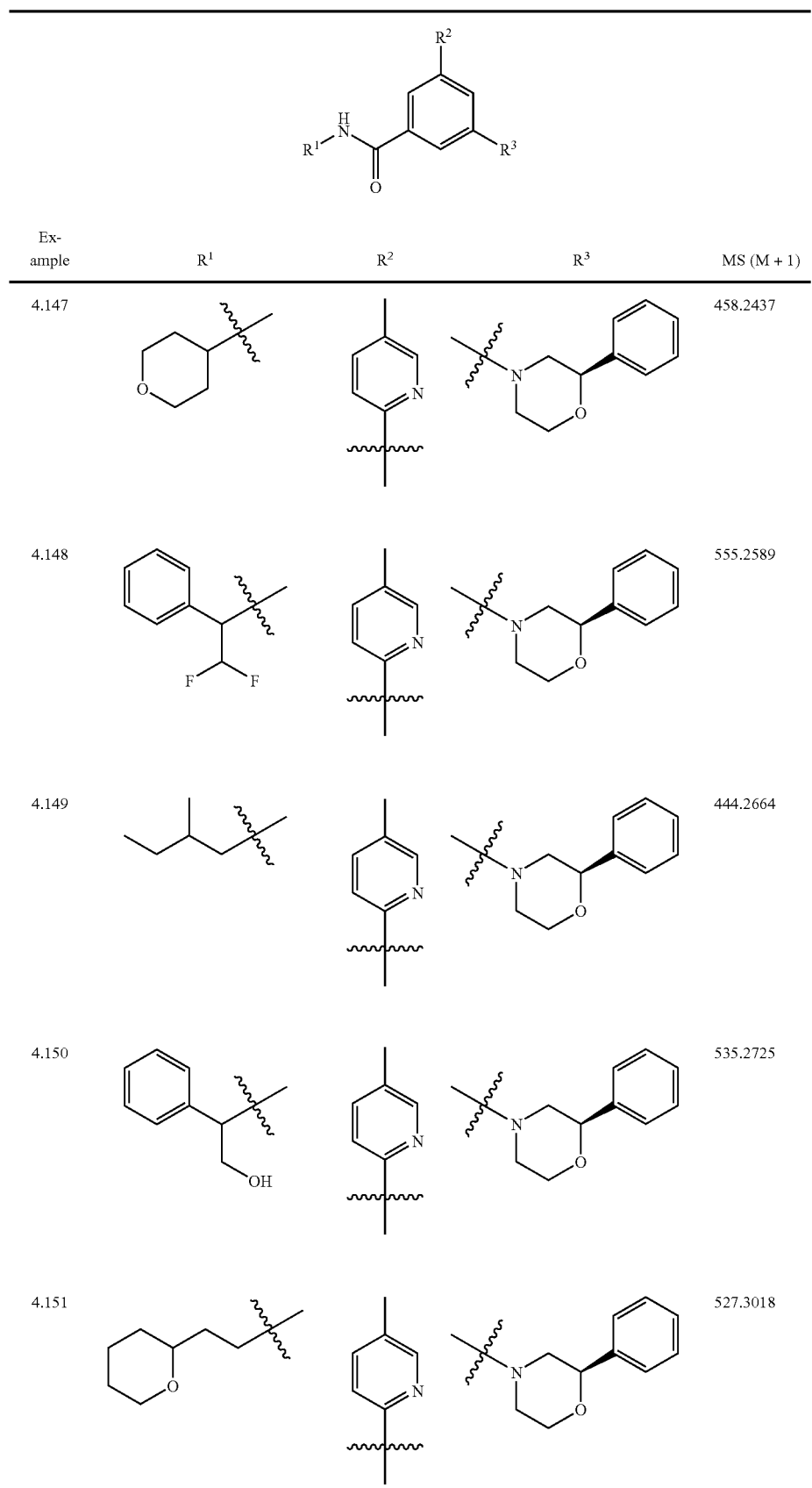
| Example | R¹ | R² | R³ | MS (M + 1) |
|---|---|---|---|---|
| 4.147 | | | | 458.2437 |
| 4.148 | | | | 555.2589 |
| 4.149 | | | | 444.2664 |
| 4.150 | | | | 535.2725 |
| 4.151 | | | | 527.3018 |

TABLE 4-continued

| Example | R¹ | R² | R³ | MS (M + 1) |
|---|---|---|---|---|
| 4.152 | 2,5-dimethylpyrazol-1-yl (sec-butyl linker) | 5-methylpyridin-2-yl | 2-phenylmorpholin-4-yl | 510.2866 |
| 4.153 | 2-oxopyrrolidin-1-yl (propyl linker) | 5-methylpyridin-2-yl | 2-phenylmorpholin-4-yl | 499.2725 |
| 4.154 | 3,5-dimethylisoxazol-4-yl (ethyl linker) | 5-methylpyridin-2-yl | 2-phenylmorpholin-4-yl | 497.2570 |
| 4.155 | 4H-1,2,4-triazol-3-yl (chiral methyl) | 4-methyl-2-fluorophenyl | 2-phenylmorpholin-4-yl | 486.2326 |
| 4.156 | tert-butyl | 4-methyl-2-fluorophenyl | 2-phenylmorpholin-4-yl | 433.2272 |

TABLE 4-continued
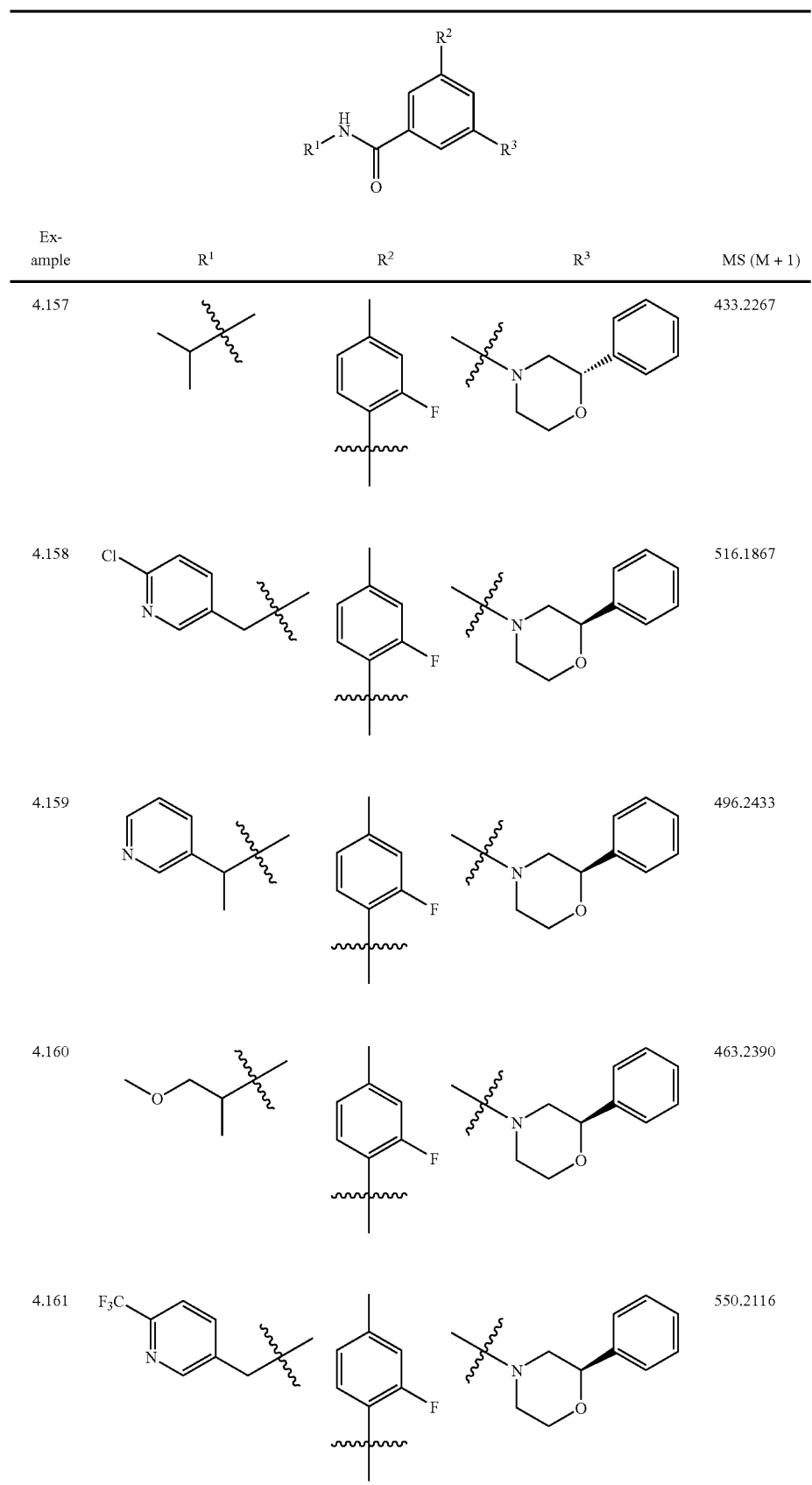
| Example | R¹ | R² | R³ | MS (M + 1) |
|---|---|---|---|---|
| 4.157 | | | | 433.2267 |
| 4.158 | | | | 516.1867 |
| 4.159 | | | | 496.2433 |
| 4.160 | | | | 463.2390 |
| 4.161 | | | | 550.2116 |

TABLE 4-continued
| Example | R¹ | R² | R³ | MS (M + 1) |
|---|---|---|---|---|
| 4.162 | 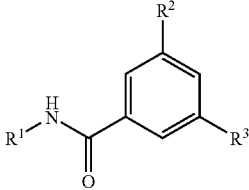 | 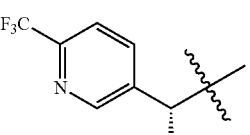 | 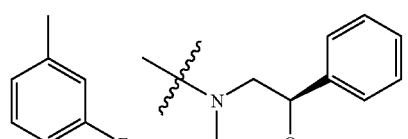 | 564.2326 |
| 4.163 | 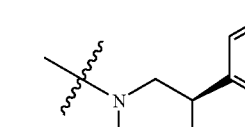 | 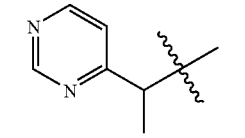 | 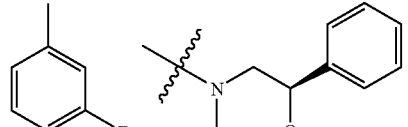 | 497.2376 |
| 4.164 | 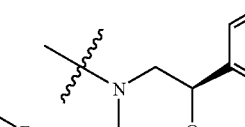 | 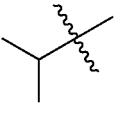 | 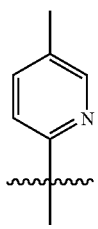 | 416.2365 |
| 4.165 | 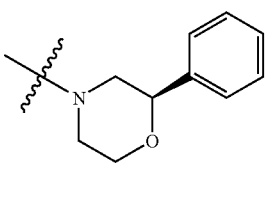 | 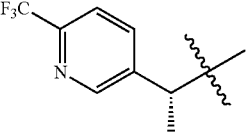 | 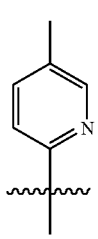 | 547.0 |
| 4.166 | 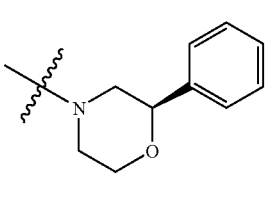 | 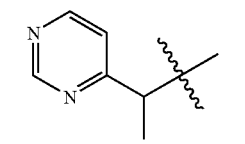 | 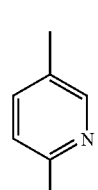 | 480.2404 |

TABLE 4-continued
| Example | R¹ | R² | R³ | MS (M + 1) |
|---|---|---|---|---|
| 4.167 | 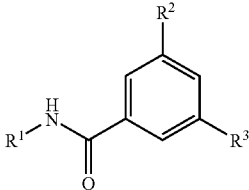 | 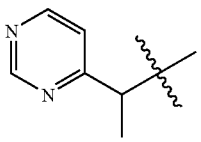 | 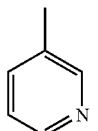 | 478.2620 |
| 4.168 | 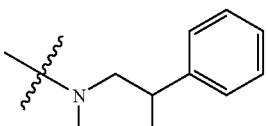 | 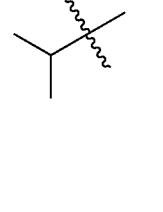 | 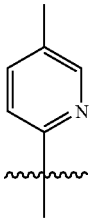 | 414.2564 |
| 4.169 | 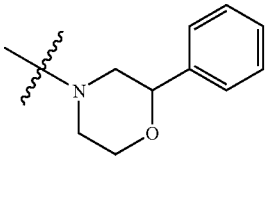 | 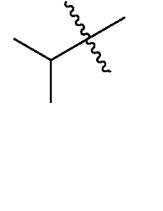 | 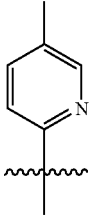 | 352.2390 |
| 4.170 | 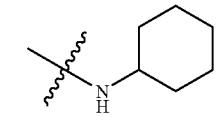 | 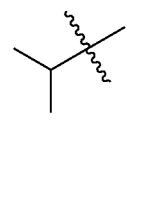 | 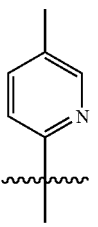 | 415.2508 |
| 4.171 | 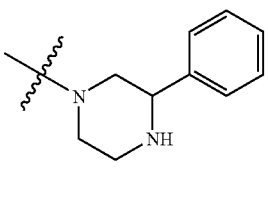 | 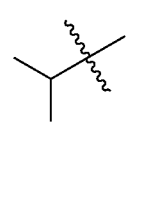 | 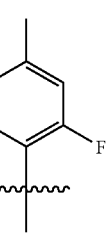 | 432.2446 |

TABLE 4-continued
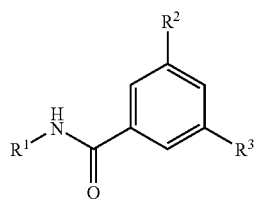
| Example | R¹ | R² | R³ | MS (M + 1) |
|---|---|---|---|---|
| 4.172 | isobutyl | 5-pyridyl | 4-methyl-3-phenylpiperazin-1-yl | 429.2659 |
| 4.173 | isobutyl | 5-pyridyl | 4-acetyl-3-phenylpiperazin-1-yl | 457.2604 |
| 4.174 | isobutyl | 5-pyridyl | 2-(4-methylphenyl)morpholin-4-yl | 430.2491 |
| 4.175 | tert-butyl | 5-pyridyl | (3S)-3-methylmorpholin-4-yl | 354.2178 |
| 4.176 | tert-butyl | 5-pyridyl | (3R)-3-methylmorpholin-4-yl | 354.2178 |

TABLE 4-continued

| Example | R¹ | R² | R³ | MS (M + 1) |
|---|---|---|---|---|
| 4.177 | isobutyl | 5-methylpyridin-2-yl | (S)-3-phenylmorpholin-4-yl | 416.2334 |
| 4.178 | isobutyl | 5-methylpyridin-2-yl | 2,2-dimethylmorpholin-4-yl | 368.2335 |
| 4.179 | isobutyl | 5-methylpyridin-2-yl | 3,3-dimethylmorpholin-4-yl | 368.2335 |
| 4.180 | tert-butyl | 5-methylpyridin-2-yl | (3S,5S)-3,5-dimethylmorpholin-4-yl | 365.2335 |
| 4.181 | tert-butyl | 3-fluoro-4-methylphenyl | 4-acetyl-3-phenylpiperazin-1-yl | 474.2596 |

TABLE 4-continued

| Example | R¹ | R² | R³ | MS (M + 1) |
|---|---|---|---|---|
| 4.182 | isopropyl-dimethyl | 4-methyl-2-fluorophenyl | 3-phenyl-4-methylpiperazin-1-yl | 446.2360 |
| 4.183 | isopropyl | 5-methylpyridin-2-yl | tert-butylamino | 326.2241 |
| 4.184 | 1-(4-methylthiazol-2-yl)ethyl | 4-methyl-2-fluorophenyl | 1H-1,2,3-triazol-1-yl | 422.1 |
| 4.185 | 1-(4-methylthiazol-2-yl)ethyl | 4-methyl-2-fluorophenyl | 1H-1,2,3-triazol-1-yl | 422.1 |
| 4.186 | 1-(4H-1,2,4-triazol-3-yl)ethyl | 4-methyl-2-fluorophenyl | 1H-1,2,3-triazol-1-yl | 392.1 |

TABLE 4-continued

| Example | R¹ | R² | R³ | MS (M + 1) |
|---|---|---|---|---|
| 4.187 | 5-(trifluoromethyl)pyridin-3-yl, CH(CH₃) | 4-substituted-3-F-phenyl | 1H-1,2,3-triazol-1-yl | 470.1587 |
| 4.188 | 5-fluoropyridin-2-yl, CH(CH₃) | 4-substituted-3-F-phenyl | 1H-1,2,3-triazol-1-yl | 420.1626 |
| 4.189 | 2,4-dimethylthiazol-5-yl, CH₂ | 4-substituted-3-F-phenyl | 1H-1,2,3-triazol-1-yl | 422.1450 |
| 4.190 | isopropyl-C(CH₃) | 4-substituted-3-F-phenyl | 1H-1,2,3-triazol-1-yl | 339.1606 |
| 4.191 | 5-fluoropyridin-2-yl, CH(CH₃) | 5-methylpyridin-2-yl | 1H-1,2,3-triazol-1-yl | 403.1678 |

TABLE 4-continued

| Example | R¹ | R² | R³ | MS (M + 1) |
|---|---|---|---|---|
| 4.192 | (5-fluoropyridin-2-yl, CH(CH₃)-) | 5-fluoropyridin-2-yl | 1H-1,2,3-triazol-1-yl | 407.1 |
| 4.193 | isopropyl-C(CH₃)- | 3-fluoro-4-methylphenyl | 2H-1,2,3-triazol-2-yl | 339.1609 |
| 4.194 | (5-methyl-4H-1,2,4-triazol-3-yl)CH(CH₃)- | 3-fluoro-4-methylphenyl | 2H-1,2,3-triazol-2-yl | 406.1778 |
| 4.195 | 2-phenyl-1-hydroxymethyl-ethyl | 3-fluoro-4-methylphenyl | 2H-1,2,3-triazol-2-yl | 417.1719 |
| 4.196 | (1,2,5-thiadiazol-3-yl)CH₂C(CH₃)- | 3-fluoro-4-methylphenyl | 2H-1,2,3-triazol-2-yl | 395.1081 |

TABLE 4-continued

| Example | R¹ | R² | R³ | MS (M + 1) |
|---|---|---|---|---|
| 4.197 | (4H-1,2,4-triazol-3-yl)(methyl)methyl | 3-fluorophenyl | 2H-1,2,3-triazol-2-yl | 392.1 |
| 4.198 | (4-methylthiazol-2-yl)(methyl)methyl | 3-fluorophenyl | 2H-1,2,3-triazol-2-yl | 422.1 |
| 4.199 | (2,4-dimethylthiazol-5-yl)methyl | 3-fluorophenyl | 2H-1,2,3-triazol-2-yl | 422.1442 |
| 4.200 | (5-fluoropyridin-2-yl)(methyl)methyl | 3-fluorophenyl | 2H-1,2,3-triazol-2-yl | 420.1620 |
| 4.201 | (6-(trifluoromethyl)pyridin-3-yl)(methyl)methyl | 3-fluorophenyl | 2H-1,2,3-triazol-2-yl | 470.1587 |

TABLE 4-continued
| Example | R¹ | R² | R³ | MS (M + 1) |
|---|---|---|---|---|
| 4.202 | 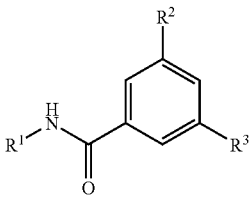 | 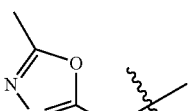 | 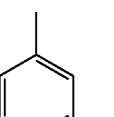 | 393.1469 |
| 4.203 | 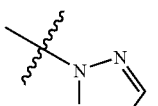 | 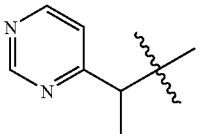 | 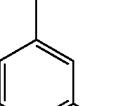 | 403.1679 |
| 4.204 | 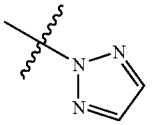 | 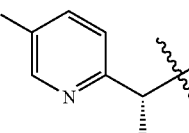 | 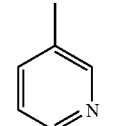 | 403.1676 |
| 4.205 | 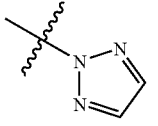 | 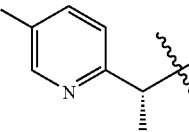 | 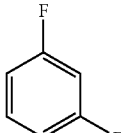 | 424.1388 |
| 4.206 | 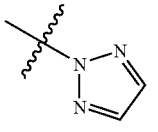 | 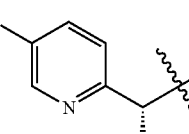 | 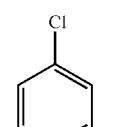 | 422.1191 |

TABLE 4-continued

| Example | R¹ | R² | R³ | MS (M + 1) |
|---|---|---|---|---|
| 4.207 | 5-fluoropyridin-2-yl (S)-CH(CH₃)– | 4-fluorophenyl | 2H-1,2,3-triazol-2-yl | 406.1473 |
| 4.208 | 5-fluoropyridin-2-yl (S)-CH(CH₃)– | 4-fluoro-2-methylphenyl | 2H-1,2,3-triazol-2-yl | 420.1629 |
| 4.209 | 5-fluoropyridin-2-yl (S)-CH(CH₃)– | 2,4-dichlorophenyl | 2H-1,2,3-triazol-2-yl | 456.1 |
| 4.210 | 4-methylthiazol-2-yl (S)-CH(CH₃)– | 2-fluoro-4-methylphenyl | 2H-1,2,3-triazol-2-yl | 422.1 |
| 4.211 | 4-methylthiazol-2-yl (S)-CH(CH₃)– | 5-methylpyridin-2-yl | 2H-1,2,3-triazol-2-yl | 405.1 |

TABLE 4-continued

| Example | R¹ | R² | R³ | MS (M + 1) |
|---|---|---|---|---|
| 4.212 | 5-fluoropyridin-2-yl (CH(CH₃)-) | 5-pyridyl (2-linked) | 1-methylbenzimidazol-2-yl | 466.2060 |
| 4.213 | 6-(trifluoromethyl)pyridin-3-yl (CH(CH₃)-) | 5-pyridyl (2-linked) | 1-methylbenzimidazol-2-yl | 516.2036 |
| 4.214 | 5-methylpyrazin-2-yl (CH(CH₃)-) | 5-pyridyl (2-linked) | 1-methylbenzimidazol-2-yl | 463.2267 |
| 4.215 | pyrazin-2-yl (CH(CH₃)-) | 5-pyridyl (2-linked) | 1-methylbenzimidazol-2-yl | 449.2105 |
| 4.216 | pyrimidin-4-yl (CH(CH₃)-) | 5-pyridyl (2-linked) | 1-methylbenzimidazol-2-yl | 449.2107 |

TABLE 4-continued
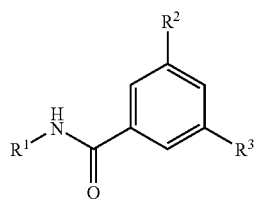
| Example | R¹ | R² | R³ | MS (M + 1) |
|---|---|---|---|---|
| 4.217 | 4-methylthiazol-2-yl isopropyl | 5-pyridyl | 1-methylbenzimidazol-2-yl | 468.1881 |
| 4.218 | 2-methylthiazol-4-yl isopropyl | 5-pyridyl | 1-methylbenzimidazol-2-yl | 468.1883 |
| 4.219 | isopropyl | 3-fluoro-4-methylphenyl | benzimidazol-2-yl | |
| 4.220 | isopropyl | 3-fluoro-4-methylphenyl | 1-methylbenzimidazol-2-yl | |
| 4.221 | isobutyl | 3-fluoro-4-methylphenyl | 1-phenylbenzimidazol-2-yl | |

TABLE 4-continued

| Example | R¹ | R² | R³ | MS (M + 1) |
|---|---|---|---|---|
| 4.222 | tert-butyl | 4-fluorophenyl | 5,6-dimethyl-1H-benzimidazol-2-yl | |
| 4.223 | tert-butyl | 4-fluorophenyl | 4,5-difluoro-1H-benzimidazol-2-yl | |
| 4.224 | 1-(5-fluoropyridin-2-yl)ethyl | 4-fluorophenyl | 1-methyl-1H-benzimidazol-2-yl | |
| 4.225 | 1-(4H-1,2,4-triazol-3-yl)ethyl | 4-fluorophenyl | 1-methyl-1H-benzimidazol-2-yl | |
| 4.226 | 1-(6-(trifluoromethyl)pyridin-3-yl)ethyl | 4-fluorophenyl | 1-methyl-1H-benzimidazol-2-yl | |

TABLE 4-continued

| Example | R¹ | R² | R³ | MS (M + 1) |
|---|---|---|---|---|
| 4.227 | tetrahydropyran-4-yl | 3-fluoro-4-yl phenyl | 1-methylbenzimidazol-2-yl | |
| 4.228 | tert-butyl | 3-fluoro-4-yl phenyl | 3-hydroxypyridin-2-yl | 379.1815 |
| 4.229 | tert-butyl | 3-fluoro-4-yl phenyl | 5-nitropyridin-2-yl | 408.1722 |
| 4.230 | 1-(pyridin-2-yl)cyclopropyl | 3-fluoro-4-yl phenyl | 3-fluoropyridin-2-yl | 442.1739 |
| 4.231 | tert-pentyl | 3-fluoro-4-yl phenyl | 3-fluoropyridin-2-yl | 367.1610 |

TABLE 4-continued

| Example | R¹ | R² | R³ | MS (M + 1) |
|---|---|---|---|---|
| 4.232 | 1H-1,2,4-triazol-5-yl-CH(CH₃)- | 3-F-phenyl (attached at 4) | 3-F-pyridin-2-yl | 420.1642 |
| 4.233 | pyridin-4-yl-CH(CH₃)- | 3-F-phenyl (attached at 4) | 3-F-pyridin-2-yl | 430.1736 |
| 4.234 | pyrimidin-5-yl-CH₂- | 3-F-phenyl (attached at 4) | 3-F-pyridin-2-yl | 417.1540 |
| 4.235 | pyridin-3-yl-C(CF₃)H- | 3-F-phenyl (attached at 4) | 3-F-pyridin-2-yl | 484.1419 |
| 4.236 | 1,2,3-thiadiazol-5-yl-CH₂- | 3-F-phenyl (attached at 4) | 3-F-pyridin-2-yl | 422.1117 |

TABLE 4-continued

| Example | R¹ | R² | R³ | MS (M + 1) |
|---|---|---|---|---|
| 4.237 | phenylcyclopropyl | 4-F-phenyl | 3-F-pyridin-2-yl | 441.1755 |
| 4.238 | cyclopropyl | 4-F-phenyl | 3-F-pyridin-2-yl | 365.1468 |
| 4.239 | $F_3C$-C(CH$_3$)$_2$- | 4-F-phenyl | 3-F-pyridin-2-yl | 407.1162 |
| 4.240 | 1-(4-methylthiazol-2-yl)ethyl | 4-F-phenyl | 3-F-pyridin-2-yl | 450.1464 |
| 4.241 | 1-(2-methylthiazol-4-yl)ethyl | 4-F-phenyl | 3-F-pyridin-2-yl | 450.1472 |

TABLE 4-continued

| Example | R¹ | R² | R³ | MS (M + 1) |
|---|---|---|---|---|
| 4.242 | 5-F-pyridin-2-yl, CH(CH₃)- | 4-F-phenyl | 3-F-pyridin-2-yl | 448.1642 |
| 4.243 | pyrimidin-4-yl, CH(CH₃)- | 4-F-phenyl | 3-F-pyridin-2-yl | 431.1666 |
| 4.244 | pyridin-2-yl, CH(CH₃)- | 4-F-phenyl | 3-F-pyridin-2-yl | 460.1725 |
| 4.245 | 6-CF₃-pyridin-3-yl, CH(CH₃)- | 4-F-phenyl | 3-F-pyridin-2-yl | 498.1605 |
| 4.246 | 2-CF₃-pyrimidin-5-yl, CH(CH₃)- | 4-F-phenyl | 3-F-pyridin-2-yl | 485.1425 |

TABLE 4-continued

| Example | R¹ | R² | R³ | MS (M + 1) |
|---|---|---|---|---|
| 4.247 | 2-CF₃-pyridin-5-yl, CH(CH₃)- | 5-methyl-pyridin-2-yl | 3-fluoro-pyridin-2-yl | 481.1691 |
| 4.248 | pyridin-2-yl, CH(CH₃)- | 5-methyl-pyridin-2-yl | 3-fluoro-pyridin-2-yl | 413.1801 |
| 4.249 | 4-methyl-thiazol-2-yl, CH(CH₃)- | 5-methyl-pyridin-2-yl | 3-fluoro-pyridin-2-yl | 433.1525 |
| 4.250 | 4H-1,2,4-triazol-3-yl, CH(CH₃)- | 5-methyl-pyridin-2-yl | 3-fluoro-pyridin-2-yl | 403.1702 |
| 4.251 | 2-CF₃-pyrimidin-5-yl, CH₂- | 5-methyl-pyridin-2-yl | 3-fluoro-pyridin-2-yl | 468.1481 |

TABLE 4-continued

| Example | R¹ | R² | R³ | MS (M + 1) |
|---|---|---|---|---|
| 4.252 | 5-fluoropyridin-2-yl with methyl | 5-pyridyl | 3-fluoropyridin-2-yl | 431.1706 |
| 4.253 | pyrimidin-5-ylmethyl | 5-pyridyl | 3-fluoropyridin-2-yl | 400.1597 |
| 4.254 | 2-methylthiazol-4-yl with methyl | 5-pyridyl | 3-fluoropyridin-2-yl | 433.1526 |
| 4.255 | pyrimidin-4-yl with methyl | 5-pyridyl | 3-fluoropyridin-2-yl | 414.1764 |
| 4.256 | cyclopropyl with methyl | 5-pyridyl | 3-fluoropyridin-2-yl | 348.1530 |

TABLE 4-continued

| Example | R¹ | R² | R³ | MS (M + 1) |
|---|---|---|---|---|
| 4.257 | F₃C-pyrimidine-CH(CH₃)- | 5-pyridyl (N at 2) | 3-F-2-pyridyl | 482.1632 |
| 4.258 | 4H-1,2,4-triazol-3-yl-CH(CH₃)- | 5-pyridyl (N at 2) | 3-F-2-pyridyl | 403.1710 |
| 4.259 | 4H-1,2,4-triazol-3-yl-CH(CH₃)- | 5-pyridyl (N at 2) | 3-F-2-pyridyl | 403.1710 |
| 4.260 | F₃C-pyrimidine-CH(CH₃)- | 5-pyridyl (N at 2) | 3-F-2-pyridyl | 482.1615 |
| 4.261 | 5-F₃C-2-pyridyl-CH(CH₃)- | 5-pyridyl (N at 2) | 3-F-2-pyridyl | 481.1692 |

TABLE 4-continued

| Example | R¹ | R² | R³ | MS (M + 1) |
|---|---|---|---|---|
| 4.262 | 5-(trifluoromethyl)pyridin-2-yl CH(CH₃)- | 5-methylpyridin-2-yl | 3-fluoropyridin-2-yl | 481.1658 |
| 4.263 | 3-fluoropyridin-2-yl CH(CH₃)- | 5-methylpyridin-2-yl | 3-fluoropyridin-2-yl | 431.1693 |
| 4.264 | 3-fluoropyridin-2-yl CH(CH₃)- | 5-methylpyridin-2-yl | 3-fluoropyridin-2-yl | 431.0 |
| 4.265 | 5-oxo-4,5-dihydro-1H-1,2,4-triazol-3-yl CH(CH₃)- | 5-methylpyridin-2-yl | 3-fluoropyridin-2-yl | 419.1643 |
| 4.266 | (5-methylpyrazin-2-yl)CH₂- | 5-methylpyridin-2-yl | 3-fluoropyridin-2-yl | 414.1735 |

TABLE 4-continued

| Example | R¹ | R² | R³ | MS (M + 1) |
|---|---|---|---|---|
| 4.267 | 4H-1,2,4-triazol-3-yl CH(CH₃)- | 4-(attach), 3-F phenyl | 3-F pyridin-2-yl | 420.1634 |
| 4.268 | pyrazin-2-yl CH(CH₃)- | 5-methyl, 2-(attach) pyridin-2-yl | 3-F pyridin-2-yl | 414.1730 |
| 4.269 | pyrazin-2-yl CH(CH₃)- | 5-methyl, 2-(attach) pyridin-2-yl | 3-F pyridin-2-yl | 414.1735 |
| 4.270 | 5-Cl pyridin-2-yl CH(CH₃)- | 5-methyl, 2-(attach) pyridin-2-yl | 3-F pyridin-2-yl | 447.1402 |
| 4.271 | 5-Cl pyridin-2-yl CH(CH₃)- | 5-methyl, 2-(attach) pyridin-2-yl | 3-F pyridin-2-yl | 447.1413 |

TABLE 4-continued

| Example | R¹ | R² | R³ | MS (M + 1) |
|---|---|---|---|---|
| 4.272 | pyrazin-2-ylmethyl | 5-methylpyridin-2-yl | 3-fluoropyridin-2-yl | 400.1590 |
| 4.273 | 1-(5-fluoropyridin-2-yl)ethyl N-oxide | 5-methylpyridin-2-yl | 3-fluoropyridin-2-yl | 447.1632 |
| 4.274 | 1-(6-trifluoromethylpyridin-3-yl)ethyl N-oxide | 5-methylpyridin-2-yl | 3-fluoropyridin-2-yl | 497.1616 |
| 4.275 | (3,5-difluoropyridin-2-yl)methyl | 5-methylpyridin-2-yl | 3-fluoropyridin-2-yl | 435.1431 |
| 4.276 | 1-(5-methylpyrazin-2-yl)ethyl | 5-methylpyridin-2-yl | 3-fluoropyridin-2-yl | 428.1885 |

TABLE 4-continued
| Example | R¹ | R² | R³ | MS (M + 1) |
|---|---|---|---|---|
| 4.277 | 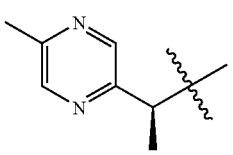 | 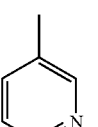 | 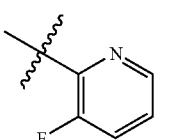 | 428.1884 |
| 4.278 | 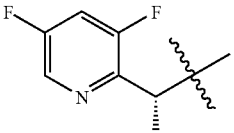 | 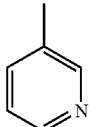 | 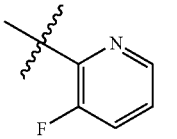 | 449.1583 |
| 4.279 | 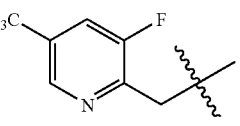 | 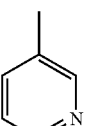 | 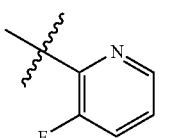 | 485.1396 |
| 4.280 | 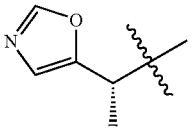 | 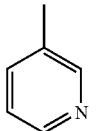 | 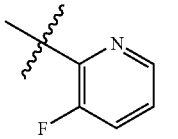 | 403.1578 |
| 4.281 | 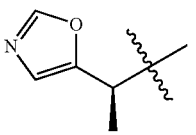 | 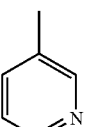 | 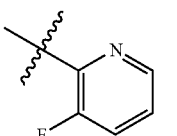 | 403.1556 |

TABLE 4-continued

| Example | R¹ | R² | R³ | MS (M + 1) |
|---|---|---|---|---|
| 4.282 | pyrazinyl-C(CH₃)₂- | 5-pyridyl (2-linked) | 3-fluoropyridin-2-yl | 428.1888 |
| 4.283 | 5-methyl-1,3,4-oxadiazol-2-yl-C(CH₃)₂- | 5-pyridyl (2-linked) | 3-fluoropyridin-2-yl | 404.1516 |
| 4.284 | pyridin-2-yl-C(CH₃)₂- | 5-pyridyl (2-linked) | 3-fluoropyridin-2-yl | 427.1935 |
| 4.285 | 4-methylthiazol-2-yl-C(CH₃)₂- | 5-pyridyl (2-linked) | 3-fluoropyridin-2-yl | 447.1662 |
| 4.286 | 5-fluoropyridin-2-yl N-oxide-CH(CH₃)- | 3-fluoro-4-phenyl | 3-fluoropyridin-2-yl | 464.1591 |

TABLE 4-continued
| Example | R¹ | R² | R³ | MS (M + 1) |
|---|---|---|---|---|
| 4.287 | 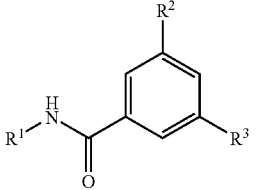 | 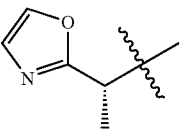 | 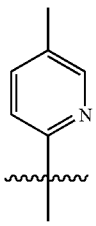 | 403.1574 |
| 4.288 | 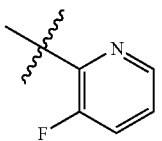 | 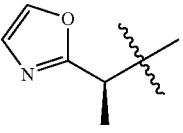 | 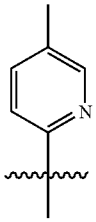 | 403.1585 |
| 4.289 | 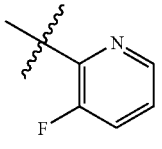 | 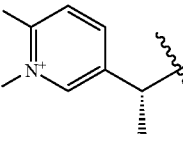 | 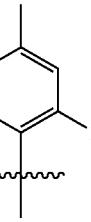 | 514.1553 |
| 4.290 | 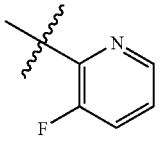 | 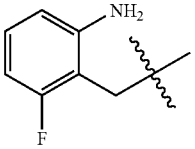 | 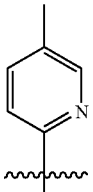 | 431.1671 |
| 4.291 | 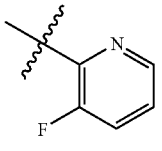 | 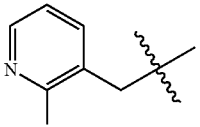 | 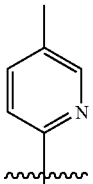 | 415.1565 |

TABLE 4-continued
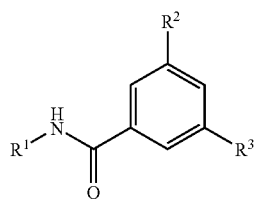
| Example | R¹ | R² | R³ | MS (M + 1) |
|---|---|---|---|---|
| 4.292 | naphthalen-1-yl-CH(CH₃)– | 5-methylpyridin-2-yl | 3-fluoropyridin-2-yl | 462.1978 |
| 4.293 | (3-fluoropyridin-4-yl)-CH(CH₃)– | 5-methylpyridin-2-yl | 3-fluoropyridin-2-yl | 431.1675 |
| 4.294 | (5-fluoropyridin-3-yl)-CH(CH₃)– | 5-methylpyridin-2-yl | 3-fluoropyridin-2-yl | 431.1676 |
| 4.295 | (5-trifluoromethylpyrazin-2-yl)-CH(CH₃)– | 5-methylpyridin-2-yl | 3-fluoropyridin-2-yl | 482.1620 |
| 4.296 | (5-trifluoromethylpyrazin-2-yl)-CH(CH₃)– | 5-methylpyridin-2-yl | 3-fluoropyridin-2-yl | 482.1606 |

TABLE 4-continued
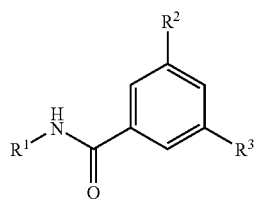
| Example | R¹ | R² | R³ | MS (M + 1) |
|---|---|---|---|---|
| 4.297 | | | | 403.1381 |
| 4.298 | | | | 360.1510 |
| 4.299 | | | | 402.1726 |
| 4.300 | | | | 402.1725 |
| 4.301 | | | | 418.1672 |

TABLE 4-continued
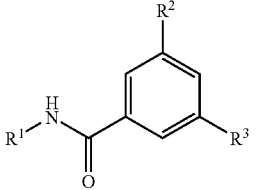
| Example | R¹ | R² | R³ | MS (M + 1) |
|---|---|---|---|---|
| 4.302 | 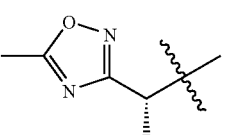 | 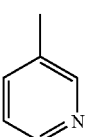 | 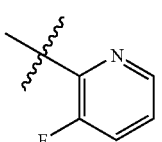 | 418.1699 |
| 4.303 | 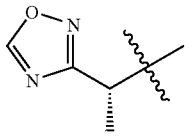 | 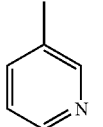 | 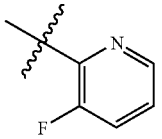 | 404.1521 |
| 4.304 | 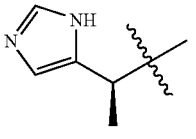 | 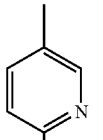 | 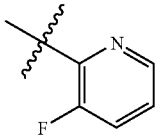 | 402.1741 |
| 4.305 | 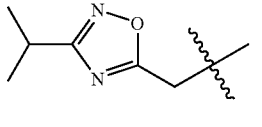 | 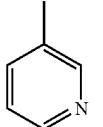 | 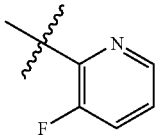 | 432.1831 |
| 4.306 | 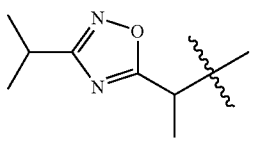 | 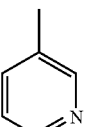 | 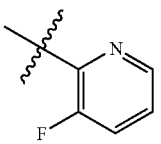 | 446.1989 |

TABLE 4-continued

| Example | R¹ | R² | R³ | MS (M + 1) |
|---|---|---|---|---|
| 4.307 | 3-ethyl-1,2,4-oxadiazol-5-ylmethyl | 5-pyridyl (via 2-) | 3-fluoropyridin-2-yl | 418.1678 |
| 4.308 | 1,3,4-oxadiazol-2-ylmethyl | 5-pyridyl (via 2-) | 3-fluoropyridin-2-yl | 390.1358 |
| 4.309 | 5-ethyl-1,2,4-oxadiazol-3-ylmethyl | 5-pyridyl (via 2-) | 3-fluoropyridin-2-yl | 418.1677 |
| 4.310 | 5-(ethoxymethyl)-1,2,4-oxadiazol-3-ylmethyl | 5-pyridyl (via 2-) | 3-fluoropyridin-2-yl | 448.1780 |
| 4.311 | 5-(2-methoxyethyl)-1,2,4-oxadiazol-3-ylmethyl | 5-pyridyl (via 2-) | 3-fluoropyridin-2-yl | 448.1781 |

TABLE 4-continued

| Example | R¹ | R² | R³ | MS (M + 1) |
|---|---|---|---|---|
| 4.312 | F₃C-pyridine | 4-F-phenyl | 3-F-pyridine | 484.1443 |
| 4.313 | F₃C-pyridine | phenyl | 3-F-pyridine | 466.1544 |
| 4.314 | F₃C-pyridine | 2-F-phenyl | 3-F-pyridine | 484.1456 |
| 4.315 | F₃C-pyridine | 2,4-diF-phenyl | 3-F-pyridine | 502.1365 |
| 4.316 | F₃C-pyridine | 4-cyclopropyl-phenyl | 3-F-pyridine | 506.1866 |
| 4.317 | F₃C-pyridine | pyridine | 3-F-pyridine | 467.1499 |

TABLE 4-continued

| Example | R¹ | R² | R³ | MS (M + 1) |
|---|---|---|---|---|
| 4.318 | 6-CF₃-pyridin-3-yl-CH(CH₃)- | 4-(2-hydroxypropan-2-yl)phenyl | 3-fluoropyridin-2-yl | 524.1973 |
| 4.319 | 6-CF₃-pyridin-3-yl-CH(CH₃)- | 5-fluoropyridin-2-yl | 3-fluoropyridin-2-yl | 485.1411 |
| 4.320 | 6-CF₃-pyridin-3-yl-CH(CH₃)- | 3-fluoropyridin-2-yl | 3-fluoropyridin-2-yl | 485.1395 |
| 4.321 | 6-CF₃-pyridin-3-yl-CH(CH₃)- | 5-chloropyridin-2-yl | 3-fluoropyridin-2-yl | 501.1121 |
| 4.322 | 6-CF₃-pyridin-3-yl-CH(CH₃)- | 5-CF₃-pyridin-2-yl | 3-fluoropyridin-2-yl | 535.1419 |

TABLE 4-continued

| Example | R¹ | R² | R³ | MS (M + 1) |
|---|---|---|---|---|
| 4.323 | pyrazinyl-CH(CH₃)- | 4-F-phenyl | 3-F-pyridin-2-yl | 431.1669 |
| 4.324 | isobutyl | 4-F-phenyl | pyridin-2-yl | 349.1730 |
| 4.325 | isobutyl | 4-F-phenyl | 3-Cl-pyridin-2-yl | 383.1320 |
| 4.326 | tert-butyl | 4-F-phenyl | 6-CN-pyridin-2-yl | 374.1670 |
| 4.327 | isopropyl-CH- | 4-F-phenyl | 3-CN-pyridin-2-yl | 374.1671 |

TABLE 4-continued

| Example | R¹ | R² | R³ | MS (M + 1) |
|---|---|---|---|---|
| 4.328 | tert-pentyl | 4-methyl-3-F-phenyl | 5-F-pyridin-2-yl | 367.1620 |
| 4.329 | tert-pentyl | 4-methyl-3-F-phenyl | 5-Cl-pyridin-2-yl | 383.1330 |
| 4.330 | tert-pentyl | 4-methyl-3-F-phenyl | 5-methyl-pyridin-2-yl | 363.1867 |
| 4.331 | tert-pentyl | 4-methyl-3-F-phenyl | 5-CF₃-pyridin-2-yl | 417.1596 |
| 4.332 | tert-pentyl | 4-methyl-3-F-phenyl | 3-CF₃-pyridin-2-yl | 417.1605 |

TABLE 4-continued

| Example | R¹ | R² | R³ | MS (M + 1) |
|---|---|---|---|---|
| 4.333 | tert-pentyl | 4-F-phenyl | 1,8-naphthyridin-2-yl | 400.1817 |
| 4.334 | tert-pentyl | 4-F-phenyl | 5-amino-pyridin-2-yl | 364.1818 |
| 4.335 | tert-pentyl | 4-F-phenyl | 4-methoxy-pyridin-2-yl | 379.1811 |
| 4.336 | tert-pentyl | 4-F-phenyl | 6-amino-pyridin-2-yl | 364.1818 |
| 4.337 | tert-pentyl | 4-F-phenyl | 3-amino-pyridin-2-yl | 364.1816 |

TABLE 4-continued

| Example | R¹ | R² | R³ | MS (M + 1) |
|---|---|---|---|---|
| 4.338 | isobutyl | 3-F-phenyl | 2-oxo-1,2-dihydro-1,5-naphthyridin-6-yl | 416.1769 |
| 4.339 | isobutyl | 3-F-phenyl | 6-(methoxycarbonyl)pyridin-2-yl | 407.1784 |
| 4.340 | isobutyl | 3-F-phenyl | 6-acetylpyridin-2-yl | 391.1822 |
| 4.341 | isobutyl | 3-F-phenyl | 5-(methylsulfonyl)pyridin-2-yl | 427.1486 |
| 4.342 | isobutyl | 3-F-phenyl | 5-cyanopyridin-2-yl | 374.1660 |

TABLE 4-continued

| Example | R¹ | R² | R³ | MS (M+1) |
|---|---|---|---|---|
| 4.343 | pyrimidinyl-CH(CH₃)- | 3-fluorophenyl | 6-(carboxy)pyridin-2-yl | 471.1864 |
| 4.344 | (5-fluoropyridin-2-yl)-CH(CH₃)- | 5-methylpyridin-2-yl | 1,8-naphthyridin-2-yl | 464.1900 |
| 4.345 | (5-fluoropyridin-2-yl)-CH(CH₃)- | 5-methylpyridin-2-yl | 6-cyanopyridin-2-yl | 438.1733 |
| 4.346 | (5-fluoropyridin-2-yl)-CH(CH₃)- | 5-methylpyridin-2-yl | 3-cyanopyridin-2-yl | 438.1731 |
| 4.347 | (5-fluoropyridin-2-yl)-CH(CH₃)- | 5-methylpyridin-2-yl | 4-methoxypyridin-2-yl | 443.1883 |

TABLE 4-continued
| Example | R¹ | R² | R³ | MS (M + 1) |
|---|---|---|---|---|
| 4.348 | 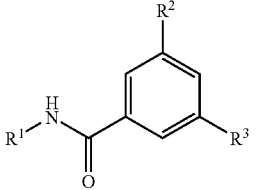 | 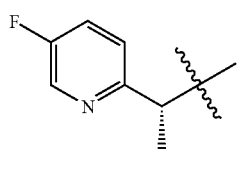 | 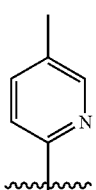 | 471.2208 |
| 4.349 | 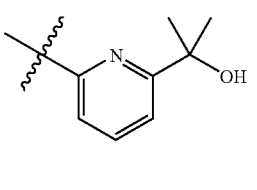 | 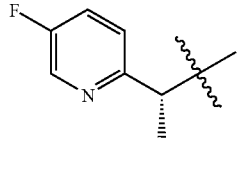 | 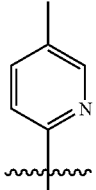 | 413.1773 |
| 4.350 | 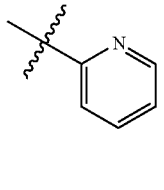 | 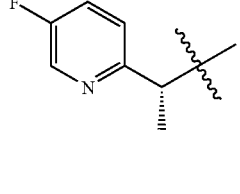 | 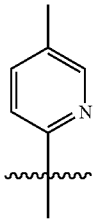 | 427.1932 |
| 4.351 | 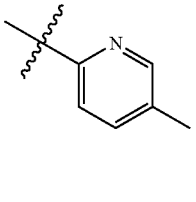 | 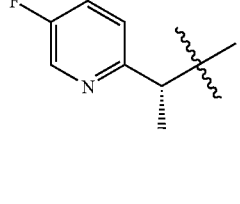 | 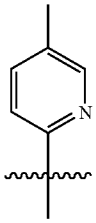 | 481.1657 |
| 4.352 | 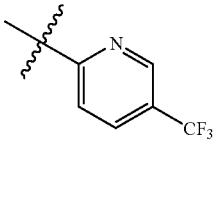 | 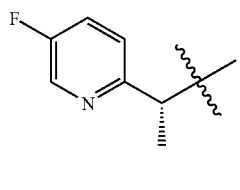 | 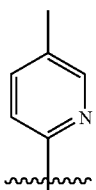 | 431.1681 |

TABLE 4-continued
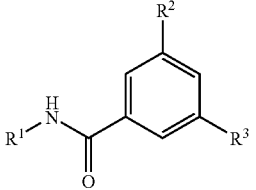
| Example | R¹ | R² | R³ | MS (M + 1) |
|---|---|---|---|---|
| 4.353 | 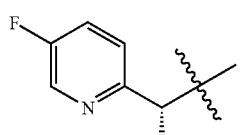 | 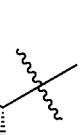 |  | 438.1737 |
| 4.354 |  |  |  | 457.1711 |
| 4.355 | 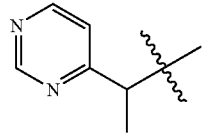 | 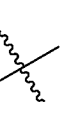 | 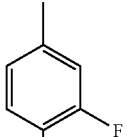 | 438.1714 |
| 4.356 |  | 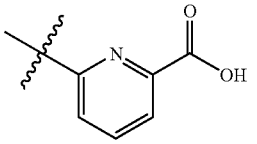 | 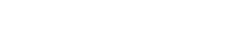 | 428.1877 |
| 4.357 | 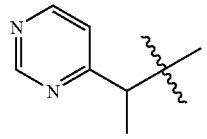 | 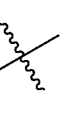 | 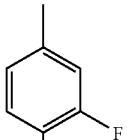 | 462.1800 |

TABLE 4-continued

| Example | R¹ | R² | R³ | MS (M + 1) |
|---|---|---|---|---|
| 4.358 | 5-fluoropyridin-2-yl with chiral methyl | 5-methylpyridin-2-yl | 3-fluoro-5-methylpyridin-2-yl | 445.1843 |
| 4.359 | 2-(trifluoromethyl)pyrimidin-5-yl with chiral methyl | 5-methylpyridin-2-yl | 3-fluoro-5-methylpyridin-2-yl | 496.1768 |
| 4.360 | 3-fluoropyridin-2-yl with chiral methyl | 5-methylpyridin-2-yl | 3-fluoro-5-methylpyridin-2-yl | 445.1844 |
| 4.361 | 5-(trifluoromethyl)pyridin-2-yl with chiral methyl | 5-methylpyridin-2-yl | 3-fluoro-5-methylpyridin-2-yl | 495.1810 |
| 4.362 | 4H-1,2,4-triazol-3-yl with chiral methyl | 5-methylpyridin-2-yl | 3-fluoro-5-methylpyridin-2-yl | 417.1837 |

TABLE 4-continued

| Example | R¹ | R² | R³ | MS (M + 1) |
|---|---|---|---|---|
| 4.363 | (6-trifluoromethylpyridin-3-yl)-CH(CH₃)- | 5-pyridin-2-yl | 3-fluoro-5-methylpyridin-2-yl | 495.1817 |
| 4.364 | (5-methylpyrazin-2-yl)-CH₂- | 5-pyridin-2-yl | 3-fluoro-5-methylpyridin-2-yl | 428.1893 |
| 4.365 | (5-oxo-4,5-dihydro-1H-1,2,4-triazol-3-yl)-CH(CH₃)- | 5-pyridin-2-yl | 3-fluoro-5-methylpyridin-2-yl | 433.1795 |
| 4.366 | (5-fluoropyridin-2-yl)-CH(CH₃)- | 5-methylpyridin-2-yl | 2-isopropylphenyl | 454.2292 |
| 4.367 | (5-fluoropyridin-2-yl)-CH(CH₃)- | 5-methylpyridin-2-yl | 2-cyclopropylphenyl | 452.2137 |

TABLE 4-continued

| Example | R¹ | R² | R³ | MS (M + 1) |
|---|---|---|---|---|
| 4.368 | 5-F-pyridin-2-yl (S-methyl) | 5-pyridinyl | 2,6-dichlorophenyl | 480.1047 |
| 4.369 | 5-F-pyridin-2-yl (S-methyl) | 5-pyridinyl | 2-methylphenyl | 426.1979 |
| 4.370 | 4H-1,2,4-triazol-3-yl (methyl) | 4-phenyl | 4-methylphenyl | 397.2033 |
| 4.371 | 4H-1,2,4-triazol-3-yl (methyl) | 4-F-phenyl | 2-F-4-methylphenyl | 433.1859 |
| 4.372 | 4H-1,2,4-triazol-3-yl (methyl) | 4-F-phenyl | 4-F-phenyl | 405.1527 |
| 4.373 | 4H-1,2,4-triazol-3-yl (methyl) | 2-F-phenyl | 2-F-phenyl | 405.1527 |

TABLE 4-continued
| Example | R¹ | R² | R³ | MS (M + 1) |
|---|---|---|---|---|
| 4.374 | 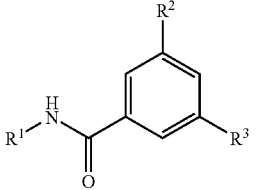 | 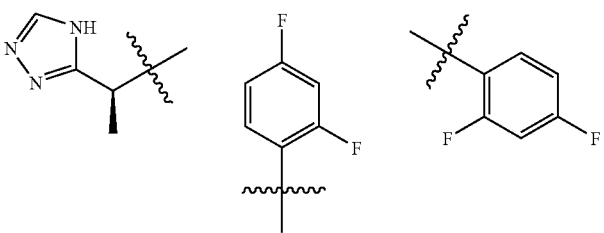 | 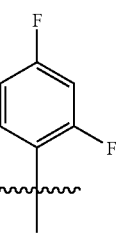 | 441.1344 |
| 4.375 | 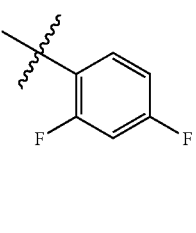 | 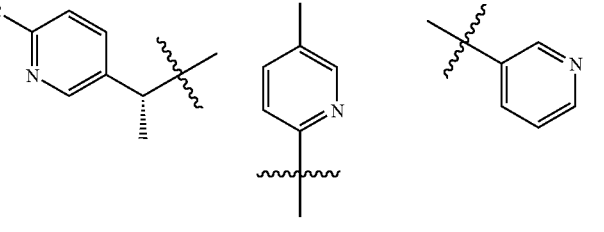 | 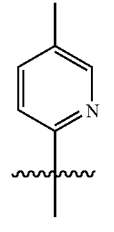 | 463.1765 |
| 4.376 | 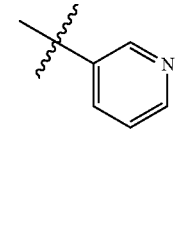 | 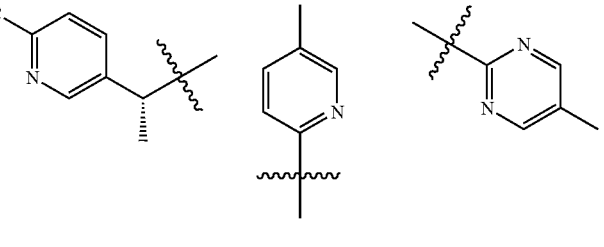 | 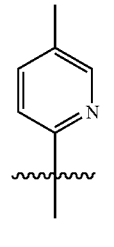 | 478.1861 |
| 4.377 | 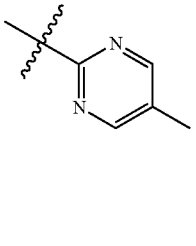 | 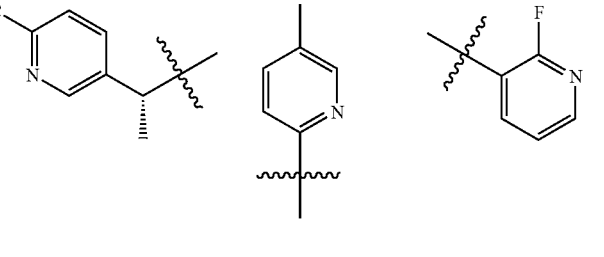 | 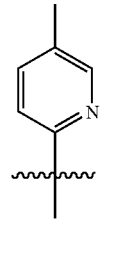 | 481.1660 |
| 4.378 | 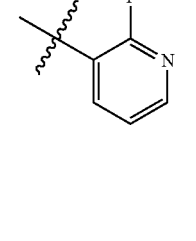 | 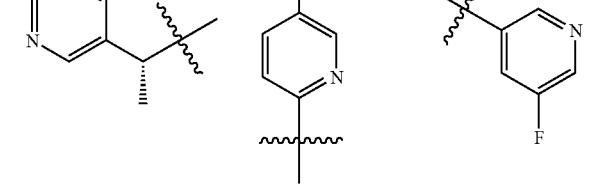 | 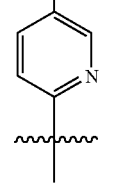 | 481.1656 |

TABLE 4-continued
| Example | R¹ | R² | R³ | MS (M + 1) |
|---|---|---|---|---|
| 4.379 | 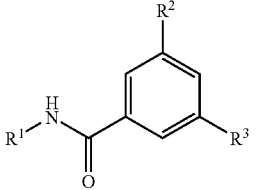 | 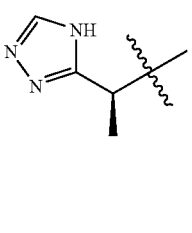 | 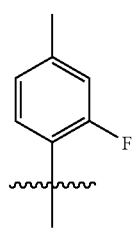 | 419.1678 |
| 4.380 | 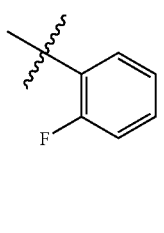 | 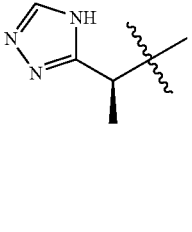 | 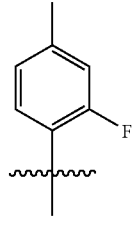 | 470.1618 |
| 4.381 | 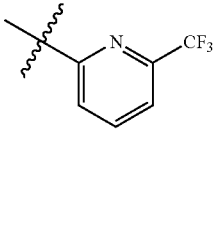 | 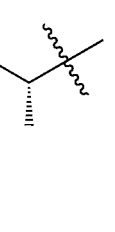 | 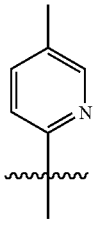 | 464.1693 |
| 4.382 | 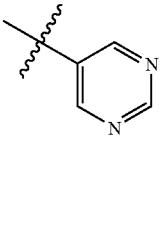 | 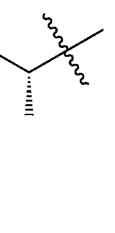 | 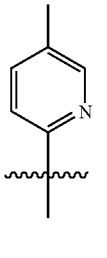 | 494.1785 |
| 4.383 | 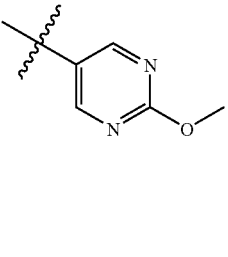 | 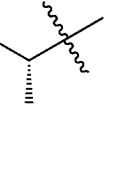 | 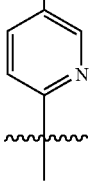 | 479.1786 |

TABLE 4-continued
| Example | R¹ | R² | R³ | MS (M + 1) |
|---|---|---|---|---|
| 4.384 | 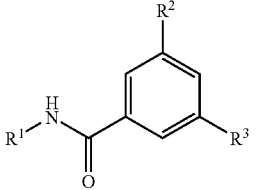 | 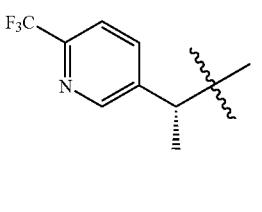 | 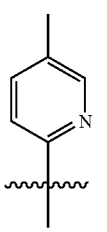 | 463.1728 |
| 4.385 | 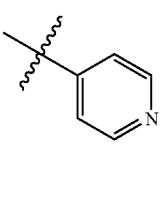 | 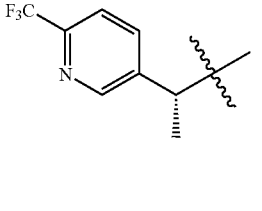 | 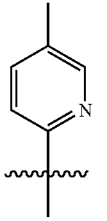 | 481.1632 |
| 4.386 | 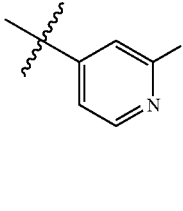 | 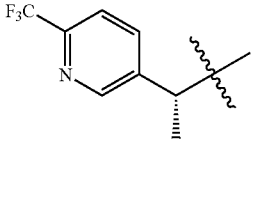 | 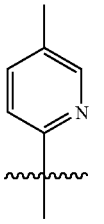 | 464.1683 |
| 4.387 | 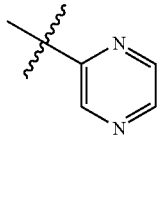 | 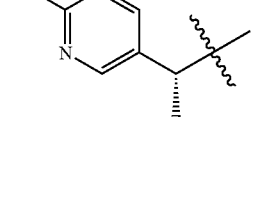 | 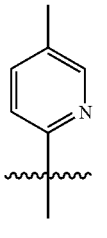 | 481.1633 |
| 4.388 | 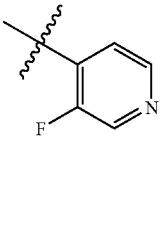 | 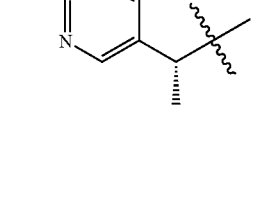 | 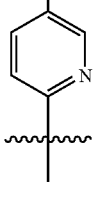 | 480.1626 |

TABLE 4-continued

| Example | R¹ | R² | R³ | MS (M + 1) |
|---|---|---|---|---|
| 4.389 | F₃C-pyridyl-CH(CH₃)- | 5-pyridyl (2-linked) | 5-amino-pyrazin-2-yl | 479.1789 |
| 4.390 | F₃C-pyridyl-CH(CH₃)- | 5-pyridyl (2-linked) | 6-methoxy-pyridazin-3-yl | 479.1786 |
| 4.391 | F₃C-pyridyl-CH(CH₃)- | 5-pyridyl (2-linked) | 6-chloro-pyridazin-3-yl | 498.1330 |
| 4.392 | F₃C-pyridyl-CH(CH₃)- | 5-methyl-pyridin-2-yl | pyridazin-3-yl | 464.1708 |
| 4.393 | F₃C-pyridyl-CH(CH₃)- | 5-pyridyl (2-linked) | 3,5-difluoro-pyridin-2-yl | 499.1555 |

TABLE 4-continued

| Example | R¹ | R² | R³ | MS (M + 1) |
|---|---|---|---|---|
| 4.394 | F₃C-pyridyl | pyridyl | difluoropyridine N-oxide | 515.1515 |
| 4.395 | F₃C-pyridyl | pyridyl | pyrimidinyl | 464.1693 |
| 4.396 | F₃C-pyridyl | pyridyl | methylpyridazinyl | 478.1847 |
| 4.397 | F₃C-pyridyl | pyridyl | hydroxypyridyl | 479.1695 |
| 4.398 | F₃C-pyridyl | pyridyl | hydroxypyrimidinyl | 480.1693 |

TABLE 4-continued

| Example | R¹ | R² | R³ | MS (M + 1) |
|---|---|---|---|---|
| 4.399 | F₃C-pyridine-CH(CH₃)- | 5-pyridyl (N at 2) | 3-(6-hydroxy)pyridazinyl | 480.1656 |
| 4.400 | F₃C-pyridine-CH(CH₃)- | 5-pyridyl (N at 2) | 3-(2-hydroxy)pyridinyl | 479.1689 |
| 4.401 | F₃C-pyridine-CH(CH₃)- | 5-pyridyl (N at 2) | 2-(4-hydroxy)pyrimidinyl | 480.1 |
| 4.402 | F₃C-pyridine-CH(CH₃)- | 5-pyridyl (N at 2) | 2-(6-hydroxy)pyridinyl | 479.1695 |
| 4.403 | F₃C-pyridine-CH(CH₃)- | 5-pyridyl (N at 2) | 2-(3-hydroxy)pyrazinyl | 480.1637 |

TABLE 4-continued

| Example | R¹ | R² | R³ | MS (M + 1) |
|---|---|---|---|---|
| 4.404 | 5-CF₃-pyridin-3-yl (with CH methyl) | 5-methyl-pyridin-2-yl | 6-hydroxy-pyrazin-2-yl | 480.1650 |
| 4.405 | 4H-1,2,4-triazol-3-yl (with CH methyl) | 5-methyl-pyridin-2-yl | 3,5-difluoro-pyridin-2-yl | 421.1593 |
| 4.406 | 4H-1,2,4-triazol-3-yl (with CH methyl) | 2-fluoro-4-methyl-phenyl | 5-fluoro-pyridin-3-yl | 420.1627 |
| 4.407 | 4H-1,2,4-triazol-3-yl (with CH methyl) | 2-fluoro-4-methyl-phenyl | 5-methyl-pyrimidin-2-yl | 417.1827 |
| 4.408 | 4H-1,2,4-triazol-3-yl (with CH methyl) | 2-fluoro-4-methyl-phenyl | 3,5-difluoro-pyridin-2-yl | 438.1563 |

TABLE 4-continued

| Example | R¹ | R² | R³ | MS (M + 1) |
|---|---|---|---|---|
| 4.409 | 3,5-difluoropyridin-2-yl with CH(CH₃) linker | 5-pyridyl (2-attached) | pyrazin-2-yl | 432.1634 |
| 4.410 | 4H-1,2,4-triazol-3-yl with CH(CH₃) linker | 5-pyridyl (2-attached) | pyrazin-2-yl | 386.1724 |
| 4.411 | 2-(trifluoromethyl)pyrimidin-5-yl with CH(CH₃) linker | 5-pyridyl (2-attached) | pyrazin-2-yl | 465.1649 |
| 4.412 | 5-(trifluoromethyl)pyrazin-2-yl with CH(CH₃) linker | 5-pyridyl (2-attached) | pyrazin-2-yl | 465.1647 |
| 4.413 | 3-methyl-1,2,4-oxadiazol-5-yl with CH(CH₃) linker | 5-pyridyl (2-attached) | pyrazin-2-yl | 401.1723 |

TABLE 4-continued

| Example | R¹ | R² | R³ | MS (M + 1) |
|---|---|---|---|---|
| 4.414 | 3,5-difluoropyridin-2-yl (with CH(CH₃)) | 5-methylpyridin-2-yl | 6-methylpyridazin-3-yl | 446.1789 |
| 4.415 | 4H-1,2,4-triazol-3-yl (with CH(CH₃)) | 5-methylpyridin-2-yl | 6-methylpyridazin-3-yl | 400.1885 |
| 4.416 | 2-(trifluoromethyl)pyrimidin-5-yl (with CH(CH₃)) | 5-methylpyridin-2-yl | 6-methylpyridazin-3-yl | 479.1815 |
| 4.417 | 5-(trifluoromethyl)pyrazin-2-yl (with CH(CH₃)) | 5-methylpyridin-2-yl | 6-methylpyridazin-3-yl | 479.1813 |
| 4.418 | 3-methyl-1,2,4-oxadiazol-5-yl (with CH(CH₃)) | 5-methylpyridin-2-yl | 6-methylpyridazin-3-yl | 415.1878 |

TABLE 4-continued

| Example | R¹ | R² | R³ | MS (M + 1) |
|---|---|---|---|---|
| 4.419 | 3,5-difluoropyridin-2-yl-CH(CH₃)- | 5-pyridyl (2-linked) | 2-aminopyrimidin-5-yl | 447.1749 |
| 4.420 | 4H-1,2,4-triazol-3-yl-CH(CH₃)- | 5-pyridyl (2-linked) | 2-aminopyrimidin-5-yl | 401.1840 |
| 4.421 | 2-(trifluoromethyl)pyrimidin-5-yl-CH(CH₃)- | 5-pyridyl (2-linked) | 2-aminopyrimidin-5-yl | 480.1765 |
| 4.422 | 5-(trifluoromethyl)pyrazin-2-yl-CH(CH₃)- | 5-pyridyl (2-linked) | 2-aminopyrimidin-5-yl | 480.1766 |
| 4.423 | 3-methyl-1,2,4-oxadiazol-5-yl-CH(CH₃)- | 5-pyridyl (2-linked) | 2-aminopyrimidin-5-yl | 416.1838 |

TABLE 4-continued

| Example | R¹ | R² | R³ | MS (M + 1) |
|---|---|---|---|---|
| 4.424 | (6-trifluoromethylpyridin-3-yl)(methyl)methyl | 6-pyridyl (5-) | 2-methylpyrimidin-5-yl | 478.1 |
| 4.425 | (4H-1,2,4-triazol-3-yl)(methyl)methyl | 6-pyridyl (5-) | 2-methylpyrimidin-5-yl | 400.1 |
| 4.426 | (3-methyl-1,2,4-oxadiazol-5-yl)(methyl)methyl | 6-pyridyl (5-) | 2-methylpyrimidin-5-yl | 415.1 |
| 4.427 | (6-trifluoromethylpyridin-3-yl)(methyl)methyl | 6-pyridyl (5-) | 2-trifluoromethylpyrimidin-5-yl | 532.0 |
| 4.428 | (5-trifluoromethylpyridin-2-yl)(methyl)methyl | 6-pyridyl (5-) | 2-trifluoromethylpyrimidin-5-yl | 482.0 |

TABLE 4-continued

| Example | R¹ | R² | R³ | MS (M + 1) |
|---|---|---|---|---|
| 4.429 | 4H-1,2,4-triazol-3-yl-CH(CH₃)– | 5-pyridin-2-yl | 2-(trifluoromethyl)pyrimidin-5-yl | 453.9 |
| 4.430 | 3-methyl-1,2,4-oxadiazol-5-yl-CH(CH₃)– | 5-pyridin-2-yl | 2-(trifluoromethyl)pyrimidin-5-yl | 468.9 |
| 4.431 | 2-(trifluoromethyl)pyrimidin-5-yl-CH(CH₃)– | 5-pyridin-2-yl | isopropenyl | 413.1 |
| 4.432 | 4H-1,2,4-triazol-3-yl-CH(CH₃)– | 2-fluoro-4-methylphenyl | isopropenyl | 365.1747 |
| 4.433 | 4H-1,2,4-triazol-3-yl-CH(CH₃)– | 3-fluoro-4-methylphenyl | isopropyl | 367.1930 |

TABLE 4-continued
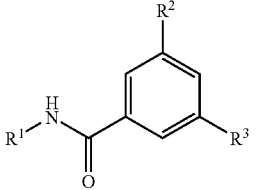
| Example | R¹ | R² | R³ | MS (M + 1) |
|---|---|---|---|---|
| 4.434 | 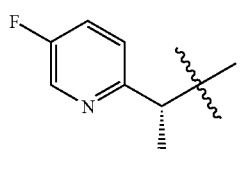 | 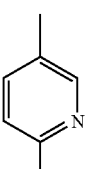 | 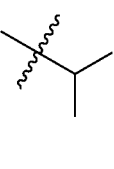 | 378.1974 |
| 4.435 | 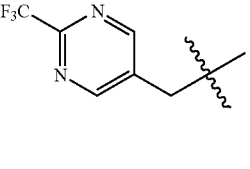 | 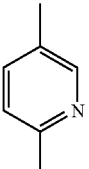 | 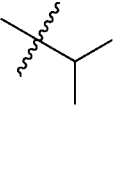 | 415.1755 |
| 4.436 | 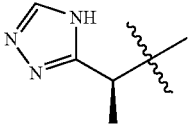 | 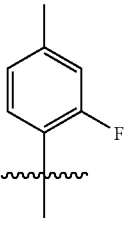 |  | 339.1610 |
| 4.437 | 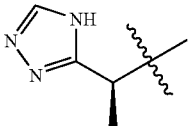 | 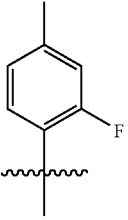 | 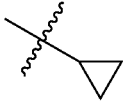 | 365.1773 |
| 4.438 | 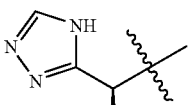 | 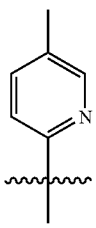 | 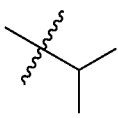 | 350.1972 |

TABLE 4-continued

| Example | R¹ | R² | R³ | MS (M + 1) |
|---|---|---|---|---|
| 4.439 | 5-fluoropyridin-2-yl (methyl, stereo) | 5-methylpyridin-2-yl | sec-butyl | 364.1818 |
| 4.440 | 5-fluoropyridin-2-yl (methyl, stereo) | 5-methylpyridin-2-yl | 2-methylbutyl (gem-dimethyl propyl) | 378.1975 |
| 4.441 | 5-fluoropyridin-2-yl (methyl, stereo) | 5-methylpyridin-2-yl | 1-methylcyclopropyl | 376.1816 |
| 4.442 | 5-fluoropyridin-2-yl (methyl, stereo) | 5-methylpyridin-2-yl | C(CH₃)₂OH | 352.1 |
| 4.443 | 3,5-difluoropyridin-2-yl (methyl, stereo) | 5-methylpyridin-2-yl | C(CH₃)₂CF₃ | 422.1 |

TABLE 4-continued

| Example | R¹ | R² | R³ | MS (M + 1) |
|---|---|---|---|---|
| 4.444 | 3-methyl-1,2,4-oxadiazol-5-yl CH(CH₃)- | 5-pyridyl (linked at 2) | -C(CH₃)₂CF₃ | 391.1 |
| 4.445 | 4H-1,2,4-triazol-3-yl CH(CH₃)- | 5-pyridyl (linked at 2) | -C(CH₃)₂CF₃ | 376.1 |
| 4.446 | (5-fluoropyridin-2-yl)CH(CH₃)- | 5-pyridyl (linked at 2) | -C(CH₃)₂CF₃ | 404.1 |
| 4.447 | 4H-1,2,4-triazol-3-yl CH(CH₃)- | 5-methylpyridin-2-yl | -C(CH₃)₂OH | 366.1923 |
| 4.448 | (5-fluoropyridin-2-yl)CH(CH₃)- | 5-pyridyl (linked at 2) | -C(CH₃)₂OH | 394.1938 |

TABLE 4-continued

| Example | R¹ | R² | R³ | MS (M + 1) |
|---|---|---|---|---|
| 4.449 | 3-methyl-1,2,4-oxadiazol-5-yl with CH(CH₃) linker | 5-pyridyl (2-attached) | C(CH₃)₂OH | 381.1 |
| 4.450 | 3,5-difluoropyridin-2-yl with CH(CH₃) linker | 5-pyridyl (2-attached) | C(CH₃)₂OH | 412.1 |
| 4.451 | 5-methyl-1,2,4-oxadiazol-3-yl with CH(CH₃) linker | 5-pyridyl (2-attached) | C(CH₃)₂OH | 381.1 |
| 4.452 | 2-(trifluoromethyl)pyrimidin-5-yl with CH(CH₃) linker | 5-methyl-pyridin-2-yl | C(CH₃)₂OH | 445.0 |
| 4.453 | 4H-1,2,4-triazol-3-yl with CH(CH₃) linker | 2-fluorophenyl | C(CH₃)₂OH | 383.1 |

TABLE 4-continued
| Example | R¹ | R² | R³ | MS (M + 1) |
|---|---|---|---|---|
| 4.454 | 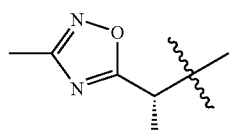 | 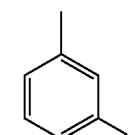 | 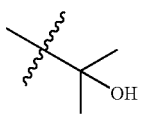 | 398.1 |
| 4.455 | 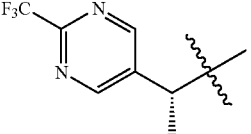 | 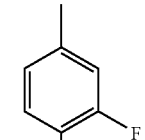 | 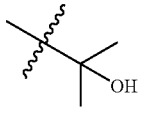 | 462.0 |
| 4.456 | 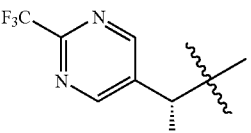 | 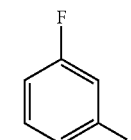 | 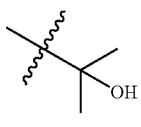 | 466.0 |
| 4.457 | 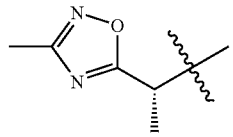 | 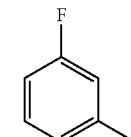 | 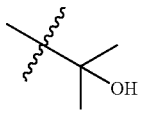 | 402.1 |
| 4.458 | 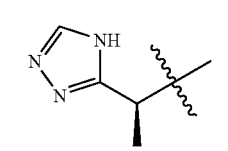 | 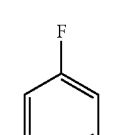 | 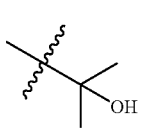 | 387.1 |

TABLE 4-continued
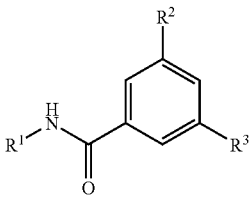
| Ex-ample | R¹ | R² | R³ | MS (M + 1) |
|---|---|---|---|---|
| 4.459 | 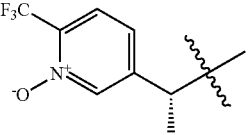 | 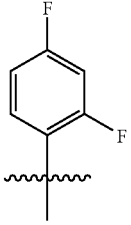 | 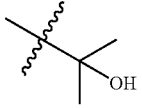 | 481.1562 |
| 4.460 | 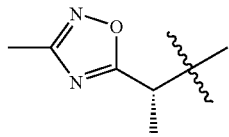 | 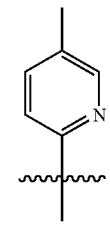 | 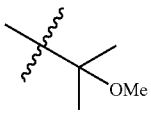 | 395.2092 |
| 4.461 | 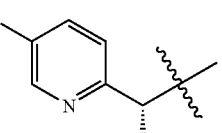 | 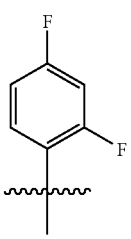 | 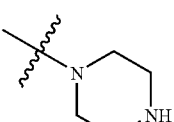 | 441.1906 |
| 4.462 | 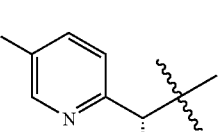 | 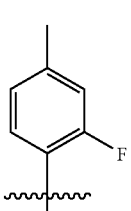 | 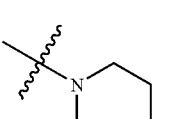 | 437.2155 |
| 4.463 | 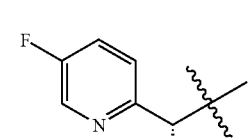 | 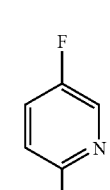 | 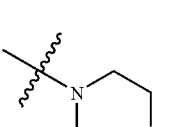 | 424.1943 |

TABLE 4-continued

| Example | R¹ | R² | R³ | MS (M + 1) |
|---|---|---|---|---|
| 4.464 | 3-methyl-1,2,4-oxadiazol-5-yl CH(CH₃) | 5-F-pyridin-2-yl | piperazin-1-yl | 411.1942 |
| 4.465 | 2-(trifluoromethyl)pyrimidin-5-yl CH(CH₃) | 5-F-pyridin-2-yl | piperazin-1-yl | 475.1862 |
| 4.466 | 3-methyl-1,2,4-oxadiazol-5-yl CH(CH₃) | 3-F-phenyl | morpholin-4-yl | 425.1984 |
| 4.467 | 1H-pyrazol-5-yl CH(CH₃) | 3-F-phenyl | morpholin-4-yl | 409.2038 |
| 4.468 | 2-(trifluoromethyl)pyrimidin-5-yl CH(CH₃) | 3-F-phenyl | morpholin-4-yl | 489.1911 |

TABLE 4-continued

| Example | R¹ | R² | R³ | MS (M + 1) |
|---|---|---|---|---|
| 4.469 | 3,5-difluoropyridin-2-yl (S)-CH(CH₃)- | 5-methylpyridin-2-yl | 4-acetylpiperazin-1-yl | 480.2200 |
| 4.470 | 3-methyl-1,2,4-oxadiazol-5-yl (S)-CH(CH₃)- | 5-methylpyridin-2-yl | morpholin-4-yl | 408.2029 |
| 4.471 | 4H-1,2,4-triazol-3-yl (S)-CH(CH₃)- | 3-fluoro-4-methylphenyl | 4-acetylpiperazin-1-yl | 451.2276 |
| 4.472 | 3-methyl-1,2,4-oxadiazol-5-yl (S)-CH(CH₃)- | 2,4-difluorophenyl | morpholin-4-yl | 429.1734 |
| 4.473 | 2-(trifluoromethyl)pyrimidin-5-yl (S)-CH(CH₃)- | 2,4-difluorophenyl | morpholin-4-yl | 493.1669 |

TABLE 4-continued

| Example | R¹ | R² | R³ | MS (M + 1) |
|---|---|---|---|---|
| 4.474 | 3-methyl-1,2,4-oxadiazol-5-yl CH(CH₃)- | 5-pyridyl | 2,2-dimethyl-4-acetylpiperazin-1-yl | 477.2620 |
| 4.475 | 4H-1,2,4-triazol-3-yl CH(CH₃)- | 2,4-difluorophenyl | morpholin-4-yl | 414.1748 |
| 4.476 | 3,5-difluoropyridin-2-yl CH(CH₃)- | 5-pyridyl | morpholin-4-yl | 439.1948 |
| 4.477 | 5-(trifluoromethyl)pyridin-2-yl CH(CH₃)- | 5-pyridyl | morpholin-4-yl | 471.2007 |
| 4.478 | 3-methyl-1,2,4-oxadiazol-5-yl CH(CH₃)- | 5-pyridyl | 2-(trifluoromethyl)morpholin-4-yl | 476.1917 |

TABLE 4-continued

| Example | R¹ | R² | R³ | MS (M + 1) |
|---|---|---|---|---|
| 4.479 | | | | 513.2284 |
| 4.480 | | | | 507.1820 |
| 4.481 | | | | 539.1876 |
| 4.482 | | | | 487.2123 |
| 4.483 | | | | 529.2207 |

TABLE 4-continued
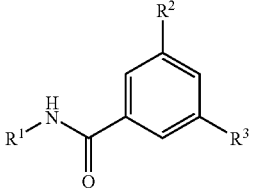
| Example | R¹ | R² | R³ | MS (M + 1) |
|---|---|---|---|---|
| 4.484 | 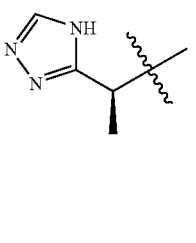 | 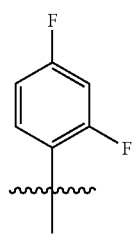 | 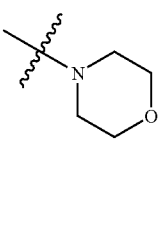 | 414.1740 |
| 4.485 | 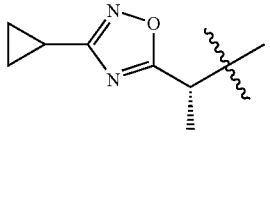 | 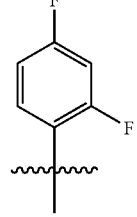 | 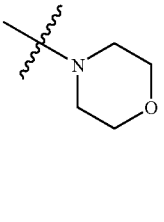 | 455.1886 |
| 4.486 | 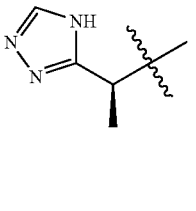 | 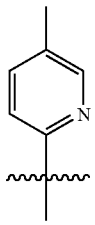 | 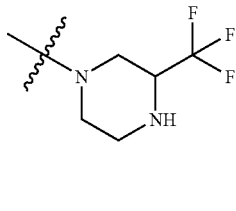 | 460.2072 |
| 4.487 | 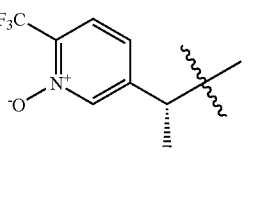 | 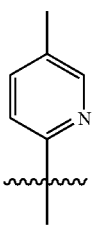 | 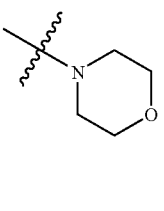 | 487.1950 |
| 4.488 | 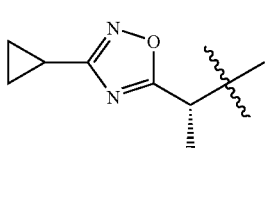 | 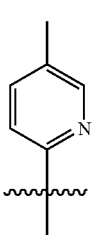 | 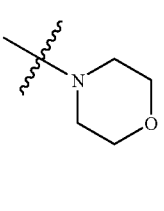 | 434.2186 |

TABLE 4-continued

| Example | R¹ | R² | R³ | MS (M + 1) |
|---|---|---|---|---|
| 4.489 | | | | 475.2063 |
| 4.490 | | | | 538.2045 |
| 4.491 | | | | 506.1981 |
| 4.492 | | | | 508.1656 |
| 4.493 | | | | 413.1492 |

TABLE 4-continued
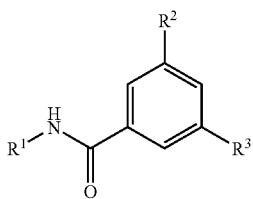
| Example | R¹ | R² | R³ | MS (M + 1) |
|---|---|---|---|---|
| 4.494 | 3-methyl-1,2,4-oxadiazol-5-yl CH(CH₃) | Cl (pyridin-5-yl, attached at 3-position) | morpholin-4-yl C(CH₃)₂ | 428.1492 |
| 4.495 | 2-(trifluoromethyl)pyridin-5-yl N-oxide CH(CH₃) | Cl (pyridin-5-yl) | morpholin-4-yl C(CH₃)₂ | 507.1417 |
| 4.496 | 4H-1,2,4-triazol-3-yl CH(CH₃) | methyl-pyridinyl | 2-(trifluoromethyl)morpholin-4-yl C(CH₃)₂ | 461.1920 |
| 4.497 | 1H-pyrazol-5-yl CH(CH₃) | methyl-pyridinyl | C(CH₃)₂OH | 365.1976 |
| 4.498 | 3-methyl-1,2,4-oxadiazol-5-yl CH(CH₃) | F (pyridinyl) | C(CH₃)₂OH | 385.1673 |

TABLE 4-continued

| Example | R¹ | R² | R³ | MS (M + 1) |
|---|---|---|---|---|
| 4.499 | 2-CF₃-pyrimidin-5-yl (CH(CH₃)) | 5-F-pyridin-2-yl | C(CH₃)₂OH | 449.1596 |
| 4.500 | 5-CF₃-pyridin-2-yl (CH(CH₃)) | 5-Me-pyridin-2-yl | C(CH₃)₂OH | 444.1889 |
| 4.501 | 2-CF₃-pyrimidin-5-yl (CH(CH₃)) | 5-Me-pyridin-2-yl | C(CH₃)₂OH | 431.1690 |
| 4.502 | 2-CF₃-pyrimidin-5-yl (CH(CH₃)) | 5-Me-pyridin-2-yl | C(CH₃)₂OMe | 459.2002 |
| 4.503 | 2-CF₃-pyrimidin-5-yl (CH(CH₃)) | 5-Me-pyridin-2-yl | C(CH₃)₂NH₂ | 444.2002 |

TABLE 4-continued

| Example | R¹ | R² | R³ | MS (M + 1) |
|---------|----|----|----|------------|
| 4.504 | | | | 416.1836 |
| 4.505 | | | | 380.2085 |
| 4.506 | | | | 479.1809 |
| 4.507 | | | | 415.1883 |
| 4.508 | | | | 365.2094 |

TABLE 4-continued
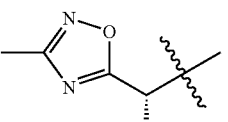
| Example | R¹ | R² | R³ | MS (M + 1) |
|---|---|---|---|---|
| 4.509 | 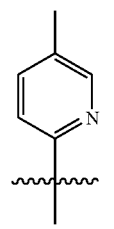 | 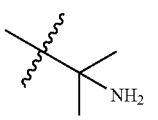 | 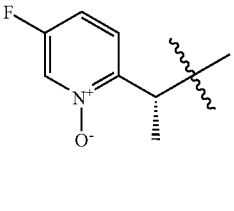 | 380.2083 |
| 4.510 | 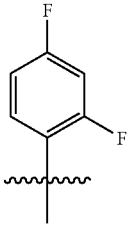 | 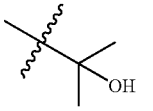 | 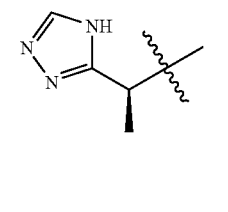 | 431.1563 |
| 4.511 | 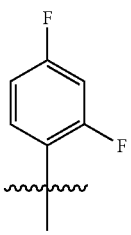 | 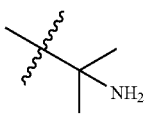 | 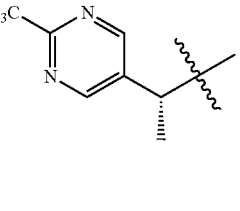 | 386.1789 |
| 4.512 | 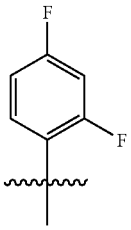 | 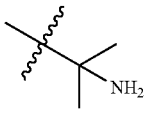 | 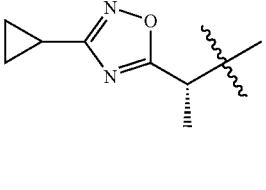 | 465.1713 |
| 4.513 | 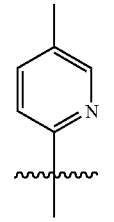 | 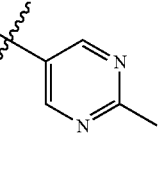 | | 441.2025 |

TABLE 4-continued

| Example | R¹ | R² | R³ | MS (M + 1) |
|---|---|---|---|---|
| 4.514 | 2-CF₃-pyridine 1-oxide, 5-yl with CH(CH₃) linker | 5-pyridyl (2-attached) | C(CH₃)₂OMe | 474.1991 |
| 4.515 | 5-methyl-1,2,4-oxadiazol-3-yl with CH(CH₃) linker | 5-pyridyl (2-attached) | C(CH₃)₂OMe | 395.2080 |
| 4.516 | 4H-1,2,4-triazol-3-yl with CH(CH₃) linker | 5-pyridyl (2-attached) | C(CH₃)₂OMe | 380.2073 |
| 4.517 | 5-fluoropyridine 1-oxide, 2-yl with CH(CH₃) linker | 5-pyridyl (2-attached) | C(CH₃)₂OMe | 424.2028 |
| 4.518 | 3-cyclopropyl-1,2,4-oxadiazol-5-yl with CH(CH₃) linker | 5-pyridyl (2-attached) | C(CH₃)₂OMe | 421.22392 |

TABLE 4-continued

| Example | R¹ | R² | R³ | MS (M + 1) |
|---|---|---|---|---|
| 4.519 | 3-cyclopropyl-1,2,4-oxadiazol-5-yl-CH(CH₃)- | 5-methylpyridin-2-yl | -C(CH₃)₂OH | 407.2079 |
| 4.520 | 3-cyclopropyl-1,2,4-oxadiazol-5-yl-CH(CH₃)- | 5-methylpyridin-2-yl | 2-aminopyrimidin-5-yl-C(CH₃)- | 442.1990 |
| 4.521 | 3-methyl-1,2,4-oxadiazol-5-yl-CH(CH₃)- | 2,4-difluorophenyl | -C(CH₃)₂OMe | 416.1803 |
| 4.522 | 5-(2,2,2-trifluoroethyl)-1,2,4-oxadiazol-3-yl-CH(CH₃)- | 5-methylpyridin-2-yl | -C(CH₃)₂OH | 449.1791 |
| 4.523 | 2-trifluoromethylpyridin-1-oxide-5-yl-CH(CH₃)- | 5-fluoropyridin-2-yl | -C(CH₃)₂OH | 464.1586 |

TABLE 4-continued

| Example | R¹ | R² | R³ | MS (M + 1) |
|---|---|---|---|---|
| 4.524 | 4H-1,2,4-triazol-3-yl-CH(CH₃)- | 5-fluoropyridin-2-yl | -C(CH₃)₂OH | 370.1674 |
| 4.525 | 5-methyl-1,2,4-oxadiazol-3-yl-CH(CH₃)- | 5-fluoropyridin-2-yl | -C(CH₃)₂OH | 385.1668 |
| 4.526 | 5-methyl-1,2,4-oxadiazol-3-yl-CH(CH₃)- | 2,4-difluorophenyl | -C(CH₃)₂OH | 402.1630 |
| 4.527 | 6-(trifluoromethyl)pyridin-3-yl 1-oxide-CH(CH₃)- | 4-methylphenyl | -C(CH₃)₂OH | 459.1888 |
| 4.528 | 4H-1,2,4-triazol-3-yl-CH(CH₃)- | 4-chlorophenyl | -C(CH₃)₂OH | 385.1431 |

TABLE 4-continued

| Example | R¹ | R² | R³ | MS (M + 1) |
|---|---|---|---|---|
| 4.529 | 2-(trifluoromethyl)pyridin-5-yl N-oxide, CH(CH₃) | 4-chlorophenyl | C(CH₃)₂OH | 479.1354 |
| 4.530 | 3-methyl-1,2,4-oxadiazol-5-yl, CH(CH₃) | 4-chlorophenyl | C(CH₃)₂OH | 400.1428 |
| 4.531 | 2-(trifluoromethyl)pyrimidin-5-yl, CH(CH₃) | 4-chlorophenyl | C(CH₃)₂OH | 464.1357 |
| 4.532 | 2-(trifluoromethyl)pyridin-5-yl N-oxide, CH(CH₃) | 5-methylpyridin-2-yl | 2-methylpyrimidin-5-yl | 494.1803 |
| 4.533 | 2-(trifluoromethyl)pyridin-5-yl N-oxide, CH(CH₃) | 5-methylpyridin-2-yl | isopropyl | 444.1897 |

TABLE 4-continued
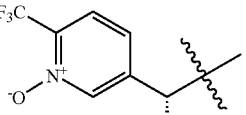
| Example | R¹ | R² | R³ | MS (M + 1) |
|---|---|---|---|---|
| 4.534 | 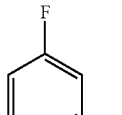 | 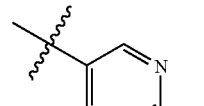 | 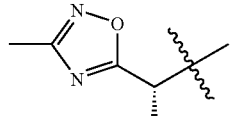 | 515.1521 |
| 4.535 | 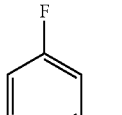 | 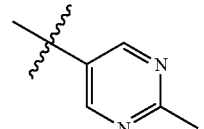 | 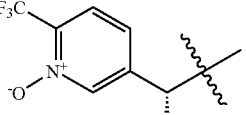 | 436.1601 |
| 4.536 | 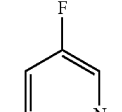 | 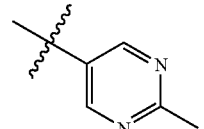 | 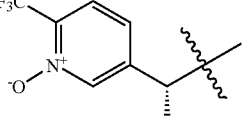 | 498.1559 |
| 4.537 | 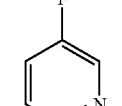 | 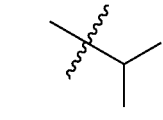 | 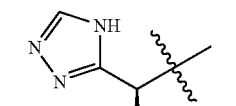 | 448.1655 |
| 4.538 | 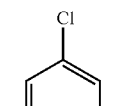 | 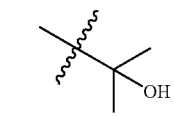 | | 386.1386 |

TABLE 4-continued

| Example | R¹ | R² | R³ | MS (M + 1) |
|---|---|---|---|---|
| 4.539 | F₃C-pyridine N-oxide, CH(CH₃)- | Cl, pyridine | C(CH₃)₂OH | 480.1302 |
| 4.540 | methyl-1,2,4-oxadiazole, CH(CH₃)- | Cl, pyridine | C(CH₃)₂OH | 401.1380 |
| 4.541 | F₃C-pyrimidine, CH(CH₃)- | Cl, pyridine | C(CH₃)₂OH | 465.1296 |
| 4.542 | methyl-pyrimidine, CH(CH₃)- | F, F phenyl | C(CH₃)₂OH | 412.1842 |
| 4.543 | methyl-pyrimidine, CH(CH₃)- | F, F phenyl | C(CH₃)₂OH | 412.1840 |

TABLE 4-continued

| Example | R¹ | R² | R³ | MS (M + 1) |
|---|---|---|---|---|
| 4.544 | | | | 425.2100 |
| 4.545 | | | | 367.1894 |
| 4.546 | | | | 417.1832 |
| 4.547 | | | | 468.1757 |
| 4.548 | | | | 389.1835 |

TABLE 4-continued

| Example | R¹ | R² | R³ | MS (M + 1) |
|---|---|---|---|---|
| 4.549 | pyrazinyl-CH(CH₃)- | 5-pyridyl | 1-methyl-1,2,3-triazol-5-yl | 400.1877 |
| 4.550 | 3-methyl-1,2,4-oxadiazol-5-yl-CH(CH₃)- | 5-pyridyl | 1-methyl-1,2,3-triazol-5-yl | 404.1833 |
| 4.551 | 5-fluoropyridin-2-yl-CH(CH₃)- | 2,4-difluorophenyl | 4-methyl-4H-1,2,4-triazol-3-yl | 438.1536 |
| 4.552 | 6-trifluoromethylpyridin-3-yl-CH(CH₃)- | 2,4-difluorophenyl | 4-methyl-4H-1,2,4-triazol-3-yl | 488.1493 |
| 4.553 | 4H-1,2,4-triazol-3-yl-CH(CH₃)- | 2,4-difluorophenyl | 4-methyl-4H-1,2,4-triazol-3-yl | 410.1534 |

TABLE 4-continued

| Example | R¹ | R² | R³ | MS (M + 1) |
|---|---|---|---|---|
| 4.554 | | | | 489.1462 |
| 4.555 | | | | 456.1440 |
| 4.556 | | | | 425.1533 |
| 4.557 | | | | 425.1533 |
| 4.558 | | | | 478.1833 |

TABLE 4-continued

| Example | R¹ | R² | R³ | MS (M + 1) |
|---|---|---|---|---|
| 4.559 | | F | | 450.1841 |
| 4.560 | | F | | 529.1760 |
| 4.561 | | F | | 465.1834 |
| 4.562 | | F | | 465.1834 |
| 4.563 | | F | | 454.1483 |

TABLE 4-continued

| Example | R¹ | R² | R³ | MS (M + 1) |
|---|---|---|---|---|
| 4.564 | 5-fluoro-2-pyridyl N-oxide with chiral methyl | 2,4-difluorophenyl | 4-methyl-5-cyclopropyl-4H-1,2,4-triazol-3-yl | 494.1789 |
| 4.565 | 5-fluoropyridin-2-yl with chiral methyl | 5-fluoropyridin-2-yl | 4-methyl-4H-1,2,4-triazol-3-yl | 421.1575 |
| 4.566 | 6-(trifluoromethyl)pyridin-3-yl with chiral methyl | 5-fluoropyridin-2-yl | 4-methyl-4H-1,2,4-triazol-3-yl | 471.1546 |
| 4.567 | 4H-1,2,4-triazol-3-yl with chiral methyl | 5-fluoropyridin-2-yl | 4-methyl-4H-1,2,4-triazol-3-yl | 393.1574 |
| 4.568 | 2-(trifluoromethyl)pyrimidin-5-yl with chiral methyl | 5-fluoropyridin-2-yl | 4-methyl-4H-1,2,4-triazol-3-yl | 472.1498 |

TABLE 4-continued

| Example | R¹ | R² | R³ | MS (M + 1) |
|---|---|---|---|---|
| 4.569 | | | | 439.1481 |
| 4.570 | | | | 408.1572 |
| 4.571 | | | | 408.1750 |
| 4.572 | | | | 461.1888 |
| 4.573 | | | | 433.1886 |

TABLE 4-continued

| Example | R¹ | R² | R³ | MS (M + 1) |
|---|---|---|---|---|
| 4.574 | 2-(trifluoromethyl)pyrimidin-5-yl (chiral methyl) | 5-fluoropyridin-2-yl | 4-methyl-5-cyclopropyl-4H-1,2,4-triazol-3-yl | 512.1804 |
| 4.575 | 3-methyl-1,2,4-oxadiazol-5-yl (chiral methyl) | 5-fluoropyridin-2-yl | 4-methyl-5-cyclopropyl-4H-1,2,4-triazol-3-yl | 488.1886 |
| 4.576 | 5-methyl-1,2,4-oxadiazol-3-yl (chiral methyl) | 5-fluoropyridin-2-yl | 4-methyl-5-cyclopropyl-4H-1,2,4-triazol-3-yl | 488.1885 |
| 4.577 | 5-fluoropyridin-2-yl N-oxide (chiral methyl) | 5-fluoropyridin-2-yl | 4-methyl-5-cyclopropyl-4H-1,2,4-triazol-3-yl | 477.1836 |
| 4.578 | 2-(trifluoromethyl)pyridin-5-yl N-oxide (chiral methyl) | 5-fluoropyridin-2-yl | 4-methyl-5-cyclopropyl-4H-1,2,4-triazol-3-yl | 527.1802 |

TABLE 4-continued

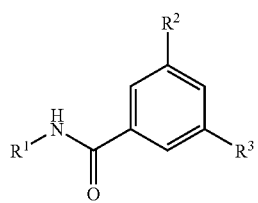

| Example | R¹ | R² | R³ | MS (M + 1) |
|---|---|---|---|---|
| 4.579 | F₃C-pyridin-3-yl-CH(CH₃)- | 5-methyl-pyridin-2-yl | 4-methyl-5-(2,2,2-trifluoroethyl)-4H-1,2,4-triazol-3-yl | 549.1819 |
| 4.580 | 5-fluoro-pyridin-2-yl N-oxide-CH(CH₃)- | 5-methyl-pyridin-2-yl | 1-methyl-1H-1,2,3-triazol-5-yl | 433.1781 |
| 4.581 | 6-(trifluoromethyl)pyridin-3-yl N-oxide-CH(CH₃)- | 5-methyl-pyridin-2-yl | 1-methyl-1H-1,2,3-triazol-5-yl | 483.1753 |
| 4.582 | 6-(trifluoromethyl)pyridin-3-yl N-oxide-CH(CH₃)- | 2,4-difluorophenyl | 4-methyl-4H-1,2,4-triazol-3-yl | 504.1461 |
| 4.583 | 6-(trifluoromethyl)pyridin-3-yl N-oxide-CH(CH₃)- | 2,4-difluorophenyl | 5-cyclopropyl-4-methyl-4H-1,2,4-triazol-3-yl | 544.1760 |

TABLE 4-continued
| Example | R¹ | R² | R³ | MS (M + 1) |
|---|---|---|---|---|
| 4.584 | 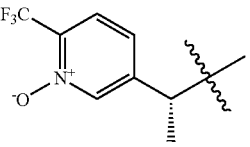 | 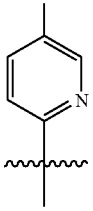 | 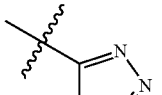 | 487.1501 |
| 4.585 | 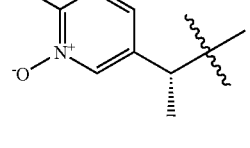 | 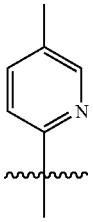 | 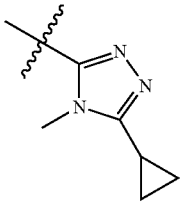 | 523.2064 |
| 4.586 | 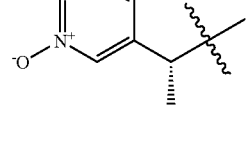 | 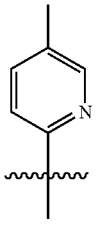 | 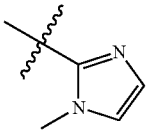 | 482.1797 |
| 4.587 | 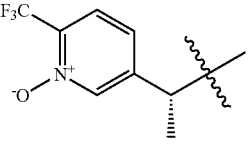 | 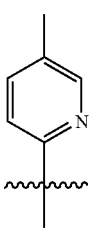 | 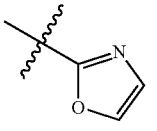 | 469.1482 |
| 4.588 | 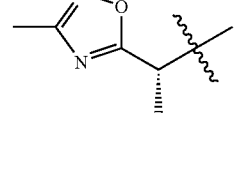 | 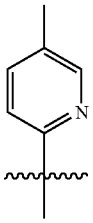 | 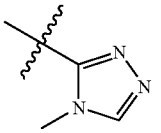 | 404.1826 |

TABLE 4-continued

| Example | R¹ | R² | R³ | MS (M + 1) |
|---|---|---|---|---|
| 4.589 | 5-fluoropyridin-2-yl with CH(CH₃) linker | 5-pyridyl (attached at 2-position) | 4-methyl-5-(2,2,2-trifluoroethyl)-4H-1,2,4-triazol-3-yl with C(CH₃) linker | 499.1858 |
| 4.590 | 4H-1,2,4-triazol-3-yl with CH(CH₃) linker | 5-pyridyl (attached at 2-position) | 4-methyl-5-(2,2,2-trifluoroethyl)-4H-1,2,4-triazol-3-yl with C(CH₃) linker | 471.1874 |
| 4.591 | 2-(trifluoromethyl)pyrimidin-5-yl with CH(CH₃) linker | 5-pyridyl (attached at 2-position) | 4-methyl-5-(2,2,2-trifluoroethyl)-4H-1,2,4-triazol-3-yl with C(CH₃) linker | 550.1776 |
| 4.592 | 3,5-difluoropyridin-2-yl with CH(CH₃) linker | 5-pyridyl (attached at 2-position) | 4-methyl-5-(2,2,2-trifluoroethyl)-4H-1,2,4-triazol-3-yl with C(CH₃) linker | 517.1761 |
| 4.593 | 3-methyl-1,2,4-oxadiazol-5-yl with CH(CH₃) linker | 5-pyridyl (attached at 2-position) | 4-methyl-5-(2,2,2-trifluoroethyl)-4H-1,2,4-triazol-3-yl with C(CH₃) linker | 486.1852 |

TABLE 4-continued

| Example | R¹ | R² | R³ | MS (M + 1) |
|---|---|---|---|---|
| 4.594 | | | | 486.1851 |
| 4.595 | | | | 549.1828 |
| 4.596 | | | | 515.1801 |
| 4.597 | | | | 550.1789 |
| 4.598 | | | | 565.1803 |

TABLE 4-continued

| Example | R¹ | R² | R³ | MS (M + 1) |
|---|---|---|---|---|
| 4.599 | | | | 404.1836 |
| 4.600 | | | | 470.2295 |
| 4.601 | | | | 488.2403 |
| 4.602 | | | | 474.2237 |
| 4.603 | | | | 537.2026 |

TABLE 4-continued
| Example | R¹ | R² | R³ | MS (M + 1) |
|---|---|---|---|---|
| 4.604 | 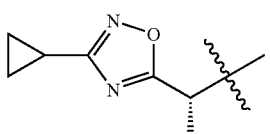 | 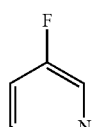 | 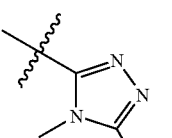 | 474.2047 |
| 4.605 | 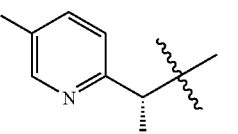 | 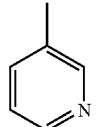 | 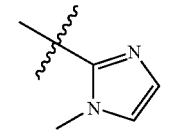 | 416.1886 |
| 4.606 | 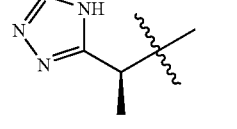 | 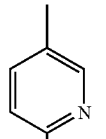 | 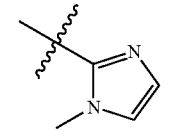 | 388.1883 |
| 4.607 | 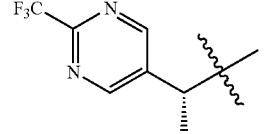 | 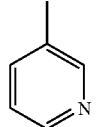 | 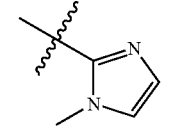 | 467.1809 |
| 4.608 | 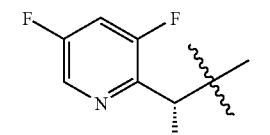 | 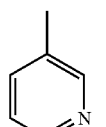 | 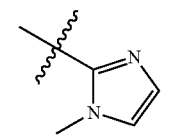 | 434.1787 |

TABLE 4-continued

| Example | R¹ | R² | R³ | MS (M + 1) |
|---|---|---|---|---|
| 4.609 | | | | 403.1876 |
| 4.610 | | | | 403.1875 |
| 4.611 | | | | 466.1852 |
| 4.612 | | | | 387.1928 |
| 4.613 | | | | 432.1836 |

TABLE 4-continued

| Example | R¹ | R² | R³ | MS (M + 1) |
|---|---|---|---|---|
| 4.614 | (S)-1-(oxazol-2-yl)ethyl | 5-pyridyl | 1-methylimidazol-2-yl | 388.1770 |
| 4.615 | (S)-1-(3-cyclopropyl-1,2,4-oxadiazol-5-yl)ethyl | 2,4-difluorophenyl | 4-methyl-5-cyclopropyl-1,2,4-triazol-3-yl | 491.1985 |
| 4.616 | (R)-1-(3-methyl-1,2,4-oxadiazol-5-yl)ethyl | 5-pyridyl | 3-fluoropyridin-2-yl | 418.1664 |
| 4.617 | 2-(3-methyl-1,2,4-oxadiazol-5-yl)-1-hydroxymethyl-ethyl | 5-pyridyl | 3-fluoropyridin-2-yl | 434.1624 |
| 4.618 | 2-(3-methyl-1,3,4-oxadiazol-5-yl)ethyl | 5-pyridyl | 3-fluoropyridin-2-yl | 418.1671 |

TABLE 4-continued

| Example | R¹ | R² | R³ | MS (M + 1) |
|---|---|---|---|---|
| 4.619 | | | | 430.1669 |
| 4.620 | | | | 444.1826 |
| 4.621 | | | | 486.1540 |
| 4.622 | | | | 432.1821 |
| 4.623 | | | | 448.1769 |

TABLE 4-continued

| Example | R¹ | R² | R³ | MS (M + 1) |
|---|---|---|---|---|
| 4.624 | 3-methyl-1,2,4-oxadiazol-5-yl isopropyl | 5-pyridyl | 3-fluoro-2-pyridyl | 418.1672 |
| 4.625 | 3-cyclopropyl-1,2,4-oxadiazol-5-yl (S)-ethyl | 5-pyridyl | 4-methyl-5-(2,2,2-trifluoroethyl)-4H-1,2,4-triazol-3-yl | 512.2027 |
| 4.626 | 5-(2,2,2-trifluoroethyl)-1,2,4-oxadiazol-3-yl (S)-ethyl | 5-pyridyl | 3-fluoro-2-pyridyl | 486.1560 |
| 4.627 | 5-(2,2,2-trifluoroethyl)-1,2,4-oxadiazol-3-yl (S)-ethyl | 5-pyridyl | 5-cyclopropyl-4-methyl-4H-1,2,4-triazol-3-yl | 512.2031 |
| 4.628 | 5-(2,2,2-trifluoroethyl)-1,2,4-oxadiazol-3-yl (S)-ethyl | 2,4-difluorophenyl | 5-cyclopropyl-4-methyl-4H-1,2,4-triazol-3-yl | 533.1733 |

TABLE 4-continued

| Example | R¹ | R² | R³ | MS (M + 1) |
|---|---|---|---|---|
| 4.629 | F₃C-CH₂-[oxadiazole]-CH(CH₃)- | 5-F-pyridin-2-yl | 4-methyl-5-cyclopropyl-1,2,4-triazol-3-yl | 516.1780 |
| 4.630 | F₃C-CH₂-[oxadiazole]-CH(CH₃)- | 5-methyl-pyridin-2-yl | 4-methyl-5-(CH₂CF₃)-1,2,4-triazol-3-yl | 554.1747 |
| 4.631 | F₃C-pyrimidin-5-yl-CH(CH₃)- | 2,4-difluorophenyl | 4,5-dimethyl-1,2,4-triazol-3-yl | 503.1604 |
| 4.632 | 4H-1,2,4-triazol-3-yl-CH(CH₃)- | 2,4-difluorophenyl | 1-methyl-1,2,3-triazol-5-yl | 410.1542 |
| 4.633 | F₃C-pyrimidin-5-yl-CH(CH₃)- | 2,4-difluorophenyl | 1-methyl-1,2,3-triazol-5-yl | 489.1464 |

TABLE 4-continued

| Example | R¹ | R² | R³ | MS (M + 1) |
|---|---|---|---|---|
| 4.634 | 3-methyl-1,2,4-oxadiazol-5-yl isopropyl | 2,4-difluorophenyl | 1-methyl-1,2,3-triazol-5-yl | 425.1537 |
| 4.635 | 5-methyl-1,2,4-oxadiazol-3-yl isopropyl | 2,4-difluorophenyl | 1-methyl-1,2,3-triazol-5-yl | 425.1538 |
| 4.636 | 5-fluoropyridin-2-yl N-oxide isopropyl | 2,4-difluorophenyl | 1-methyl-1,2,3-triazol-5-yl | 454.1493 |
| 4.637 | 6-trifluoromethylpyridin-3-yl N-oxide isopropyl | 2,4-difluorophenyl | 1-methyl-1,2,3-triazol-5-yl | 504.1466 |
| 4.638 | 1H-1,2,4-triazol-5-yl isopropyl | 4-methylphenyl | 1-methyl-1,2,3-triazol-5-yl | 388.1890 |

TABLE 4-continued
| Example | R¹ | R² | R³ | MS (M + 1) |
|---|---|---|---|---|
| 4.639 | 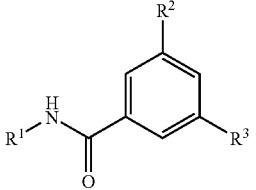 | 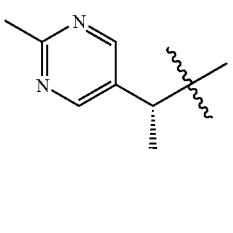 | 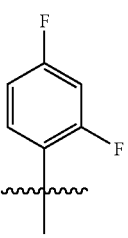 | 475.2052 |
| 4.640 | 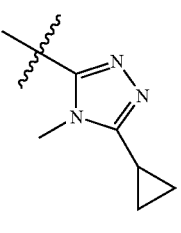 | 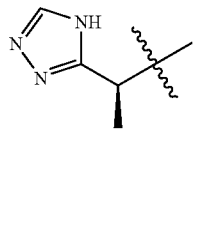 | 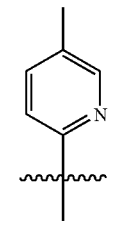 | 390.1535 |
| 4.641 | 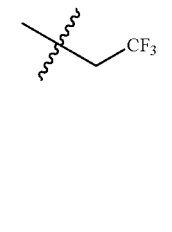 | 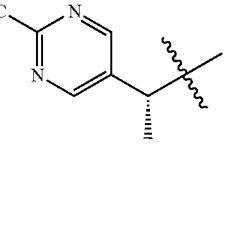 | 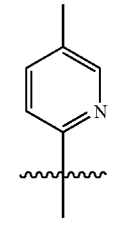 | 469.1456 |
| 4.642 | 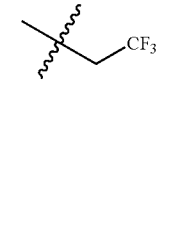 | 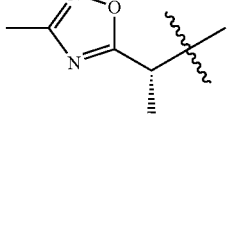 | 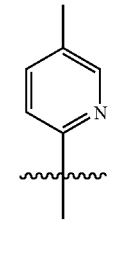 | 405.1531 |
| 4.643 | 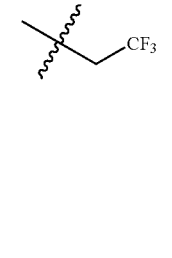 | 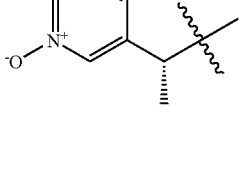 | 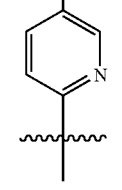 | 484.1452 |

TABLE 5

| EX | Structure | MS M + H | Stereochemistry |
|---|---|---|---|
| 5.1 | 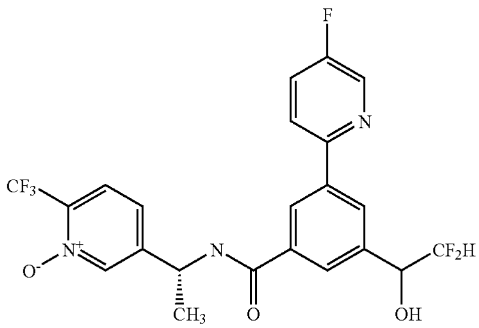 | 485.9 | R, R/S |
| 5.2 | 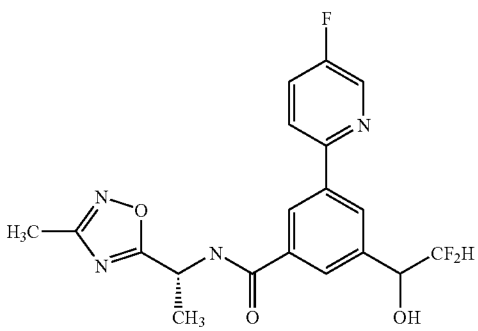 | 407.0 | R, R/S |
| 5.3 | 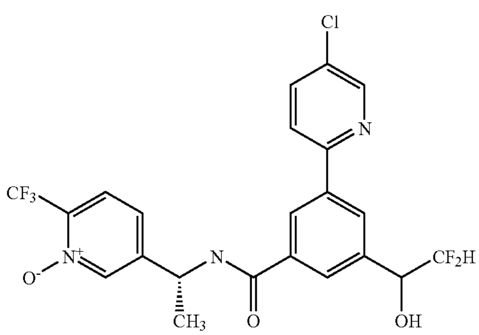 | 502.0 | R, R/S |
| 5.4 | 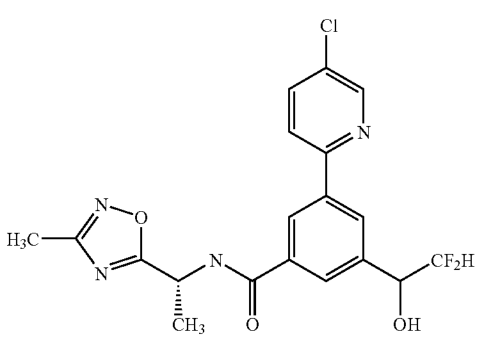 | 423.0 | R, R/S |

TABLE 5-continued

| EX | Structure | MS M + H | Stereochemistry |
|---|---|---|---|
| 5.5 | 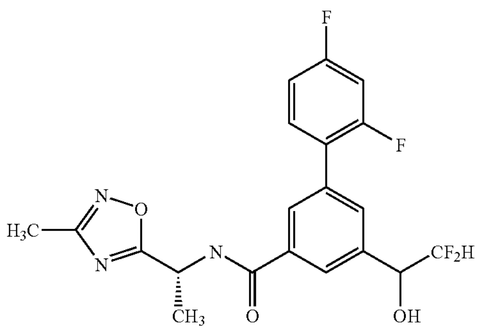 | 424.0 | R, R/S |
| 5.6 | 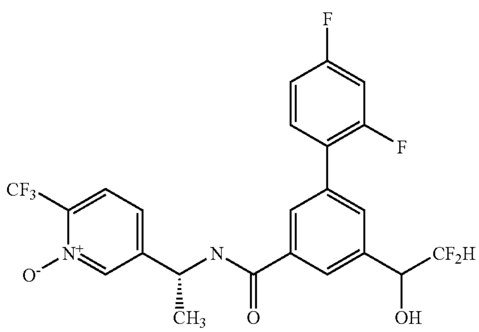 | 503.0 | R, R/S |
| 5.7 | 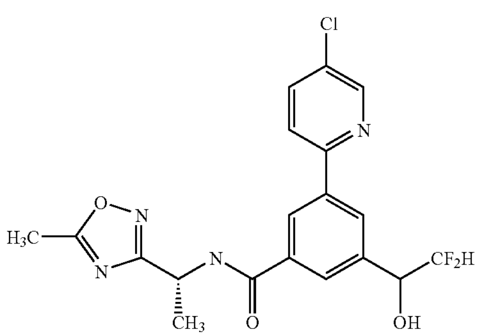 | 423.1 | R, R/S |
| 5.8 | 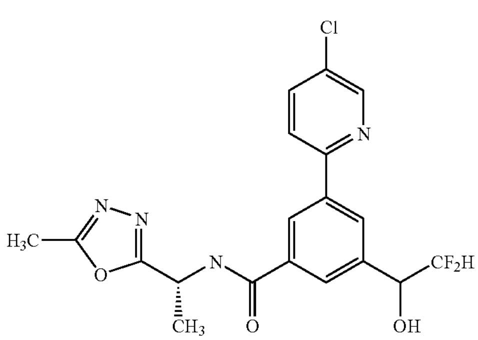 | 423.0 | R, R/S |

TABLE 5-continued

| EX | Structure | MS M + H | Stereochemistry |
|---|---|---|---|
| 5.9 | 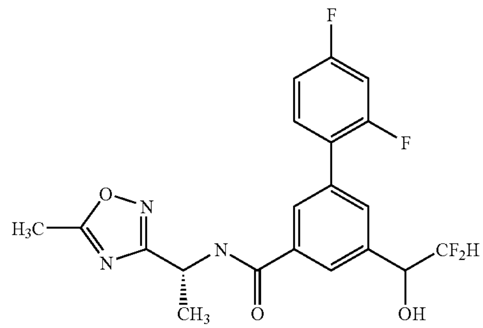 | 424.1 | R, R/S |
| 5.10 | 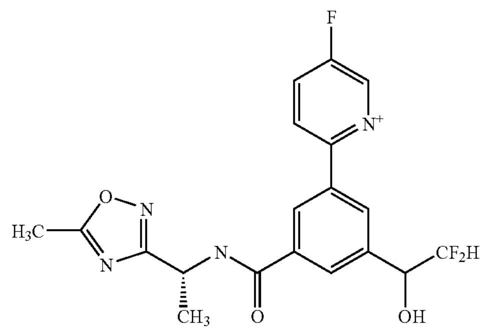 | 407.1 | R, R/S |

TABLE 6

| EX | Structure | MS M + H | Stereochemistry |
|---|---|---|---|
| 6.1 | 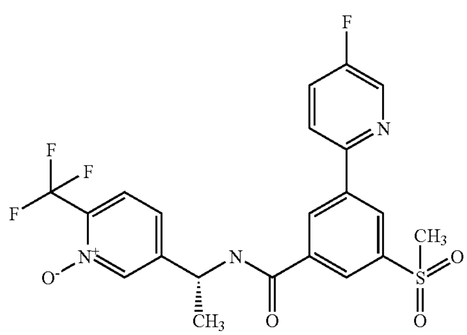 | 484.3 | R |
| 6.2 | 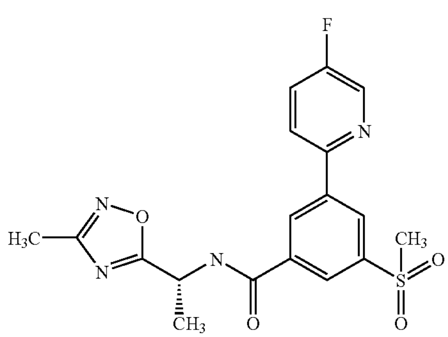 | 405.3 | R |

TABLE 6-continued

| EX | Structure | MS M + H | Stereochemistry |
|---|---|---|---|
| 6.3 | 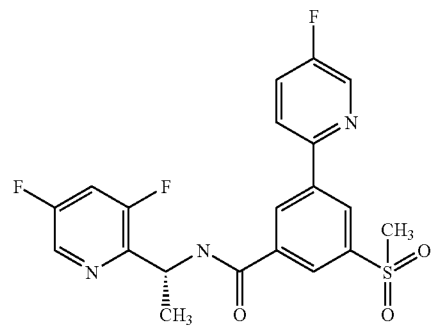 | 436.3 | R |
| 6.4 | 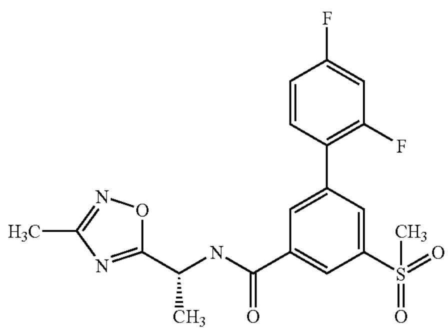 | 422.3 | R |
| 6.5 | 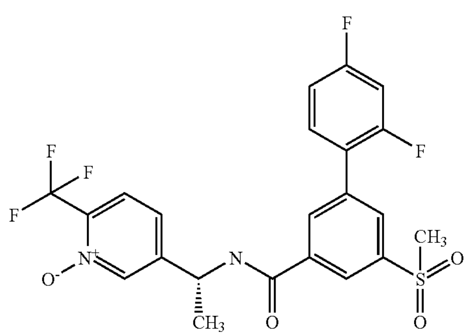 | 501.3 | R |
| 6.6 | 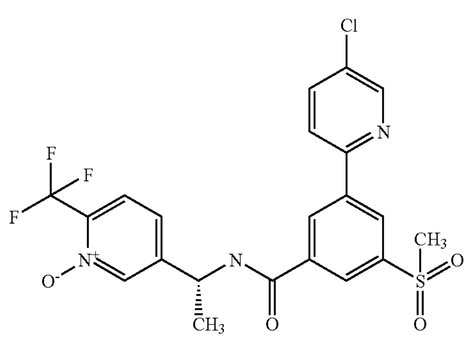 | 500.3 | R |

TABLE 6-continued
| EX | Structure | MS M + H | Stereochemistry |
|---|---|---|---|
| 6.7 | 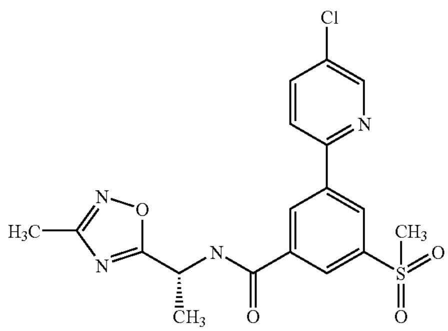 | 421.3 | R |
| 6.8 | 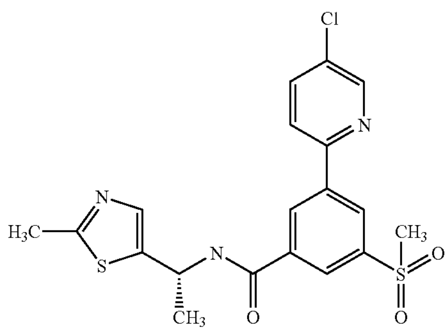 | 436.3 | R |
| 6.9 | 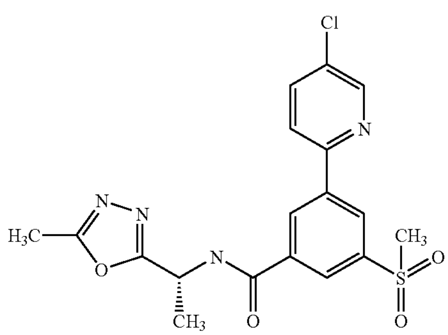 | 421.3 | R |
TABLE 7
| EX | Structure | MS M + H | Stereochemistry |
|---|---|---|---|
| 7.1 | 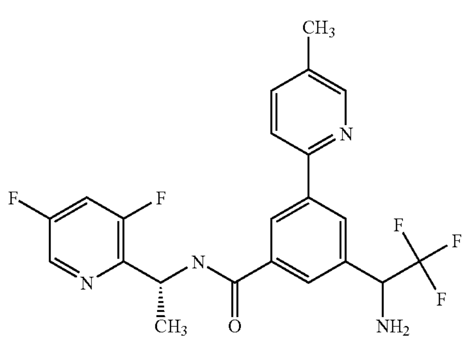 | 451.3 | R, R/S |
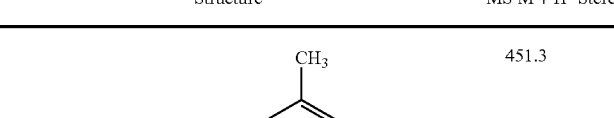

TABLE 7-continued

| EX | Structure | MS M + H | Stereochemistry |
|---|---|---|---|
| 7.2 | 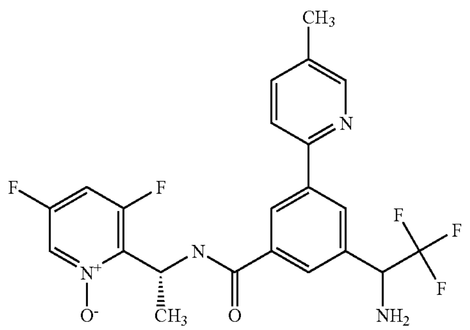 | 467.3 | R,R/S |
| 7.3 | 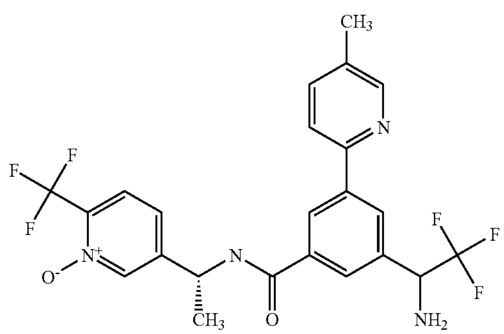 | 499.3 | R, R/S |
| 7.4 | 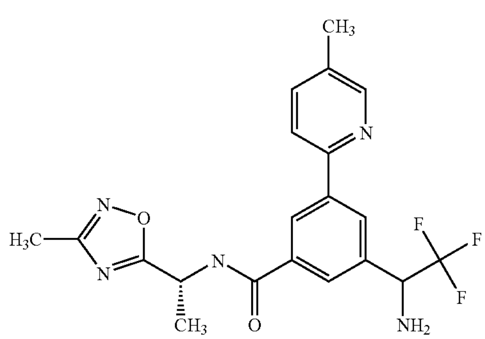 | 420.3 | R, R/S |
| 7.5 | 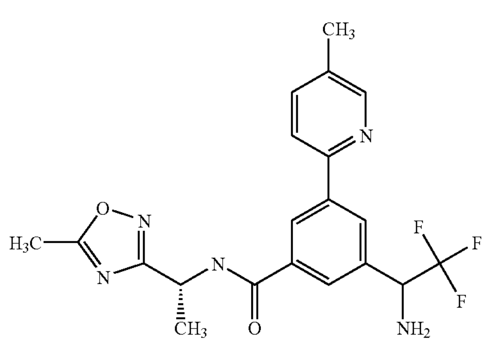 | 420.3 | R, R/S |

TABLE 7-continued

| EX | Structure | MS M + H | Stereochemistry |
|---|---|---|---|
| 7.6 | 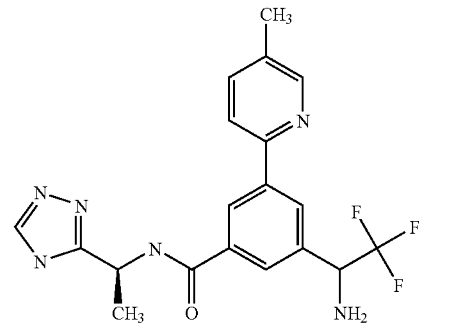 | 405.3 | S, R/S |
| 7.7 | 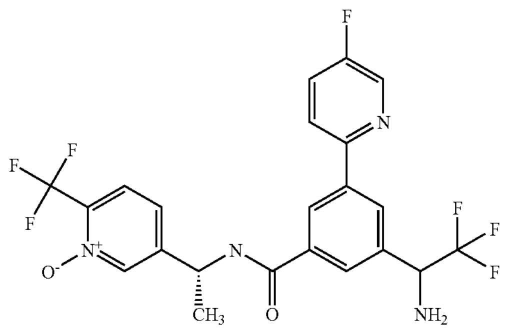 | 503.0 | R, R/S |
| 7.8 | 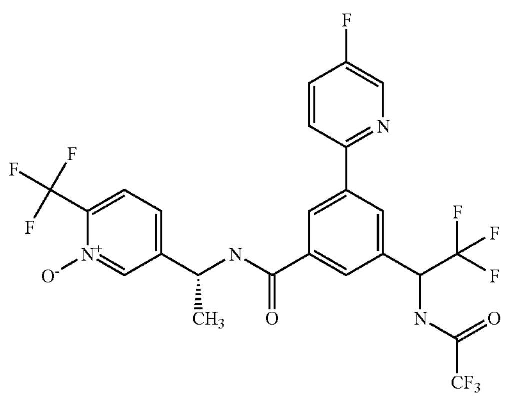 | 599.2 | R, R/S |

Particular examples of the compounds of formula I are:
N-[(1R)-1-(5-Fluoropyridin-2-yl)ethyl]-3-(5-methylpyridin-2-yl)-5-[(R/S)-2,2,2-trifluoro-1-hydroxyethyl]benzamide;
4'-Methyl-N-(2,2,2-trifluoroethyl)-5-(2,2,2-trifluoro-1-hydroxyethyl)biphenyl-3-carboxamide;
3-(5-Fluoropyridin-2-yl)-N-{(1R)-1-[1-oxido-6-(trifluoromethyl)pyridin-3-yl]ethyl}-5-[(R/S)-2,2,2-trifluoro-1-hydroxyethyl]benzamide;
4'-Methyl-N-{(1R)-1-[1-oxido-6-(trifluoromethyl)pyridyn-3-yl]ethyl}-5-[2,2,2-trifluoro-1-hydroxy-1-(trifluoromethyl)ethyl]biphenyl-3-carboxamide;
N-[(1R)-1-(4-Fluorophenyl)ethyl]-3-(5-methylpyridin-2-yl)-5-[2,2,2-trifluoro-1-hydroxy-1-(trifluoromethyl)ethyl]benzamide;
2'-Fluoro-5-[hydroxy(phenyl)methyl]-N-isopropyl-4'-methylbiphenyl-3-carboxamide;
3-(5-Cyclopropyl-4-methyl-4H-1,2,4-triazol-3-yl)-N-[(1R)-1-(5-fluoropyridin-2-yl)ethyl]-5-(5-methylpyridin-2-yl)benzamide;
3-(5-Cyclopropyl-4-methyl-4H-1,2,4-triazol-3-yl)-N-[(1R)-1-(3,5-difluoropyridin-2-yl)ethyl]-5-(5-methylpyridin-2-yl)benzamide;
3-(5-Methylpyridin-2-yl)-5-(4-methyl-4H-1,2,4-triazol-3-yl)-N-{(1R)-1-[5-(trifluoromethyl)pyridin-2-yl]ethyl}benzamide;
N-[(1R)-1-(3,5-Difluoropyridin-2-yl)ethyl]-3-(5-methylpyridin-2-yl)-5-(1-methyl-1H-1,2,3-triazol-5-yl)benzamide;
2',4'-Difluoro-5-piperazin-1-yl-N-{(1R)-1-[2-(trifluoromethyl)pyrimidin-5-yl]ethyl}biphenyl-3-carboxamide;
2'-Fluoro-4'-methyl-5-morpholin-4-yl-N-[(1R)-1-(1H-1,2,4-triazol-3-yl)ethyl]biphenyl-3-carboxamide;
3-(3-Fluoropyridin-2-yl)-N-[(1R)-1-(5-fluoropyridin-2-yl)ethyl]-5-(5-methylpyridin-2-yl)benzamide;
3-(3-Fluoropyridin-2-yl)-N-[(1R)-1-(5-methyl-1,2,4-oxadiazol-3-yl)ethyl]-5-(5-methylpyridin-2-yl)benzamide;
N-[(1R)-1-(3-Methyl-1,2,4-oxadiazol-5-yl)ethyl]-3-(5-methylpyridin-2-yl)-5-(2-methylpyrimidin-5-yl)benzamide;
3-Isopropyl-5-(5-methylpyridin-2-yl)-N-[(1S)-1-(4H-1,2,4-triazole-3-yl)ethyl]benzamide;

3-(1-Hydroxy-1-methylethyl)-5-(5-methylpyridin-2-yl)-N-{(1R)-1-[2-(trifluoromethyl)pyrimidin-5-yl]ethyl}benzamide;

2',4'-Difluoro-5-(1-hydroxy-1-methylethyl)-N-[(1R)-1-(3-methyl-1,2,4-oxadiazol-5-yl)ethyl]biphenyl-3-carboxamide;

or pharmaceutically acceptable salts and individual enantiomers and diastereomers thereof.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

When $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyla are $C_2$-$C_6$ alkynyl. "Alkenyl," "alkynyl" and other like terms include carbon chains containing at least one unsaturated C—C bond.

As used herein, "fluoroalkyl" refers to an alkyl substituent as described herein containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. As used herein, the term "heteroaryl" refers to groups having 5 to 14 ring atoms, preferably 5, 6, 9, or ring atoms; having 6, 10, or 14 π electrons shared in a cyclic array; and having, in addition to carbon atoms, between one and about three heteroatoms selected from the group consisting of N, 0, and S. heteroaryl groups include, without limitation, thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-fluor-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, arylalkylsulfonyl, arylsulfonyl, $C_0$-$C_6$N-alkylcarbamoyl, $C_2$-$C_{15}$N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" refers to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The phrases "effective amount" or "therapeutically effective amount" mean a concentration of P2X receptor complex modulator sufficient to inhibit or enhance the effect of the P2X receptor complex.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, tissue injury pain, and the like (Dorland's Illustrated Medical Dictionary, 28th Edition, W. B. Saunders Company, Philadelphia, Pa.). The goal of treatment of pain is to reduce the degree or severity of pain perceived by a treatment subject.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise compounds of the invention (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x)tricyclic antidepressant drugs, xi) norepinephrine modulators, xii) lithium, xiii) valproate, xiv) neurontin (gabapentin), xv) pregabalin, and xvi) sodium channel blockers. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present compounds and compositions are useful for the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, small fiber neuropathy, and diabetic neuropathy. The present compounds and compositions are also useful for the treatment of chronic lower back pain, phantom limb pain, chronic pelvic pain, neuroma pain, complex regional pain syndrome, chronic arthritic pain and related neuralgias, and pain associated with cancer, chemotherapy, HIV and HIV treatment-induced neuropathy. Compounds of this invention may also be utilized as local anesthetics. Compounds of this invention are useful for the treatment of irritable bowel syndrome and related disorders, as well as Crohn's disease.

The instant compounds have clinical uses for the treatment of epilepsy and partial and generalized tonic seizures. They are also useful for neuroprotection under ischaemic conditions caused by stroke or neural trauma and for treating multiple sclerosis. The present compounds are useful for the treatment of tachy-arrhythmias. Additionally, the instant compounds are useful for the treatment of neuropsychiatric disorders, including mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders. Thus, another aspect of this invention is the use of the compounds of formula I in the manufacture of a medicament to treat pain and other diseases associated with pain.

In addition to primates, such as humans, a variety of other mammals can be treated according to the method of the present invention. For instance, mammals including, but not limited to, cows, sheep, goats, horses, dogs, cats guinea pigs, or other bovine, ovine, equine, canine, feline, rodent such as mouse, species can be treated. However, the method can also be practiced in other species, such as avian species (e.g., chickens).

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5\text{-}HT_{1A}$ agonists or antagonists, especially $5\text{-}HT_{1A}$ partial agonists, neurokinin-1 receptor antagonists, corticotropin releasing factor (CRF) antagonists, and pharmaceutically acceptable salts thereof.

Further, it is understood that compounds of this invention can be administered at prophylactically effective dosage levels to prevent the above-recited conditions and disorders, as well as to prevent other conditions and disorders associated with calcium channel activity.

Creams, ointments, jellies, solutions, or suspensions containing the instant compounds can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to about 75 mg of the compound per kilogram of body weight per day, or alternatively about 0.5 mg to about 3.5 g per patient per day. Neuropathic pain may be effectively treated by the administration of from about 0.01 mg to about 125 mg of the compound per kilogram of body weight per day, or alternatively about 0.5 mg to about 5.5 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may ary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors. Such patient-related factors include the age, body weight, general health, sex, and diet of the patient. Other factors include the time and route of administration, rate of excretion, drug combination, and the severity of the particular disease undergoing therapy.

In practice, the compounds of the invention, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt. The compounds of the invention, or pharmaceutically acceptable salts thereof, can also be included in pharmaceutical compositions in combination with one or more therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. As described previously, in preparing the compositions for oral dosage form, any of the usual pharmaceutical media can be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which solid pharmaceutical carriers are employed. If desired, tablets may be coated by standard aqueous or nonaqueous techniques. In addition to the common dosage forms set out above, controlled release means and/or delivery devices may also be used in administering the instant compounds and compositions.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, and disintegrating agents can be used to form oral solid preparations such as powders, capsules and tablets. Because of their ease of administration, tablets and capsules are advantageous oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet advantageously contains from about 0.1 mg to about 500 mg of the active ingredient and each cachet or capsule advantageously containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

Further, as described above, the instant compounds can be utilized in combination with one or more therapeutically active compounds. In particular, the inventive compounds can be advantageously used in combination with i) opiate agonists or antagonists, ii) other calcium channel antagonists, iii) 5HT receptor agonists or antagonists, including 5-$HT_{1A}$ agonists or antagonists, and 5-$HT_{1A}$ partial agonists, iv) sodium channel antagonists, v) N-methyl-D-aspartate (NMDA) receptor agonists or antagonists, vi) COX-2 selective inhibitors, vii) neurokinin receptor 1 (NK1) antagonists, viii) non-steroidal anti-inflammatory drugs (NSAID), ix) selective serotonin reuptake inhibitors (SSRI) and/or selective serotonin and norepinephrine reuptake inhibitors (SSNRI), x)tricyclic antidepressant drugs, xi) norepinephrine modulators, xii) lithium, xiii) valproate, xiv) norepinephrine reuptake inhibitors, xv) monoamine oxidase inhibitors (MAOIs), xvi) reversible inhibitors of monoamine oxidase (RIMAs), xvii) alpha-adrenoreceptor antagonists, xviii) atypical anti-depressants, xix) benzodiazepines, xx) corticotropin releasing factor (CRF) antagonists, xxi) neurontin (gabapentin) and xxii) pregabalin.

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosonium hexafluorophosphate, CAMP (cyclic adenosine-3',5'-monophosphate), DAST ((diethylamino)sulfur trifluoride), DBU (1,8-diazabicyclo[5.4.0]undec-7-ene), DIBAL (diisobutylaluminum hydride), DIEA (diisopropylethyl amine), DMAP (4-(dimethylamino)pyridine), DMF (N,N-dimethylformamide), DPPF (1,1'-bisdiphenylphosphino ferrocene), EDC (1-(3-dimethylaminopropyl)-3-ethylcarbodiimide hydrochloride), Et$_3$N (triethylamine), GST (glutathione transferase), HOBt (1-hydroxybenzotriazole), LAH (lithium aluminum hydride), Ms (methanesulfonyl; mesyl; or SO$_2$Me), MsO (methanesulfonate or mesylate), MCPBA (meta-chloro perbenzoic acid), NaHMDS (sodium hexamethyldisilazane), NBS (N-bromosuccinimide), NCS(N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or SO$_2$NH$_2$), SPA (scintillation proximity assay), Th (2- or 3-thienyl), TFA (trifluoroacetic acid), THF (Tetrahydrofuran), Thi (Thiophenediyl), TLC (thin layer chromatography), TMEDA (N,N,N',N'-tetramethylethylenediamine), TMSI (trimethylsilyl iodide), Tr or trityl (N-triphenylmethyl), C$_3$H$_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the procedures provided in the Examples. The following Examples further describe, but do not limit, the scope of the invention.

Unless specifically stated otherwise, the experimental procedures were performed under the following conditions: All operations were carried out at room or ambient temperature; that is, at a temperature in the range of 18-25° C. Inert gas protection was used when reagents or intermediates were air and moisture sensitive. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter (s)), mL (milliliters), g (gram(s)), mg (milligrams(s)), mol (moles), mmol (millimoles), eq (equivalent(s)).

The procedures described herein for synthesizing the compounds may include one or more steps of protecting group manipulations and of purification, such as, re-crystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultra-violet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyllithium, phenyllithium, alkyl magnaesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the examples below can be further manipulated, when appropriate, using the standard functional group transformation techniques available to those skilled in the art, to provide desired compounds described in this invention.

It is also understood that compounds of this invention contain one or more stereocenters that may be prepared as single enantiomers or diastereomers, or as mixtures containing two or more enantiomers or diastereomers in any proportion.

Other variations or modifications, which will be obvious to those skilled in the art, are within the scope and teachings of this invention. This invention is not to be limited except as set forth in the following claims.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Reaction Schemes

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Amine intermediates of type 1.4 can be prepared from one of several intermediates as shown in Scheme 1. This method utilizes diastereoselective Ellman sulfinimine addition chemistry to generate a pair of diastereomeric sulfinamides. The diastereomers are separated by silica chromatography prior to HCl deprotection to give 1.4. Depending on the substrate either the R or S Ellman reagent is utilized to favor the desired alpha methyl amino compound with the preferred stereo configuration shown.

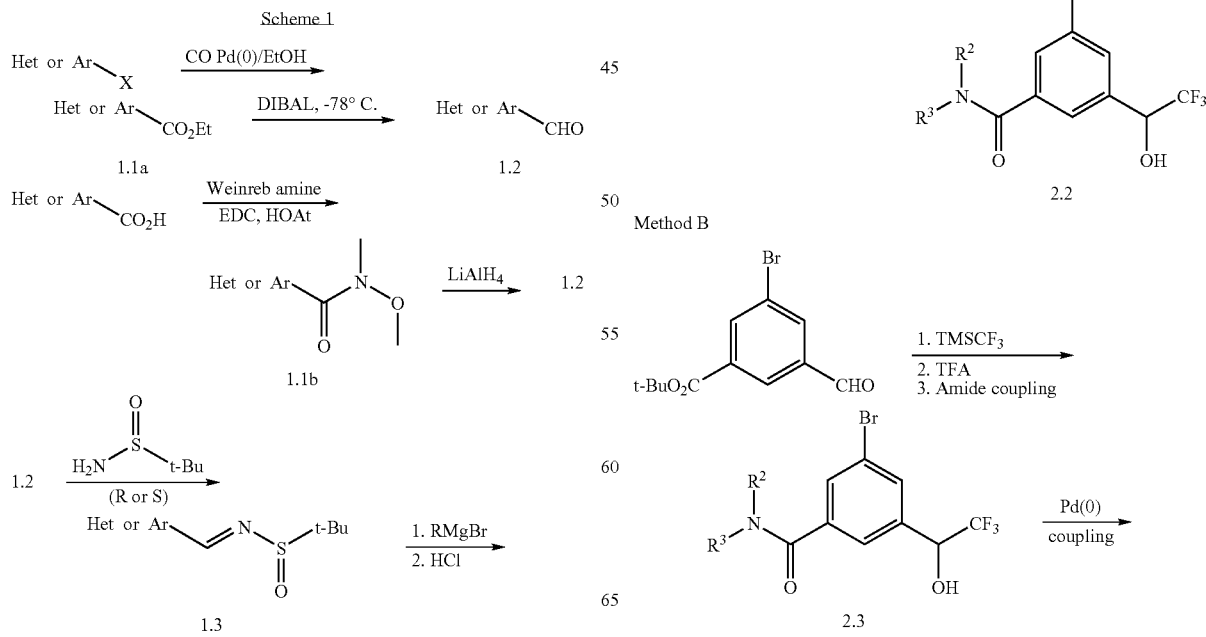

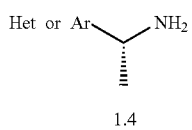

Examples of type 2.2 can be prepared as outlined in Scheme 2 starting from tert-butyl 3-bromo-5-formylbenzoate. Depending on the desired penultimate, using either method A or B, the respective acid intermediate 2.1 or halide intermediates of type 2.3 can be prepared prior to preparation of final trifluoromethylcarbinols of type 2.2

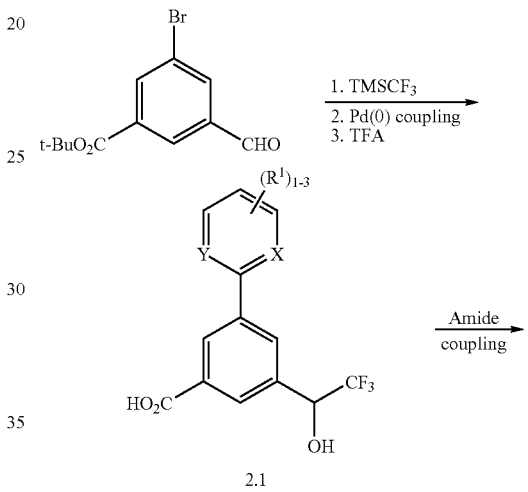

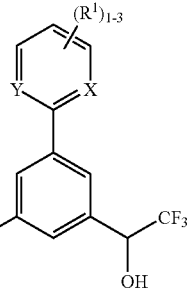

-continued

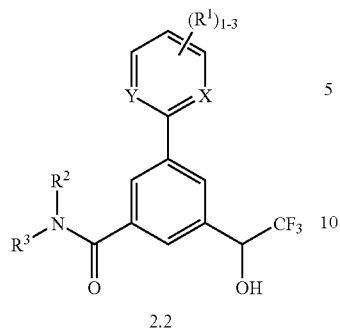

2.2

Examples of type 3.4 can be prepared as outlined in Scheme 3 starting from the same 1,3,5-tri-substituted benzene compound. Introduction of the first trifluoromethyl, subsequent oxidation gives 3.1. Treatment once again with Ruppert's reagent and TFA deprotection of the tert-butyl ester gives key acid 3.3. Final amide bond formation give examples of type 3.4.

Scheme 3

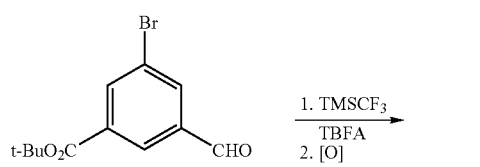

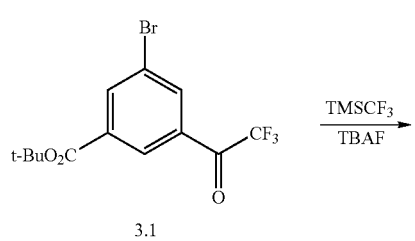

3.1

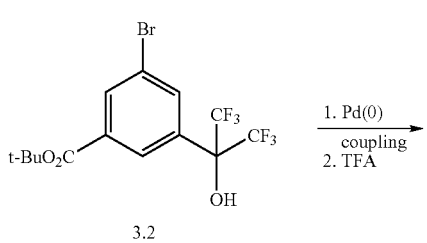

3.2

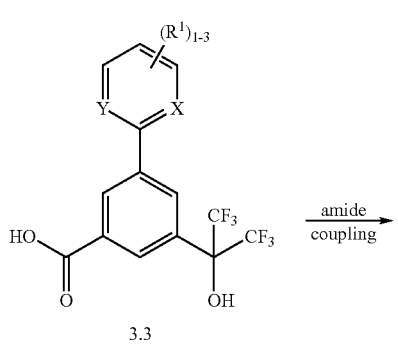

3.3

-continued

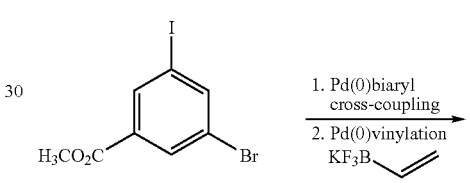

3.4

Examples of secondary carbinols of type 4.4 can be prepared as outline in Scheme 4. Starting from 3-bromo-5-iodo-methylbenzoate Suzuki biaryl coupling and subsequent vinylation gives intermediate 4.1. Saponification, amide coupling and ozonolysis gives aldehyde of type 4.3. Addition with either Grignard reagents or boronate ester/boronic acids under Rh(I) catalysis gives final carbinols of type 4.4.

Scheme 4

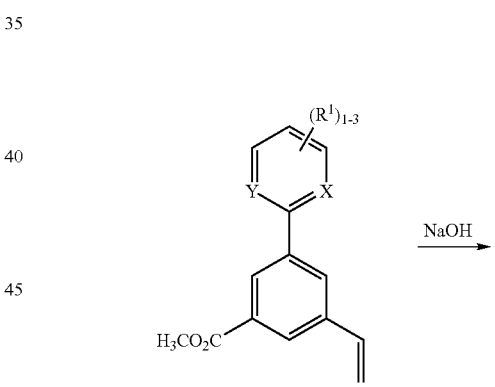

4.1

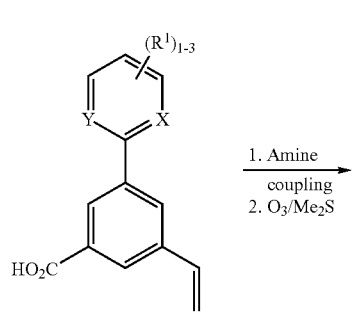

4.2

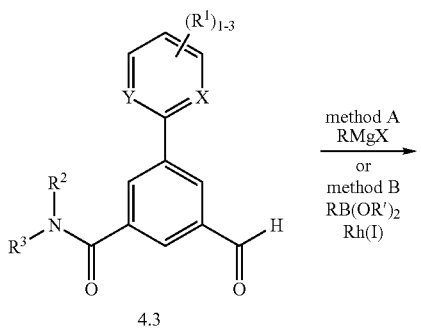

4.3

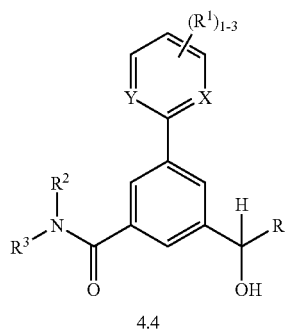

4.4

R = alkyl, aryl substituted alkyl, heteroaryl

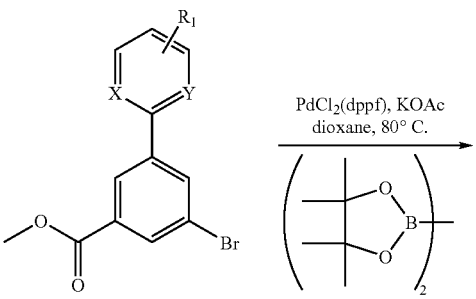

5.2

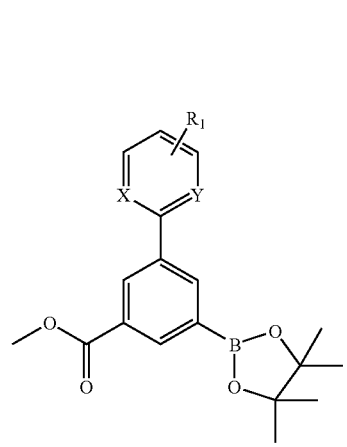

5.3

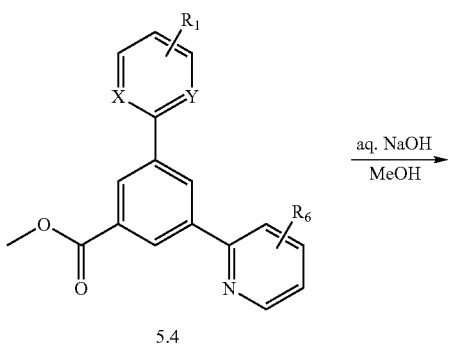

5.4

The synthesis of 2-pyridyl analogs is shown in Scheme 5. Iodide 5.1 can be selectively cross-coupled under palladium catalysis with either substituted aryl boronic acids using Suzuki conditions or substituted pyridyl zinc halides using Negishi conditions. Bromide 5.2 can then undergo a second cross-coupling reaction with various 5- and 6-membered aryl or heteroaryl boronic acids or stannanes to arrive at appropriately substituted tricyclic intermediates. Alternatively, borylation of bromide 2 gives boronate ester 5.3 which can undergo facile cross-couplings with a variety of heteroarenes such as 2-halopyridines, 2-halopyrazines, 2-halopyrimidines, and 2-halopyridazines. Ester hydrolysis and amide bond formation using EDC gives final targets 5.6.

SCHEME 5

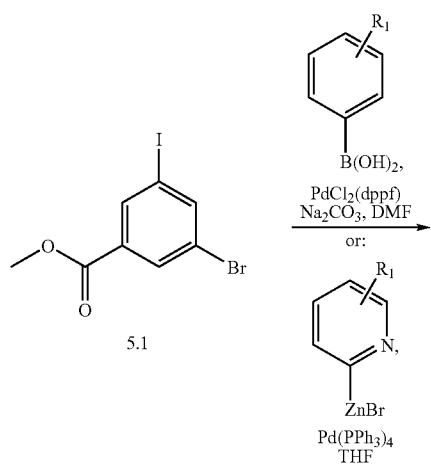 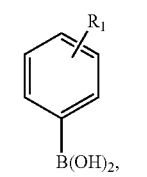 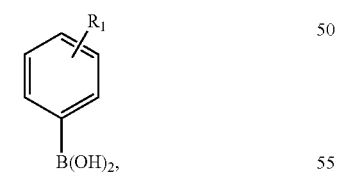 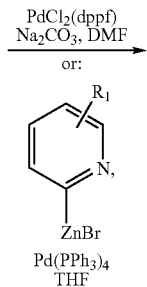 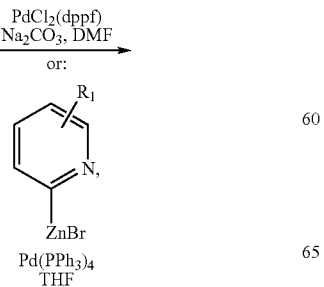

5.5

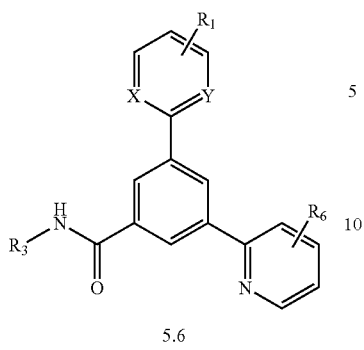

5.6

N-linked biaryl compounds are prepared as shown in Scheme 6. Bromide 6.2 can undergo palladium catalyzed N-arylation of substituted morpholines, piperidines, and piperazines which after in situ ester hydrolysis yields acid 6.3. Amide bond formation under standard conditions gives final targets 6.4.

SCHEME 6

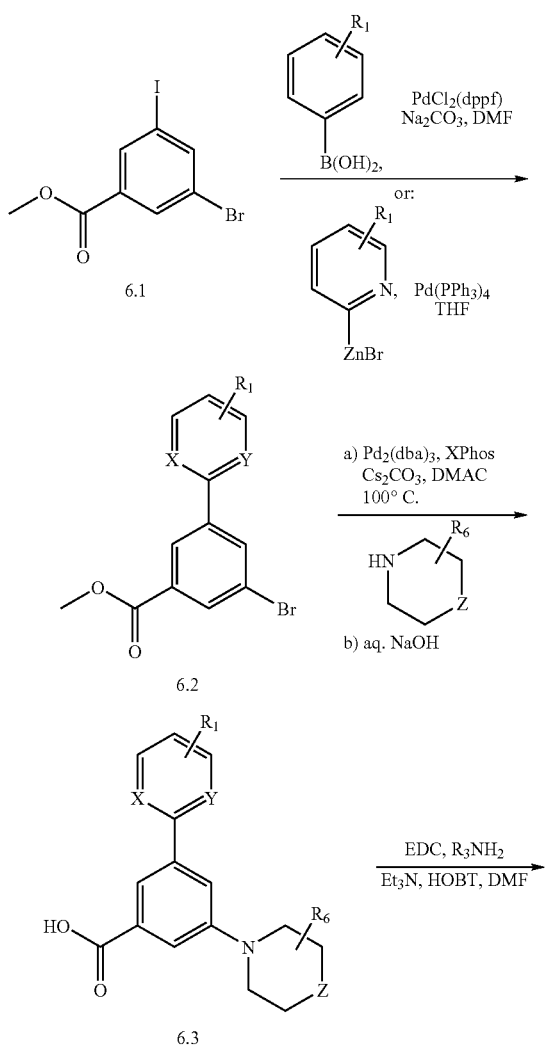

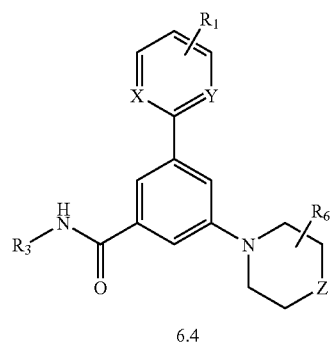

6.4

1,2,4-Triazoles are prepared according to Scheme 7. Bromide 7.1 is cross-coupled under palladium catalysis with either substituted aryl boronic acids using Suzuki conditions or substituted pyridyl zinc halides using Negishi conditions. The methyl ester of diester 7.2 can be selectively hydrolyzed and reacted with amines under standard conditions providing amide 7.3. Treatment with Lawesson's reagent forms the thioamide, which can undergo addition of a substituted hydrazide using mercury acetate or mercury chloride. Continued heating provides the cyclized 1,2,4-triazole 7.4. Deprotection of the tert-butyl ester followed by amide bond formation affords final targets 7.5.

SCHEME 7

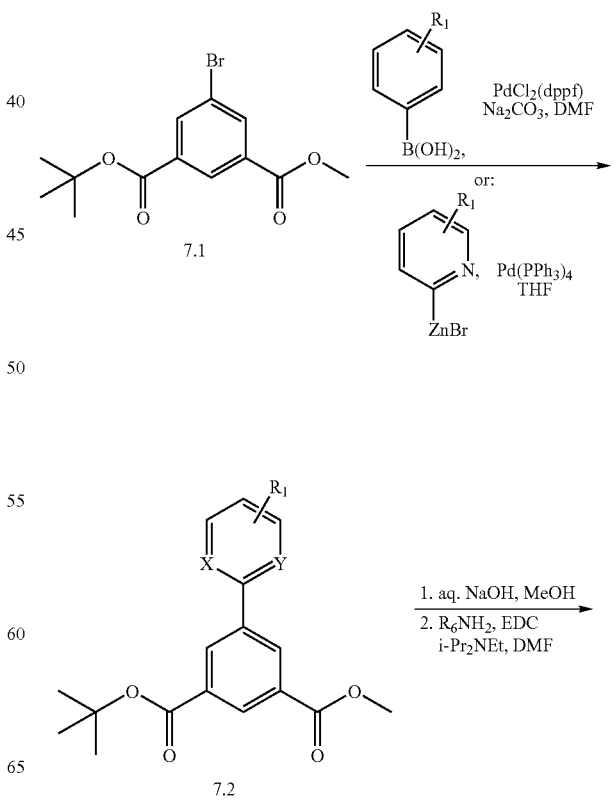

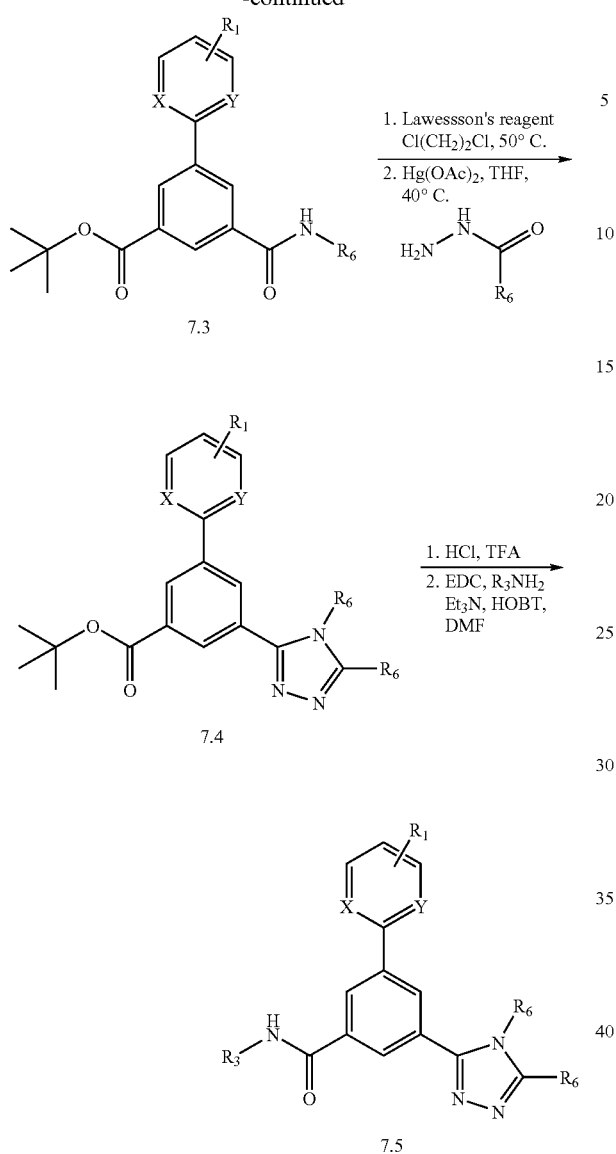

The synthetic scheme utilized to prepare difluoromethyl carbinols of type 8.4 is depicted in Scheme 8. Use of an excess of i-PrMgCl in the presence of 8.1 followed by treatment with difluoroethyl acetate allows for reductive formation of carbinol 8.2 (Li, H.; Balsells, J. Tetrahedron Lett., 2008, 49, 2034-2037). Suzuki cross-coupling using Pd(0) catalysis installs the biaryl moiety and ester removal using TFA provides penultimate acid 8.3. Final amide coupling gives examples of type 8.4.

The general synthetic scheme utilized to prepare sulfones of type 9.5 is depicted in Scheme 9. Intermediate 9.1 is treated with a sulfinic acid salt in the presence of CuI and L-proline at ca. 90° C. in DMSO to give the sulfones of type 9.2 (Wei, Z; Dawei, M. *J. Org. Chem.*, 2005, 2696-2700). Treatment of 9.2 with Ir-catalyzed C—H activation conditions (Murphy, J.; Tzschucke, C.; Hartwig, *J. Org. Lett.*, 2007, 9, 757-760) gives the pinacol boronate ester intermediate 9.3 which is subsequently used in a Suzuki cross-coupling, followed by ester deprotection and final amide coupling to give examples of type 9.5.

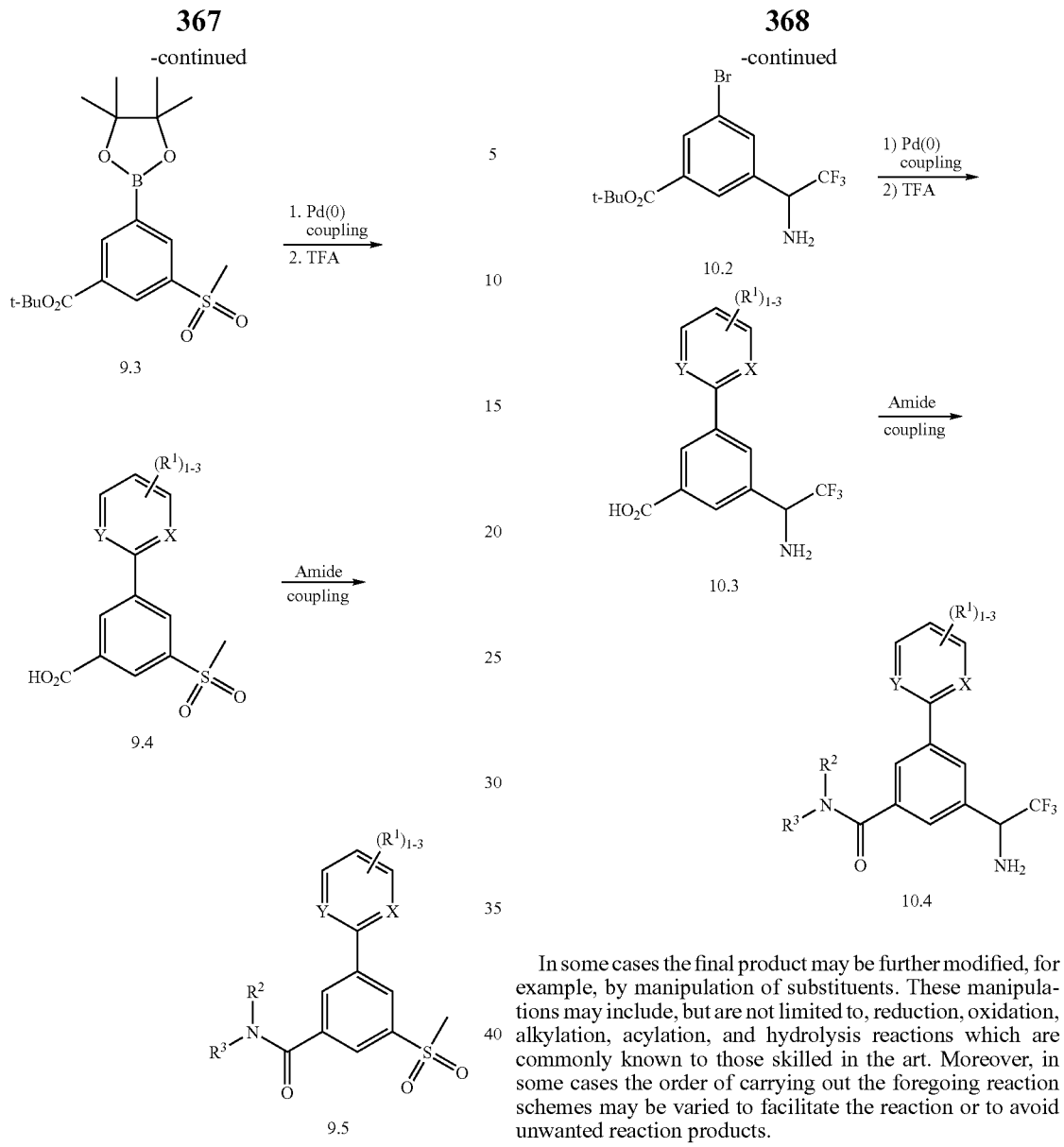

Scheme 10 depicts the general synthetic route utilized to prepare alpha-trifluoromethyl benzyl amine examples of type 10.4. Starting from intermediate 3.1 (described in Scheme 3) and treatment with LiHMDS followed by borane dimethyl sulfide gives racemic intermediate 10.2 (Gosselin, G. et al. *Org. Lett.*, 2005, 355-358). Suzuki coupling, deprotection and amide coupling as described previously gives examples of type 10.4.

In some cases the final product may be further modified, for example, by manipulation of substituents. These manipulations may include, but are not limited to, reduction, oxidation, alkylation, acylation, and hydrolysis reactions which are commonly known to those skilled in the art. Moreover, in some cases the order of carrying out the foregoing reaction schemes may be varied to facilitate the reaction or to avoid unwanted reaction products.

INTERMEDIATES AND EXAMPLES

The following examples are provided so that the invention might be more fully understood. These examples are illustrative only and should not be construed as limiting the invention in any way.

INTERMEDIATE 1

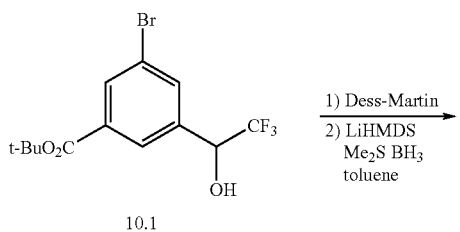

(1R)-1-(5-Fluoropyridin-2-yl)ethanamine

Step A: Ethyl 5-fluoropyridine-2-carboxylate

To a degassed solution of ethyl alcohol (400 mL) in a Parr steel bomb was added sodium acetate (43.3 g, 528 mmol), 2-bromo-5-fluoropyridine (20 g, 114 mmol), 1,1'-bis(diphenylphosphino)ferrocene (2.27 g, 4.09 mmol) and palladium acetate (204 mg, 0.91 mmol). The vessel was put under nitrogen and sealed with Parr top. The atmosphere was displaced with carbon monoxide gas and the pressure was adjusted to 300 psi. The mixture was heated to 90° C. After 3 h, the pressure dropped to below 100 psi. The vessel was cooled to ambient temperature and the reaction was repressurized with carbon monoxide to 300 psi. The vessel was heated to 90° C. for an additional 4 h. The vessel was cooled to ambient temperature and the remaining carbon monoxide was vented. The mixture was concentrated to half of the volume. Ethyl acetate (500 mL) and water (300 mL) were added. The organic layer was isolated and the aqueous layer was extracted with ethyl acetate (2×). The combined organic extracts were washed with brine, dried over sodium sulfate, filtered and concentrated. Purification by silica gel chromatography (100% hexanes→70% hexanes/ethyl acetate) gave the title compound. MS 170.0 (M+1).

Step B: 5-Fluoropyridine-2-carbaldehyde

To a solution of ethyl 5-fluoropyridine-2-carboxylate (25 g, 148 mmol) in tetrahydrofuran (250 mL) at −78° C. was added dropwise diisobutylaluminum hydride (1.0 M in hexanes; 296 mL, 296 mmol). After 1 h, the reaction was quenched with ethyl alcohol (10 mL). Saturated aqueous sodium potassium tartrate tetrahydrate (1.3 L) was added and the aqueous layer was extracted with ethyl acetate (2×). The combined organic extracts were washed with brine, dried over sodium sulfate, filtered. The solution mixture (1.4 L) was carried onto the next step without concentration. MS 125.9 (M+1).

Step C: N-[(1E)-(5-Fluoropyridin-2-yl)methylene]-2-methylpropane-2-sulfinamide

To a solution of 5-fluoropyridine-2-carbaldehyde (18.49 g, 148 mmol) in ethyl acetate (850 mL), THF (250 mL) and hexanes (300 mL) were added (R)-(+)-2-methyl-2-propanesulfinamide (19.71 g, 163 mmol) and anhydrous copper(II) sulfate (59.0 g, 370 mmol). The mixture was stirred at ambient temperature. After 18 h, the mixture was filtered through Celite. The filtered cake was washed with ethyl acetate and the filtrate was concentrated. Purification by silica gel chromatography (100% dichloromethane→98% dichloromethane/methanol) gave the title compound.

Step D: N-[(1R)-1-(5-Fluoropyridin-2-yl)ethyl]-2-methylpropane-2-sulfinamide

To a solution of N-[(1E)-(5-fluoropyridin-2-yl)methylene]-2-methylpropane-2-sulfinamide (52.12 g, 228 mmol) in dichloromethane (1000 mL) at −78° C. was added methylmagnesium bromide (3.0 M in THF; 198 mL, 594 mmol). The mixture was allowed to warm to ambient temperature. After 30 min, the mixture was cooled down to −78° C. and was quenched with saturated aqueous ammonium chloride (100 mL). The mixture was allowed to warm to ambient temperature. The organic layer was separated and the aqueous layer was extracted with dichloromethane (3×). The combined organic extracts were washed with brine, dried over sodium sulfate, filtered and concentrated. Purification by silica gel chromatography (100% ethyl acetate) gave the title compound. MS 245 (M+1).

Step E: (1R)-1-(5-Fluoropyridin-2-yl)ethanamine

To a solution of N-[(1R)-1-(5-fluoropyridin-2-yl)ethyl]-2-methylpropane-2-sulfinamide (34.3 g, 140 mmol) in methyl alcohol (700 mL) at 0° C. was added hydrogen chloride (4.0 M in dioxane; 105 mL, 421 mmol). After 30 min, the mixture was concentrated to dryness. The residue was recrytalized using ethyl alcohol (15 mL) and ether (40 mL). The white solid was filtered and dried under reduced pressure to give the hydrochloride salt of the title compound. MS 141.1 (M+1).

INTERMEDIATE 2

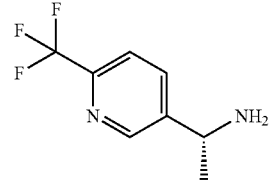

(1R)-1-[6-(Trifluoromethyl)pyridin-3-yl]etanamine

Step A: 2-methyl-N-{(1E)-[6-(trifluoromethyl)-3-pyridinyl]methylene}-2-propanesulfinamide To a solution of 6-(trifluoromethyl)nicotinaldehyde (45.0 g, 257 mmol) in dichloroethane (640 mL) were added (S)-(−)-2-methyl-2-propanesulfinamide (34.3 g, 283 mmol) and anhydrous copper(II) sulfate (82 g, 514 mmol). The mixture was stirred at 50° C. After 48 h, the mixture cooled to ambient temperature. The reaction mixture was filtered through Celite. The filtered cake was washed with dichloromethane and the filtrate was concentrated to give the title compound (76.8 g). MS 223.1 (M-tert-butyl+1)

Step B: 2-methyl-N-{(1R)-1-[6-(trifluoromethyl)-3-pyridinyl]ethyl}-2-propanesulfinamide To a solution of 2-methyl-N-{(1E)-[6-(trifluoromethyl)-3-pyridinyl]methylene}-2-propanesulfinamide (76.8 g, 276 mmol) in dichloromethane (920 mL) at −45° C. was added methylmagnesium bromide (3.0 M in THF; 184 mL, 552 mmol). The mixture was stirred at −45° C. for 4 h. The reaction mixture was warmed to −20° C. Additional methylmagnesium bromide (3.0 M in THF; 276 mL, 828 mmol) was added at −20° C. The reaction mixture was warmed to 0° C. and was quenched with saturated aqueous ammonium chloride (300 mL). The mixture was allowed to warm to ambient temperature. The organic layer was separated and the aqueous layer was extracted with dichloromethane (3×). The combined organic extracts were washed with brine, dried over magnesium sulfate, filtered and concentrated. The concentrate was recrystallized using ethyl alcohol (500 mL). Then white solid was filtered and dried under reduced pressure (41.6 g). MS 295.0 (M+1).

Step C: (1R)-1-[6-(trifluoromethyl)-3-pyridinyl]ethanamine

To a solution of 2-methyl-N-{(1R)-1-[6-(trifluoromethyl)-3-pyridinyl]ethyl}-2-propanesulfinamide (41.6 g, 141 mmol) in methyl alcohol (470 mL) at 0° C. was added hydrogen chloride (4.0 M in dioxane; 106 mL, 424 mmol). After 30 min, the mixture was concentrated to dryness. The residue was recrystallized using ethyl alcohol (15 mL) and ether (40 mL). The white solid was filtered and dried under reduced pressure to give the hydrochloride salt of the title compound (26.3 g). MS 191.2 (M+1). $^1$H NMR (500 MHz, CD$_3$ OD): δ

8.83 (d, J=2.2 Hz, 1H); 8.17 (d, J=8.2 Hz, 1H); 7.93 (d, J=8.2 Hz, 1H); 4.69 (q, J=6.9 Hz, 1H); 1.70 (d, J=6.9 Hz, 3H).

INTERMEDIATE 3

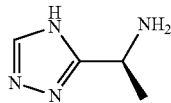

(1S)-1-(4H-1,2,4-Triazol-3-yl)ethanamine

Step A: Benzyl[(1S)-2-amino-1-methyl-2-thioxoethyl]carbamate

To a solution of [(1S)-2-amino-1-methyl-2-oxoethyl]carbamate (15.0 g, 67.5 mmol) in dichloromethane (337 mL) was added 2,4-bis-(4-methoxyphenyl)-1,3-dithia-2,4-diphosphetane 2,4-disulfide (15.01 g, 37.1 mmol) and the mixture was heated to 55° C. After 1.5 h, the reaction was allowed to cool to ambient temperature and concentrated. Recrystallization from dichloromethane gave the title compound (13.4 g). MS 239.1 (M+1).

Step B: Benzyl[(1S)-1-(4H-1,2,4-triazol-3-yl)ethyl]carbamate

To a solution of benzyl[(1S)-2-amino-1-methyl-2-thioxoethyl]carbamate (13.4 g, 56.2 mmol) in ethanol (1.125 L) was added formic acid hydrazide (20.26 g, 337 mmol) and mercury(II) chloride (19.85 g, 73.1 mmol). After 1 h the reaction was filtered and concentrated. Saturated aqueous sodium carbonate and ethyl acetate were added. The organic layer was isolated and the aqueous layer was extracted with ethyl acetate (2×). The combined organic extracts were washed with brine, dried over magnesium sulfate, filtered, and concentrated. A solution of the resulting residue in ethanol (1.125 L) was heated to 80° C. After 16 h, the reaction was concentrated. Purification by silica gel chromatography (100% dichloromethane→90% dichloromethane/methanol with 1% ammonium hydroxide) gave the title compound (8.7 g). MS 247.1 (M+1).

Step C: (1S)-1-(4H-1,2,4-Triazol-3-yl)ethanamine

To a solution of benzyl[(1S)-1-(4H-1,2,4-triazol-3-yl)ethyl]carbamate (8.6 g, 34.9 mmol) in ethanol (140 mL) was added 4 M hydrochloric acid in 1,4-dioxane (43.7 mL, 175 mmol) and 10% palladium on carbon (1.858 g, 1.746 mmol) and the mixture was pressurized to 47 psi under hydrogen. After 4 h, the reaction was depressurized and filtered. Concentration gave the title compound as a hydrochloride salt (6.6 g). MS 113.0 (M+1). $^1$H NMR (500 MHz, CD$_3$OD): δ 8.82 (s, 1H); 4.67 (q, J=6.9 Hz, 1H); 1.70 (dd, J=6.9, 1.0 Hz, 3H).

INTERMEDIATE 4

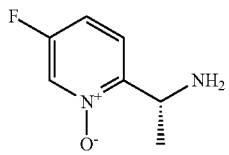

(1R)-1-(5-Fluoro-1-oxidopyrindin-2-yl)ethanamine

Step A: tert-Butyl[(1R)-1-(5-fluoropyridin-2-yl)ethyl]carbamate

To a solution of the toluene sulfonic acid salt of (1R)-1-(5-fluoropyridin-2-yl)ethanamine (7.5 g, 24.0 mmol) in dichloromethane (96 mL) at 0° C. was added triethylamine (7.03 mL, 50.0 mmol) and di-tert-butyl dicarbonate (6.13 mL, 26.4 mmol). The mixture was allowed to warm to ambient temperature. After 16 hours, saturated aqueous sodium bicarbonate was added. The organic layer was isolated and the aqueous layer was extracted with dichloromethane (2×). The combined organic extracts were washed with brine, dried over magnesium sulfate, and filtered. Concentration gave the title compound (7.72 g). MS 241.1 (M+1).

Step B: tert-Butyl[(1R)-1-(5-fluoro-1-oxidopyridin-2-yl)ethyl]carbamate

To a solution of tert-butyl[(1R)-1-(5-fluoropyridin-2-yl)ethyl]carbamate (5.77 g, 24.0 mmol) in dichloromethane (96 mL) was added 3-chloroperbenzoic acid (6.51 g, 26.4 mmol). After 4.5 h, excess 3-chloroperbenzoic acid (0.59 g, 2.6 mmol) was added. After 72 h, saturated aqueous sodium sulfite was added. After 1 h, saturated aqueous sodium bicarbonate was added. The organic layer was isolated and the aqueous layer was extracted with dichloromethane (2×). The combined organic extracts were washed with brine, dried over magnesium sulfate, filtered, and concentrated. Purification by silica gel chromatography (100% dichloromethane→90% dichloromethane/methanol with 1% ammonium hydroxide) gave the title compound (5.45 g). MS 257.1 (M+1).

Step C: (1R)-1-(5-Fluoro-1-oxidopyrindin-2-yl)ethanamine

To a solution of tert-butyl[(1R)-1-(5-fluoro-1-oxidopyridin-2-yl)ethyl]carbamate (1.47 g, 5.74 mmol) in dichloromethane (28.7 mL) was added 4 M hydrochloric acid in 1,4-dioxane (43.0 mL, 172 mmol). After 2 h, concentration gave the title compound as a hydrochloride salt (1.396 g). MS 157.1 (M+1). $^1$H NMR (500 MHz, CD$_3$OD): δ 8.55 (dd, J=4.3, 2.4 Hz, 1H); 7.70 (dd, J=9.0, 6.7 Hz, 1H); 7.52 (ddd, J=9.1, 7.1, 2.4 Hz, 1H); 4.80 (q, J=7.0 Hz, 1H); 1.74 (d, J=7.0 Hz, 3H).

INTERMEDIATE 5

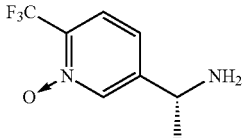

(1R)-1-[1-Oxido-6-(trifluoromethyl)-3-pyridinyl]ethanamine

Step A: tert-Butyl {(1R)-1-[6-(trifluoromethyl)-3-pyridinyl]ethyl}carbamate

To a solution of (1R)-1-[6-(trifluoromethyl)pyridin-3-yl]ethanamine hydrochloride salt (0.554 g, 0.21 mmol) in dichloromethane (7.0 mL) were added di-tert-butyl dicarbonate (0.506 g, 2.32 mmol) and triethylamine (0.969 mL, 6.95 mmol). The reaction mixture was stirred at ambient temperature for 4 h. Saturated aqueous ammonium chloride was added. The mixture was extracted with dichloromethane (3×). The combined organics extracts were washed with brine, dried over magnesium sulfate, filtered and concentrated to give the title compound which was used directly in Step B (0.626 g).

Step B: tert-Butyl {(1R)-1-[1-oxido-6-(trifluoromethyl)-3-pyridinyl]ethyl}carbamate To a solution of tert-butyl {(1R)-1-[6-(trifluoromethyl)-3-pyridinyl]ethyl}carbamate (0.626 g, 2.157 mmol) in chloroform (10.0 mL) were added 2,6-di-tert-butyl-4-methylphenol (24 mg, 0.108 mmol) and 3-chloroperbenzoic acid (0.665 g, 2.70 mmol). The reaction mixture was stirred at 50° C. for 48 h. The reaction mixture was cooled to ambient temperature. Saturated aqueous sodium thiosulfate and saturated aqueous sodium bicarbonate were added. The mixture was extracted with dichloromethane (3×). The combined organics extracts were washed with brine, dried over magnesium sulfate, filtered and concentrated. Purification by silica gel chromatography (75% hexanes/ethyl acetate→100% ethyl acetate) gave the title compound (140 mg). MS 307.0 (M+1).

Step C: (1R)-1-[1-Oxido-6-(trifluoromethyl)-3-pyridinyl]ethanamine hydrochloride To a solution of tert-butyl {(1R)-1-[1-oxido-6-(trifluoromethyl)-3-pyridinyl]ethyl}carbamate (140 mg, 0.457 mmol) in dioxane (2 mL) was added hydrogen chloride (4.0 M in dioxane; 0.343 mL, 1.371 mmol). The reaction mixture was stirred for 4 h. The reaction mixture was concentrated to dryness to give the hydrochloride salt of the title compound (118 mg). MS 207.1 (M+1).

INTERMEDIATE 6

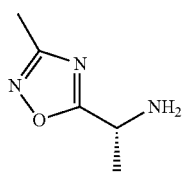

(1R)-1-(3-Methyl-1,2,4-oxadiazol-5-yl)ethanamine

Step A: tert-Butyl[(1R)-1-(3-methyl-1,2,4-oxadiazol-5-yl)ethyl]carbamate

To a solution of N-(tert-butoxycarbonyl)-D-alanine (20 g, 106 mmol), acetamide oxime (17.3 g, 234 mmol) in 120 mL of 1,4-dioxane and 30 mL of N,N-dimethylformamide were added EDC (44.8 g, 234 mmol). The mixture was heated at 60° C. for 4 h then at 100° C. for 16 h. After cooling to ambient temperature, 300 mL of ethyl acetate was added. The mixture was washed with aqueous saturated sodium bicarbonate (2×). The combined organic extracts were dried over magnesium sulfate, filtered and concentrated. The residue was purified by silica gel chromatography (100% dichloromethane→90% dichloromethane/methanol) to give pure tert-butyl[(1R)-1-(3-methyl-1,2,4-oxadiazol-5-yl)ethyl]carbamate (6.0 g). MS 172.1 ((M-t-butyl+H)+1).

Step B: (1R)-1-(3-Methyl-1,2,4-oxadiazol-5-yl)ethanamine

To a solution of tert-butyl[(1R)-1-(3-methyl-1,2,4-oxadiazol-5-yl)ethyl]carbamate (6.0 g, 26.4 mmol) in dioxane (40 mL) was added 4 M hydrochloric acid in dioxane (30 mL). The reaction mixture was stirred for 16 h. The solution was concentrated and dried by vacuum to give hydrochloride salt of (1R)-1-(3-methyl-1,2,4-oxadiazol-5-yl)ethanamine (5.1 g). $^1$H NMR (500 MHz, CD$_3$OD): δ 4.90-4.83 (m, 1H); 2.41 (s, 3H); 1.72 (d, J=7.0 Hz, 3H). MS 128.2 (M+1).

INTERMEDIATE 7

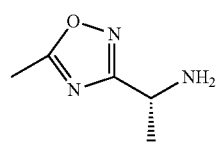

(1R)-1-(5-Methyl-1,2,4-oxadiazol-3-yl)ethanamine

Step A: Benzyl[(1R)-1-cyanoethyl]carbamate

To a solution of benzyl[(1R)-2-amino-1-methyl-2-oxoethyl]carbamate (10 g, 45 mmol) in 50 mL of N,N-dimethylformamide was added 2,4,6-trichloro-1,3,5-triazine (4.15 g, 22.5 mmol). After 2 h, 100 mL of water was added and the mixture was filtered. The solids were washed with 100 mL aqueous sodium bicarbonate (2×) and dried under vacuum to give pure benzyl[(1R)-1-cyanoethyl]carbamate (7.2 g). MS 205.2 ((M+1).

Step B: Benzyl[(1R,2Z)-2-amino-2-(hydroxyimino)-1-methylethyl]carbamate

To a solution of benzyl[(1R)-1-cyanoethyl]carbamate (2.52 g, 12.3 mmol) in ethanol (30 ml) was added hydroxylamine hydrochloride salt (0.90 g, 13.0 mmol) and triethylamine (3.43 ml, 24.6 mmol) and the mixture heated to 75° C. After 16 h, the solution was concentrated and the residue was dissolved in 200 mL of dichloromethane. The mixture was washed with 100 mL of saturated aqueous sodium bicarbonate (2×) and brine (100 mL). The combined organic extracts were dried over sodium sulfate, filtered and concentrated to give benzyl[(1R,2Z)-2-amino-2-(hydroxyimino)-1-methylethyl]carbamate (2.9 g). MS 238.2 (M+1).

Step C: Benzyl[(1R)-1-(5-methyl-1,2,4-oxadiazol-3-yl)ethyl]carbamate

To a solution of benzyl[(1R,2Z)-2-amino-2-(hydroxyimino)-1-methylethyl]carbamate (2.25 g, 9.48 mmol) in dioxane (80 ml) was added 1-acetyl-1H-imidazole (3.13 g, 28.5 mmol) and the mixture heated to 90° C. After 16 h, the solution was concentrated and the residue was dissolved in 200 mL of dichloromethane. The mixture was washed with 100 mL of aqueous saturated sodium bicarbonate (2×) and brine (100 mL). The organic layer was dried over sodium sulfate, filtered and concentrated. The residue was purified by silica gel chromatography (100% dichloromethane→95% dichloromethane/methanol) to give the title compound (1.1 g). MS 262.1 (M+1).

Step D: (1R)-1-(5-Methyl-1,2,4-oxadiazol-3-yl)ethanamine

To a solution of benzyl[(1R)-1-(5-methyl-1,2,4-oxadiazol-3-yl)ethyl]carbamate (1.10 g, 4.21 mmol) in dichloromethane (40 mL) was added 1 M boron trichloride solution in dichloromethane (21.1 mL, 21.1 mmol) at 0° C. The reaction mixture was allowed to warm from 0° C. to 20° C. over 4 h. The solution was quenched by 5 ml of methanol at 0° C. After warming to ambient temperature, the mixture was concentrated and the residue was washed with 100 mL of diethyl ether (2×) to give the hydrochloride salt of (1R)-1-(5-methyl-1,2,4-oxadiazol-3-yl)ethanamine was obtained as solid (0.84 g). $^1$H NMR (500 MHz, CD$_3$OD): δ 4.70-4.61 (m, 1H); 2.63 (s, 3H); 1.67 (d, J=6.9 Hz, 3H).

INTERMEDIATE 8

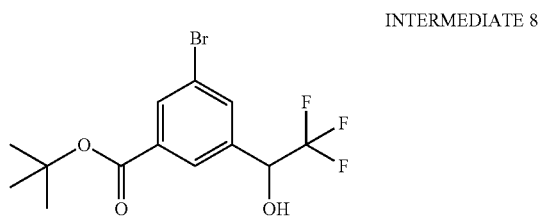

Step A: tert-Butyl 3-bromo-5-[(R/S)-2,2,2-trifluoro-1-hydroxyethyl]benzoate

To a solution of tert-butyl 3-bromo-5-formylbenzoate (Merck patent case No. 22407 PV; 5.7 g, 20.0 mmol) in THF (133 mL) at 0° C. were added trimethyl(trifluoromethyl)silane (4.44 mL, 30.0 mmol) and activated 4 Å molecular sieves. Tetrabutylammonium fluoride (1.0 M in THF; 6.0 mL, 6.0 mmol) was added dropwise. The reaction mixture was warmed to ambient temperature. After 3 h, aqueous 1N HCl (25 mL) and tert-butyl methyl ether (100 mL) were added. The organic layer was separated, washed with brine, dried over sodium sulfate, filtered and concentrated.

INTERMEDIATE 9

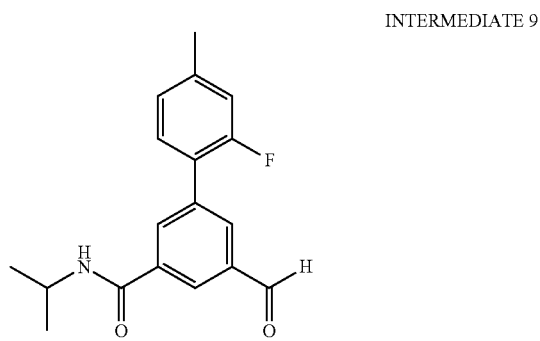

2'-Fluoro-5-formyl-N-isopropyl-4'-methylbiphenyl-3-carboxamide

Step A: Methyl 3-bromo-5-iodo-benzoate

Methanol (50 mL) was added into a solution of 3-bromo-5-iodo-benzoic acid (25 g) in 2M HCl/ether (100 mL). The reaction mixture was then stirred at room temperature for 18 hrs. The solution was dried down under reduced pressure. The residue was then re-dissolved in ethyl ether (300 mL). The ether solution was washed with sat. Na$_2$CO$_3$ (3×200 mL), and water (3×200 mL). The organic layer was dried with sodium sulfate and evaporated to dryness to give the crude product. The crude product was then purified through a short silica column (eluted with 20% EtOAc/hexane) to give pure compound by TLC.

Step B: Methyl 5-bromo-2'-fluoro-4'-methylbiphenyl-3-carboxylate

Methyl 3-bromo-5-iodo-benzoate (13 g) and 2-fluoro-4-methylphenylboronic acid (6 g) were dissolved in DMF (120 mL) at room temperature. The solution was then cooled down to 0° C. with ice bath. To this solution was added aq. sodium carbonate (6 g in 50 mL of water), Pd(dppf)Cl$_2$ (3 g) and DMF (10 mL). After the addition, the reaction was warmed up slowly to room temperature. The reaction mixture was then stirred at room temperature for 4 hrs. Solvent was evaporated under reduced pressure. The residue was re-dissolved in EtOAc (200 mL) washed with HCl (1M) 3×200 mL), sat. NaHCO$_3$ (3×100 mL), brine (3×100 mL) and water (3×100 mL). The organic layer was separated and concentrated. The crude product was then purified with column chromatography (silica gel, eluted with EtOAc/Hexane, 0 to 1%) to give pure compound. Note a second column can be done to further remove unwanted bis cross coupled by-product.

Step C: Methyl 2'-fluoro-4'-methyl-5-vinylbiphenyl-3-carboxylate

To Biotage Advancer MW reactor was charged methyl 5-bromo-2'-fluoro-4'-methylbiphenyl-3-carboxylate (20 g, 61.9 mmol), PdCl$_2$(dppf) (0.20 g, 0.273 mmol), potassium vinyl trifluoroborate (12.4 g, 93 mmol), Et$_3$N (13.0 ml, 93 mmol) and EtOH (150 ml). The reactor was sealed and heated at 140° C. for 10 min followed by flash cooling. Removed mixture from the cooling reservoir via vacuum and reaction repeated 5× (120 g, 371 mmol processed). All runs were combined and concentrated to dryness. The crude was partitioned between water and dichloromethane. The layers were separated and the aqueous extracted 2× w/DCM. The combined organic layers were dried over Na$_2$SO$_4$, filtered and concentrated via rotary evaporation to give 116 g amber oil. The crude was purified by automated silica gel chromatography (750 g SiO2, EtOAc/hexanes) to give nearly colorless oil which solidified to white solid upon cooling (99.7 g, 99%).

Step D: 2'-Fluoro-4'-methyl-5-vinylbiphenyl-3-carboxylic acid

In a 500 mL flask charged with methyl ester from step C above (20 g, 74 mmol) in THF (250 mL) was added MeOH (100 mL) and aq. 3N NaOH (74 mmol, 25 mL). The mixture was stirred overnight at rt and an additional 15 mL NaOH added. Reaction stirred for 16 h, the pH was then adjusted 4-5 and the mixture extracted repeatedly with EtOAc. The combined organic layers were washed with brine, dried over Na$_2$SO$_4$ and concentrated to dryness to give 18.5 g of product as a white solid.

Step E: 2'-Fluoro-N-isopropyl-4'-methyl-5-vinylbiphenyl-3-carboxamide

In a 500 mL flask charged with carboxylic acid from step D (12 g, 46.8 mmol) in THF (300 mL) at 0° C. was added carbonyl diimidazole (9.1 g, 56.2 mmol) portionwise. Upon complete addition (10 min.) the ice bath was removed and the reaction stirred for 1 h. At this time the mixture was re-cooled to 0° C. and isopropylamine added dropwise (4.98 g, 84 mmol). The mixture was warmed to rt and the reaction complete within 2 h as indicated by LC-MS. The mixture was concentrated and treated with EtOAc and aq. Na$_2$HCO$_3$. The organic layer was washed with brine; dried over Na$_2$SO$_4$ and concentrated to via rotary evaporation and further dried in vacuo. The crude product was re-crystallized from EtOAc/hexanes to give 11.7 g of final product as a colorless solid (84%): LC-MS (M+H)=298.0.

Step F: 2'-Fluoro-5-formyl-N-isopropyl-4'-methylbiphenyl-3-carboxamide

Amide 2'-fluoro-N-isopropyl-4'-methyl-5-vinylbiphenyl-3-carboxamide from step E was dissolved in DCM and cooled to −78° C. in an acetone/dry ice bath. Ozone was bubbled into the solution. After ~40 minutes, the solution turned blue (indicating that the olefin had been consumed and that the solution was now concentrated with ozone) and the ozone turned off. Nitrogen was bubbled through the solution briefly and the mixture allowed to warm to rt. At this time the reaction was carefully quenched with dimethyl sulfide and the mixture allowed to stand for 1 h. The mixture was concentrated via rotary evaporation and the solid dissolved in ethyl acetate. The organic solution was washed with water (3×), followed by brine and then dried over sodium sulfate and the volatiles removed in vacuo to yield 7.6 g of product as a colorless solid (97%): $^1$H NMR (CDCl$_3$, 400 MHz) δ 10.1 (s, 1H), 8.22 (s, 1H) 8.18 (s, 1H), 8.15 (s, 1H), 7.38 (t, J=8.0, 1H), 7.06 (d, J=8.0, 1H), 7.02 (d, J=12, 1H), 6.12 (br d, J=6.8, 1H), 4.32 (sept, J=7.2, 1H), 2.42 (s, 3H), 1.24 (d, J=6.8, 6H); LC-MS (M+H)=298.0.

Example 1.10

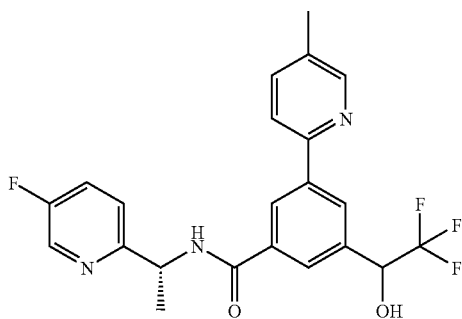

N-[(1R)-1-(5-Fluoropyridin-2-yl)ethyl]-3-(5-methylpyridin-2-yl)-5-[(R/S)-2,2,2-trifluoro-1-hydroxyethyl]benzamide Step A: tert-Butyl 3-bromo-5-[(R/S)-2,2,2-trifluoro-1-hydroxyethyl]benzoate To a solution of tert-butyl 3-bromo-5-formylbenzoate (5.7 g, 20.0 mmol) in tetrahydrofuran (133 mL) at 0° C. were added trimethyl(trifluoromethyl)silane (4.44 mL, 30.0 mmol) and activated 4 Å molecular sieves. Tetrabutylammonium fluoride (1.0 M in THF; 6.0 mL, 6.0 mmol) was added dropwise. The reaction mixture was warmed to ambient temperature. After 3 h, aqueous 1N HCl (25 mL) and tert-butyl methyl ether (100 mL) were added. The organic layer was separated, washed with brine, dried over sodium sulfate, filtered and concentrated.

Step B: tert-Butyl 3-(5-methylpyridin-2-yl)-5-[(R/S) 2,2,2-trifluoro-1-hydroxyethyl]benzoate To a solution of tert-butyl 3-bromo-5-(2,2,2-trifluoro-1-hydroxyethyl)benzoate (5.0 g, 14.1 mmol) and bis(tri-tert-butylphosphine)palladium(0) (0.22 g, 0.42 mmol) in dioxane (70 mL) was added 5-methyl-2-pyridylzinc bromide (0.5 M in THF; 56.3 mL, 28.2 mmol). The reaction mixture was heated to 70° C. After 1 h, additional 5-methyl-2-pyridylzinc bromide (0.5 M in THF; 10 mL, 5.0 mmol) and bis(tri-tert-butylphosphine)palladium(0) (40 mg, 0.078 mmol) were added. After 30 min, the reaction was concentrated. Saturated aqueous sodium potassium tartrate tetrahydrate and saturated aqueous sodium bicarbonate were added. The mixture was extracted with ethyl acetate (3×). The combined organic extracts were washed with brine, dried over sodium sulfate, filtered and concentrated. Purification by silica gel chromatography (100% hexanes→70% hexanes/ethyl acetate) gave the title compound. MS 368.2 (M+1).

Step C: 3-(5-Methylpyridin-2-yl)-5-[(R/S)-2,2,2-trifluoro-1-hydroxyethyl]benzoic acid To a solution of tert-butyl 3-(5-methylpyridin-2-yl)-5-(2,2,2-trifluoro-1-hydroxyethyl)benzoate (3.25 g, 8.85 mmol) in dichloromethane (15 mL) was added hydrogen chloride (4.0 M in dioxane; 11.1 mL, 44.2 mmol). The reaction mixture was stirred at ambient temperature. After 18 h, the mixture was concentrated. Dichloromethane was added the suspension was filtered. The solid cake was washed with dihchloromethane and dried under reduced pressure to give the hydrochloride salt of the title compound. MS 312.1 (M+1).

Step D: N-[(1R)-1-(5-Fluoropyridin-2-yl)ethyl]-3-(5-methylpyridin-2-yl)-5-[(R/S)-2,2,2-trifluoro-1-hydroxyethyl)benzamide To a solution of 3-(5-methylpyridin-2-yl)-5-(2,2,2-trifluoro-1-hydroxyethyl)benzoic acid (25 mg, 0.072 mmol) in N,N-dimethylformamide (0.7 mL) were added (1R)-1-(5-fluoropyridin-2-yl)ethanamine hydrochloride salt (23 mg, 0.11 mmol), EDC (20.7 mg, 0.11 mmol), HOAT (0.5 M in DMF; 72 μL, 0.036 mmol) and triethylamine (60 μL 0.43 mmol). The reaction mixture was heated to 60° C. After 3 h, the mixture was cooled to ambient temperature and the solid in the reaction was filtered off. Purification by reverse phase chromatography (C-18, 75% water/acetonitrile→48% water/acetonitrile with 0.1% trifluoroacetic acid) gave the trifluoroacetate salt of the title compound. HRMS 434.1484 (M+1). $^1$H NMR (500 MHz, DMSO-d$_6$): δ 9.09 (d, J=7.6 Hz, 1H); 8.57 (d, J=8.0 Hz, 2H); 8.52 (d, J=3.0 Hz, 1H); 8.38 (s, 1H); 8.05 (s, 1H); 7.98 (d, J=8.1 Hz, 1H); 7.78 (dd, J=8.2, 2.2 Hz, 1H); 7.70 (td, J=8.8, 3.0 Hz, 1H); 7.52 (dd, J=8.8, 4.5 Hz, 1H); 7.01 (d, J=5.6 Hz, 1H); 5.37-5.31 (m, 1H); 5.29-5.23 (m, 1H); 2.37 (s, 3H); 1.55 (d, J=7.1 Hz, 3H).

Example 1.24

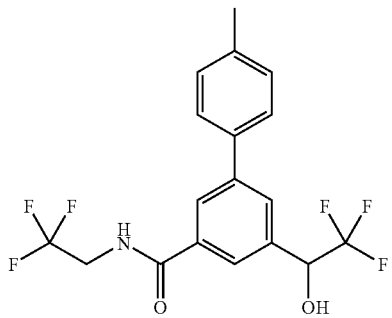

4'-Methyl-N-(2,2,2-trifluoroethyl)-5-(2,2,2-trifluoro-1-hydroxyethyl)biphenyl-3-carboxamide Step A: tert-butyl 4'-methyl-5-(2,2,2-trifluoro-1-hydroxyethyl)biphenyl-3-carboxylate To a mixture of Intermediate 3 (2.0 g, 5.6 mmol) (4-methylphenyl)boronic acid (1.0 g, 7.3 mmol), Pd[P(Ph$_3$)]$_4$ (0.32 g, 0.28 mmol), and K$_2$CO$_3$ (2.3 g, 17 mmol) under N$_2$ was added 75 mL of degassed n-Propanol/water (4:1). The reaction was heated to 85° C. overnight. The mixture was cooled to room temperature and filtered over celite. The crude material was taken up in EtOAc and water. The organic layer was extracted (3×) and washed with brine. The final organic layer was dried over Na$_2$SO$_4$, filtered and concentrated to 2.8 g of crude material. Purification using automated flash chromatography (SiO2, 120 g, 0-20% EtOAc/Hex) gave, upon concentration, title product.

Step B: 4'-methyl-5-(2,2,2-trifluoro-1-hydroxyethyl)biphenyl-3-carboxylic acid

To a DCM (22 mL) solution tert-butyl 4'-methyl-5-(2,2,2-trifluoro-1-hydroxyethyl)biphenyl-3-carboxylate (1.6 g, 4.4 mmol) from step A was added trifluoroacetic acid (22 mL). The mixture was stirred at rt for 3 h and concentrated to dryness. The crude title compound was used in step C without further purification.

Step C: 4'-methyl-N-(2,2,2-trifluoroethyl)-5-(2,2,2-trifluoro-1-hydroxyethyl)biphenyl-3-carboxamide To a DMF solution (9.7 mL) containing 4'-methyl-5-(2,2,2-trifluoro-1-hydroxyethyl)biphenyl-3-carboxylic acid (300 mg, 0.97 mmol), HOAt (1.6 mL, 0.97 mmol), DIPEA (0.34 mL, 1.9 mmol), and 2,2,2-trifluoroethanamine (0.23 mL, 2.9 mmol) was added EDC (278 mg, 1.45 mmol). The reaction was stirred at room temperature overnight. EtOAc, NaHCO$_3$ and 3M LiCl were added to the reaction and organics were extracted with EtOAc (3×). The combined organic layers were washed with 3M LiCl (3×) and followed by brine. The final organic layer was dried over Na$_2$SO$_4$, filtered and concentrated. Crude product was taken up in DMF and purified by RP-HPLC. Fractions containing product were combined and sat. NaHCO$_3$ and EtOAc were added. Organics were extracted with EtOAc and washed with brine. Final organic layer was dried over Na$_2$SO$_4$, filtered and concentrated to give a white solid: $^1$H NMR (CD$_3$OD, 400 MHz) δ 8.07 (s, 1H), 7.93 (s, 1H), 7.90 (s, 1H), 7.55 (d, J=8.2 Hz, 2H), 7.27 (d, J=7.9 Hz, 2H), 5.16 (q, J=7.1 Hz, 1H), 4.09 (q, J=9.2 Hz, 2H), 2.36 (s, 3H); HRMS (ES, M+H) calcd for C$_{18}$H$_{15}$F$_6$NO$_2$: 392.1080. found: 392.1079.

Example 1.46

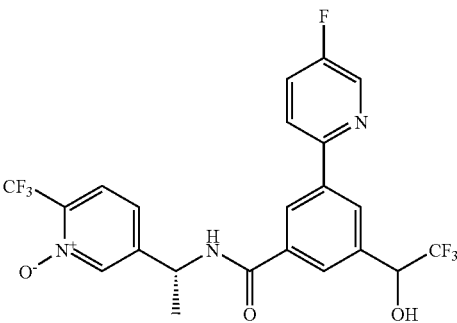

3-(5-Fluoropyridin-2-yl)-N-{(1R)-1-[1-oxido-6-(trifluoromethyl)pyridin-3-yl]ethyl}-5-[(R or S)-2,2,2-trifluoro-1-hydroxyethyl]benzamide Step A: tert-butyl 3-bromo-5-[(R or S)-2,2,2-trifluoro-1-hydroxyethyl]benzoate Intermediate 8 was separated by chiral chromatography (ChiralPak AD-H, 30×250 mm, 95/5: CO$_2$/EtOH, 70 mL/min, UV at 214 nm). The first eluded peak was carried onto the next step.

Step B: tert-butyl 3-(5-fluoropyridin-2-yl)-5-[(R or S)-2,2,2-trifluoro-1-hydroxyethyl]benzoate To a solution of tert-butyl 3-bromo-5-[(R or S)-2,2,2-trifluoro-1-hydroxyethyl]benzoate (2.0 g, 5.63 mmol) in DMF (30 mL) were added 5-fluoro-2-(4,4,5,5-tetramethyl-1,3,2-dioxaborolan-2-yl)pyridine (2.51 g, 11.3 mmol), cesium carbonate (4.59 g, 14.1 mmol), dichloro[1,1'-bis(diphenylphosphino)ferrocene] (0.31 g, 0.56 mmol) and palladium acetate (0.06 g, 0.28 mmol) and copper(I) chloride (0.56 g, 5.63 mmol). The mixture was heated to 100° C. After 1 h, the mixture was cooled to ambient temperature and filtered with Celite. Saturated aqueous NaHCO$_3$ was added to the filtrate and the mixture was extracted with ethyl acetate (3×). The combined organic extracts were washed with brine, dried over sodium sulfate, filtered and concentrated. Purification by silica gel chromatography (100% hexanes→70% hexanes/ethyl acetate) gave the title compound (1.84 g). MS 372.0 (M+1).

Step C: 3-(5-fluoropyridin-2-yl)-5-[(R or S)-2,2,2-trifluoro-1-hydroxyethyl]benzoic acid To a solution of tert-butyl 3-(5-fluoropyridin-2-yl)-5-(2,2,2-trifluoro-1-hydroxyethyl)benzoate (1.84 g, 4.96 mmol) in dichloromethane (4 mL) was added trifluoroacetic acid (4 mL). The mixture was stirred at ambient temperature. After 18 h, the mixture was concentrated to dryness to give the trifluoroacetate salt of the title compound (2.2 g). MS 316.0 (M+1).

Step D: 3-(5-Fluoropyridin-2-yl)-N-{(1R)-1-[1-oxido-6-(trifluoromethyl)pyridin-3-yl]ethyl}-5-[(R or S)-2,2,2-trifluoro-1-hydroxyethyl]benzamide To a solution of 3-(5-fluoropyridin-2-yl)-5-(2,2,2-trifluoro-1-hydroxyethyl)benzoic acid (60.0 mg, 0.14 mmol) in DMF (1.5 mL) were added hydrochloride salt of (1R)-1-[1-oxido-6-(trifluoromethyl)pyridin-3-yl]ethanamine (54.5 mg, 0.20 mmol), EDC (53.7 g, 0.28 mmol), HOAT (19.1 mg, 0.14 mmol) and triethylamine (0.14 mL, 0.98 mmol). The mixture was stirred at 60° C. After 1 h, the mixture was cooled to ambient temperature and saturated aqueous NaHCO$_3$ was added. The mixture was extracted with ethyl acetate (3×). The combined organic extracts were washed with brine, dried over sodium sulfate, filtered and concentrated. Purification by reverse phase chromatography (C-18, 95% water/acetonitrile→5% water/acetonitrile with 0.025% trifluoroacetic acid). The product was treated with HCl (2.0 M in ether) to give the hydrochloride salt of the title compound (60 mg). HRMS 504.1161 (M+1). $^1$H NMR (400 MHz, CD$_3$OD): δ 8.69 (d, J=2.8 Hz, 1H); 8.49-8.44 (m, 2H); 8.28 (s, 1H); 8.15-8.08 (m, 2H); 7.99-7.86 (m, 2H); 7.68 (d, J=8.4 Hz, 1H); 5.23 (dq, J=14.2, 6.8 Hz, 2H); 1.63 (d, J=7.1 Hz, 3H).

Example 2.9

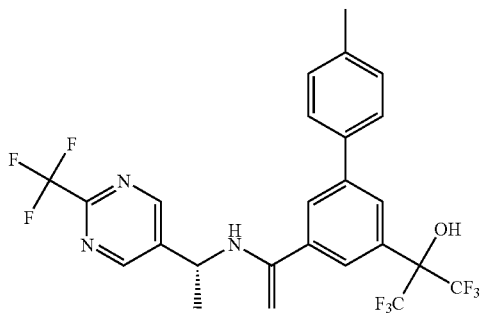

4'-Methyl-5-[2,2,2-trifluoro-1-hydroxy-(trifluoromethyl)ethyl]-N-{(1R)-1-[2-(trifluoromethyl)pyrimidine-5-yl]ethyl}biphenyl-3-carboxamide Step A: tert-butyl 4'-methyl-5-[2,2,2-trifluoro-1-hydroxy-1-(trifluoromethyl)ethyl]biphenyl-3-carboxylate To a mixture of tert-butyl 3-bromo-5-[2,2,2-trifluoro-1-hydroxy-1-(trifluoromethyl)ethyl]benzoate (1.2 g, 2.8 mmol) from Example 2.11 step B, (4-methylphenyl)boronic acid (0.5 g, 3.7 mmol), Pd[P(Ph$_3$)]$_4$ (0.16 g, 0.14 mmol), and K$_2$CO$_3$ (1.2 g, 8.5 mmol) under N$_2$ was added 28 mL of degassed n-Propanol/water (4:1). The reaction was heated to 85° C. overnight. The mixture was cooled to room temperature, filtered over celite and concentrated. The crude material was taken up in EtOAc and sat. NaHCO$_3$. The organic layer was extracted (3×) and washed with brine. The final organic layer was dried over Na$_2$SO$_4$, filtered and concentrated to 1.0 g of crude material. Purification using automated flash chromatography (SiO2, 120 g, 0-5% MeOH/DCM) gave, upon concentration, title product.

Step B: 4'-methyl-5-[2,2,2-trifluoro-1-hydroxy-1-(trifluoromethyl)ethyl]biphenyl-3-carboxylic acid To a DCM (7.8 mL) solution of tert-butyl 4'-methyl-5-[2,2,2-trifluoro-1-hydroxy-1-(trifluoromethyl)ethyl]biphenyl-3-carboxylate (0.6 g, 1.5 mmol) from step A was added trifluoroacetic acid (7.8 mL). The mixture was stirred at rt for 2 h and concentrated to dryness. The crude title compound was used in step C without further purification.

Step C: 4'-methyl-5-[2,2,2-trifluoro-1-hydroxy-(trifluoromethyl)ethyl]-N-{(1R)-1-[2-(trifluoromethyl)pyrimidine-5-yl]ethyl}biphenyl-3-carboxamide To a DMF solution (0.88 mL) containing 4'-methyl-5-[2,2,2-trifluoro-1-hydroxy-1-(trifluoromethyl)ethyl]biphenyl-3-carboxylic acid (50 mg, 0.13 mmol), HOAt (0.2 mL, 0.13 mmol), DIPEA (0.05 mL, 0.26 mmol), and (1R)-1-[2-(trifluoromethyl)pyrimidin-5-yl]ethanamine (45 mg, 0.24 mmol) was added EDC (38 mg, 0.20 mmol). The reaction was stirred at room temperature overnight, filtered and purified by RP-HPLC. The product fractions were combined and freeze-dried to give example 2B as a white solid: $^1$H NMR (CD$_3$OD, 400 MHz) δ 9.22 (d, J=6.8 Hz, 1H), 8.99 (s, 1H), 8.18 (m, 2H), 8.06 (s, 1H), 7.54 (d, J=8.15 Hz, 2H), 7.29 (d, J=7.9 Hz, 2H), 5.34 (quint, J=7.0 Hz, 1H), 2.37 (s, 3H), 1.68 (d, J=7.1 Hz, 3H); HRMS (ES, M+H) calcd for C$_{24}$H$_{18}$F$_9$N$_3$O$_2$: 552.1328. found: 552.1314.

Example 2.13

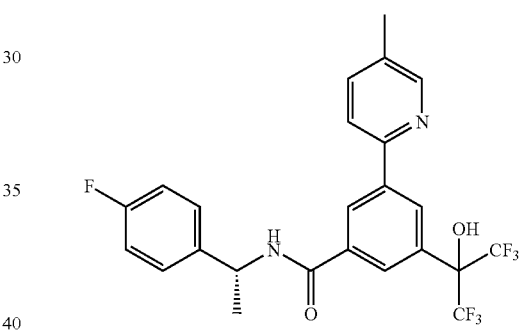

N-[(1R)-1-(4-Fluorophenyl)ethyl]-3-(5-methylpyridin-2-yl)-5-[2,2,2-trifluoro-1-hydroxy-1-(trifluoromethyl)ethyl]benzamide Step A: tert-Butyl 3-bromo-5-(trifluoroacetyl)benzoate Dess-Martin reagant (7.8 g, 18.6 mmol) was added to a solution of tert-Butyl 3-bromo-5-[(R/S)-2,2,2-trifluoro-1-hydroxyethyl]benzoate (4.4 g, 12.4 mmol) in DCM (75 mL). The reaction was stirred for one hour and saturated aq. Na$_2$S$_2$O$_3$ and aq. NaHCO$_3$ were added. The reaction was extracted with DCM (3×) and the organic layers combined and washed with brine, dried over Na$_2$SO$_4$ and concentrated to dryness. Purification using automated flash chromatography (SiO2, 120 g, 0-10% MeOH(NH$_4$OH)/DCM) gave final compound as a mixture of hydrate and ketone which was used directly in step B.

Step B: tert-butyl 3-bromo-5-[2,2,2-trifluoro-1-hydroxy-1-(trifluoromethyl)ethyl]benzoate tert-Butyl 3-bromo-5-(trifluoroacetyl)benzoate (1.0 g, 2.8 mmol) was dissolved in THF (28 mL) and trifluoromethyltrimethylsilane (2.0 g, 14.1 mmol) added. The mixture was cooled to 0° C. and TBAF (0.07 g, 0.28 mmol) was added dropwise. After stirring for 15 minute additional TBAF (0.74 g, 2.8 mmol) was added. The mixture was stirred for an additional 15 minutes, allowed to warm to rt and then quenched with 1N HCl, diluted with EtOAc and the layers separated. The organic layer was washed with brine, dried over $Na_2SO_4$ and concentrated to give title compound which was used directly step C.

Step C: tert-butyl 3-(5-methylpyridin-2-yl)-5-[2,2,2-trifluoro-1-hydroxy-1-(trifluoromethyl)ethyl]benzoate To a solution of tert-butyl 3-bromo-5-[2,2,2-trifluoro-1-hydroxy-1-(trifluoromethyl)ethyl]benzoate (1.2 g, 2.8 mmol) in 0.6 mL of dioxane under $N_2$ was added 5-methyl-2-pyridyl zinc bromide (0.5M, 11.3 mL, 5.67 mmol). The reaction was heated to 70° C. for two hours. An additional 0.5 equivalents of zinc reagent was added and the mixture stirred at 70° C. overnight. The mixture was cooled and concentrated. The crude material was taken up in EtOAc and sat. $NaHCO_3$ and sat. Rochelle's salt added. The organic layer was extracted and washed with Rochelle's salt (2×) followed by brine. The final organic layer was dried over $Na_2SO_4$, filtered and concentrated to 1.01 g of crude material. Purification using automated flash chromatography (SiO2, 120 g, 0-5% MeOH/DCM) gave, upon concentration, title product. LC-MS (M+H)=436.1

Step D: 3-(5-methylpyridin-2-yl)-5-[2,2,2-trifluoro-1-hydroxy-1-(trifluoromethyl)ethyl]benzoic acid To a 0° C. DCM (6.8 mL) solution of tert-butyl 3-(5-methylpyridin-2-yl)-5-[92,2,2-trifluoro-1-hydroxy-1-(trifluoromethyl)ethyl]benzoate (0.6 g, 1.38 mmol) from step C was added trifluoroacetic acid (6.9 mL). The mixture was warmed to rt over 2 h and concentrated to dryness to give a gummy solid. The crude title compound was used in step E without further purification. LC-MS (M+H)=380.1

Step E: N-[(1R)-1-(4-Fluorophenyl)ethyl]-3-(5-methylpyridin-2-yl)-5-[2,2,2-trifluoro-1-hydroxy-1 (trifluoromethyl)ethyl]benzamide To a DMF solution (2.6 mL) containing 3-(5-methylpyridin-2-yl)-5-[92,2,2-trifluoro-1-hydroxy-1-(trifluoromethyl)ethyl]benzoic acid (100 mg, 0.26 mmol), HOAt (17 mg, 0.13 mmol), DIPEA (0.09 mL, 0.53 mmol), and 1R-1-4-fluorophenylethyl amine (55 mg, 0.40 mmol) was added EDC (66 mg, 0.34 mmol). The reaction was heated in an Optimizer PC microwave at 150° C. for 2 min, cooled, and purified by RP-HPLC. The product fractions were combined and poured onto sat. $NaHCO_3$ and EtOAc. The organic layer was washed with brine, dried over $Na_2SO_4$ and evaporated to dryness to give example 1B as a white solid: $^1$H NMR (CDCl$_3$, 400 MHz) δ 8.46 (s, 1H), 8.36 (s, 1H), 8.27 (s, 1H), 8.15 (s, 1H), 7.59 (s, 2H), 7.31 (t, J=7.6 Hz, 2H), 6.98 (t, J=8.8 Hz, 2H), 6.75 (br s, 1H), 6.68 (d, J=7.2 Hz, 1H), 5.28 (quint, J=6.4, 1H) 2.38 (s, 3H), 1.56 (d, J=6.8 Hz, 3H); HRMS (ES, M+H) calcd for $C_{24}H_{19}F_7N_2O_2$; 501.1418. found: 501.1408.

Example 3.7

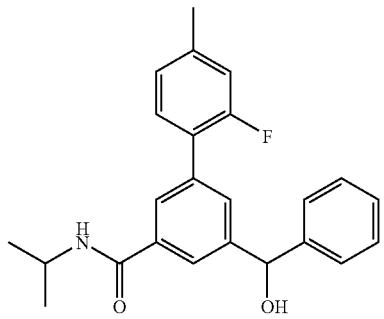

2'-Fluoro-5-[hydroxy(phenyl)methyl]-N-isopropyl-4'-methylbiphenyl-3-carboxamide

To a 0° C. THF solution (1 mL) of Intermediate 4 (2'-fluoro-5-formyl-N-isopropyl-4'-methylbiphenyl-3-carboxamide, 50 mg, 0.17 mmol) was added PhMgBr (1M, 330 μL, 0.33 mmol) dropwise. The solution was warmed to rt and allowed to stir for 16 h. At this time the mixture was quenched with aq. $NH_4Cl$ and extracted with EtOAc (2×). The combined organics washed with brine, dried over $Na_2SO_4$ and concentrated via rotary evaporation. The crude material was purified by RP-HPLC (AcCN/water with 0.1% TFA). The product containing fractions were freeze-dried to give 35 mg of final compound as a colorless powder (56%): $^1$H NMR (CD$_3$OD, 400 MHz) δ 7.83 (d, J=1.3, 1H), 7.70 (d, J=1.4, 1H), 7.41 (m, 2H), 7.2-7.4 (m, 5H), 7.04 (d, J=7.8, 1H), 7.00 (d, J=12, 1H), 5.86 (s, 1H), 4.20 (sept, J=6.4, 1H), 2.36 (s, 3H), 1.23 (d, J=6.9, 6H); HRMS (ES, M+H) calcd for $C_{24}H_{25}FNO_2$: 378.1791. found: 378.1856.

Example 4.1

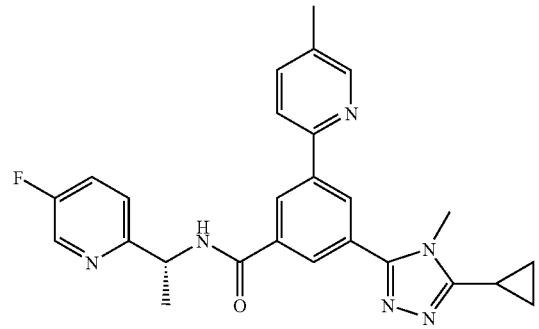

3-(5-Cyclopropyl-4-methyl-4H-1,2,4-triazol-3-yl)-N-[(1R)-1-(5-fluoropyridin-2-yl)ethyl]-5-(5-methylpyridin-2-yl)benzamide Step A: tert-Butyl methyl 5-(5-methylpyridin-2-yl)isophthalate To a solution of tert-butyl methyl 5-bromoisophthalate (10.6 g, 33.6 mmol) and bis(tri-tert-butylphosphine)palladium(0) (0.31 g, 0.61 mmol) in tetrahydrofuran (160 mL) was added 5-methyl-2-pyridylzinc bromide (0.5 M in THF; 121 mL, 60.5 mmol). The reaction mixture was heated to 60° C. After 18 h, the reaction was cooled to ambient temperature. Aqueous ethylenediaminetetraacetic acid tripotassium salt (0.4 M, 100 mL) and dichloromethane (100 mL) were added. The mixture was stirred for 15 min and the organic solvent was evaporated. The mixture was extracted with dichloromethane (3×). The combined organic extracts were washed with brine, dried over magnesium sulfate, filtered and concentrated. Purification by silica gel chromatography (99% hexanes/ethyl acetate→50% hexanes/ethyl acetate) gave the title compound. MS 328.1 (M+1).

Step B: 3-tert-Butoxycarbonyl)-5-(5-methylpyridin-2-yl)benzoic acid

To a solution of tert-butyl methyl 5-(5-methylpyridin-2-yl) isophthalate (1.2 g, 3.67 mmol) in methanol (20 mL) was added sodium hydroxide (1.0 M; 3.67 mL, 3.67 mmol). The reaction mixture was stirred at ambient temperature. After 18 h, saturated aqueous ammonium chloride was added and the mixture was extracted with dichloromethane (3×). The combined organic extracts were washed with brine, dried over magnesium sulfate, filtered and concentrated gave the title compound. MS 314.1 (M+1).

Step C: tert-Butyl 3-[(methylamino)carbonyl]-5-(5-methylpyridin-2-yl)benzoate

To a solution of 3-tert-butoxycarbonyl)-5-(5-methylpyridin-2-yl)benzoic acid (1.15 g, 3.67 mmol) in N,N-dimethylformamide (36 mL) were added methanamine (5.51 mL, 11.01 mmol), EDC (2.11 g, 11.01 mmol), HOBT (1.12 g, 7.34 mmol) and diisopropylethylamine (2.56 mL, 14.68 mmol). The reaction mixture was stirred at ambient temperature. After 18 h, water was added and the mixture was extracted with ethyl acetate (3×). The combined organic extracts were washed with water (2×), brine, dried over sodium sulfate, filtered and concentrated. Purification by silica gel chromatography (100% hexanes→30% hexanes/ethyl acetate) gave the title compound. MS 327.1 (M+1).

Step D: tert-Butyl 3-[(methylamino)carbonothioyl]-5-(5-methylpyridin-2-yl)benzoate To a solution of tert-butyl 3-[(methylamino)carbonyl]-5-(5-methylpyridin-2-yl)benzoate (1.0 g, 3.06 mmol) in dichloroethane (8 mL) was added 2,4-bis(4-methoxyphenyl)-1,3,2,4-dithiadiphosphetane 2,4-disulfide (0.68 g, 1.69 mmol). The reaction mixture was heated to 50° C. After 3 h, saturated aqueous sodium bicarbonate was added and the mixture was extracted with dichloromethane (3×). The combined organic extracts were washed with brine, dried over magnesium sulfate, filtered and concentrated. Purification by silica gel chromatography (100% dichloromethane→90% dichloromethane/methanol) gave the title compound. MS 343.0 (M+1).

Step E: tert-Butyl 3-(5-cyclopropyl-4-methyl-4H-1,2,4-triazol-3-yl)-5-(5-methylpyridin-2-yl)benzoate To a solution of tert-butyl 3-[(methylamino)carbonothioyl]-5-(5-methylpyridin-2-yl)benzoate (0.56 g, 1.64 mmol) in tetrahydrofuran (15 mL) were added cyclopropanecarbohydrazide (0.49 g, 4.92 mmol) and mercury(II) acetate (1.05 g, 3.28 mmol). The reaction mixture was heated to 40° C. After 18 h, the mixture was cooled to ambient temperature. The mixture was filtered and the filtrate was concentrated. Purification by silica gel chromatography (100% dichloromethane→95% dichloromethane/methanol) gave the title compound. MS 391.1 (M+1).

Step F: 3-(5-Cyclopropyl-4-methyl-4H-1,2,4-triazol-3-yl)-5-(5-methylpyridin-2-yl)benzoic acid To a solution of tert-butyl 3-(5-cyclopropyl-4-methyl-4H-1,2,4-triazol-3-yl)-5-(5-methylpyridin-2-yl)benzoate (0.38 g, 0.97 mmol) in methyl alcohol (10 mL) was added trifluoroacetic acid (5.0 mL, 67.3 mmol) and hydrogen chloride (4.0 M in dioxane; 5.0 mL, 20.0 mmol). The reaction mixture was stirred at ambient temperature. After 18 h, the mixture was concentrated and dried under reduced pressure gave the hydrochloride salt of the title compound. MS 335.1 (M+1).

Step G: 3-(5-Cyolopropyl-4-methyl-4H-1,2,4-triazol-3-yl)-N-[(1R)-1-(5-fluoropyridin-2-yl)ethyl]-5-(5-methylpyridin-2-yl)benzamide To a solution of 3-(5-cyclopropyl-4-methyl-4H-1,2,4-triazol-3-yl)-5-(5-methylpyridin-2-yl)benzoic acid (25 mg, 0.08 mmol) in N,N-dimethylformamide (0.7 mL) were added (1R)-1-(5-fluoropyridin-2-yl)ethanamine hydrochloride salt (15.9 mg, 0.09 mmol), EDC (43.0 mg, 0.22 mmol), HOBT (34.3 mg, 0.22 mmol) and triethylamine (65.3 μL, 0.37 mmol). The reaction mixture was stirred at ambient temperature. After 18 h, the solid in the mixture was filtered off. Purification by reverse phase chromatography (C-18, 95% water/acetonitrile→5% water/acetonitrile with 0.1% trifluoroacetic acid) gave the trifluoroacetate salt of the title compound. HRMS 457.2156 (M+1). $^1$H NMR (500 MHz, DMSO-$d_6$): δ 9.20 (d, J=7.6 Hz, 1H); 8.78-8.73 (m, 1H); 8.59 (s, 1H); 8.54-8.51 (m, 2H); 8.24-8.23 (m, 1H); 8.08 (d, J=8.1 Hz, 1H); 7.82 (dd, J=8.1, 2.2 Hz, 1H); 7.74-7.68 (m, 1H); 7.54 (dd, J=8.8, 4.5 Hz, 1H); 5.31-5.24 (m, 1H); 3.79 (s, 3H); 2.38 (s, 3H); 2.20-2.13 (m, 1H); 1.56 (d, J=7.1 Hz, 3H); 1.16-1.10 (m, 2H); 1.06-1.01 (m, 2H).

Example 4.14

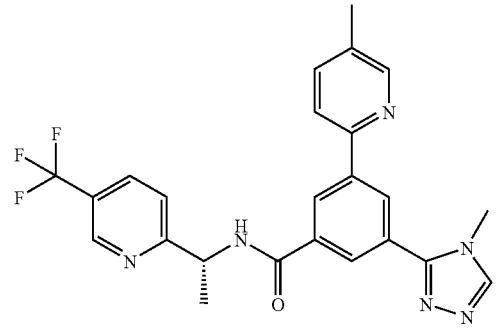

3-(5-Methylpyridin-2-yl)-5-(4-methyl-4H-1,2,4-triazol-3-yl)-N-{(1R)-1-[5-(trifluoromethyl)pyridin-2-yl]ethyl}benzamide Step A: 3-(Methoxycarbonyl)-5-(5-methylpyridin-2-yl)benzoic acid To a solution of tert-butyl methyl 5-(5-methylpyridin-2-yl) isophthalate in dichloromethane (75 mL) was added 25 mL of trifluoroacetic acid. After 16 h, the reaction was concentrated and dried under vacuum to give TFA salt of the title compound (6.5 g). MS 272.1 (M+1).

Step B: Methyl 3-[(methylamino)carbonyl]-5-(5-methylpyridin-2-yl)benzoate

To a solution of 3-(methoxycarbonyl)-5-(5-methylpyridin-2-yl)benzoic acid (1.85 g, 6.82 mmol) in N,N-dimethylformamide (20 mL) was added 2 M ammonia in dioxane (10.2 mL, 20.4 mmol), EDC (2.61 g, 13.6 mmol), HOBT (2.09 g, 13.6 mmol) and N,N-diisopropylethylamine (4.76 mL, 27.3 mmol). After 16 h, the reaction was concentrated and the residue was dissolved in 200 ml of dichloromethane. The mixture was washed with 100 mL of saturated aqueous sodium bicarbonate solution (2×) and brine (100 ml). The combined organic extracts were dried over sodium sulfate, filtered and concentrated. The residue was purified by silica gel chromatography (1% ethyl acetate/hexane→60% ethyl acetate/hexane) to give the title compound (1.82 g). MS 285.1 (M+1).

Step C: Methyl 3-[(methylamino)carbonothioyl]-5-(5-methylpyridin-2-yl)benzoate To a solution of methyl 3-[(methylamino)carbonyl]-5-(5-methylpyridin-2-yl)benzoate (2.90 g, 10.2 mmol) in dichloroethane (20 mL) was added 2,4-bis-(4-methoxyphenyl)-1,3-dithia-2,4-diphosphetane 2,4-disulfide (Lawesson's reagent) (2.27 g, 5.61 mmol) and the mixture heated to 60° C. After 2 h, the reaction was cooled to ambient temperature. Dichloromethane (200 mL) was added, and the mixture washed with 100 mL of saturated aqueous sodium bicarbonate (2×) and brine (100 mL). The combined organic extracts were dried over sodium sulfate, filtered and concentrated. The residue was purified by silica gel chromatography (100% dichloromethane→90% dichloromethane/methanol) to give the title compound (1.9 g). MS 301.0 (M+1).

Step D: Methyl 3-(5-methylpyridin-2-yl)-5-(4-methyl-4H-1,2,4-triazol-3-yl)benzoate To a solution of methyl 3-[(methylamino)carbonothioyl]-5-(5-methylpyridin-2-yl)benzoate (0.90 g, 3.00 mmol) in THF (30 mL) was added formic hydrazide (0.54 g, 8.99 mmol) and mercury acetate (1.72 g, 5.39 mmol) and the mixture heated to 40° C. After 16 h, the reaction was cooled to ambient temperature, filtered and concentrated. The organic residue was dissolved in 100 ml of dichloromethane and washed with 50 mL of saturated aqueous sodium bicarbonate (2×). The combined organic extracts were dried over sodium sulfate, filtered and concentrated. The residue was purified by silica gel chromatography (100% dichloromethane→90% dichloromethane/methanol) to give the title compound (0.37 g). MS 309.1 (M+1).

Step E: 3-(5-Methylpyridin-2-yl)-5-(4-methyl-4H-1,2,4-triazol-3-yl)benzoic acid To a solution of methyl 3-(5-methylpyridin-2-yl)-5-(4-methyl-4H-1,2,4-triazol-3-yl)benzoate (0.37 g, 1.20 mmol) in THF (5 mL) was added lithium hydroxide (86 mg, 3.60 mmol) in 5 mL of water. After 16 h, the reaction was acidified to pH 1 by 1 M HCl. The solution was concentrated and dried under vacuum to give the hydrochloride salt of the title compound (0.43 g). MS 295.0 (M+1).

Step F: 3-(5-Methylpyridin-2-yl)-5-(4-methyl-4H-1,2,4-triazol-3-yl)-N-{(1R)-1-[5-(trifluoromethyl)pyridin-2-yl]ethyl}benzamide To a solution of 3-(5-methylpyridin-2-yl)-5-(4-methyl-4H-1,2,4-triazol-3-yl)benzoic acid (30.0 mg, 0.102 mmol) in N,N-dimethylformamide (2 mL) was added the hydrochloride salt of (1R)-1-[5-(trifluoromethyl)pyridin-2-yl]ethanamine (40.0 mg, 0.153 mmol), EDC (39.1 mg, 0.204 mmol), HOBT (31.2 mg, 0.204 mmol) and N,N-diisopropylethylamine (89 µL, 0.510 mmol). After 16 h, the reaction was purified by reverse phase HPLC (C-18, 95% water/acetonitrile→5% water/acetonitrile with 0.1% trifluoroacetic acid) to give the TFA salt of the title compound (46 mg). HRMS 467.1807 (M+1). $^1$H NMR (500 MHz, DMSO-d$_6$): δ 9.30 (d, J=7.3 Hz, 1H); 8.94 (s, 1H); 8.77 (s, 1H); 8.76 (t, J=1.7 Hz, 1H); 8.59 (s, 1H); 8.57 (t, J=1.6 Hz, 1H); 8.31 (t, J=1.6 Hz, 1H); 8.20 (dd, J=8.3, 2.3 Hz, 1H); 8.08 (d, J=8.1 Hz, 1H); 7.82 (dd, J=8.1, 2.2 Hz, 1H); 7.69 (d, J=8.3 Hz, 1H); 5.36-5.27 (m, 1H); 3.84 (s, 3H); 2.38 (s, 3H); 1.59 (d, J=7.1 Hz, 3H).

Example 4.46

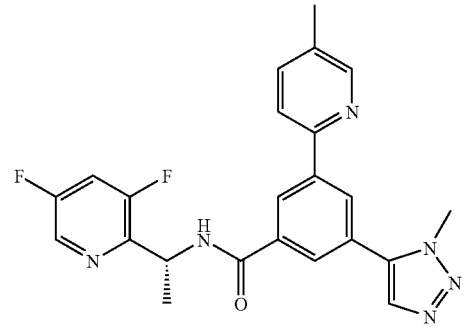

N-[(1R)-1-(3,5-Difluoropyridin-2-yl)ethyl]-3-(5-methylpyridin-2-yl)-5-(1-methyl-1H-1,2,3-triazol-5-yl)benzamide

Step A: Methyl 3-ethynyl-5-(5-methylpyridin-2-yl)benzoate

To a degassed solution of methyl 3-bromo-5-(5-methylpyridin-2-yl)benzoate (200 mg, 0.653 mmol) in dioxane (3 mL) was added tributyl(ethynyl)tin (247 mg, 0.784 mmol), cesium fluoride (198 mg, 1.31 mmol) and bis(tri-t-butylphosphine)palladium (16.7 mg, 0.033 mmol) and the mixture heated to 70° C. After 2 h, the reaction was cooled to ambient temperature and dichloromethane (50 mL was added). The organic layer was washed with 30 mL of saturated aqueous sodium bicarbonate (2×), dried over sodium sulfate, filtered and concentrated. The residue was purified by silica gel chromatography (100% dichloromethane→95% dichloromethane/methanol) to give the title compound (145 mg). MS 252.1 (M+1).

Step B: Methyl 3-(5-methylpyridin-2-yl)-5-{1-[(trimethylsily)methyl]-1H-1,2,3-triazol-5-yl}benzoate To a degassed solution of methyl 3-ethynyl-5-(5-methylpyridin-2-yl)benzoate (124 mg, 0.493 mmol) in benzene (12 mL) were added trimethylsilylmethylazide (96 mg, 0.740 mmol) and pentamethylcyclopentadienylbis(triphenylphosphine)ruthenium(II) chloride (59 mg, 0.074 mmol) and the mixture heated to 80° C. in a sealed tube. After 16 h, the title compound was showed as the major isomer (10:1 isomeric ratio) in the reaction. The reaction was concentrated and purified by reverse-phase HPLC gave the title compound (120 mg). MS 381.1 (M+1).

Step C: Methyl 3-(5-methylpyridin-2-yl)-5-(1-methyl-1H-1,2,3-triazol-5-yl)benzoate To a solution of methyl 3-(5-methylpyridin-2-yl)-5-{1-[(trimethylsilyl)methyl]-1H-1,2,3-triazol-5-yl}benzoate (122 mg, 0.321 mmol) in THF (5 mL) was added 2 M tetrabutylammonium fluoride in THF (1.60 mL, 3.20 mmol). After 16 h, the mixture was distributed between 100 ml of dichloromethane and 100 ml of 1 M ammonium chloride solution. The organic layer was washed with 50 mL of brine and concentrated to give title compound (85 mg). MS 309.1 (M+1).

Step D: 3-(5-Methylpyridin-2-yl)-5-(1-methyl-1H-1,2,3-triazol-5-yl)benzoic acid To a solution of methyl 3-(5-methylpyridin-2-yl)-5-(1-methyl-1H-1,2,3-triazol-5-yl)benzoate (85 mg, 0.276 mmol) in THF (5 mL) was added 1 M aqueous sodium hydroxide (0.827 mL, 0.827 mmol) and water (4 mL). After 16 h, the reaction was acidified to pH 1 by 1 M HCl. The solution was concentrated and dried under vacuum to give the hydrochloride salt of title compound (95 mg). MS 295.0 (M+1).

Step E: N-[(1R)-1-(3,5-Difluoropyridin-2-yl)ethyl]-3-(5-methylpyridin-2-yl)-5-(1-methyl-1H-1,2,3-triazol-5-yl)benzamide To a solution of 3-(5-methylpyridin-2-yl)-5-(1-methyl-1H-1,2,3-triazol-5-yl)benzoic acid (20 mg, 0.068 mmol) in N,N-dimethylformamide (1 mL) was added the hydrochloride salt of (1R)-1-(3,5-difluoropyridin-2-yl)ethanamine (31.4 mg, 0.136 mmol), EDC (39.1 mg, 0.204 mmol), HOBT (31.2 mg, 0.204 mmol) and N,N-diisopropylethylamine (59.3 µL, 0.340 mmol). After 16 h, the reaction mixture was purified by reverse phase HPLC (C-18, 95% water/acetonitrile→5% water/acetonitrile with 0.1% trifluoroacetic acid) to give the TFA salt of the title compound (27.2 mg). HRMS 435.1739 (M+1). $^1$H NMR (500 MHz, DMSO-$d_6$) δ 9.13 (d, J=7.2 Hz, 1H); 8.67-8.64 (m, 1H); 8.57 (s, 1H); 8.49 (d, J=2.4 Hz, 1H); 8.39-8.37 (m, 1H); 8.10 (t, J=1.6 Hz, 1H); 8.07 (d, J=8.1 Hz, 1H); 8.04 (s, 1H); 7.96-7.89 (m, 1H); 7.79 (dd, J=8.1, 2.2 Hz, 1H); 5.54-5.46 (m, 1H); 4.13 (s, 3H); 2.37 (s, 3H); 1.54 (d, J=7.0 Hz, 3H).

Example 4.105

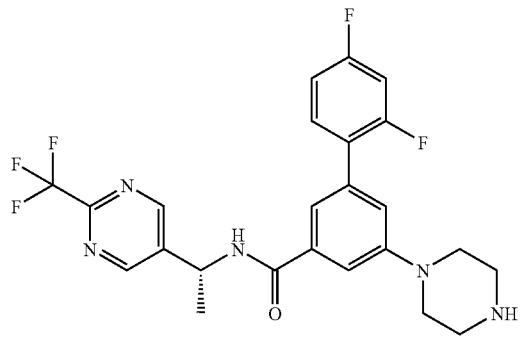

2',4'-Difluoro-5-piperazin-1-yl-N-{(1R)-1-[2-(trifluoromethyl)pyrimidin-5-yl]ethyl}biphenyl-3-carboxamide

Step A: Methyl 5-bromo-2',4'-fluoro-4'-difluorobiphenyl-3-carboxylate

To a solution of methyl-3-bromo-5-iodobenzoate (2.12 g, 6.21 mmol) in N,N-dimethylformamide (31 mL) and water (10 mL) was added (2,4-difluorophenyl)boronic acid (1.03 g, 6.53 mmol), palladium acetate (70 mg, 0.31 mmol), triphenylphosphine-3,3',3"-trisulfonic acid trisodium salt hydrate (529 mg, 0.93 mmol), and diisopropylamine (1.33 mL, 9.31 mmol) and the mixture heated to 80° C. After 1.5 h, the reaction was cooled to ambient temperature. Ethyl acetate was added and the mixture was extracted with water (3x). The organic layer was washed with brine, dried over sodium sulfate, filtered and concentrated to give the title compound (1.92 g).

Step B: tert-Butyl 4-[2',4'-difluoro-5-methoxycarbonyl)biphenyl-3-yl]piperazine-1-carboxylate To a solution of methyl 5-bromo-2',4'-fluoro-4'-difluorobiphenyl-3-carboxylate (388 mg, 1.19 mmol) in N,N-dimethylacetamide (5 mL) was added tert-butyl piperazine-1-carboxylate (276 mg, 1.48 mmol), cesium carbonate (773 mg, 2.37 mmol), palladium dibenzylidene acetone (27.2 mg, 0.030 mmol), and 2-dicyclohexylphosphino-2',4',6'-triisopropyl-1,1'biphenyl (XPhos; 42.4 mg, 0.089 mmol) and the mixture heated to 90° C. After 2 h the reaction was allowed to cool to ambient temperature. Ethyl acetate was added and the mixture was extracted with water (3x). The organic layer was washed with brine, dried over sodium sulfate, filtered and concentrated. Purification by silica gel chromatography (100% hexanes→75% hexanes/ethyl acetate) gave the title compound (493 mg). MS 433.2 (M+1).

Step C: 5-[4-(tert-Butoxycarbonyl)piperazin-1-yl]-2',4'-difluorobiphenyl-3-carboxylic acid To a solution of tert-butyl 4-[2',4'-difluoro-5-methoxycarbonyl)biphenyl-3-yl]piperazine-1-carboxylate (493 mg, 1.14 mmol) in tetrahydrofuran (10 mL) and water (5 mL) was added 1 M sodium hydroxide (1.71 mL, 1.71 mmol) and stirred at ambient temperature. After 16 h, the reaction was acidified with 1 M hydrochloric acid (1.71 mL, 1.71 mmol).

Extraction with dichloromethane gave the title compound (483 mg). MS 319.1 (M-Boc).

Step D: 2',4'-Difluoro-5-piperazin-1-yl-N-{(1R)-1-[2-(trifluoromethyl)pyrimidin-5-yl]ethyl}biphenyl-3-carboxamide To a solution of 5-[4-(tert-butoxycarbonyl)piperazin-1-yl]-2',4'-difluorobiphenyl-3-carboxylic acid (30.0 mg, 0.072 mmol), in N,N-dimethylformamide (1.0 mL) was added (1R)-1-[2-(trifluoromethyl)pyrimidin-5-yl]ethanamine dihydrochloride (22.7 mg, 0.086 mmol), EDC (17.8 mg, 0.093 mmol), HOBT (11.0 mg, 0.072 mmol) and diisopropylethylamine (0.038 mL, 0.215 mmol). After 16 h, the mixture was acidified with hydrochloric acid gas. After 15 min, the mixture was concentrated and purified by reverse phase HPLC (C-18, 95% water/acetonitrile→25% water/acetonitrile with 0.1% trifluoroacetic acid) to give the title compound (28.4 mg). HRMS 492.1833 (M+1). $^1$H NMR (500 MHz, CD$_3$OD): δ 9.00 (s, 2H); 7.57-7.50 (m, 1H); 7.47-7.43 (m, 2H); 7.24 (q, J=1.7 Hz, 1H); 7.09-7.03 (m, 2H); 5.33 (q, J=7.1 Hz, 1H); 3.25 (t, J=4.9 Hz, 4H); 3.00 (t, J=4.7 Hz, 4H); 1.68 (d, J=7.2 Hz, 3H).

Example 4.109

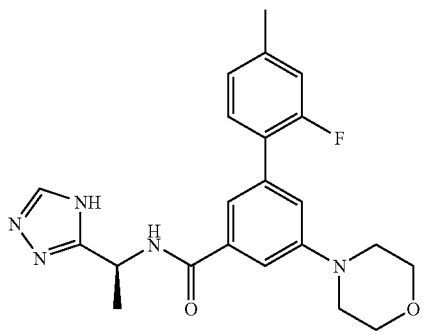

2'-Fluoro-4'-methyl-5-morpholin-4-yl-N-[(1R)-1-(1H-1,2,4-triazol-3-yl)ethyl]biphenyl-3-carboxamide Step A: Methyl 5-bromo-2'-fluoro-4'-methylbiphenyl-3-carboxylate To a solution of methyl-3-bromo-5-iodobenzoate (10.0 g, 29.3 mmol) in N,N-dimethylformamide (163 mL) at 0° C. was added 2-fluoro-4-methylphenyl)boronic acid (4.74 g, 30.8 mmol), sodium carbonate (2M in water; 22.0 mL, 44.0 mmol) and PdCl$_2$(dppf)·CH$_2$Cl$_2$ adduct and the mixture was allowed to warm to ambient temperature. After 16 h, the reaction was concentrated. Water and saturated aqueous sodium bicarbonate were added and the mixture was extracted with dichloromethane (3×). The combined organic extracts were washed with brine, dried over magnesium sulfate, filtered and concentrated. Purification by silica gel chromatography (100% hexanes→85% hexanes/ethyl acetate) gave the title compound. MS 323.0 (M).

Step B: 2'-Fluoro-4'methyl-5-morpholin-4-ylbiphenyl-3-carboxylic acid

To a solution of methyl 5-bromo-2'-fluoro-4'-methylbiphenyl-3-carboxylate (408.0 mg, 1.263 mmol) in N,N-dimethylacetamide (5 mL) was added morpholine (0.17 mL, 1.9 mmol), cesium carbonate (1.23 g, 3.79 mmol), palladium dibenzylidene acetone (116.0 mg, 0.13 mmol), and 2-dicyclohexylphosphino-2',4',6'-triisopropyl-1,1'biphenyl (XPhos; 90.0 mg, 0.19 mmol) and the mixture heated to 100° C. After 16 h the reaction was allowed to cool to ambient temperature, filtered with methanol, and sodium hydroxide (1M in water; 3.0 mL, 3.0 mmol) was added. After 16 h, reaction was concentrated, acidified with trifluoroacetic acid, and purified by reverse phase HPLC (C-18, 95% water/acetonitrile→20% water/acetonitrile with 0.1% trifluoroacetic acid). Extraction with dichloromethane and 1M aqueous hydrochloric acid gave the title compound. MS 316.1 (M+1).

Step C: 2'-Fluoro-4'-methyl-5-morpholin-4-yl-N-[(1R)-1-(1H-1,2,4-triazol-3-yl)ethyl]biphenyl-3-carboxamide To a solution of 2'-fluoro-4'methyl-5-morpholin-4-ylbiphenyl-3-carboxylic acid (52.0 mg, 0.15 mmol) in N,N-dimethylformamide (1.0 mL) was added (1R)-1-(1H-1,2,4-triazol-3-yl)ethanamine dihydrochloride (30.1 mg, 0.16 mmol), EDC (36.8 mg, 0.19 mmol), HOBT (22.6 mg, 0.15 mmol) and diisopropylethylamine (0.10 mL, 0.59 mmol). After 16 h, the mixture was purified by reverse phase HPLC (C-18, 95% water/acetonitrile→25% water/acetonitrile with 0.1% trifluoroacetic acid) to give the title compound. HRMS 410.1990 (M+1).). $^1$H NMR (500 MHz, CD$_3$OD): δ 9.37 (s, 1H); 7.86 (d, J=7.6 Hz, 2H); 7.67 (s, 1H); 7.45 (t, J=8.1 Hz, 1H); 7.13 (d, J=7.9 Hz, 1H); 7.07 (d, J=12.0 Hz, 1H); 5.52-5.47 (m, 1H); 4.00 (t, J=4.6 Hz, 4H); 3.52 (t, J=4.5 Hz, 4H); 2.40 (s, 3H); 1.79 (d, J=7.1 Hz, 3H).

Example 4.252

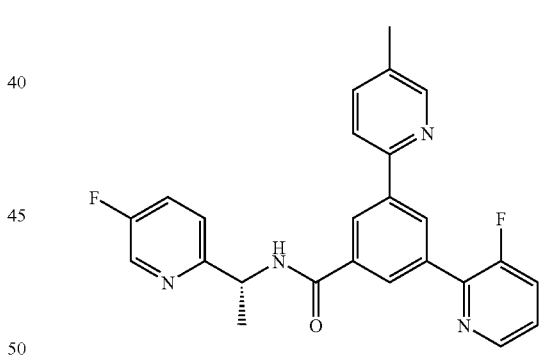

3-(3-Fluoropyridin-2-yl)-N-[(1R)-1-(5-fluoropyridin-2-yl)ethyl]-5-(5-methylpyridin-2-yl)benzamide Step A: Methyl 3-bromo-5-(5-methylpyridin-2-yl)benzoate To a solution methyl-3-bromo-5-iodobenzoate (10.0 g, 29.3 mmol) and 5-methyl-2-pyridylzinc bromide (0.5 M in THF; 64.5 mL, 32.3 mmol) in tetrahydrofuran (84 mL) was added tetrakis(triphenylphosphine)palladium(0) (1.70 g, 1.47 mmol). The reaction mixture was stirred at ambient temperature. After 6 h, saturated aqueous sodium bicarbonate was added. The mixture was extracted with ethyl acetate (3×). The combined organic extracts were washed with sodium potassium tartrate tetrahydrate (2×), brine, dried over magnesium sulfate, filtered and concentrated. Purification by silica gel chromatography (100% dichloromethane→95% dichloromethane/ethyl acetate) gave the title compound. MS 306.0 (M).

Step B: Methyl 3-(5-methylpyridin-2-yl)-5-(4,4,5,5-tetramethyl-1,3,2-dioxaborolan-2-yl)benzoate To a solution of methyl 3-bromo-5-(5-methylpyridin-2-yl)benzoate (3.5 g, 11.43 mmol) in dioxane (45.7 mL) were added bis(pinacolato)diboron (3.63 g, 14.29 mmol), dichloro[1,1'-bis(diphenylphosphino)ferrocene]palladium(II) dichloromethane adduct (0.47 g, 0.57 mmol) and potassium acetate (2.24 g, 22.86 mmol). The reaction mixture was heated to 80° C. After 18 h, the reaction was cooled to ambient temperature and the mixture was filtered through Celite. The filtrate was concentrated and saturated aqueous sodium bicarbonate was added. The mixture was extracted with ethyl acetate (3×). The combined organic extracts were washed with brine, dried over magnesium sulfate, filtered and concentrated. Purification by silica gel chromatography (100% dichloromethane→85% dichloromethane/ethyl acetate) gave the title compound. MS 354.1 (M+1).

Step C: Methyl 3-(3-fluoropyridin-2-yl)-5-(5-methylpyridin-2-yl)benzoate

To a solution of methyl 3-(5-methylpyridin-2-yl)-5-(4,4,5,5-tetramethyl-1,3,2-dioxaborolan-2-yl)benzoate (0.80 g, 2.27 mmol) in N,N-dimethylformamide (6.8 mL) and water (2.3 mL) were added 2-bromo-3-fluoropyridine (0.44 g, 2.49 mmol), palladium acetate (25.4 mg, 0.11 mmol), 3,3',3"-phosphinidynetris(benzenesulfonic acid)trisodium salt (0.19 g, 0.34 mmol) and diisopropylamine (0.81 mL, 5.66 mmol). The reaction mixture was heated to 80° C. After 18 h, the mixture was cooled to ambient temperature and the solid was filtered off. Purification by reverse phase HPLC (C-18, 95% water/acetonitrile→5% water/acetonitrile with 0.1% trifluoroacetic acid) gave the title compound. MS 323.0 (M+1).

Step D: 3-(3-Fluoropyridin-2-yl)-5-(5-methylpyridin-2-yl)benzoic acid

To a solution of methyl 3-(3-fluoropyridin-2-yl)-5-(5-methylpyridin-2-yl)benzoate (0.50 g, 1.55 mmol) in methyl alcohol (10 mL) was added sodium hydroxide (1.0 M; 4.65 mL, 4.65 mmol). After 2.5 h, hydrogen chloride (1.0 M; 4.65 mL, 4.65 mmol) was added and the mixture was concentrated to give the sodium chloride salt of the title compound. MS 309.1 (M+1).

Step E: 3-(3-Fluoropyridin-2-yl)-N-[(1R)-1-(5-fluoropyridin-2-yl)ethyl]-5-(5-methylpyridin-2-yl)benzamide To a solution of the sodium chloride salt of 3-(3-fluoropyridin-2-yl)-5-(5-methylpyridin-2-yl)benzoic acid (25.0 mg, 0.05 mmol) in N,N-dimethylformamide (0.35 mL) were added (1R)-1-(5-fluoropyridin-2-yl)ethanamine hydrochloride salt (16.5 mg, 0.08 mmol), EDC (14.9 mg, 0.08 mmol), HOBT (7.92 mg, 0.05 mmol) and triethylamine (21.6 µL, 0.16 mmol). The reaction mixture was stirred at ambient temperature. After 18 h, the mixture was cooled to ambient temperature. Purification by reverse phase HPLC (C-18, 95% water/acetonitrile→50% water/acetonitrile with 0.1% trifluoroacetic acid) gave the title compound. HRMS 431.1706 (M+1). $^1$H NMR (500 MHz, CDCl$_3$): δ 8.73 (q, J=1.6 Hz, 1H); 8.57-8.54 (m, 2H); 8.52 (t, J=1.7 Hz, 1H); 8.45 (q, J=1.5 Hz, 1H); 8.44 (d, J=2.8 Hz, 1H); 7.78 (d, J=8.1 Hz, 1H); 7.62-7.52 (m, 3H); 7.43-7.31 (m, 3H); 5.43 (p, J=7.0 Hz, 1H); 2.40 (s, 3H); 1.61 (d, J=6.8 Hz, 3H).

Example 4.302

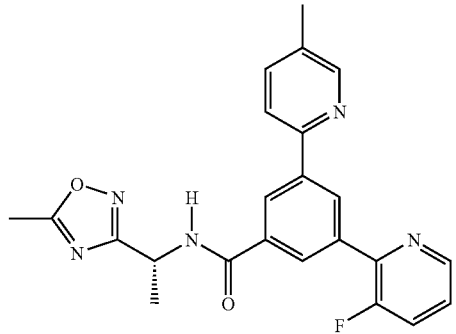

3-(3-Fluoropyridin-2-yl)-N-[(1R)-1-(5-methyl-1,2,4-oxadiazol-3-yl)ethyl]-5-(5-methylpyridin-2-yl)benzamide To a solution of 3-(3-fluoropyridin-2-yl)-5-(5-methylpyridin-2-yl)benzoic acid (37.8 mg, 0.113 mmol) in N,N-dimethylformamide (2 mL) was added (1R)-1-(5-methyl-1,2,4-oxadiazol-3-yl)ethanamine hydrochloride salt (23 mg, 0.141 mmol), EDC (54.2 mg, 0.283 mmol), HOBT (43.3 mg, 0.283 mmol) and N,N-diisopropylethylamine (74.1 µL, 0.424 mmol). After 16 h, the reaction mixture was purified by reverse phase HPLC (C-18, 95% water/acetonitrile→5% water/acetonitrile with 0.1% trifluoroacetic acid) to give the TFA salt of the title compound (51.6 mg). HRMS 418.1669 (M+1). $^1$H NMR (500 MHz, DMSO-d$_6$): δ 9.27 (d, J=7.8 Hz, 1H); 8.80 (d, J=1.8 Hz, 1H); 8.66-8.59 (m, 2H); 8.58 (s, 1H); 8.48 (d, J=1.8 Hz, 1H); 8.04 (d, J=8.1 Hz, 1H); 7.92 (ddd, J=11.6, 8.3, 1.3 Hz, 1H); 7.81 (dd, J=8.1, 2.2 Hz, 1H); 7.59-7.54 (m, 1H); 5.39-5.31 (m, 1H); 2.59 (s, 3H); 2.38 (s, 3H); 1.59 (d, J=7.1 Hz, 3H).

Example 4.426

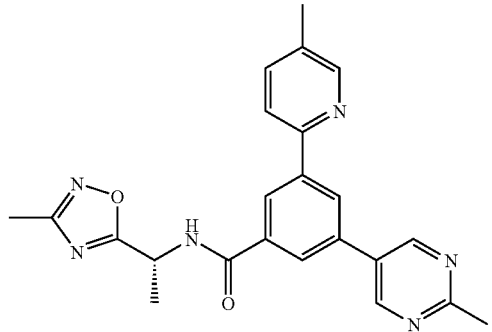

N-[(1R)-1-(3-Methyl-1,2,4-oxadiazol-5-yl)ethyl]-3-(5-methylpyridin-2-yl)-5-(2-methylpyrimidin-5-yl)benzamide

Step A: Methyl 3-(5-methylpyridin-2-yl)-5-(2-methylpyrimidin-5-yl)benzoate

To a solution of methyl 3-(5-methylpyridin-2-yl)-5-(4,4,5,5-tetramethyl-1,3,2-dioxaborolan-2-yl)benzoate (170 mg, 0.481 mmol) in N,N-dimethylformamide (1.44 mL) and water (0.481 mL) was added 5-bromo-2-methylpyrimidine (167 mg, 0.963 mmol), palladium(II) acetate (5.40 mg, 0.024 mmol), 3,3'3''-phosphinidynetris(benzenesulfonic acid)trisodium salt (41.0 mg, 0.072 mmol) and diisopropylamine (0.171 mL, 1.20 mmol) and the mixture was heated to 80° C. After 1 h, the reaction was allowed to cool to ambient temperature and filtered. Purification by reverse phase chromatography (C-18, 95% water/acetonitrile→50% water/acetonitrile with 0.1% trifluoroacetic acid) gave the title compound (100 mg). MS 320.1 (M+1).

Step B: 3-(5-Methylpyridin-2-yl)-5-(2-methylpyrimidin-5-yl)benzoic acid

To a solution of methyl 3-(5-methylpyridin-2-yl)-5-(2-methylpyrimidin-5-yl)benzoate (100 mg, 0.313 mmol) in methanol (1.57 mL) was added 1 M sodium hydroxide in water (0.939 mL, 0.939 mmol) and the mixture was heated to 45° C. After 2 h, the reaction was allowed to cool to ambient temperature and hydrochloric acid (0.078 mL, 0.939 mmol) was added. The mixture was concentrated to give the sodium chloride salt of the title compound (142 mg). MS 306.0 (M+1).

Step C: N-[(1R)-1-(3-Methyl-1,2,4-oxadiazol-5-yl)ethyl]-3-(5-methylpyridin-2-yl)-5-(2-methylpyrimidin-5-yl)benzamide To a solution of the sodium chloride salt of 3-(5-methylpyridin-2-yl)-5-(2-methylpyrimidin-5-yl)benzoic acid (35 mg, 0.073 mmol) in N,N-dimethylformamide (0.728 mL) was added the hydrochloride salt of (1R)-1-(3-methyl-1,2,4-oxadiazol-5-yl)ethanamine (17.5 mg, 0.087 mmol), EDC (16.8 mg, 0.087 mmol), HOBT (11.2 mg, 0.073 mmol), and triethylamine (0.041 mL, 0.291 mmol). After 16 h, water and trifluoroacetic acid were added. Purification by reverse phase chromatography (C-18, 95% water/acetonitrile→25% water/acetonitrile with 0.1% trifluoroacetic acid) gave the title compound (28.8 mg). HRMS 415.1880 (M+1). $^1$H NMR (500 MHz, CD$_3$OD): δ 9.21 (s, 2H); 8.78 (s, 1H); 8.57-8.53 (m, 2H); 8.49 (d, J=9.5 Hz, 2H); 8.42 (d, J=8.3 Hz, 1H); 5.51 (q, J=7.2 Hz, 1H); 2.80 (s, 3H); 2.64 (s, 3H); 2.37 (s, 3H); 1.75 (d, J=7.1 Hz, 3H).

Example 4.438

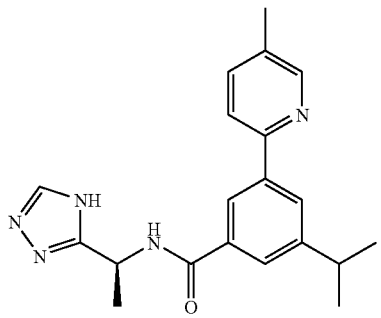

3-Isopropyl-5-(5-methylpyridin-2-yl)-N-[(1S)-1-(4H-1,2,4-triazole-3-yl)ethyl]benzamide Step A: Methyl 3-isopropenyl-5-(5-methylpyridin-2-yl)benzoate To a solution of methyl 3-bromo-5-(5-methylpyridin-2-yl)benzoate (1.00 g, 3.27 mmol) in N,N-dimethylformamide (9.80 mL) and water (3.27 mL) was 2-isopropenyl-4,4,5,5-tetramethyl-1,3,2-dioxaborolane (0.921 mL, 4.90 mmol), palladium(II) acetate (37.0 mg, 0.163 mmol), 3,3'3''-phosphinidynetris(benzenesulfonic acid)trisodium salt (278 mg, 0.490 mmol) and diisopropylamine (1.16 mL, 8.17 mmol) and the mixture was heated to 80° C. After 50 min, the reaction was allowed to cool to ambient temperature and filtered. Purification by reverse phase chromatography (C-18, 90% water/acetonitrile→40% water/acetonitrile with 0.1% trifluoroacetic acid) gave the title compound (864 mg). MS 268.2 (M+1).

Step B: 3-Isopropenyl-5-(5-methylpyridin-2-yl)benzoic acid

To a solution of methyl 3-isopropenyl-5-(5-methylpyridin-2-yl)benzoate (864 mg, 3.23 mmol) in methanol (10 mL) was added 1 M sodium hydroxide in water (9.70 mL, 9.70 mmol). After 16 h, hydrochloric acid (0.801 mL, 9.70 mmol) was added. The mixture was concentrated to give the sodium chloride salt of the title compound (1.352 g). MS 254.1 (M+1).

Step C: 3-Isopropyl-5-(5-methylpyridin-2-yl)benzoic acid

To a solution of 3-isopropenyl-5-(5-methylpyridin-2-yl)benzoic acid (150 mg, 0.592 mmol) in ethanol (11.8 mL) was added 10% palladium on carbon (50.0 mg, 0.047 mmol) and the mixture was placed under 1 atm of hydrogen. After 1 h, filtration and concentration gave the crude title compound (150 mg). MS 256.2 (M+1).

Step D: 3-Isopropyl-5-(5-methylpyridin-2-yl)-N-[(1S)-1-(4H-1,2,4-triazole-3-yl)ethyl]benzamide To a solution of 3-isopropyl-5-(5-methylpyridin-2-yl)benzoic acid (100 mg, 0.392 mmol) in N,N-dimethylformamide (3.0 mL) was added the hydrochloride salt of (1S)-1-(4H-1,2,4-triazol-3-yl)ethanamine (107 mg, 0.578 mmol), EDC (90.0 mg, 0.470 mmol), HOBT (60.0 mg, 0.392 mmol) and triethylamine (0.164 mL, 1.175 mmol) and the mixture was heated to 45° C. After 1 h, water and trifluoroacetic acid were added. The mixture was purified by reverse phase chromatography (C-18, 95% water/acetonitrile→25% water/acetonitrile with 0.1% trifluoroacetic acid). Treatment with 2 M hydrochloric acid in diethyl ether gave the title compound as a hydrochloride salt (153 mg). HRMS 350.1976 (M+1). $^1$H NMR (500 MHz, CD$_3$OD): δ 9.21 (s, 1H); 8.73 (s, 1H); 8.55 (d, J=8.4 Hz, 1H); 8.36 (d, J=8.4 Hz, 1H); 8.30 (s, 1H); 8.12 (s, 1H); 8.01 (s, 1H); 5.52 (q, J=7.1 Hz, 1H); 3.20-3.12 (m, 1H); 2.63 (s, 3H); 1.79 (d, J=7.1 Hz, 3H); 1.39 (d, J=6.9 Hz, 6H).

Example 4.452

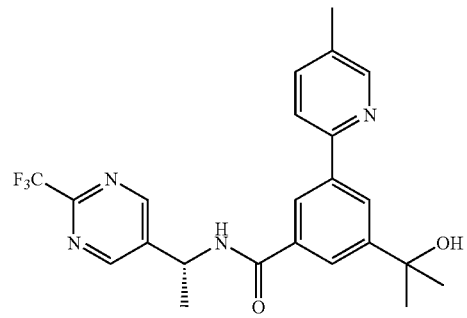

3-(1-Hydroxy-1-methylethyl)-5-(5-methylpyridin-2-yl)-N-{(1R)-1-[2-(trifluoromethyl)pyrimidin-5-yl]ethyl}benzamide Step A: 3-(1-Hydroxy-1-methylethyl)-5-(5-methylpyridin-2-yl)benzoic acid To a solution of the sodium chloride salt of 3-isopropenyl-5-(5-methylpyridin-2-yl)benzoic acid (2.114 g, 4.93 mmol) in water (49.3 mL) at 0° C. was added methanesulfonic acid (23.7 mL, 247 mmol) and the mixture was heated to 50° C. After 16 h, the mixture was cooled to 0° C. and sodium hydroxide (9.86 g, 247 mmol) added. The mixture was extracted with ethyl acetate (3×). The combined organic extracts were washed with brine, dried over magnesium sulfate, filtered and concentrated. The mixture was purified by reverse phase chromatography (C-18, 95% water/acetonitrile→65% water/acetonitrile with 0.1% trifluoroacetic acid). Treatment with 2 M hydrochloric acid in diethyl ether gave the title compound as a hydrochloride salt (1.252 g). MS 272.0 (M+1).

Step B: 3-(1-Hydroxy-1-methylethyl)-5-(5-methylpyridin-2-yl)-N-{(1R)-1-[2-(trifluoromethyl)pyrimidin-5-yl]ethyl}benzamide To a solution of the hydrochloride salt of 3-(1-hydroxy-1-methylethyl)-5-(5-methylpyridin-2-yl)benzoic acid (165 mg, 0.536 mmol) in N,N-dimethylformamide (2.1 mL) was added the hydrochloride salt of (1R)-1-[2-(trifluoromethyl)pyrimidin-5-yl]ethanamine (170 mg, 0.643 mmol), EDC (123 mg, 0.643 mmol), HOBT (82.0 mg, 0.536 mmol) and triethylamine (0.374 mL, 2.68 mmol) and the mixture was heated to 60° C. After 1 h the mixture was allowed to cool to ambient temperature, water and trifluoroacetic acid were added. The mixture was purified by reverse phase chromatography (C-18, 95% water/acetonitrile→50% water/acetonitrile with 0.1% trifluoroacetic acid). Treatment with 2 M hydrochloric acid in diethyl ether gave the title compound as a hydrochloride salt (179 mg). HRMS 445.1845 (M+1). $^1$H NMR (500 MHz, CD$_3$OD): δ 9.04 (s, 2H); 8.69 (s, 1H); 8.46 (d, J=8.4 Hz, 1H); 8.28-8.21 (m, 4H); 5.37 (q, J=7.2 Hz, 1H); 2.60 (s, 3H); 1.73 (d, J=7.2 Hz, 3H); 1.64 (s, 6H).

Example 4.457

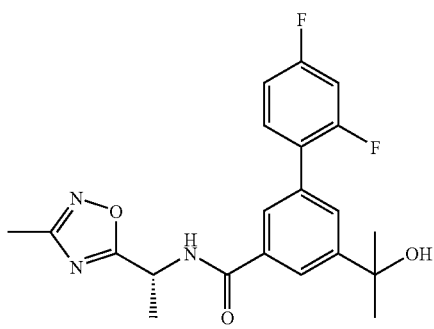

2',4'-Difluoro-5-(1-hydroxy-1-methylethyl)-N-[(1R)-1-(3-methyl-1,2,4-oxadiazol-5-yl)ethyl]biphenyl-3-carboxamide Step A: Methyl 3-bromo-5-isopropenylbenzoate To a solution of methyl 3-bromo-5-iodobenzoate (2.50 g, 7.33 mmol) in acetonitrile (22.0 mL) and water (7.33 mL) was 2-isopropenyl-4,4,5,5-tetramethyl-1,3,2-dioxaborolane (1.378 mL, 7.33 mmol), palladium(II) acetate (41.0 mg, 0.183 mmol), 3,3'3''-phosphinidynetris(benzenesulfonic acid)trisodium salt (313 mg, 0.550 mmol) and diisopropylamine (2.61 mL, 18.33 mmol) and the mixture was heated to 80° C. After 2.5 h, the reaction was allowed to cool to ambient temperature and saturated aqueous sodium bicarbonate was added. The mixture was extracted with ethyl acetate (3×). The combined organic extracts were washed with brine, dried over magnesium sulfate, filtered and concentrated. Purification by silica gel chromatography (100% hexanes→80% hexanes/ethyl acetate) gave the title compound (1.71 g).

Step B: 3-Bromo-5-isoprpenylbenzoic acid

To a solution of methyl 3-bromo-5-isopropenylbenzoate (1.71 g, 6.70 mmol) in methanol (33.5 mL) was added 1 M aqueous sodium hydroxide (20.11 mL, 20.11 mmol) and the mixture was heated to 50° C. After 30 min, 1 M aqueous hydrochloric acid was added and the mixture was extracted with dichloromethane (3×). The combined organic extracts were washed with brine, dried over magnesium sulfate, and filtered. Concentration gave the title compound (1.48 g).

Step C: 3-Bromo-5-(1-hydroxy-1-methylethyl)benzoic acid

To a solution of 3-bromo-5-isoprpenylbenzoic acid (1.22 g, 5.06 mmol) in 1,4-dioxane (33.7 mL) and water (16.9 mL) at 0° C. was added methanesulfonic acid (32.8 mL, 506 mmol) and the mixture was allowed to warm to ambient temperature. After 48 h, the mixture was cooled to 0° C. and sodium hydroxide was added. The mixture was extracted with ethyl acetate (3×). The combined organic extracts were washed with brine, dried over magnesium sulfate, filtered and concentrated. Purification by reverse phase chromatography (C-18, 90% water/acetonitrile→40% water/acetonitrile with 0.1% trifluoroacetic acid) gave the title compound (536 mg).

Step D: 2',4'-Difluoro-5-(1-hydroxy-1-methylethyl)biphenyl-3-carboxylic acid

To a solution of 3-bromo-5-(1-hydroxy-1-methylethyl)benzoic acid (150 mg, 0.579 mmol) in N,N-dimethylformamide (2.90 mL) and water (0.97 mL) was added (2,4-difluorophenyl)boronic acid (110 mg, 0.695 mmol), palladium(II) acetate (6.5 mg, 0.029 mmol), 3,3'3''-phosphinidynetris(benzenesulfonic acid)trisodium salt (49.4 mg, 0.087 mmol) and diisopropylamine (0.206 mL, 1.45 mmol) and the mixture was heated to 80° C. After 3 h, filtration and purification by reverse phase chromatography (C-18, 90% water/acetonitrile→30% water/acetonitrile with 0.1% trifluoroacetic acid) gave the title compound (156 mg).

Step E: 2',4'-Difluoro-5-(1-hydroxy-1-methylethyl)-N-[(1R)-1-(3-methyl-1,2,4-oxadiazol-5-yl)ethyl]biphenyl-3-carboxamide To a solution of 2',4'-difluoro-5-(1-hydroxy-1-methylethyl)biphenyl-3-carboxylic acid (34 mg, 0.116 mmol) in N,N-dimethylformamide (1.2 mL) was added the hydrochloride salt of (1R)-1-(3-methyl-1,2,4-oxadiazol-5-yl)ethanamine, EDC (26.8 mg, 0.140 mmol), HOBT (17.8 mg, 0.116 mmol) and triethylamine (0.065 mL, 0.465 mmol). After 16 h, water and trifluoroacetic acid were added. The mixture was purified by reverse phase chromatography (C-18, 95% water/acetonitrile→5% water/acetonitrile with 0.1% trifluoroacetic acid). Treatment with 2 M hydrochloric acid in diethyl ether gave the title compound as a hydrochloride salt (50.1 mg). HRMS 402.1633 (M+1). ¹H NMR (500 MHz, CD₃OD): δ 8.03 (t, J=1.8 Hz, 1H); 7.89-7.86 (m, 2H); 7.58 (q, J=7.6 Hz, 1H); 7.12-7.07 (m, 2H); 5.46 (q, J=7.1 Hz, 1H); 2.37 (s, 3H); 1.71 (d, J=7.1 Hz, 3H); 1.61 (s, 6H).

Example 4.539

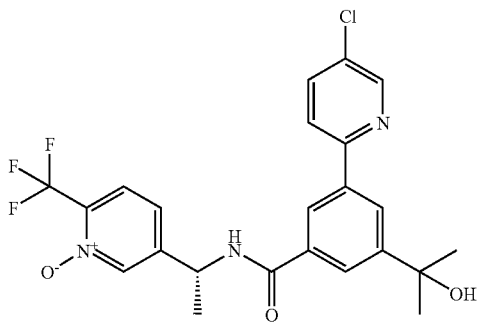

3-(5-Chloropyridin-2-yl)-5-(1-hydroxy-1-methyl-ethyl)-N-{(1R)-1-[1-oxido-6-(trifluoromethyl)pyridin-3-yl]-ethyl}benzamide Step A: methyl 3-bromo-5-iodobenzoate To a suspension of 3-bromo-5-iodobenzoic acid (993 g, 3.04 mol) in methanol (6.0 L) was added hydrochloric acid (37%; 20.0 mL, 244 mmol). The mixture was heated to 70° C. After 72 h, the mixture was cooled to ambient temperature. Dichloromethane (2.5 L) was added and the mixture was partially concentrated. The suspension was filtered and the filtered cake was washed with cold methanol to give the title compound as a white solid (846 g).

Step B: methyl 3-bromo-5-(4,4,5,5-tetramethyl-1,3,2-dioxaborolan-2-yl)benzoate

To a solution of methyl 3-bromo-5-iodobenzoate (2.06 g, 6.04 mmol) in dioxane (40 mL) were added bis(pinacolato)diboron (1.92 g, 7.55 mmol), potassium acetate (1.19 g, 12.1 mmol) and dichloro[1,1'-bis(diphenylphosphino)ferrocene]palladium(II) dichloromethane adduct (0.22 g, 0.30 mmol). The mixture was degassed with argon and stirred at 80° C. After 42 h, the mixture was cooled to ambient temperature and filtered through Celite. The filtered cake was washed with ethyl acetate and the filtrate was concentrated. Purification by silica gel chromatography (100% hexanes→50% hexanes/ethyl acetate) gave the title compound (1.74 g). MS 341.0 (M).

Step C: methyl 3-bromo-5-(5-chloropyridin-2-yl)benzoate

To a solution of methyl 3-bromo-5-(4,4,5,5-tetramethyl-1,3,2-dioxaborolan-2-yl)benzoate (0.10 g, 0.29 mmol) in DMF (1.5 mL) and water (0.49 mL) were added 2-bromo-5-chloropyridine (0.17 g, 0.88 mmol), palladium(II) aceate (3.3 mg, 0.015 mmol), 3,3'3"-phosphinidynetris(benzenesulfonic acid)trisodium salt (25.0 mg, 0.044 mmol) and diisopropylamine (0.10 mL, 0.73 mmol). The mixture was heated to 80° C. After 1 h, the mixture was filtered and the filtrate was purified by reverse phase chromatography (C-18, 85% water/acetonitrile→5% water/acetonitrile with 0.1% trifluoroacetic acid) gave the title compound (78 mg). MS 326.0 (M).

Step D: methyl 3-(5-chloropyridin-2-yl)-5-isopropenylbenzoate

To a solution of methyl 3-bromo-5-(5-chloropyridin-2-yl)benzoate (78.0 mg, 0.24 mmol)) in DMF (1.2 mL) and water (0.4 mL) was 2-isopropenyl-4,4,5,5-tetramethyl-1,3,2-dioxaborolane (53.9 µL, 0.29 mmol), palladium(II) acetate (2.68 mg, 0.012 mmol), 3,3'3"-phosphinidynetris(benzenesulfonic acid)trisodium salt (20.4 mg, 0.036 mmol) and diisopropylamine (85.0 µL, 0.60 mmol) and the mixture was heated to 80° C. After 1 h, the reaction was filtered and the filtrate was purified by reverse phase chromatography (C-18, 85% water/acetonitrile→5% water/acetonitrile with 0.1% trifluoroacetic acid) gave the title compound (59 mg). MS 388.0 (M+1).

Step E: 3-(5-chloropyridin-2-yl)-5-isopropenylbenzoic acid

To a solution of methyl 3-(5-chloropyridin-2-yl)-5-isopropenylbenzoate (0.13 g, 0.46 mmol) in methanol (3.1 mL) was added 1 M aqueous sodium hydroxide (0.92 mL, 0.92 mmol) and the mixture was heated to 60° C. After 45 min, hydrochloric acid (76 uL, 092 mmol) was added and the mixture was concentrated to dryness gave the bis sodium chloride salt of the title compound. MS 274.0 (M+1).

Step F: 3-(5-chloropyridin-2-yl)-5-(1-hydroxy-1-methylethyl)benzoic acid

To a solution of 3-(5-chloropyridin-2-yl)-5-isopropenylbenzoic acid (0.18 g, 0.46 mmol) in water (4.6 mL) was added methanesulfonic acid (1.5 mL, 23.1 mmol). The mixture was heated to 50° C. After 18 h, the mixture was cooled to ambient temperature and sodium carbonate was added to adjust pH to 3-4. The mixture was extracted with ethyl acetate (3×). The combined organic extracts were washed with brine, dried over magnesium sulfate, filtered and concentrated. Purification by reverse phase chromatography (C-18, 100% water/acetonitrile→25% water/acetonitrile with 0.1% trifluoroacetic acid) gave the title compound (80 mg). MS 292.1 (M+1).

Step G: 3-(5-Chloropyridin-2-yl)-5-(1-hydroxy-1-methylethyl)-N-{(1R)-1-[1-oxido-6-(trifluoromethyl)pyridin-3-yl]ethyl}benzamide To a solution of 3-(5-chloropyridin-2-yl)-5-(1-hydroxy-1-methylethyl)benzoic acid (20 mg, 0.07 mmol) in DMF (0.7 mL) were added the potassium chloride salt of (1R)-1-[1-oxido-6-(trifluoromethyl)pyridin-3-yl]ethanamine (33.6 mg, 0.09 mmol), HATU (0.05 M in DMA; 0.21 mL, 0.10 mmol) and diisopropylamine (60 µL, 0.34 mmol). The mixture was stirred at ambient temperature. After 30 min, the mixture was filtered and the filtrate was purified by reverse phase chromatography (C-18, 95% water/acetonitrile→25% water/acetonitrile with 0.1% trifluoroacetic acid) gave the title compound (25 mg). FIRMS 480.1302 (M+1). ¹H NMR (400 MHz, CDCl₃): δ 8.58 (s, 1H); 8.36 (s, 1H); 8.20 (d, J=4.9 Hz, 2H);

8.04 (s, 1H); 7.78-7.61 (m, 3H); 7.42-7.30 (m, 2H); 5.33-5.23 (m, 1H); 1.69 (s, 6H), 1.63 (d, J=7.1 Hz, 3H).

Example 5.5

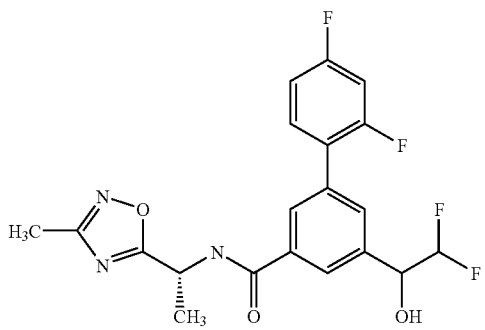

5-(2,2-Difluoro-1-hydroxyethyl)-2',4'-difluoro-N-[(1R)-1-(3-methyl-1,2,4-oxadiazol-5-yl)ethyl]biphenyl-3-carboxamide Step A: tert-butyl 3-bromo-5-(2,2-difluoro-1-hydroxyethyl)benzoate To a solution of tert-butyl 3,5-dibromobenzoate (18.43 g, 54.9 mmol) in tetrahydrofuran (137 mL) at 0° C. was added isopropylmagnessium chloride (2.0 M in THF; 46.6 mL, 93 mmol). The reaction mixture was warmed to ambient temperature. The reaction was monitor by LC-MS for disappearance of tert-butyl 3,5-dibromobenzoate. The mixture was cooled back to 0° C. and ethyl difluoroacetate (13.7 mL, 137 mmol) was added. The mixture was stirred at 0° C. for 1 h, then warmed to ambient temperature. After 18 h, methanol and saturated ammonium chloride were added and the mixture was concentrated to remove organic solvents. Water was added and the mixture was extracted with dichloromethane (3×). The combined organic extracts were washed with brine, dried over magnesium sulfate, filtered and concentrated. Purification by silica gel chromatography (100% hexanes→75% hexanes/ethyl acetate) gave the title compound (4.04 g).

Step B: tert-butyl 5-(2,2-difluoro-1-hydroxyethyl)-2',4'-difluorobiphenyl-3-carboxylate To a solution of tert-butyl 3-bromo-5-(2,2-difluoro-1-hydroxyethyl)benzoate (1.0 g, 2.97 mmol) in N,N-dimethylformamide (11.9 mL) and water (2.97 mL) was added (2,4-difluorophenyl)boronic acid (0.61 g, 3.86 mmol), palladium (II) acetate (67 mg, 0.3 mmol), 3,3'3"-phosphinidynetris (benzenesulfonic acid)trisodium salt (0.51 g, 0.89 mmol) and diisopropylamine (1.27 mL, 8.9 mmol). The mixture was stirred at ambient temperature. After 1 h, brine was added and mixture was extracted with ethyl acetate (3×). The combined organic extracts were washed with brine, dried over magnesium sulfate, filtered and concentrated. Purification by silica gel chromatography (100% hexanes→60% hexanes/ethyl acetate) gave the title compound (1.03 g). MS 315.0 (M-t-butyl group).

Step C: 5-(2,2-difluoro-1-hydroxyethyl)-2',4'-difluorobiphenyl-3-carboxylic acid To a solution of tert-butyl 5-(2,2-difluoro-1-hydroxyethyl)-2',4'-difluorobiphenyl-3-carboxylate (1.03 g, 2.79 mmol) in dichloromethane (5.6 mL) was added trifluoroacetic acid (5.4 mL). The mixture was stirred at ambient temperature. After 48 h, the mixture was concentrated to dryness to give the title compound (0.85 g). MS 315.0 (M+1).

Step D: 5-(2,2-Difluoro-1-hydroxyethyl)-2',4'-difluoro-N-[(1R)-1-(3-methyl-1,2,4-oxadiazol-5-yl)ethyl]biphenyl-3-carboxamide To a solution of 5-(2,2-difluoro-1-hydroxyethyl)-2',4'-difluorobiphenyl-3-carboxylic acid (0.25 g, 0.80 mmol) in N,N-dimethylformamide (2.7 mL) were added (1R)-1-(3-methyl-1,2,4-oxadiazol-5-yl)ethanamine (0.18 g, 0.88 mmol), EDC (0.27 g, 1.39 mmol), HOAT (51.1 mg, 0.40 mmol) and triethylamine (0.67 mL, 4.77 mmol). The mixture was stirred at 50 C. After 2 h, saturated sodium bicarbonate was added the mixture was extracted with dichloromethane (3×). The combined organic extracts were washed with brine, dried over magnesium sulfate, filtered and concentrated. Purification by silica gel chromatography (100% hexanes→85% dichloromethane/methanol). Product obtained was not pure therefore it was purified again by reverse phase chromatography (C-18, 95% water/acetonitrile→30% water/acetonitrile with 0.1% trifluoroacetic acid) gave the title compound (201 mg). HRMS 424.1283 (M+1). $^1$H NMR δ (ppm) (DMSO-$d_6$): 9.28 (1H, d, J=7.3 Hz), 8.01 (2H, s), 7.76 (1H, s), 7.66 (1H, dd, J=15.6, 9.0 Hz), 7.43 (1H, m), 7.26 (1H, m), 6.11 (1H, dt, J=11.2, 0.7 Hz), 5.40 (1H, m), 4.93 (1H, m), 2.33 (3H, s), 1.61 (3H, d, J=7.3 Hz).

Example 6.5

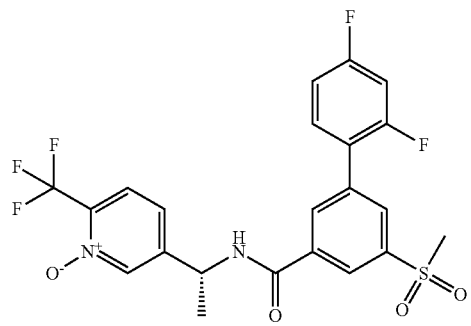

2',4'-Difluoro-5-(methylsulfonyl)-N-{(1R)-1-[1-oxido-6-(trifluoromethyl)pyridin-3-yl]ethyl}biphenyl-3-carboxamide Step A: tert-butyl 3-(methylsulfonyl)benzoate The mixture of tert-butyl 3-bromobenzoate (7.0 g, 27.2 mmol), sodium methanesulfinate (4.45 g, 43.6 mmol), copper (I) iodide (0.52 g, 2.72 mmol), L-proline (0.63 g, 5.44 mmol) and sodium hydroxide (0.22 g, 5.44 mmol) was purged with nitrogen and DMSO was added. The mixture was heated to 80° C. After 18 h, the mixture was cooled to ambient temperature. Additional sodium methanesulfinate (2.78 g, 27.2 mmol), copper(I) iodide (0.52 g, 2.72 mmol), L-proline (0.63 g, 5.44 mmol) were added and the mixture was stirred at 80° C. for another 18 h. The mixture was cooled to ambient temperature and filtered with Celite. Lithium chloride (3.0 M in water) was added and the mixture was extracted with ethyl acetate (3×). The combined organic extracts were washed with LiCl (3.0 M in water), brine, dried over sodium sulfate, filtered and concentrated. Purification by silica gel chromatography (100% hexanes→75% hexanes/ethyl acetate) gave the title compound (5.05 g).

Step B: tert-butyl 3-(methylsulfonyl)-5-(4,4,5,5-tetramethyl-1,3,2-dioxaborolan-2-yl)benzoate tert-Butyl 3-(methylsulfonyl)benzoate (1.0 g, 3.9 mmol), bis(pinacolato) diboron (0.99 g, 3.9 mmol), methoxy(cyclooctadiene)iridium(I) dimer (0.26 g, 0.39 mmol), 4,4'-di-tert-butyl-2,2'-bipyridine (0.21 g, 0.78 mmol) and sodium periodate (1.25 g, 5.85 mmol) were mixed together in the dry box under nitrogen atmosphere. Anhydrous THF was added and the mixture was heated to 80° C. After 6 h, the mixture was cooled to ambient temperature and aqueous Cu(II) SO$_4$ was added. The mixture was extracted with ethyl acetate (3×). The combined organic extracts were washed with Cu(II) SO$_4$ (2×), brine, dried over sodium sulfate, filtered and concentrated. Purification by silica gel chromatography (100% dichloromethane→80% dichloromethane/methanol) gave the title compound (1.0 g).

Step C: tert-butyl 2',4'-difluoro-5-(methylsulfonyl)biphenyl-3-carboxylate

The mixture of tert-butyl 3-(methylsulfonyl)-5-(4,4,5,5-tetramethyl-1,3,2-dioxaborolan-2-yl)benzoate (0.125 g, 0.33 mmol), 1-bromo-2,4-difluorobenzene (36.9 μL, 0.33 mmol), dichloro[1,1'-bis(diphenylphosphino)ferrocene]palladium (II) dichloromethane adduct (6.68 mg, 8.2 μmol) and cesium carbonate (0.32 g, 0.98 mmol) was purged with nitrogen. A degas solution of THF (1.6 mL) and water (1.6 mL) was added. The mixture was heated in a microwave reactor at 120° C. for 15 min. The mixture was filtered with Celite. Water was added and the mixture was extracted with ethyl acetate (3×). The combined organic extracts were washed with brine, dried over sodium sulfate, filtered and concentrated. Purification by silica gel chromatography (100% hexanes→70% hexanes/ethyl acetate) gave the title compound (77 mg).

Step D: 2',4'-difluoro-5-(methylsulfonyl)biphenyl-3-carboxylic acid

To a solution of tert-butyl 2',4'-difluoro-5-(methylsulfonyl)biphenyl-3-carboxylate (77 mg, 0.21 mmol) in dichloromethane (1.05 mL) was added trifluoroacetic acid (1.05 mL). The mixture was stirred at ambient temperature for 30 min. The mixture was concentrated to dryness to give the title compound.

Step E: 2',4'-Difluoro-5-(methylsulfonyl)-N-{(1R)-1-[1-oxido-6-(trifluoromethyl)pyridin-3-yl]ethyl}biphenyl-3-carboxamide To a solution of 2',4'-difluoro-5-(methylsulfonyl)biphenyl-3-carboxylic acid (25 mg, 0.08 mmol)) in N,N-dimethylformamide (0.8 mL) were added hydrochloride salt of (1R)-1-[1-oxido-6-(trifluoromethyl)pyridin-3-yl]ethanamine (38.7 mg, 0.16 mmol), EDC (23.0 g, 0.12 mmol), HOAT (10.9 mg, 0.08 mmol) and triethylamine (66.2 μL, 0.4 mmol). The mixture was stirred at ambient temperature. After 18 h, the mixture was filtered and the filtrate was purified by reverse phase chromatography (C-18, 95% water/acetonitrile→5% water/acetonitrile with 0.025% trifluoroacetic acid) gave the trifluoroacetate salt of the title compound (28 mg). HRMS 501.0913 (M+1). $^1$H NMR (400 MHz, CD$_3$OD): δ 8.48 (s, 1H); 8.43 (s, 1H); 8.31 (s, 1H); 8.24 (s, 1H); 7.88 (d, J=8.4 Hz, 1H); 7.67-7.62 (m, 2H); 7.13-7.08 (m, 2H); 5.24 (m, 1H); 3.18 (s, 3H); 1.62 (d, J=7.1 Hz, 3H).

Example 7.1

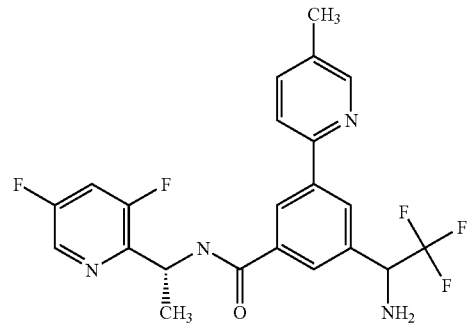

3-(1-Amino-2,2,2-trifluoroethyl)-N-[(1R)-1-(3,5-difluoropyridin-2-yl)ethyl]-5-(5-methylpyridin-2-yl)benzamide

Step A: tert-butyl 3-bromo-5-(trifluoroacetyl)benzoate

To a solution of tert-butyl 3-bromo-5-(2,2,2-trifluoro-1-hydroxyethyl)benzoate (8.8 g, 24.8 mmol) in dichloromethane (124 mL) was added Dess-MartinPeriodinane (15.8 g, 37.2 mmol). The mixture was stirred at ambient temperature. After 2 h, saturated NaHCO$_3$ and saturated Na$_2$SO$_3$. The mixture was extracted with dichloromethane (3×). The combined organic extracts were washed with water (6×), brine, dried over sodium sulfate, filtered and concentrated.

Step B: tert-butyl 3-(1-amino-2,2,2-trifluoroethyl)-5-bromobenzoate

To a solution of tert-butyl 3-bromo-5-(trifluoroacetyl)benzoate (3.0 g, 8.5 mmol) in toluene (mL) was slowly added lithium bis(trimethylsilyl)amide (1.0 M in toluene; 25.5 mL, 25.5 mmol). The reaction was stirred at ambient temperature. After 1 h, the reaction was checked by TLC for disappearance of tert-butyl 3-bromo-5-(trifluoroacetyl)benzoate. Borane dimethyl sulfide complex (2.0 M in toluene; 25.5 mL, 51.0 mmol) was added and the mixture was stirred at ambient temperature. After 1 h, aqueous NaOH (1.0 M) was added slowly to quench the reaction. The mixture was extracted with ethyl acetate (3×). The combined organic extracts were washed with brine, dried over sodium sulfate, filtered and concentrated. Purification by silica gel chromatography (100% hexanes→70% hexanes/ethyl acetate) gave the title compound (1.48 g).

Step C: tert-butyl 3-(1-amino-2,2,2-trifluoroethyl)-5-(5-methylpyridin-2-yl)benzoate To a solution of tert-butyl 3-(1-amino-2,2,2-trifluoroethyl)-5-bromobenzoate (1.4 g, 3.95 mmol) in dioxane (20 mL) was added bis(tri-t-butylphosphine)palladium(0) (0.06 g, 0.12 mmol). The mixture was degassed with nitrogen and bromo(5-methylpyridin-2-yl)zinc (0.5 M in THF; 23.7 mL, 11.9 mmol) was added. The mixture was heated to 70° C. After 1 h, the mixture was cooled to ambient temperature and filtered with Celite. The filtrate was concentrated to remove dioxane and saturated NaHCO$_3$ was added. The mixture was extracted with ethyl acetate (3×). The combined organic extracts were washed with brine, dried over sodium sulfate, filtered and concentrated. Purification by silica gel chromatography (100% dichloromethane→60% dichloromethane/ ethyl acetate) gave the title compound (1.39 g). MS 367.1 (M+1).

Step D: 3-(1-amino-2,2,2-trifluoroethyl)-5-(5-methylpyridin-2-yl)benzoic acid

To a solution of tert-butyl 3-(1-amino-2,2,2-trifluoroethyl)-5-(5-methylpyridin-2-yl)benzoate (30.0 mg, 0.08 mmol) in dichloromethane (0.5 mL) was added trifluoroacetic acid (0.3 mL). The mixture was stirred at ambient temperature. After 5 h, the mixture was concentrated to dryness to give the trifluoracetate salt of the title compound (35 mg).

Step E: 3-(1-Amino-2,2,2-trifluoroethyl)-N-[(1R)-1-(3,5-difluoropyridin-2-yl)ethyl]-5-(5-methylpyridin-2-yl)benzamide To a solution of trifluoroacetic salt of 3-(1-amino-2,2,2-trifluoroethyl)-5-(5-methylpyridin-2-yl)benzoic acid (35 mg, 0.08 mmol) in N,N-dimethylformamide (0.8 mL) were added hydrochloride salt of (1R)-1-(3,5-difluoropyridin-2-yl)ethanamine (38.1 mg, 0.17 mmol), EDC (31.6 g, 0.17 mmol), HOAT (11.2 mg, 0.08 mmol) and triethylamine (80.0 µL, 0.58 mmol). The mixture was stirred at ambient temperature. After 5 h, the mixture was filtered and the filtrate was purified by reverse phase chromatography (C-18, 95% water/acetonitrile→5% water/acetonitrile with 0.025% trifluoroacetic acid) gave the trifluoroacetate salt of the title compound (33 mg). HRMS 451.1559 (M+1). $^1$H NMR (400 MHz, CD$_3$OD): δ 8.59 (t, J=1.7 Hz, 1H); 8.60-8.47 (m, 1H); 8.33 (dd, J=4.7, 2.3 Hz, 2H); 8.05 (s, 1H); 7.91 (d, J=8.1 Hz, 1H); 7.84-7.80 (m, 1H); 7.56 (ddd, J=9.9, 8.5, 2.5 Hz, 1H); 5.57 (q, J=6.8 Hz, 1H); 5.47 (q, J=7.3 Hz, 1H); 2.41 (s, 3H); 1.58 (d, J=7.0 Hz, 3H).

Assay

In Vivo Rat Visceral Pain Model

Male Sprague-Dawley rats, weighing 150-180 g (max. range per experiment=40 g) at the beginning of the experiments. Animals will be delivered to the laboratory at least 5 days before the experiments during which time they are acclimatized to laboratory conditions. Rats will be housed in groups of 4, 5 or 6 in macrolon cages (41×25×14 cm or 44×28×19 cm) on wood with free access to food and water until tested (or as indicated otherwise). The animal house will be maintained under artificial lighting (12 hours) between 7.00 and 19.00 in a controlled ambient temperature of 21±3° C., and relative humidity maintained at 40-70%. Information related to any clinical signs and mortality will be archived with the study materials.

After overnight food-deprivation, male Sprague-Dawley rats are slightly anesthetized (isoflurane) and injected with 1% acetic acid into the colon (1.5 ml) using a cannula of 5 cm in length. After a recovery period of 75 minutes, rats are again slightly anesthetized (isoflurane) and a latex balloon of 1.5 cm in length tightly attached to a catheter is inserted via the anus into the descending colon and rectum. Anesthesia is then immediately discontinued. 15 minutes later, the test substance is administered p.o. 60 minutes after administration, the balloon is filled with 1.2 ml of water and the number of abdominal contractions is counted for 10 minutes.

10 rats are studied per group. The test is performed blind. The test substance will be evaluated at 3 doses, and compared with the vehicle group. Rats will be euthanized at the end of the experiments by exposure to a mixture of O$_2$/CO$_2$ (20%/ 80%) followed by CO$_2$. Data will be analyzed by comparing treated groups with vehicle control using Mann Whitney U tests.

In Vivo L5 Spinal Nerve Ligation Model a. Surgery and Post-Operative Care

For the spinal nerve ligation (SNL) procedure, male Sprague Dawley rats (100-200 g; Harlan) are anesthetized using isoflurane (1-5%; inhalation). Using aseptic technique, a dorsal midline incision is made from approximately spinal nerve L3 to S2. A combination of sharp and blunt dissection is used to expose the L6/S1 posterior interarticular process. The L6 transverse process is visualized and removed, and the L4 and L5 spinal nerves are exposed distal to their emergence from the intervertebral foramina. The L5 nerve is then tightly ligated with 6-0 silk suture. The muscle is closed with 4-0 absorbable suture and the skin is closed with wound clips. Postoperative monitoring is carried out to assure that animals are exposed to the least amount of pain as possible. Animals are housed in pairs on bedding and are monitored (2×) daily for three days post-operatively by Laboratory Animal Resource staff and then daily by investigator for any signs of possible distress.

b. Behavioral Testing

Prior to surgery, rats are tested for pre-surgery mechanical hind paw withdrawal thresholds by applying a series of calibrated von Frey filaments (0.25-15 g) to the left hind paw and determining the median withdrawal threshold using the Dixon "up-down" method (Chaplan et al., J Neurosci Meth 53:55, 1994). Rats are placed in individual plastic chambers on an elevated mesh galvanized steel platform and allowed to acclimate for 60 min. Pre-surgery mechanical hind paw withdrawal thresholds are determined, and rats having a threshold <15 g are excluded from the study. Following determination of pre-surgery withdrawal thresholds, rats undergo the SNL procedure described above. Between 28-35 days following the surgical procedure, rats are tested for post-surgery thresholds using the procedure described above, and animals displaying a hind paw withdrawal threshold <4.0 g are considered allodynic (i.e. mechanical hypersensitivity). Effects of test compounds on SNL-induced mechanical hypersensitivity are determined by dosing the compound along with a vehicle control group and a group receiving the positive comparator pregabalin (20 mg/kg, p.o.). Efficacy in the SNL model is evaluated by determining the % reversal of mechanical hypersensitivity using the formula:

$$\% \text{ reversal} = \frac{(\text{post-drug threshold} - \text{post-surgery threshold})}{(\text{pre-surgery threshold} - \text{post-surgery threshold})} \times 100$$

At the conclusion of the study, all rats are euthanized using CO$_2$ and plasma and brain tissue are collected for bioanalytical analysis of drug exposures.

In Vivo Complete Freunds Adjuvant (CFA) Model

Male Sprague Dawley rats (300-400 g; Charles River) receive an intradermal injection of CFA (200 ul, 0.5 mg/ml) into the plantar aspect of the left hind paw and are subsequently returned to their cages where they are maintained on soft bedding. 72 hrs following CFA injection rats are tested for post-CFA mechanical hind paw withdrawal thresholds by wrapping the rat in a towel and placing the hind paw (either left or right) in a modified Randall-Sellito paw pinch apparatus (Stoelting, Wood Dale, Ill.). A plastic bar attached to a lever is placed on the dorsum of the hind paw, and an increasing force is applied to the hind paw until the rat vocalizes or pulls its hind paw away from the bar. The rat's hind paw withdrawal threshold is recorded at that point. The mechanical stimulus is applied to each hind paw 2 times, and the average post-CFA mechanical hind paw withdrawal thresholds are determined for both the left and right hind paw. Following determination of post-CFA withdrawal thresholds, rats receive test compound, vehicle, or the positive comparator naproxen (30 mg/kg, p.o.), and effects of compounds on withdrawal thresholds for the inflamed (CFA) hind paw are determined. Efficacy in the CFA model is evaluated by determining the % reversal of mechanical hypersensitivity using the formula:

$$\% \text{ reversal} = \frac{(\text{post-drug threshold}_{left\ hind\ paw} - \text{post-}CFA\ \text{threshold}_{left\ hind\ paw})}{(\text{post-}CFA\ \text{threshold}_{right\ hind\ paw} - \text{post-}CFA\ \text{threshold}_{left\ hind\ paw})} \times 100$$

At the conclusion of the study, all rats are euthanized using $CO_2$ and plasma and brain tissue are collected for bioanalytical analysis of drug exposures.

Cystometry in Normal Healthy Rats

Female Sprague-Dawley rats weighed 250-350 g were housed in a temperature- and light (12-h light/dark cycle)-controlled room, and were allowed access to food and water ad libitum. The animals were anesthetized with urethane (1.0 g/kg, i.p.). Supplemental urethane was given if necessarily. A lower abdominal midline incision was made to expose the bladder, and a polyethylene catheter (PE-50) was inserted into the bladder dome for recording the intravesical pressure and intravesical infusion of physiological saline at the rate of 0.05 ml/min. The intravesical pressure was measured using a pressure transducer, and signal was recorded using a multiple channel data acquisition system (Power lab, AD Instruments, Biopac systems, Colorado Springs, Colo.) at a sampling rate of 10 Hz. After confirming stable inter-micturtion interval and micturition pressure by intravesical infusion of saline, the drugs were administered intravenously (0.25 ml/kg). Inter-micturition interval (functional bladder capacity) and micturition pressure (maximum intravesical pressure) were obtained from micturitions prior to dosing (baseline) and between 5 to 30 min after dosing using Chart program (v5.5.4, AD Instruments), and calculated the ratio to baseline.

Cystometry in Rat Acetic Acid-Induced Hyper-Reflexia Model

Female Sprague-Dawley rats weighed 250-350 g were housed in a temperature- and light (12-h light/dark cycle)-controlled room, and were allowed access to food and water ad libitum. The animals were anesthetized with urethane (1.0 g/kg, i.p.). Supplemental urethane was given if necessarily. A lower abdominal midline incision was made to expose the bladder, and a polyethylene catheter (PE-50) was inserted into the bladder dome for recording the intravesical pressure and intravesical infusion at the rate of 0.05 ml/min. The intravesical pressure was measured using a pressure transducer, and signal was recorded using a multiple channel data acquisition system (Power lab, AD Instruments, Biopac systems, Colorado Springs, Colo.) at a sampling rate of 10 Hz. After confirming stable inter-micturtion interval and micturition pressure by intravesical infusion of saline, 0.25% of acetic acid-saline solution was infused at the same infusion rate. After 30-60 min, drugs were intravenously infused using infusion pumps at a rate of 10 μl/min. Intermicturition interval (functional bladder capacity) and micturition pressure (maximum intravesical pressure) were obtained from micturitions prior to dosing (baseline) and between 30 to 45 min after starting drug infusion using Chart program (v5.5.4, AD Instruments), and calculated the ratio to baseline.

Generation of a Human $P2X_3$ and $P2X_{2/3}$ Stable Cell Line—Human $P2X_3$ receptor cDNA (Accession number NM_002559) was subcloned as a 5'XhoI and 3'HindIII fragment into the expression vector pcDNA5/FRT (Invitrogen). Human $P2X_2$ receptor cDNA (Accession number NM_174873) was subcloned as a 5'EcoRI and 3'NotI fragment into the expression vector pIRESneo2 (BD Biosciences Clontech). The human $P2X_3$ expression construct was transfected using Lipofectamine 2000 (Invitrogen) into Flp-in—293 cells (Invitrogen) according to the manufacturer's directions. Cells positive for flp-mediated recombination of rhesus $P2X_3$ were selected using 150 μg/ml hygromycin. The stable human $P2X_3$ cell line was co-transfected with the human $P2X_2$ expression construct using Lipofectamine 2000 as above and co-transfected cells selected using 100 mg/ml hygromycin and 1 mg/ml G418. The stable $P2X_3$ cell line was propagated in DMEM, 10% FBS, 100 μg/ml hygromycin, and 100 units/ml penicillin and 100 μg/ml streptomycin, and maintained at 37° and 95% humidity. The stable $P2X_{2/3}$ cell line was propagated as above with the addition of 500 μg/ml G418.

Intracellular Calcium Measurement to Assess Antagonist Affinity—A fluorescent imaging plate reader (FLIPR; Molecular Devices) was used to monitor intracellular calcium levels using the calcium-chelating dye Fluo-4 (Molecular Probes). The excitation and emission wavelengths used to monitor fluorescence were 488 nm and 530 nm, respectively. Cells expressing either human $P2X_3$ or human $P2X_{2/3}$ were plated at a density of 20,000 cells/well (20 μl/well) in 384-well black-walled plates approximately 20 hours before beginning the assay. On the day of the assay 20 μl of loading buffer (Hank's balanced salt solution, 2.5 mM $CaCl_2$, 20 mM HEPES, 0.1% BSA, 2.5 mM probenecid, TR-40, Fluo-4, and 138 mM NMDG substituted for NaCl) is added and cells dye-loaded for 60 min in the dark at room temperature. Ten minutes prior to adding agonist, the antagonist was added in a volume of 10 μl and allowed to incubate at room temperature. During this period fluorescence data is collected at 3 sec intervals followed by 10 sec intervals. The agonist, α,β-meATP, is added at a 6× concentration ([α,β-meATP]$_{final}$=$EC_{50}$). Following agonist addition fluorescence was measured at 5 sec intervals and analyzed based on the increase in peak relative fluorescence units (RFU) compared to the basal fluorescence. Peak fluorescence was used to determine the inhibitory effect at each concentration of antagonist by the following equation:

% Inhibition=100*(1−((RFU$_{(drug)}$−RFU$_{(control)}$)/(RFU$_{(DMSO\ only)}$−RFU$_{(control)}$)))

In vitro Electrophysiological Assay—Cells expressing human $P2X_3$ receptors were grown to a confluence of 65-85% 20 to 32 hours prior to assay. The cells were dissociated with trypsin, centrifuged, and resuspended in bath solution at a cell density of 1×10$^6$ cells/ml and loaded onto PatchXpress. The bath solution contained 150 mM NaCl, 4 mM KCl, 2 mM CaCl$_2$, 1.2 mM MgCl$_2$, 10 mM HEPES, and 11.1 mM glucose, at pH 7.2. The intracellular solution contained either 140 mM K-aspartate, 20 mM NaCl, 5 mM HEPES, 10 mM EGTA, at pH 7.2 or 30 mM CsCl, 5 mM HEPES, 10 mM EGTA, 120 mM CsF, 5 mM NaF, 2 mM MgCl2, pH=7.3 with CsOH. Agonist stock solutions were prepared in H$_2$O and diluted in bath solution prior to use. All antagonists were prepared as 10 mM stock solutions in DMSO and diluted in bath solution prior to use. All experiments were performed on cells under the whole-cell patch clamp configuration at room temperature. Up to 16 individual cells could be patch clamped simultaneously on the PatchXpress instrument. A baseline response was established by repeated CTP (100 µM; for 2 sec.) followed by antagonist incubation for 2 min. in the absence of CTP. After antagonist preincubation 100 µM CTP and antagonist were co-administered to determine the inhibitory effect of the antagonist. These steps were then repeated on the same cell with a range of concentrations of the antagonist. A maximum of five concentrations of antagonist were tested on any individual cell. The control P2X$_3$ current amplitude ($I_{P2X3\text{-}(control)}$) was taken as an average of the peak current amplitude from the last two agonist additions prior to incubation with an antagonist. The peak P2X$_3$ current amplitude in the presence of an antagonist ($I_{P2X3\text{-}(drug)}$) was used to calculate the inhibitory effect at each concentration of the antagonist according to the following equation:

% inhibition of $P2X_3 = 100*(I_{P2X3\text{-}(control)} - I_{P2X3\text{-}(drug)})/I_{P2X3\text{-}(control)}$ Each concentration of an antagonist was tested on at least two independent cells.

The concentration of drug required to inhibit P2X$_3$ current by 50% (IC$_{50}$) was determined by fitting of the Hill equation to the averaged % inhibition data at each concentration:

% of Control=100●(1+([Drug]/IC$_{50}$)$^p$)$^{-1}$

In vitro Electrophysiological Assay for P2X$_{2/3}$—P2X$_{2/3}$ was assayed as above with two protocol modifications: 1) 30 µM α,β-meATP used as agonist; and 2) current amplitude was measured at the end of 2-second agonist application. Using the assays described herein the compounds of this invention were found to be active for the P2X3 receptor. The compounds of formula I have an IC$_{50}$ activity of 100 µM or less for the P2X3 receptor. Many of the compounds of formula I have an IC$_{50}$ of less than 200 nM. For example, the compounds below have IC$_{50}$<250 nM in the "Intracellular Calcium Measurement to Assess Antagonist Affinity" assay. In particular, Compound 4.3 has an IC$_{50}$=11 nM; compound 4.109 has an IC$_{50}$=20 nM; compound 4.252 has an IC$_{50}$=8 nM; and compound 4.539 has an IC$_{50}$=26 nM.

What is claimed:

1. A compound of structural formula I:

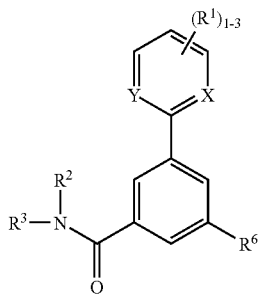

or pharmaceutically acceptable salts and individual enantiomers and diastereomers thereof wherein:

X and Y independently represent N, or CR$^1$;

R$^6$ represents OH, (CH$_2$)$_n$CF$_3$, SO$_2$R$^2$, N(R$^2$)$_2$, C(R$^2$)$_2$OR$^2$, C$_{1\text{-}6}$ alkyl, C$_{2\text{-}6}$ alkenyl, C$_{2\text{-}6}$ alkynyl, C$_{3\text{-}10}$ cycloalkyl, (CH$_2$)$_n$C$_{6\text{-}10}$ aryl, (CH$_2$)$_n$C$_{5\text{-}10}$ heterocyclyl, said alkyl substituted and said alkenyl, alkynyl, aryl and heterocyclyl optionally substituted with 1 to 3 groups of R$^a$, provided said heterocyclyl is not thiazolyl, benzthiazolyl, oxazolyl, isoxazolyl, dihydro-isoxazolyl, or oxadiazolyl, provided that when R$^6$ is (CH$_2$)$_n$C$_{5\text{-}10}$ heterocyclyl it is not tetrazolyl;

R$^1$ represents H, C$_{1\text{-}6}$ alkyl, halogen, (CH$_2$)$_n$CF$_3$, C$_{3\text{-}10}$ cycloalkyl, C(R$^2$)$_2$OH, —O—, CN, (CH$_2$)$_n$OR$^2$, (CH$_2$)$_n$C$_{5\text{-}10}$ heterocyclyl, (CH$_2$)$_n$C$_{6\text{-}10}$ aryl, or C$_{1\text{-}6}$ alkoxy; said alkyl, cycloalkyl, heterocyclyl and aryl optionally substituted with 1 to 3 groups of C$_{1\text{-}6}$ alkyl, halogen, hydroxyl, (CH$_2$)$_n$CF$_3$, or CN;

R$^2$ represents H, C$_{1\text{-}6}$ alkyl, CF$_3$, OH;

R$^3$ represents —CR$^2$R$^4$R$^5$, —(C(R$^2$)$_2$)$_n$C$_{3\text{-}10}$ cycloalkyl, —(C(R$^2$)$_2$)$_n$C$_{5\text{-}10}$ heterocycle, said cycloalkyl and heterocyclyl optionally substituted with 1 to 3 groups of R$^a$;

or R$^2$ and R$^3$ can be combined with the nitrogen to which they are attached to form a C$_{5\text{-}10}$ heterocyclyl optionally substituted with 1 to 3 groups of R$^a$;

R$^4$ and R$^5$ independently represent H, (CH$_2$)$_n$OR$^2$, (CH$_2$)$_n$C$_{5\text{-}10}$ heterocyclyl, (CH$_2$)$_n$C$_{6\text{-}10}$ aryl, C$_{3\text{-}10}$ cycloalkyl, C$_{1\text{-}6}$ alkoxy, C$_{2\text{-}6}$ alkenyl, C$_{2\text{-}6}$ alkynyl, (CH$_2$)$_n$CF$_3$, CHF$_2$, CN, C(O)$_{1\text{-}2}$R$^2$, or C$_{1\text{-}6}$ alkyl; said alkyl, cycloalkyl, heterocyclyl and aryl optionally substituted with 1 to 3 groups of R$^a$, provided that when R$^3$ is —CR$^2$R$^4$R$^5$ and the R$^4$ is substituted by R$^a$, the R$^a$ substituent is not N(R$^4$)$_2$;

R$^a$ represents C$_{1\text{-}6}$ alkyl, halogen, —CHF$_2$, —(CH$_2$)$_n$CF$_3$, —O—, C$_{3\text{-}6}$ cycloalkyl, NR$^2$C(O)R$^2$, C(O)N(R$^2$)$_2$, C(R$^2$)$_2$OR$^2$, C(O)R$^2$, NO$_2$, CN, N(R$^2$)$_2$, C(O)OR$^2$, SO$_2$R$^2$, OR$^2$, (CH$_2$)$_n$C$_{5\text{-}10}$ heterocyclyl, or (CH$_2$)$_n$C$_{6\text{-}10}$ aryl, said alkyl, heterocyclyl and aryl optionally substituted with 1 to 3 groups of C$_{1\text{-}6}$ alkyl, halogen, OR$^2$, N(R$^4$)$_2$, C(O)N(R$^2$)$_2$, (CH$_2$)$_n$CF$_3$, or CN; and n represents 0 to 4.

2. The compound according to claim 1 wherein one of X and Y is N and the other is CH.

3. The compound according to claim 2 wherein X is N and Y is CH.

4. The compound according to claim 1 wherein R$^6$ represents a substituted C$_{1\text{-}6}$ alkyl, substituted with 1 to 3 groups selected from N(R$^2$)$_2$, CF$_3$, OH, CHF$_2$, CH$_3$, phenyl and pyridyl.

5. The compound according to claim 1 wherein R$^6$ represents a (CH$_2$)$_n$C$_{6\text{-}10}$ aryl, said aryl optionally substituted with 1 to 3 groups of R$^a$.

6. The compound according to claim 1 wherein R$^6$ represents a (CH$_2$)$_n$C$_{5\text{-}10}$ heterocyclyl, said heterocyclyl optionally substituted with 1 to 3 groups of R$^a$, provided said heterocyclyl is not oxazolyl, isoxazolyl, dihydro-isoxazolyl, or oxadiazolyl.

7. The compound according to claim 1 wherein X is N, Y is CH, R$^3$ is CR$^2$R$^4$R$^5$, R$^2$ in CR$^2$R$^4$R$^5$ of R$^3$ is hydrogen, and one of R$^4$ and R$^5$ is C$_{1\text{-}6}$ alkyl and the other is (CH$_2$)$_n$C$_{5\text{-}10}$ heterocyclyl, said heterocyclyl optionally substituted with 1 to 3 groups of R$^a$.

8. The compound according to claim 7 wherein R$^6$ represents a substituted C$_{1\text{-}6}$ alkyl, substituted with 1 to 3 groups of Ra.

9. The compound according to claim 8 wherein the alkyl is substituted with 1 to 3 groups selected from N(R$^2$)$_2$, CF$_3$, OH, CHF$_2$, CH$_3$, phenyl and pyridyl.

10. The compound according to claim 6 wherein $R^6$ is imidazolyl, triazolyl, pyrazolyl, piperazinyl, pyridyl, morpholinyl, and oxazinyl optionally substituted with 1 to 3 groups of Ra, one of X and Y is nitrogen and the other is CH, the R2 in $CR^2R^4R^5$ of R3 is hydrogen, and one of R4 and R5 is C1-6 alkyl or hydrogen and the other is C5-10 heterocyclyl, said heterocyclyl optionally substituted with 1 to 3 groups of Ra.

11. The compound according to claim 6 wherein $R^6$ is imidazolyl, triazolyl, pyrazolyl, piperazinyl, pyridyl, morpholinyl, and oxazinyl optionally substituted with 1 to 3 groups of $R^a$, X and Y are CH, the $R^2$ in $CR^2R^4R^5$ of $R^3$ is hydrogen, and one of $R^4$ and $R^5$ is $C_{1-6}$ alkyl or hydrogen and the other is $(CH_2)_nC_{5-10}$ heterocyclyl, said heterocylyl optionally substituted with 1 to 3 groups of $R^a$.

12. The compound according to claim 1 wherein $R^6$ is substituted $C_{1-6}$ alkyl, X and Y are CH, the $R^2$ in $CR^2R^4R^5$ of $R^3$ is hydrogen, and one of $R^4$ and $R^5$ is $C_{1-6}$ alkyl or hydrogen and the other is $(CH_2)_nC_{5-10}$ heterocyclyl, said heterocylyl optionally substituted with 1 to 3 groups of $R^a$.

13. The compound according to claim 1 wherein $R^3$ is —$(C(R^2)_2)_nC_{3-10}$ cycloalkyl, said cycloalkyl optionally substituted with 1 to 3 groups of $R^a$.

14. The compound according to claim 1 wherein $R^3$ is —$(C(R^2)_2)_nC_{5-10}$ heterocycle, said heterocylyl optionally substituted with 1 to 3 groups of $R^a$.

15. The compound according to claim 14 wherein the heterocycle is selected from the group consisting of triazolyl, pyridyl, pyrimidinyl, oxazolyl, pyrazolyl and oxadiazolyl, optionally substituted by 1 to 3 groups of $R^a$.

16. A compound of Tables 1-7 or pharmaceutically acceptable salts and individual enantiomers and diastereomers thereof:

TABLE 1

| EX | Structure |
|---|---|
| 1.1 | |
| 1.2 | |
| 1.3 | 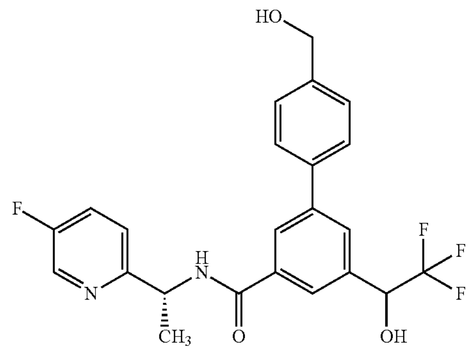 |
| 1.4 | 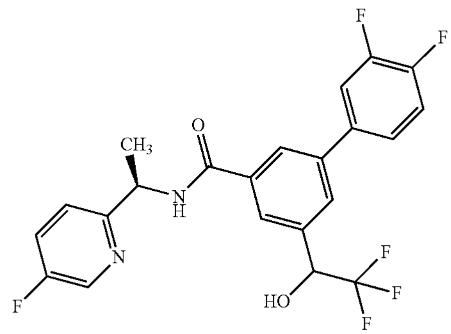 |
| 1.5 | 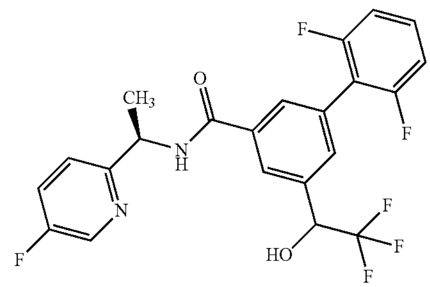 |
| 1.6 | 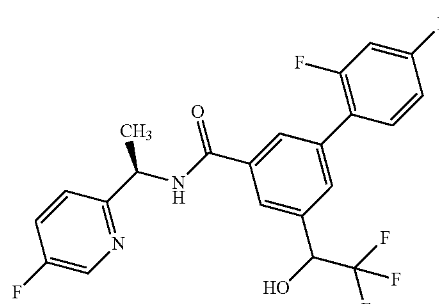 |
| 1.7 | 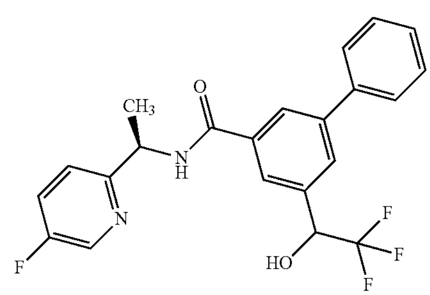 |

TABLE 1-continued
| EX | Structure |
|---|---|
| 1.8 | 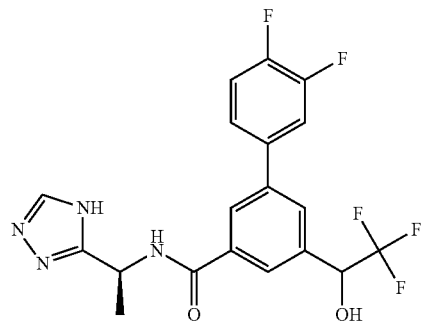 |
| 1.9 | 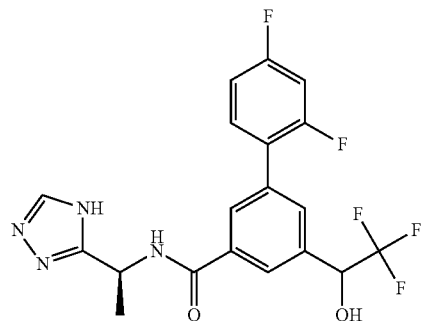 |
| 1.10 | 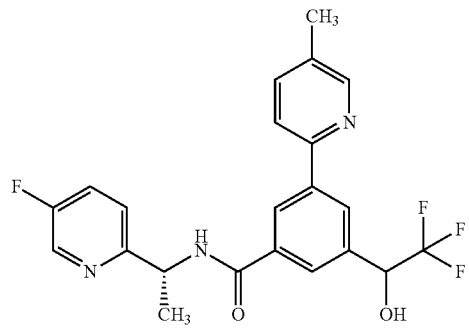 |
| 1.11 | 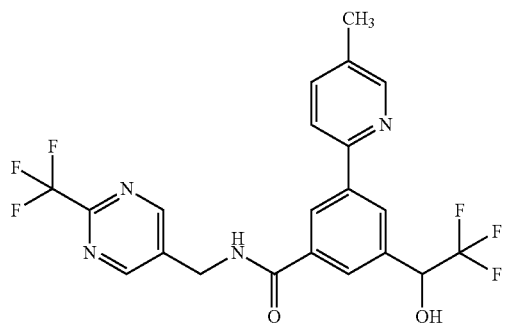 |
| 1.12 | 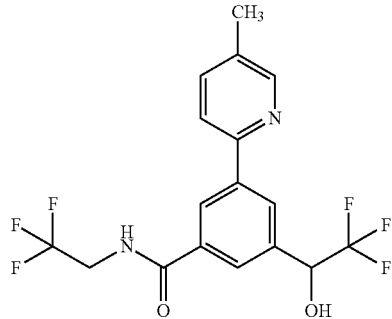 |
| 1.13 | 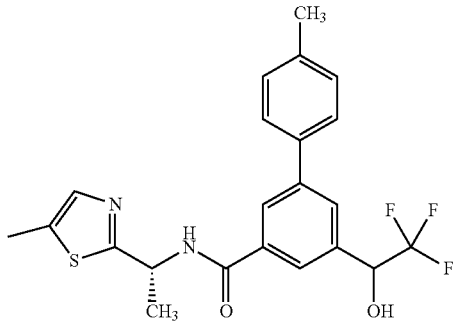 |
| 1.14 | 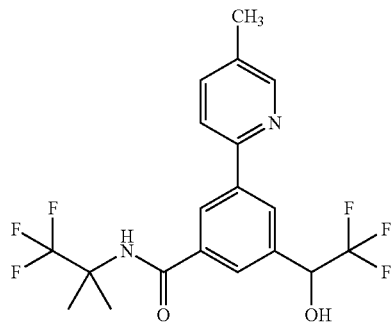 |
| 1.15 | 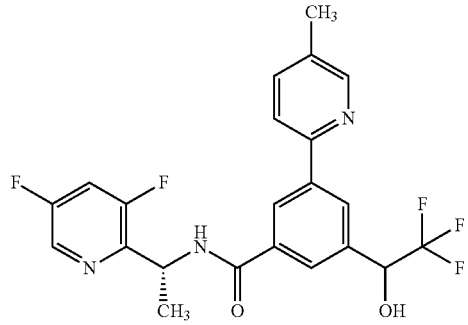 |

TABLE 1-continued
| EX | Structure |
|---|---|
| 1.16 | 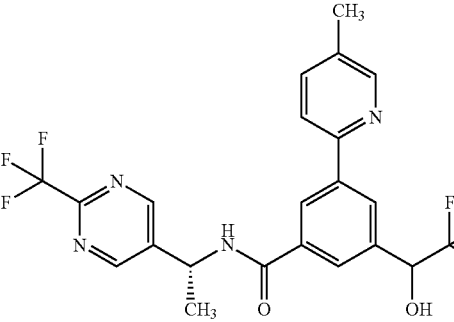 |
| 1.17 | 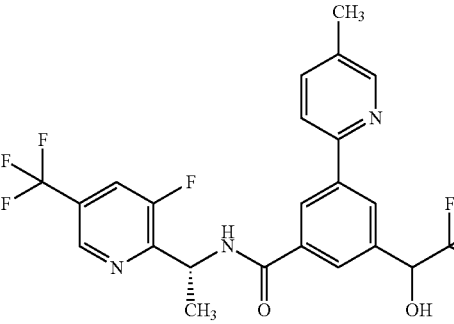 |
| 1.18 | 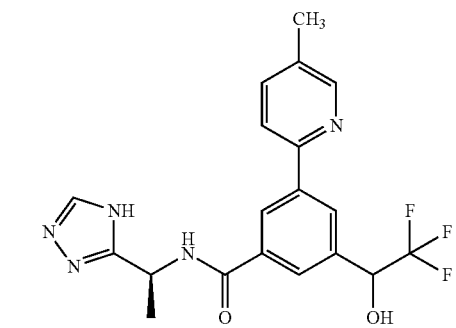 |
| 1.19 | 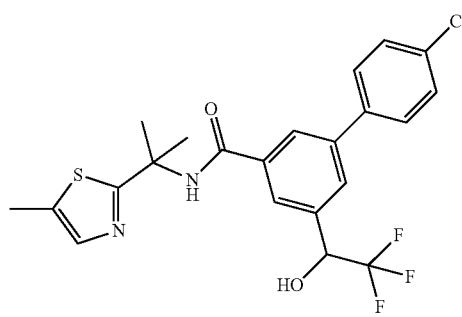 |
| 1.20 | 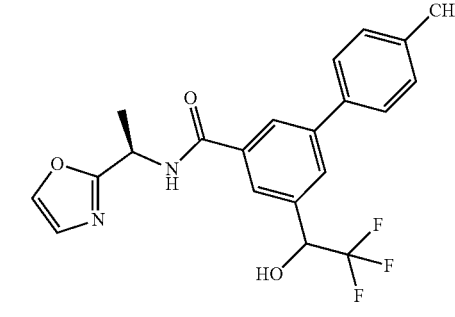 |
| 1.21 | 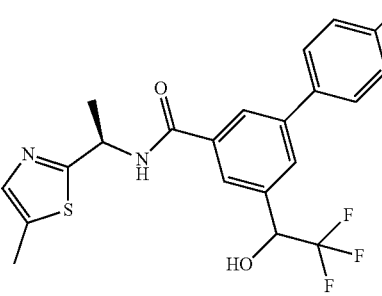 |
| 1.22 | 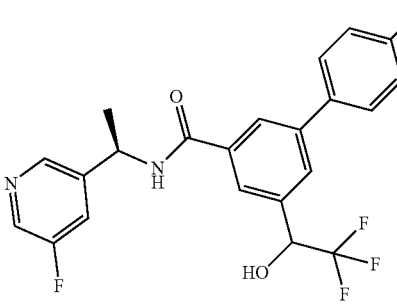 |
| 1.23 | 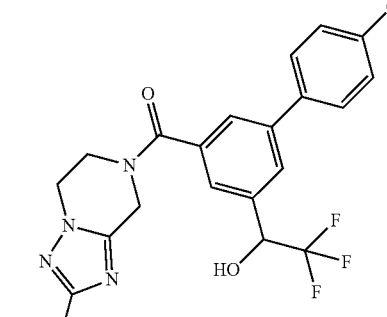 |
| 1.24 | 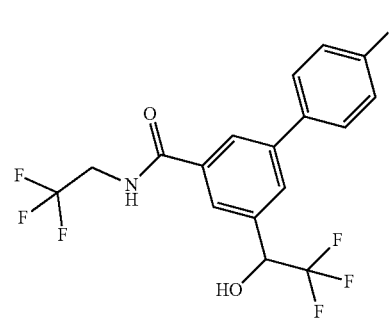 |

TABLE 1-continued

| EX | Structure |
|---|---|
| 1.25 | 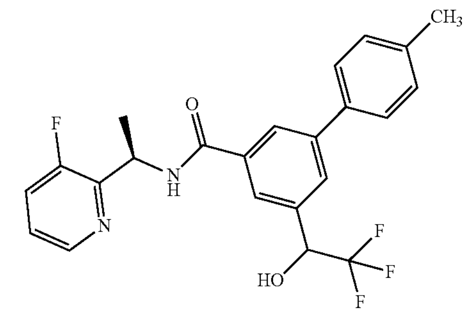 |
| 1.26 | 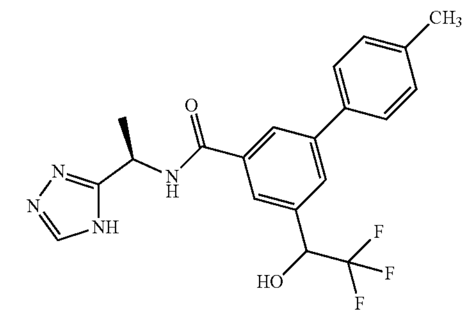 |
| 1.27 | 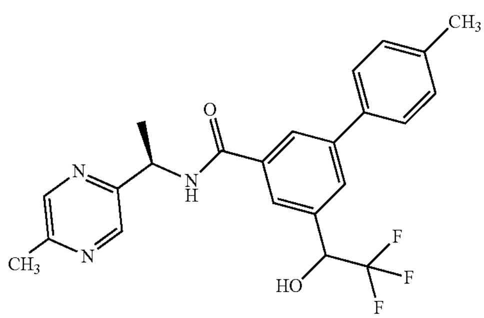 |
| 1.28 | 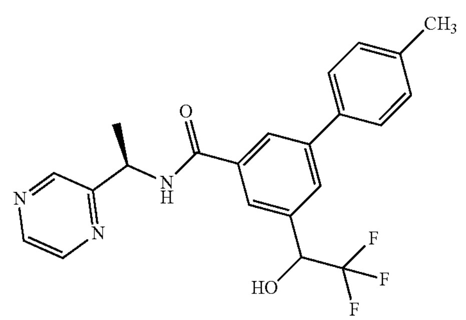 |
| 1.29 | 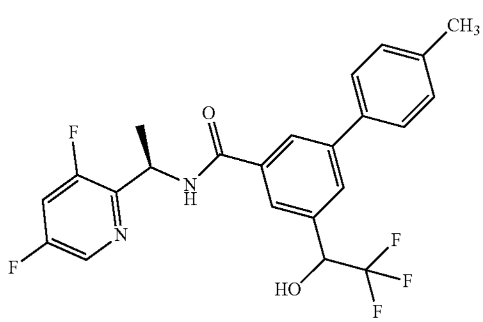 |
| 1.30 | |
| 1.31 | |
| 1.32 | |
| 1.33 | |

TABLE 1-continued
| EX | Structure |
|---|---|
| 1.34 | 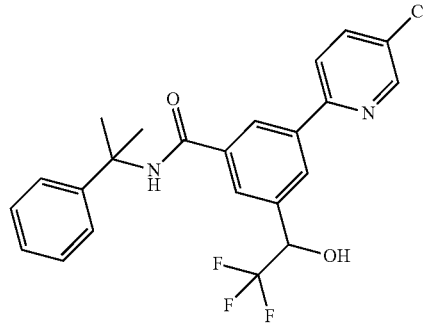 |
| 1.35 | 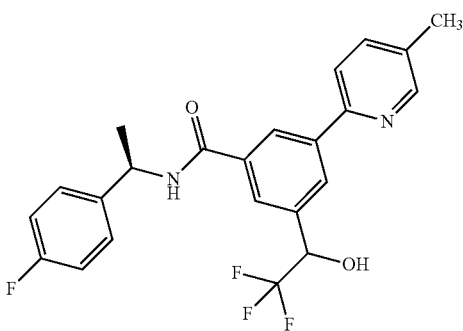 |
| 1.36 | 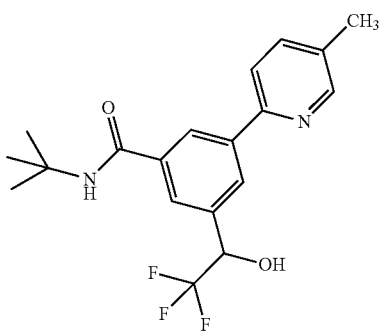 |
| 1.37 | 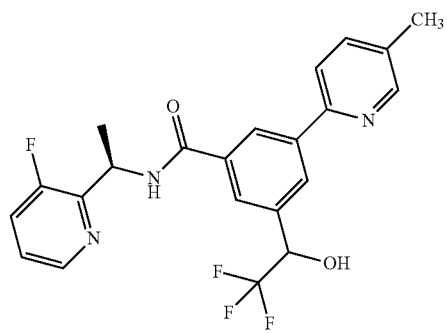 |
TABLE 1-continued
| EX | Structure |
|---|---|
| 1.38 | 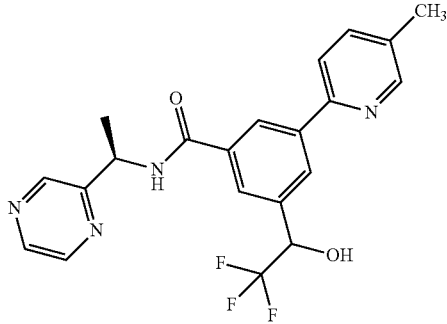 |
| 1.39 | 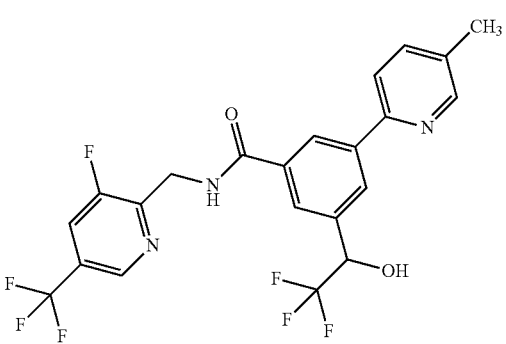 |
| 1.40 | 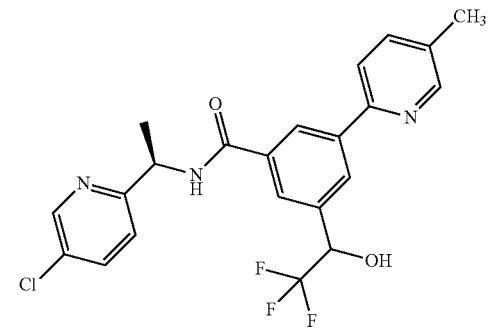 |
| 1.41 | 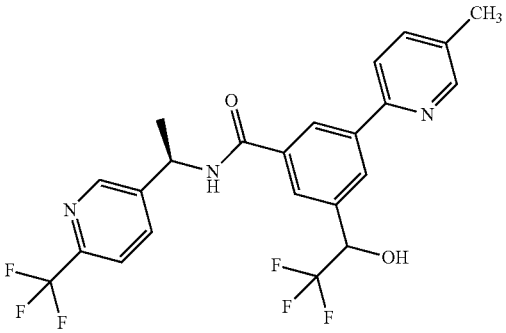 |

TABLE 1-continued

| EX | Structure |
|---|---|
| 1.42 | |
| 1.43 | |
| 1.44 | |
| 1.45 | |
| 1.46 | 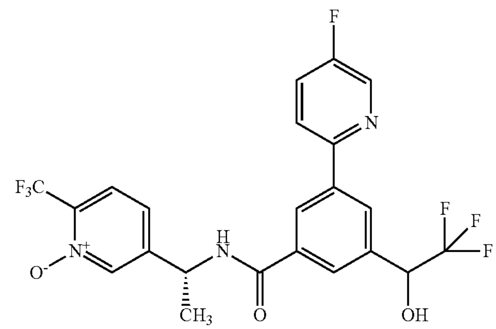 |
| 1.47 | 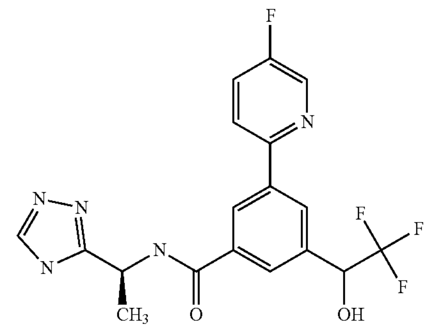 |
| 1.48 | 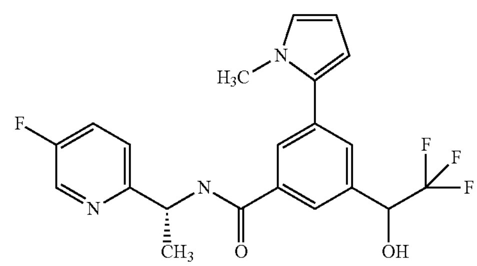 |
| 1.49 | 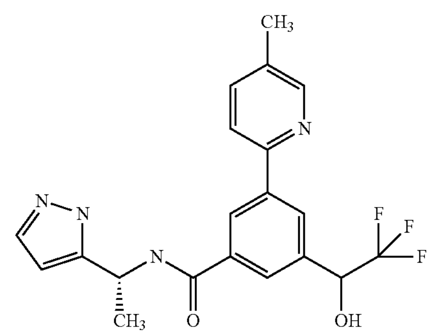 |
| 1.50 | 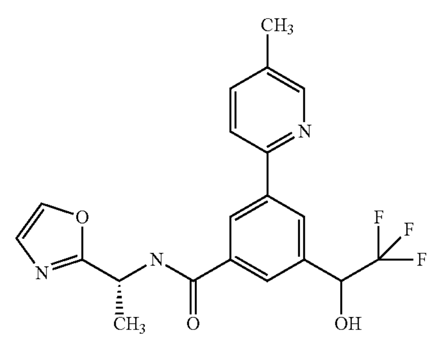 |

US 8,247,401 B2
TABLE 1-continued
| EX | Structure |
|---|---|
| 1.51 | 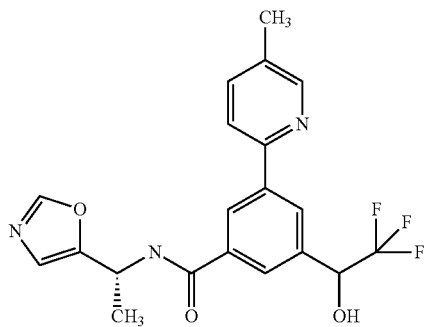 |
| 1.52 | 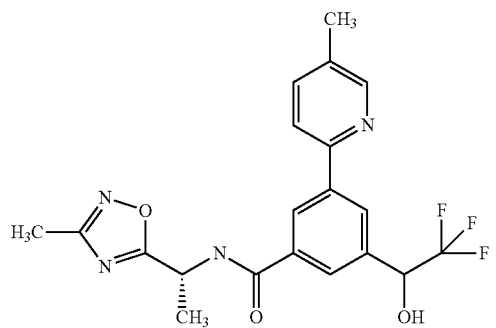 |
| 1.53 | 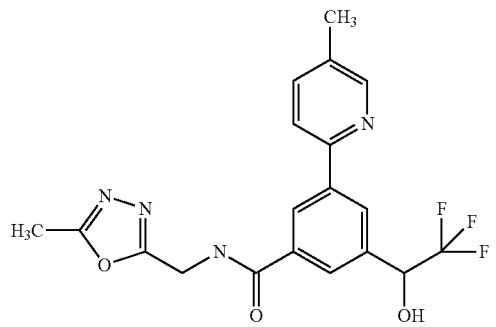 |
| 1.54 | 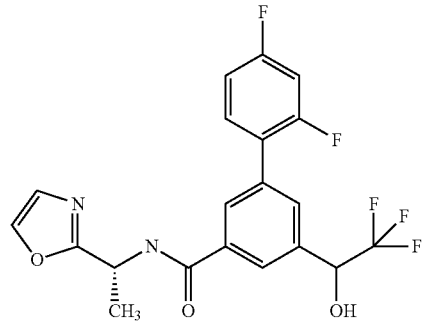 |
TABLE 1-continued
| EX | Structure |
|---|---|
| 1.55 | 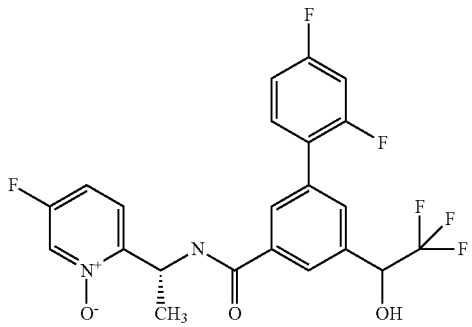 |
| 1.56 | 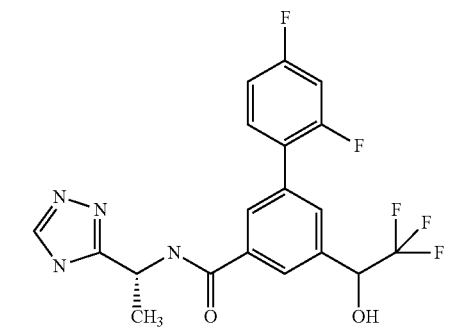 |
| 1.57 | 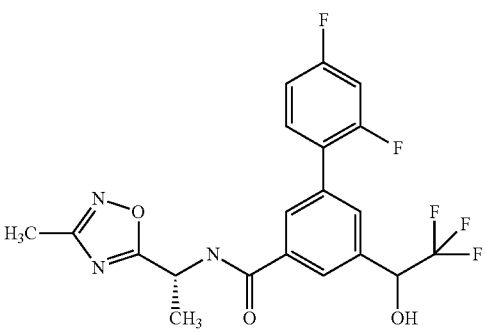 |
| 1.58 | 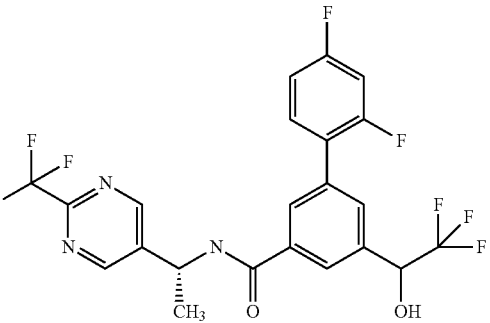 |

TABLE 1-continued
| EX | Structure |
|---|---|
| 1.59 | 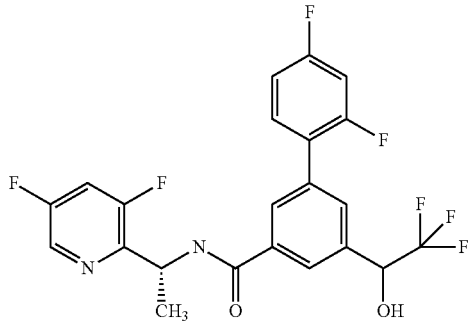 |
| 1.60 | 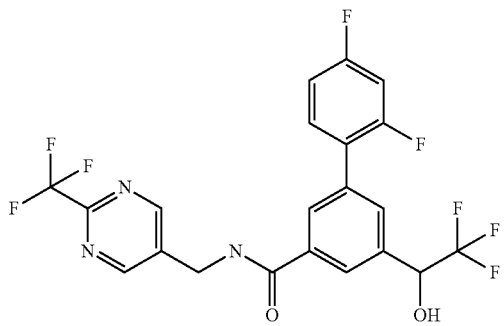 |
| 1.61 | 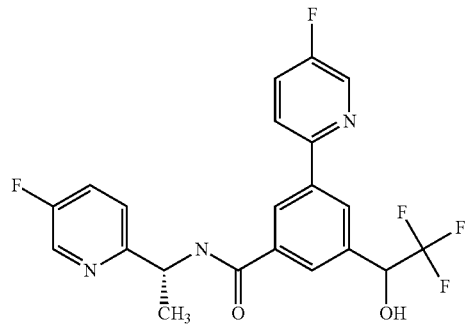 |
| 1.62 | 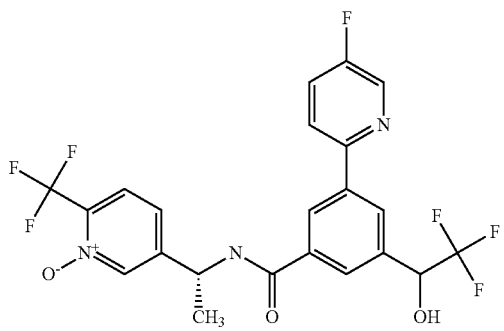 |
| 1.63 | 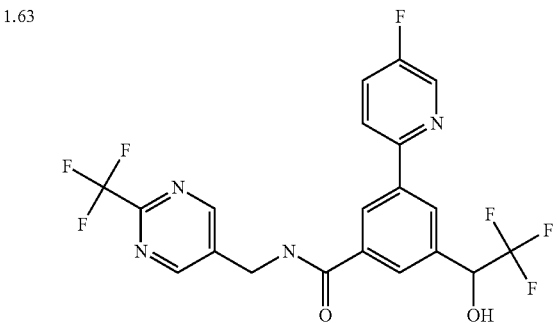 |
| 1.64 | 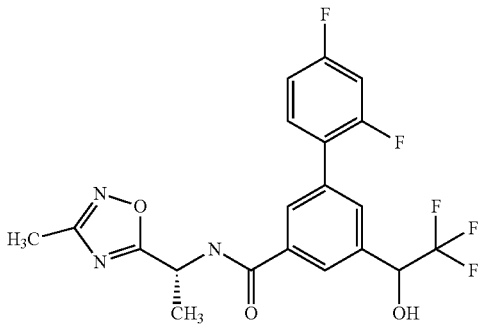 |
| 1.65 | 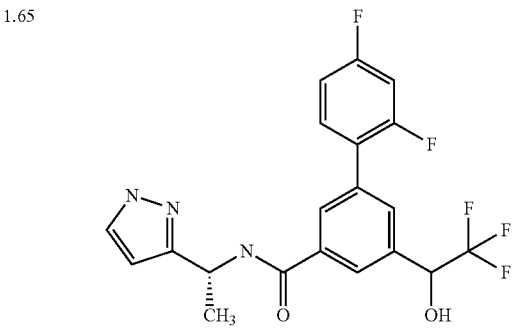 |
| 1.66 | 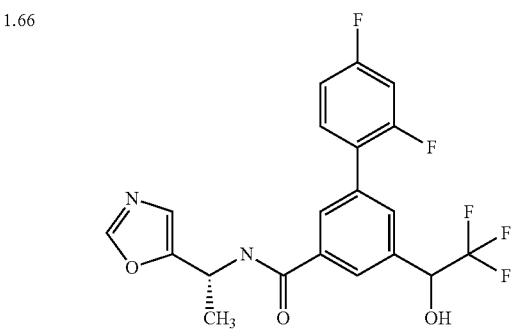 |

TABLE 1-continued
| EX | Structure |
|---|---|
| 1.67 | 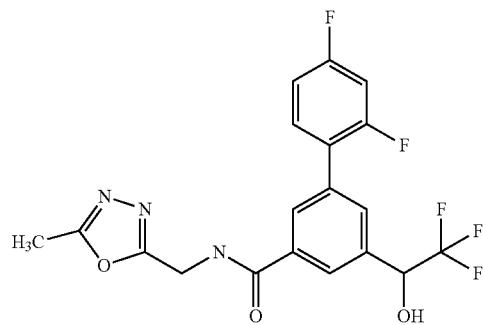 |
| 1.68 | 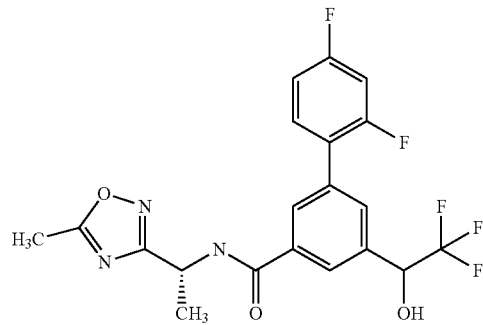 |
| 1.69 | 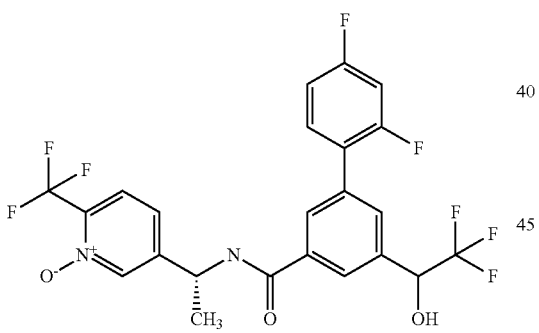 |
| 1.70 | 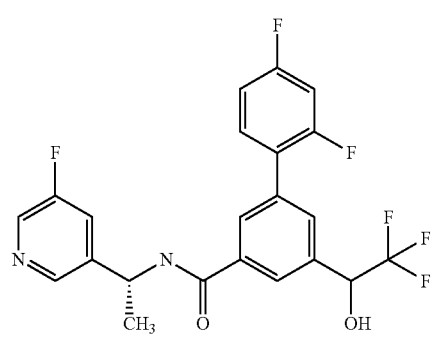 |
TABLE 1-continued
| EX | Structure |
|---|---|
| 1.71 | 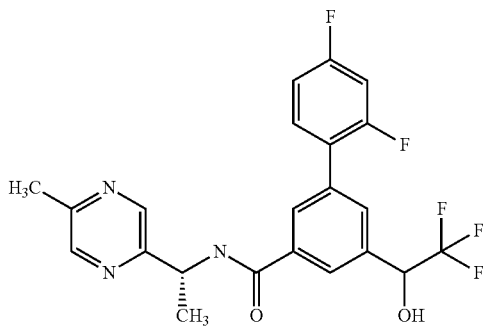 |
| 1.72 | 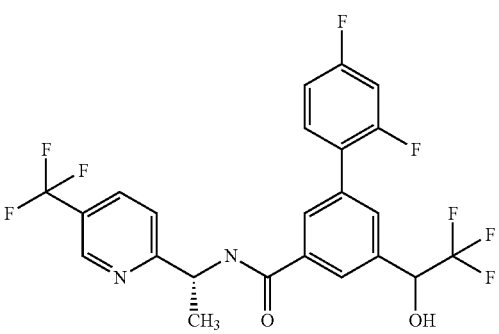 |
| 1.73 | 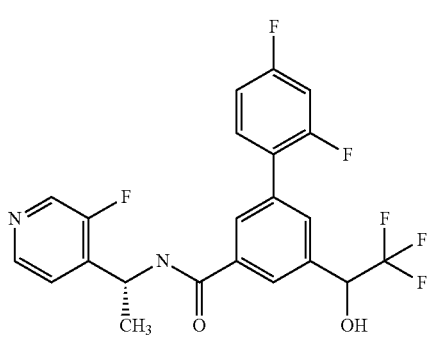 |
| 1.74 | 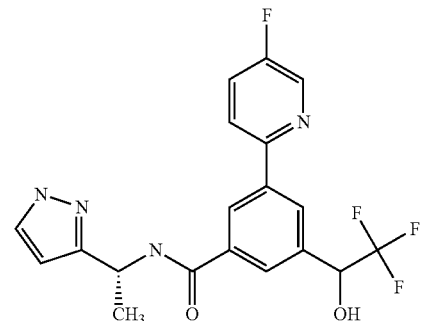 |

TABLE 1-continued
| EX | Structure |
|---|---|
| 1.75 | 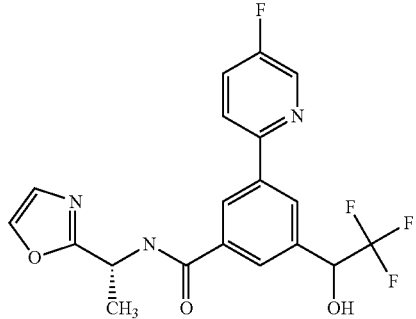 |
| 1.76 | 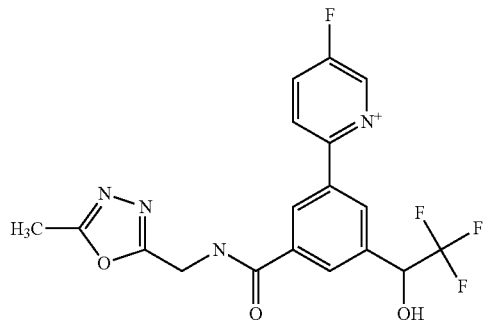 |
| 1.77 | 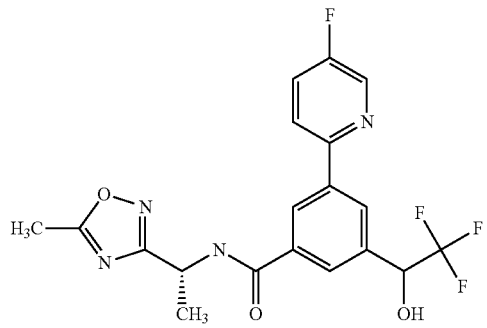 |
| 1.78 | 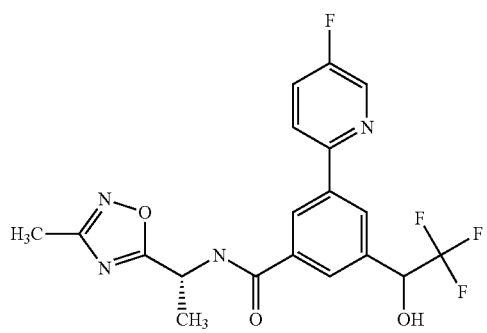 |
TABLE 1-continued
| EX | Structure |
|---|---|
| 1.79 | 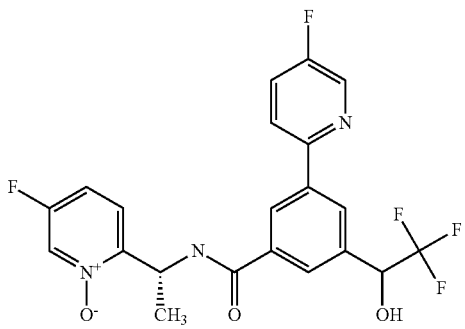 |
| 1.80 | 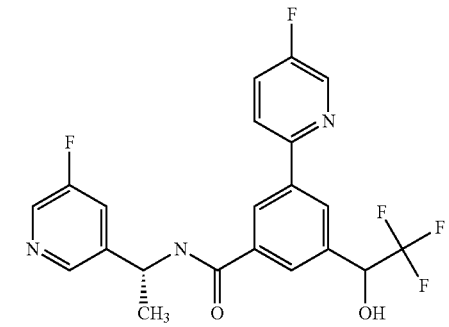 |
| 1.81 | 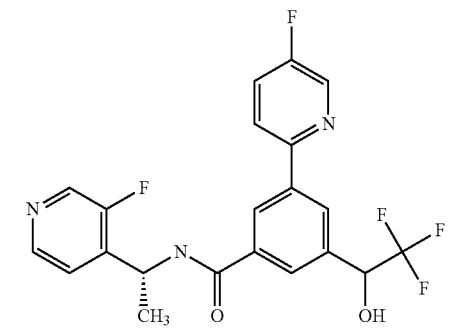 |
| 1.82 | 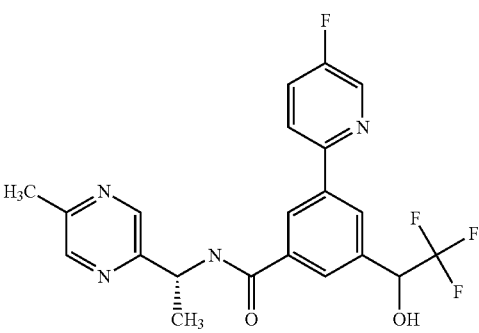 |

TABLE 1-continued
| EX | Structure |
|---|---|
| 1.83 | 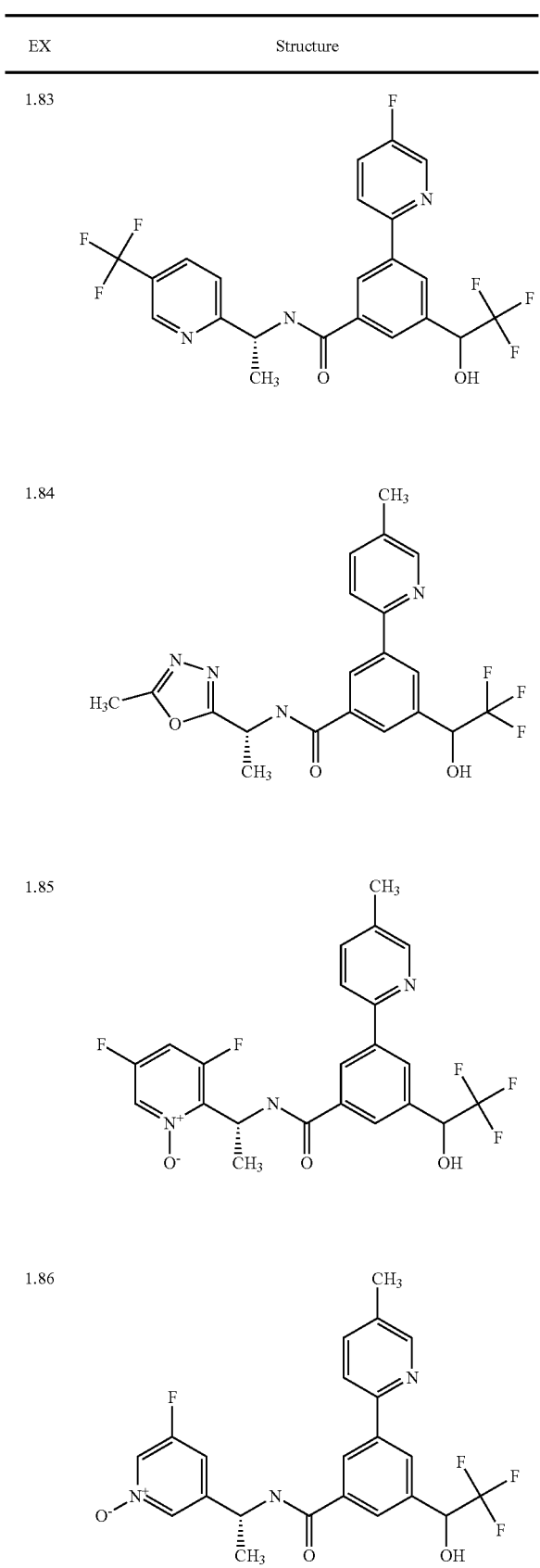 |
| 1.84 | 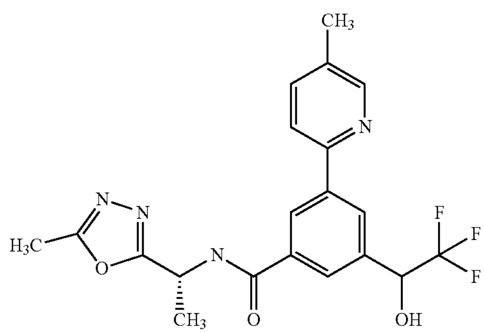 |
| 1.85 | 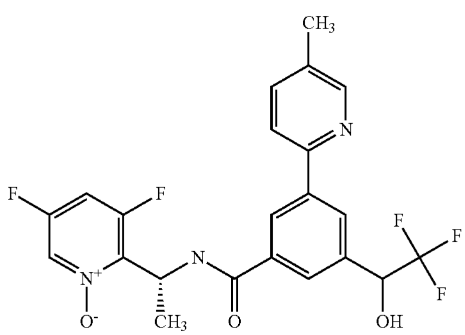 |
| 1.86 | 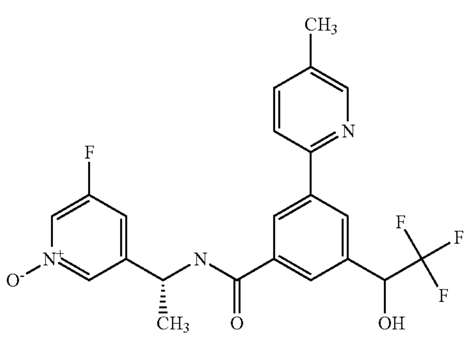 |
TABLE 1-continued
| EX | Structure |
|---|---|
| 1.87 | 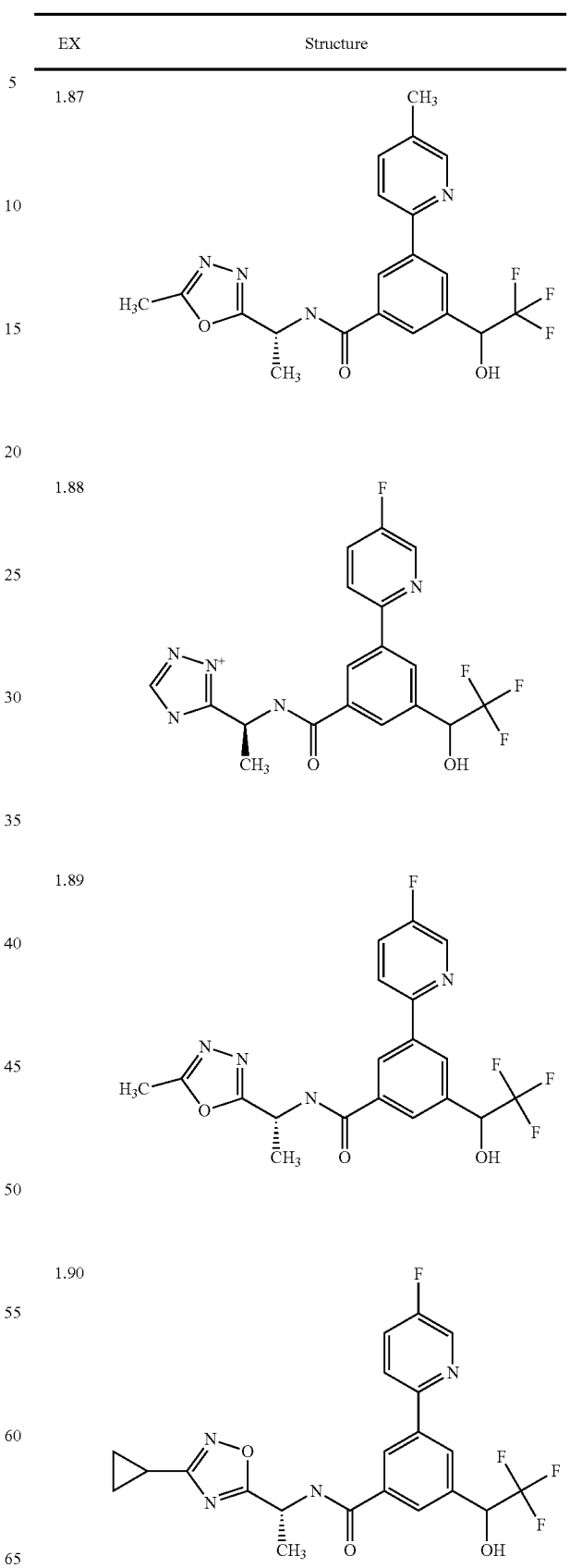 |
| 1.88 | 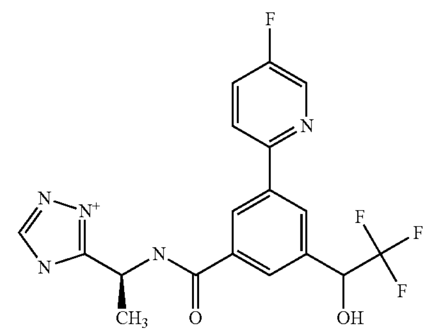 |
| 1.89 | 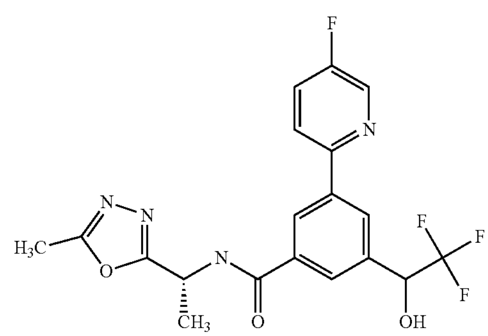 |
| 1.90 | 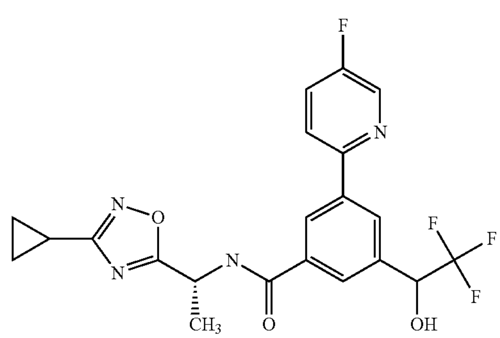 |

TABLE 1-continued
| EX | Structure |
|---|---|
| 1.91 | 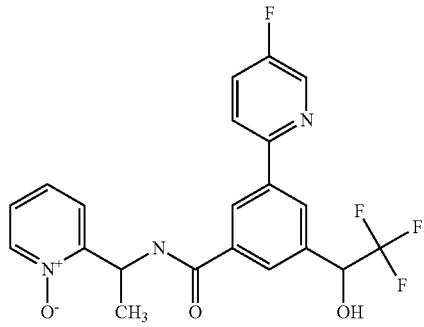 |
| 1.92 | 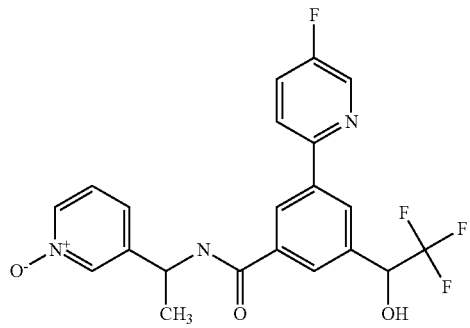 |
| 1.93 | 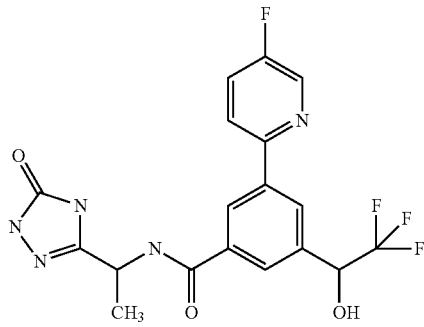 |
| 1.94 | 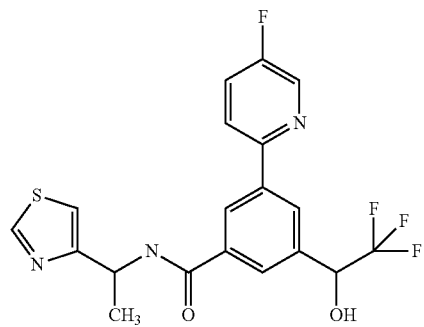 |
| 1.95 | 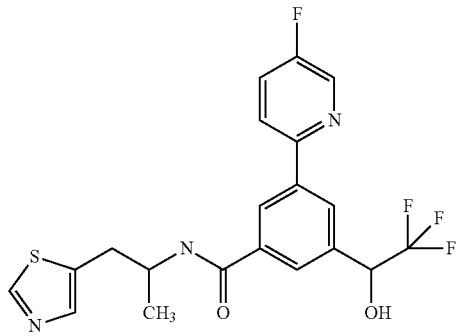 |
| 1.96 | 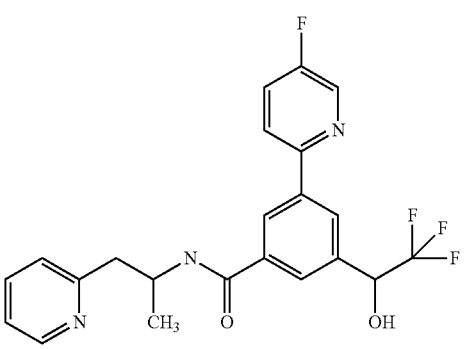 |
| 1.97 | 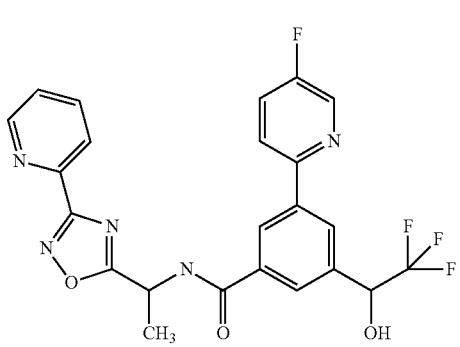 |
| 1.98 | 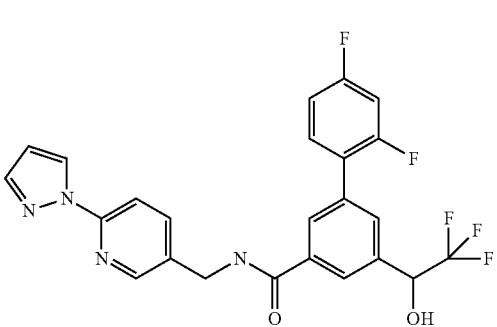 |

TABLE 1-continued
| EX | Structure |
|---|---|
| 1.99 | 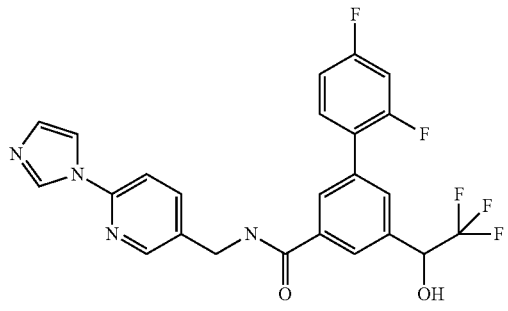 |
| 1.100 | 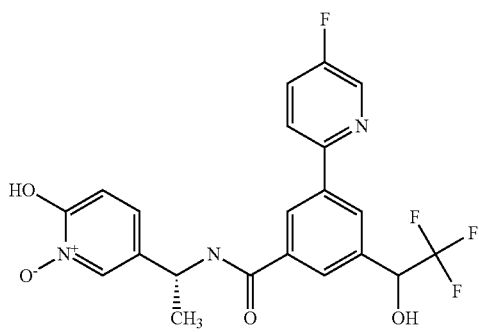 |
| 1.101 | 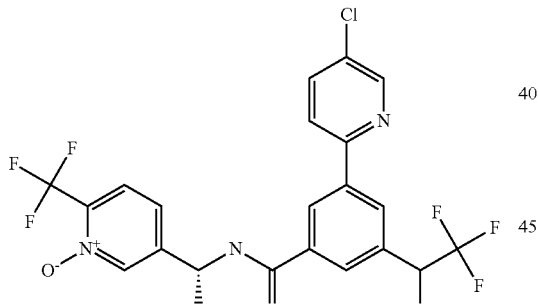 |
| 1.102 | 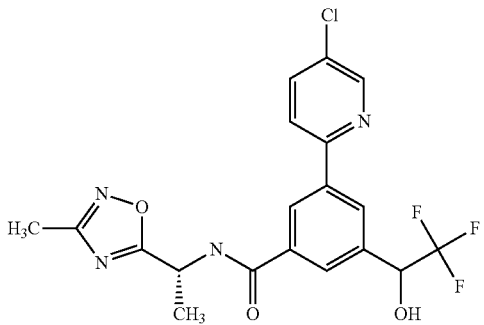 |
| 1.103 | 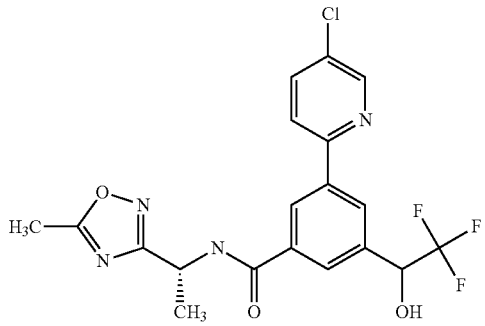 |
| 1.104 | 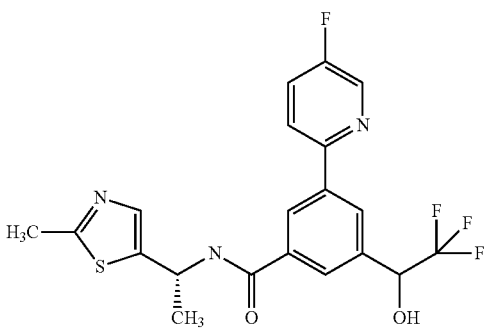 |
TABLE 2
| EX | Structure |
|---|---|
| 2.1 | 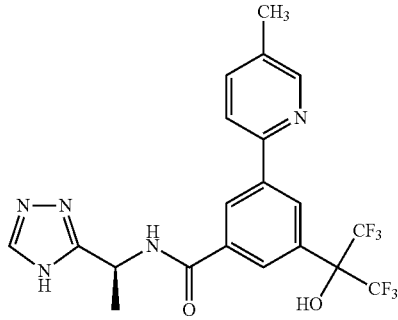 |
| 2.2 | 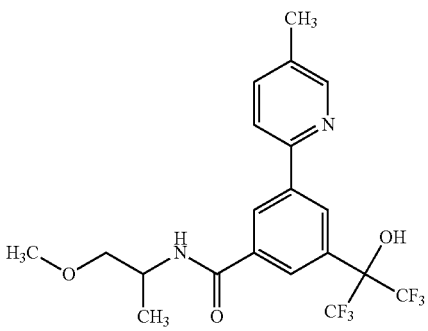 |

TABLE 2-continued

| EX | Structure |
|---|---|
| 2.3 | 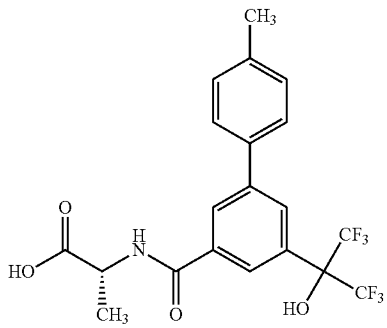 |
| 2.4 | 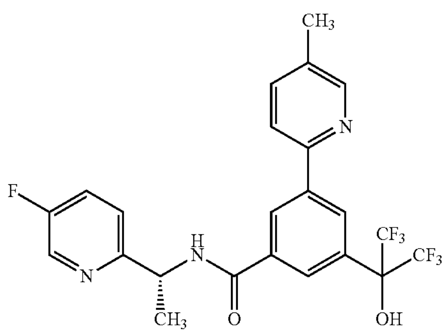 |
| 2.5 | 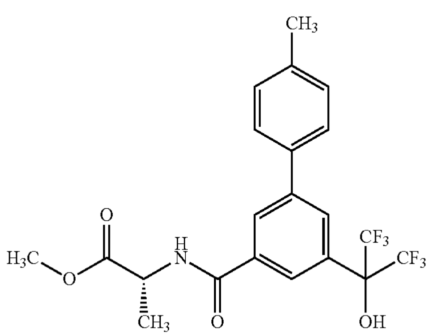 |
| 2.6 | 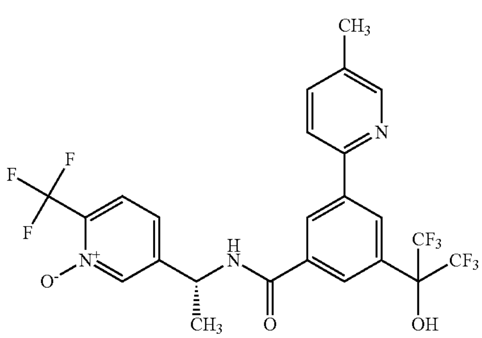 |
| 2.7 | |
| 2.8 | |
| 2.9 | |
| 2.10 | |

TABLE 2-continued
| EX | Structure |
|---|---|
| 2.11 | 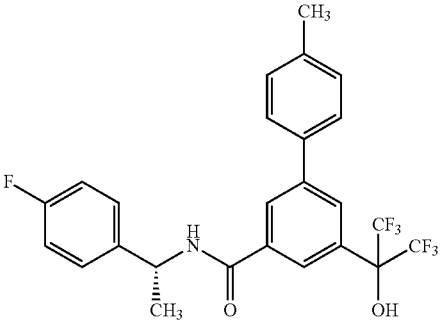 |
| 2.12 | 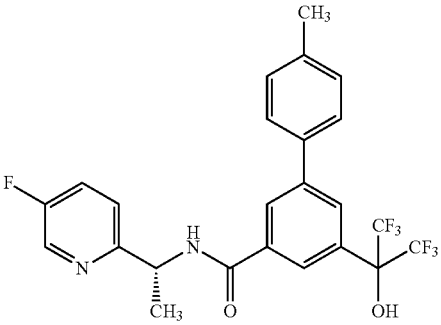 |
| 2.13 | 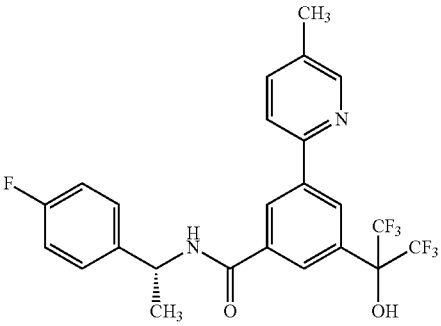 |
| 2.14 | 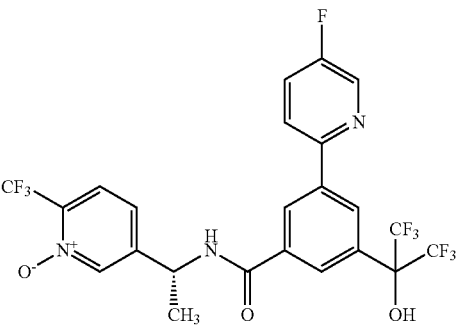 |
TABLE 3
| EX | Structure |
|---|---|
| 3.1 | 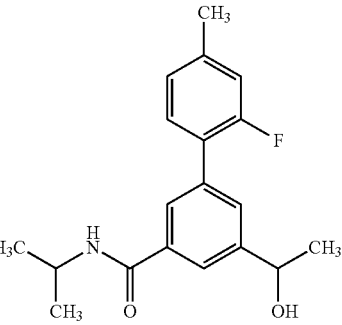 |
| 3.2 | 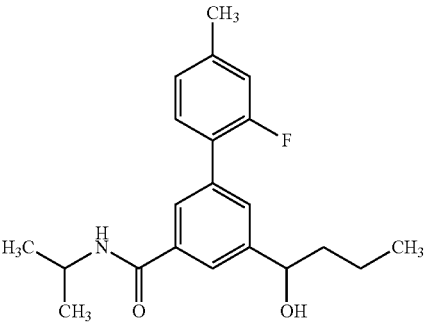 |
| 3.3 | 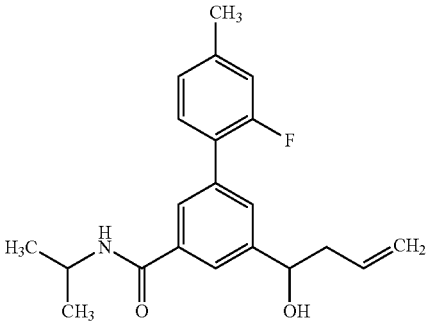 |
| 3.4 | 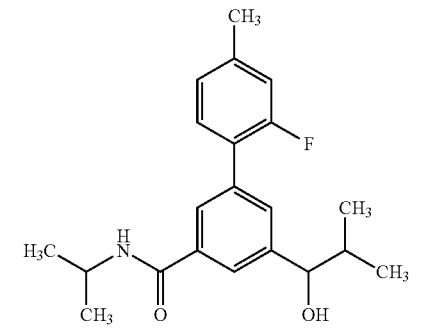 |

TABLE 3-continued
| EX | Structure |
|---|---|
| 3.5 | 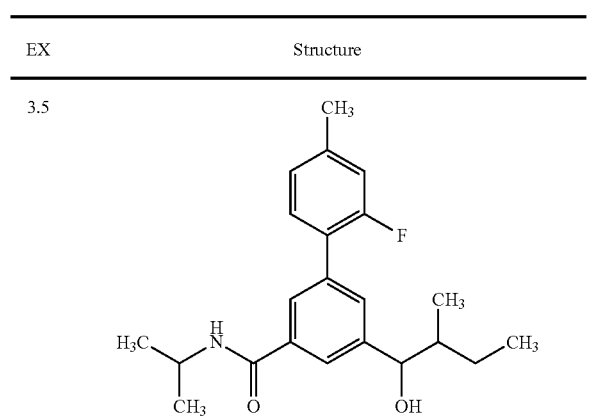 |
| 3.6 | 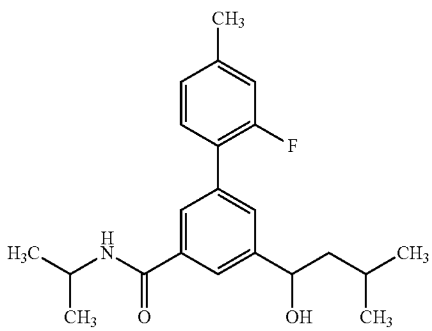 |
| 3.7 | 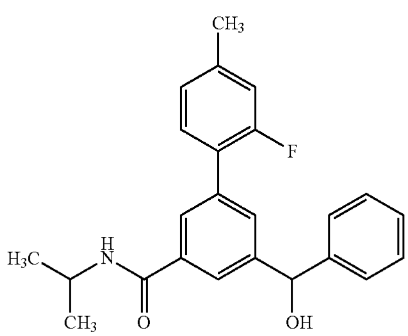 |
| 3.8 | 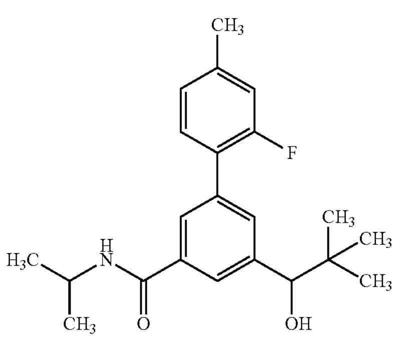 |
| 3.9 | 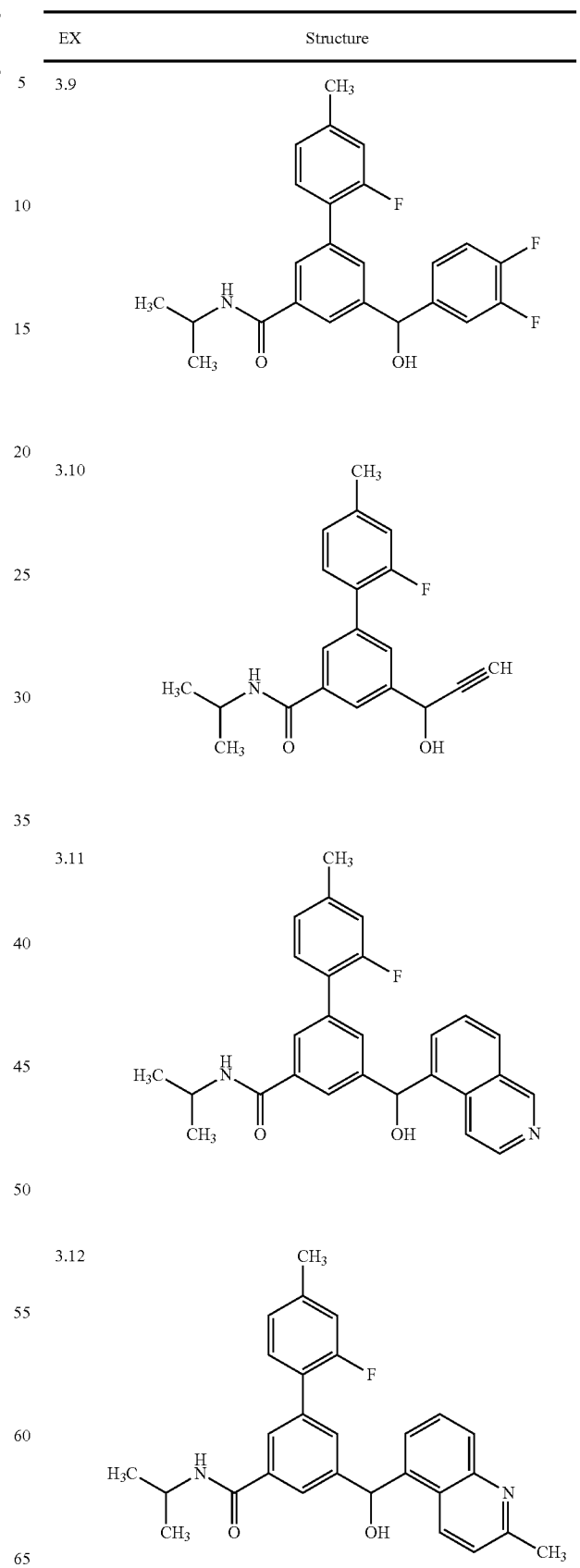 |
| 3.10 | |
| 3.11 | |
| 3.12 | |

TABLE 3-continued

| EX | Structure |
|---|---|
| 3.13 | 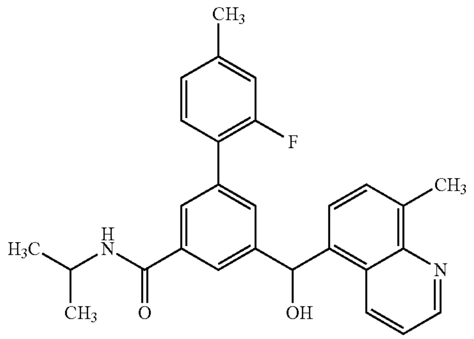 |
| 3.14 | 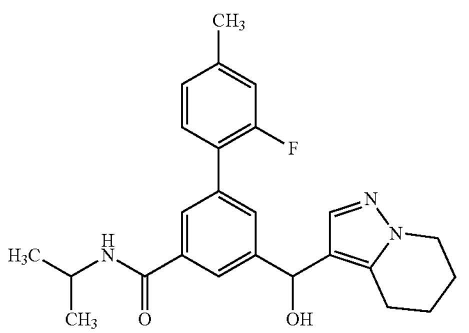 |
| 3.15 | 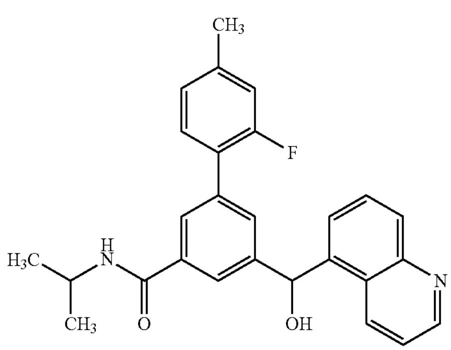 |
| 3.16 | 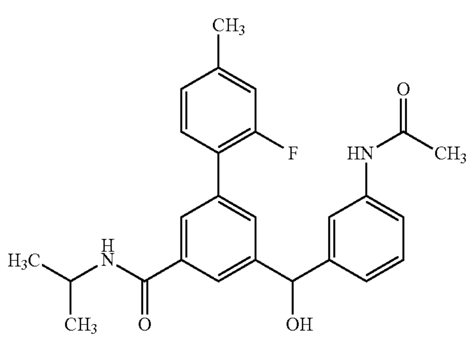 |

TABLE 3-continued

| EX | Structure |
|---|---|
| 3.17 | |
| 3.18 | |
| 3.19 | |

TABLE 3-continued
| EX | Structure |
|---|---|
| 3.20 | 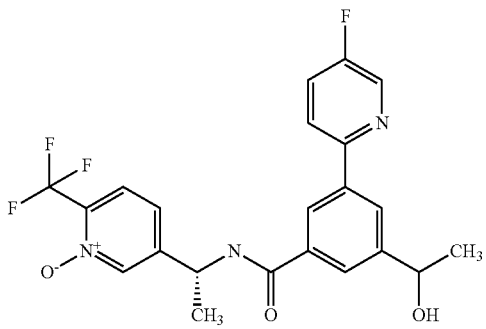 |
| 3.21 | 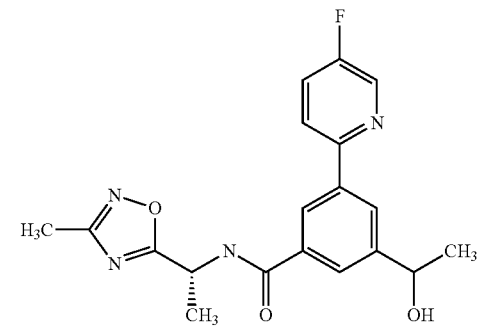 |
TABLE 4
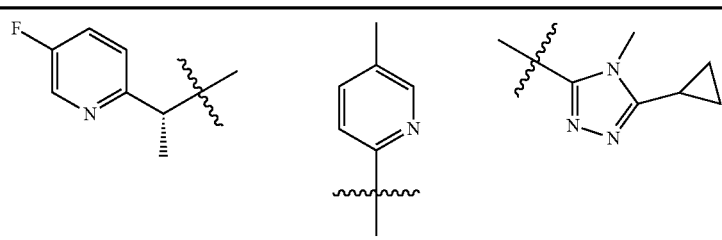
| Example | R¹ | R² | R³ |
|---|---|---|---|
| 4.1 | 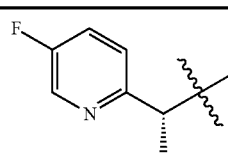 | 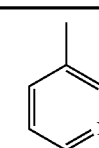 | 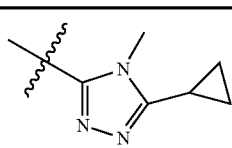 |
| 4.2 | 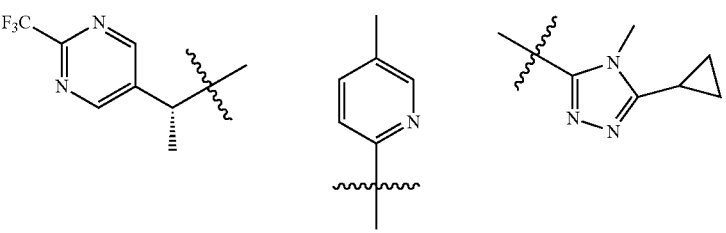 | 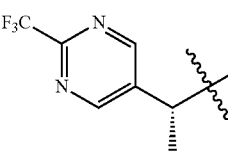 | 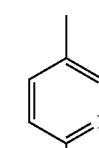 |
| 4.3 | 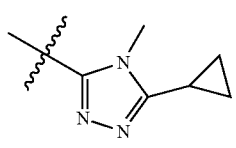 | 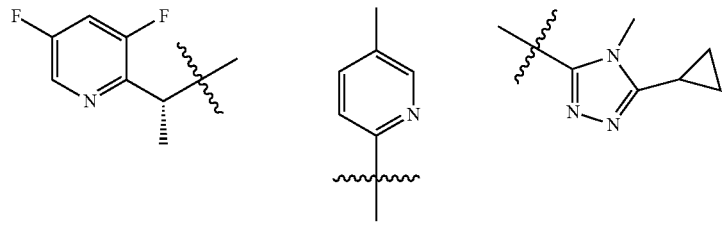 | 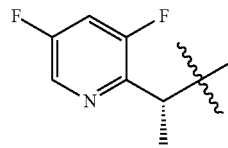 |
| 4.4 | 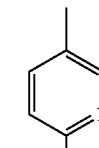 | 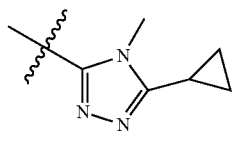 | 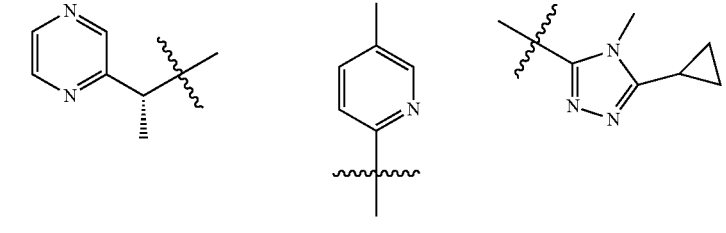 |

TABLE 4-continued

| Example | R¹ | R² | R³ |
|---|---|---|---|
| 4.5 | (4H-1,2,4-triazol-3-yl)-CH(CH₃)- | 5-pyridyl (via 2-position) | 4-methyl-5-cyclopropyl-4H-1,2,4-triazol-3-yl |
| 4.6 | (3-methyl-1,2,4-oxadiazol-5-yl)-CH(CH₃)- | 5-pyridyl (via 2-position) | 4-methyl-5-cyclopropyl-4H-1,2,4-triazol-3-yl |
| 4.7 | (1,2,4-oxadiazol-3-yl)-CH(CH₃)- | 5-pyridyl (via 2-position) | 4-methyl-5-cyclopropyl-4H-1,2,4-triazol-3-yl |
| 4.8 | (5-methyl-1,2,4-oxadiazol-3-yl)-CH(CH₃)- | 5-pyridyl (via 2-position) | 4-methyl-5-cyclopropyl-4H-1,2,4-triazol-3-yl |
| 4.9 | (5-trifluoromethyl-pyridin-2-yl)-CH(CH₃)- | 5-pyridyl (via 2-position) | 4-methyl-5-cyclopropyl-4H-1,2,4-triazol-3-yl |
| 4.10 | (6-trifluoromethyl-pyridin-3-yl)-CH(CH₃)- | 5-pyridyl (via 2-position) | 4-methyl-5-cyclopropyl-4H-1,2,4-triazol-3-yl |

TABLE 4-continued

| Example | R¹ | R² | R³ |
|---|---|---|---|
| 4.11 | 3,5-difluoropyridin-2-yl with CH(CH₃) | pyridin-2-yl (5-linked) | 4-methyl-5-(2-hydroxypropan-2-yl)-4H-1,2,4-triazol-3-yl |
| 4.12 | 2-(trifluoromethyl)pyrimidin-5-yl with CH(CH₃) | pyridin-2-yl (5-linked) | 4,5-dimethyl-4H-1,2,4-triazol-3-yl |
| 4.13 | 3,5-difluoropyridin-2-yl with CH(CH₃) | pyridin-2-yl (5-linked) | 4-methyl-4H-1,2,4-triazol-3-yl |
| 4.14 | 5-(trifluoromethyl)pyridin-2-yl with CH(CH₃) | pyridin-2-yl (5-linked) | 4-methyl-4H-1,2,4-triazol-3-yl |
| 4.15 | 5-fluoropyridin-2-yl with CH(CH₃) | pyridin-2-yl (5-linked) | 4-methyl-4H-1,2,4-triazol-3-yl |
| 4.16 | 6-(trifluoromethyl)pyridin-3-yl with CH(CH₃) | pyridin-2-yl (5-linked) | 4-methyl-4H-1,2,4-triazol-3-yl |

TABLE 4-continued

| Example | R¹ | R² | R³ |
|---|---|---|---|
| 4.17 | 3-fluoropyridin-2-yl (S)-ethyl | 5-pyridin-2-yl (methyl linker) | 4-methyl-4H-1,2,4-triazol-3-yl |
| 4.18 | 4-fluorophenyl isopropyl | 5-pyridin-2-yl (methyl linker) | 4-methyl-4H-1,2,4-triazol-3-yl |
| 4.19 | 6-(trifluoromethyl)pyridin-3-yl (S)-ethyl | 5-pyridin-2-yl (methyl linker) | 4-methyl-5-(oxazol-2-yl)-4H-1,2,4-triazol-3-yl |
| 4.20 | 6-(trifluoromethyl)pyridin-3-yl (S)-ethyl | 5-pyridin-2-yl (methyl linker) | 4-methyl-5-(trifluoromethyl)-4H-1,2,4-triazol-3-yl |
| 4.21 | 3-methyl-1,2,4-oxadiazol-5-yl (S)-ethyl | 2-fluoro-4-methylphenyl | 5-cyclopropyl-4-(2,2,2-trifluoroethyl)-4H-1,2,4-triazol-3-yl |
| 4.22 | 3-methyl-1,2,4-oxadiazol-5-yl (S)-ethyl | 2-fluoro-4-methylphenyl | 5-cyclopropyl-4-methyl-4H-1,2,4-triazol-3-yl |

TABLE 4-continued
| Example | R¹ | R² | R³ |
|---|---|---|---|
| 4.23 | 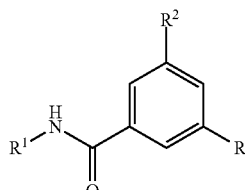 | 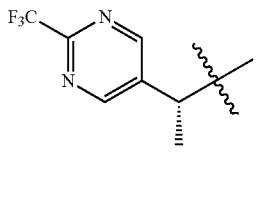 | 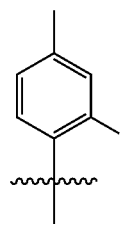 |
| 4.24 | 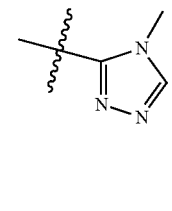 | 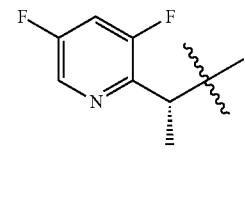 | 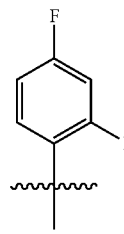 |
| 4.25 | 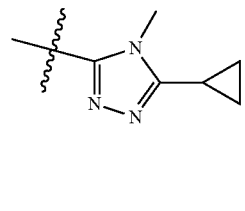 | 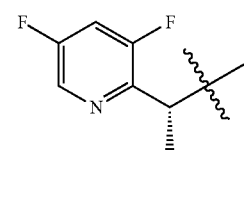 | 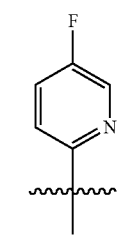 |
| 4.26 | 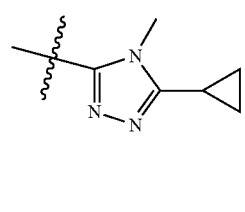 | 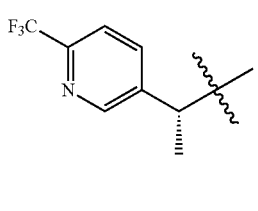 | 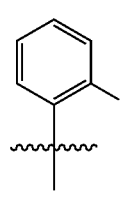 |
| 4.27 | 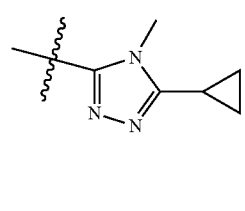 | 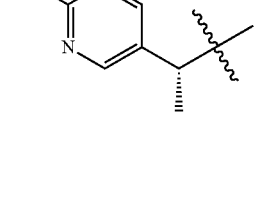 | 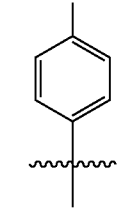 |
| 4.28 | 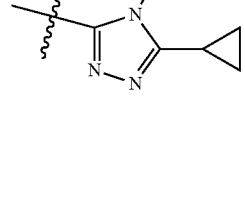 | 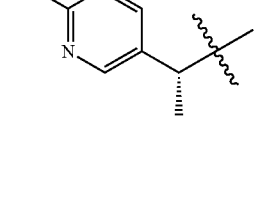 | 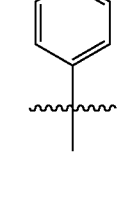 |

TABLE 4-continued

| Example | R¹ | R² | R³ |
|---|---|---|---|
| 4.29 | 2-(trifluoromethyl)pyridin-5-yl, CH(CH₃)- | 4-cyclopropylphenyl | 4-methyl-5-cyclopropyl-4H-1,2,4-triazol-3-yl |
| 4.30 | 2-(trifluoromethyl)pyridin-5-yl, CH(CH₃)- | 3-fluoro-4-yl-phenyl | 4-methyl-5-(1-methyl-1H-imidazol-2-yl)-4H-1,2,4-triazol-3-yl |
| 4.31 | 2-(trifluoromethyl)pyrimidin-5-yl, CH(CH₃)- | 3-fluoro-4-yl-phenyl | 4-methyl-5-cyclopropyl-4H-1,2,4-triazol-3-yl |
| 4.32 | pyridin-3-yl, CH(CH₃)- | 3-fluoro-4-yl-phenyl | 4-methyl-5-cyclopropyl-4H-1,2,4-triazol-3-yl |
| 4.33 | pyrimidin-4-yl, CH(CH₃)- | 3-fluoro-4-yl-phenyl | 4-methyl-5-cyclopropyl-4H-1,2,4-triazol-3-yl |
| 4.34 | tert-butyl | 3-fluoro-4-yl-phenyl | 4-methyl-5-cyclopropyl-4H-1,2,4-triazol-3-yl |

TABLE 4-continued

| Example | R¹ | R² | R³ |
|---|---|---|---|
| 4.35 | 6-(trifluoromethyl)pyridin-3-yl with (S)-methyl linker | 4-fluorophenyl | 5,6-dihydro-8H-[1,2,4]triazolo[3,4-c][1,4]oxazin-3-yl |
| 4.36 | 6-(trifluoromethyl)pyridin-3-yl with (S)-methyl linker | 4-fluorophenyl | 5,6,7,8-tetrahydro-[1,2,4]triazolo[4,3-a]pyrazin-3-yl |
| 4.37 | tert-butyl | 4-fluorophenyl | 5-cyclopropyl-4H-1,2,4-triazol-3-yl |
| 4.38 | 6-(trifluoromethyl)pyridin-3-yl with (S)-methyl linker | 4-fluorophenyl | 5-cyclopropyl-1-methyl-1H-1,2,4-triazol-3-yl |
| 4.39 | 3,5-difluoropyridin-2-yl with (S)-methyl linker | 4-fluorophenyl | 1-methyl-1H-1,2,4-triazol-3-yl |
| 4.40 | 6-(trifluoromethyl)pyridin-3-yl with (S)-methyl linker | 4-fluorophenyl | 1-methyl-1H-1,2,4-triazol-3-yl |

TABLE 4-continued

| Example | R¹ | R² | R³ |
|---|---|---|---|
| 4.41 | 5-fluoropyridin-2-yl, (S)-1-methylethyl | 3-fluorophenyl (4-linked) | 1-methyl-1H-1,2,4-triazol-5-yl |
| 4.42 | isopropyl | 3-fluorophenyl (4-linked) | 5-(trifluoromethyl)-1-methyl-1H-1,2,4-triazol-3-yl |
| 4.43 | 5-fluoropyridin-2-yl, (S)-1-methylethyl | 5-methylpyridin-2-yl | 5-cyclopropyl-1-methyl-1H-1,2,4-triazol-3-yl |
| 4.44 | 6-(trifluoromethyl)pyridin-3-yl, (S)-1-methylethyl | 5-methylpyridin-2-yl | 1-methyl-1H-1,2,3-triazol-5-yl |
| 4.45 | 5-(trifluoromethyl)pyrazin-2-yl, (S)-1-methylethyl | 5-methylpyridin-2-yl | 1-methyl-1H-1,2,3-triazol-5-yl |
| 4.46 | 3,5-difluoropyridin-2-yl, (S)-1-methylethyl | 5-methylpyridin-2-yl | 1-methyl-1H-1,2,3-triazol-5-yl |

TABLE 4-continued

| Example | R¹ | R² | R³ |
|---|---|---|---|
| 4.47 | 6-(trifluoromethyl)pyridin-3-yl (chiral methyl) | pyridin-2-yl (5-methyl) | 1-methyl-1H-1,2,3-triazol-4-yl |
| 4.48 | 2-(trifluoromethyl)pyrimidin-5-yl (chiral methyl) | pyridin-2-yl (5-methyl) | 1-methyl-1H-1,2,3-triazol-4-yl |
| 4.49 | 6-(trifluoromethyl)pyridin-3-yl (chiral methyl) | pyridin-2-yl (5-methyl) | 1-methyl-1H-imidazol-2-yl |
| 4.50 | 6-(trifluoromethyl)pyridin-3-yl (chiral methyl) | 3-fluoro-4-methylphenyl | 1-methyl-1H-imidazol-2-yl |
| 4.51 | 6-(trifluoromethyl)pyridin-3-yl (chiral methyl) | pyridin-2-yl (5-methyl) | 1-methyl-1H-imidazol-5-yl |
| 4.52 | 6-(trifluoromethyl)pyridin-3-yl (chiral methyl) | pyridin-2-yl (5-methyl) | 1-methyl-1H-imidazol-4-yl |

TABLE 4-continued
| Example | R¹ | R² | R³ |
|---|---|---|---|
| 4.53 | 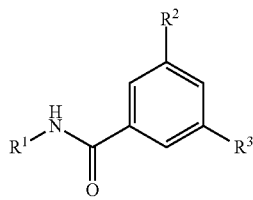 | 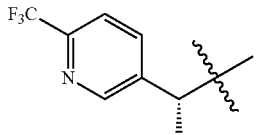 | 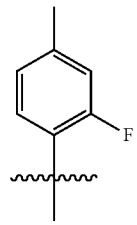 |
| 4.54 | 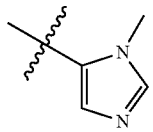 | 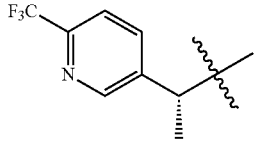 | 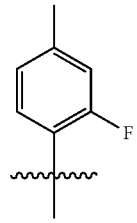 |
| 4.55 | 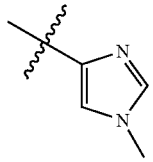 | 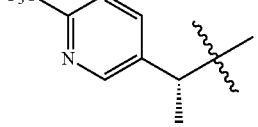 | 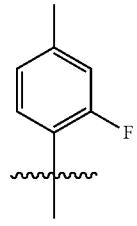 |
| 4.56 | 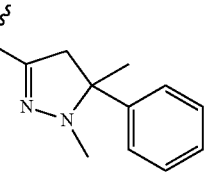 | 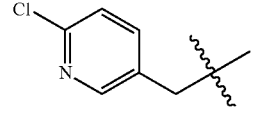 | 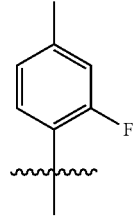 |
| 4.57 | 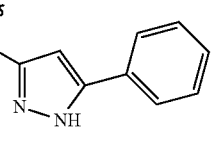 | 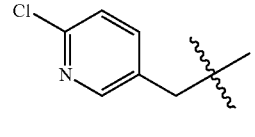 | 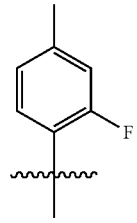 |
| 4.58 | 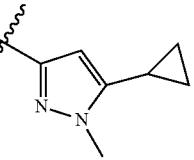 | 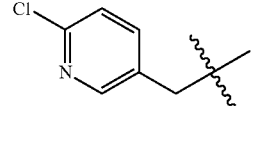 | 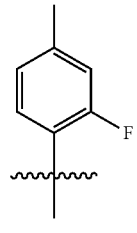 |

TABLE 4-continued
| Example | R¹ | R² | R³ |
|---|---|---|---|
| 4.59 | 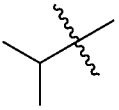 | 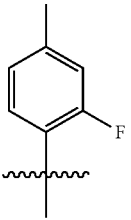 | 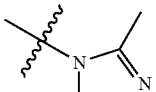 |
| 4.60 | 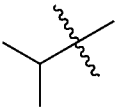 | 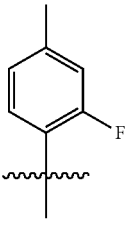 | 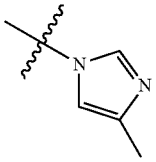 |
| 4.61 | 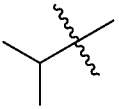 | 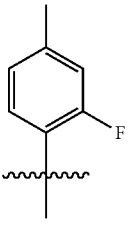 | 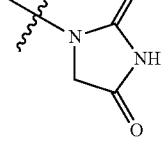 |
| 4.62 | 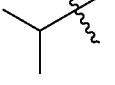 | 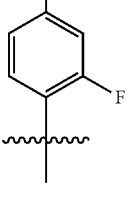 | 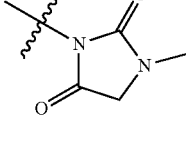 |
| 4.63 | 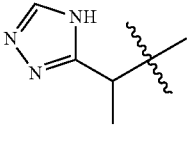 | 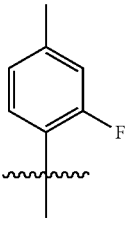 | 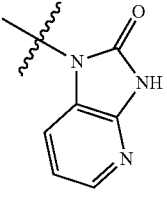 |
| 4.64 | 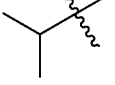 | 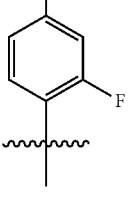 | 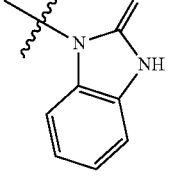 |

TABLE 4-continued
| Example | R¹ | R² | R³ |
|---|---|---|---|
| 4.65 | 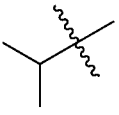 | 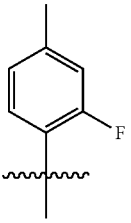 | 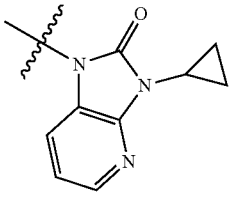 |
| 4.66 | 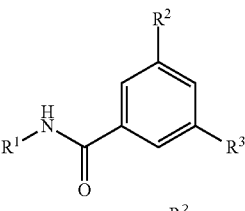 | 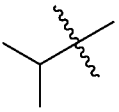 | 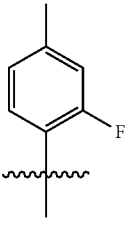 |
| 4.67 | 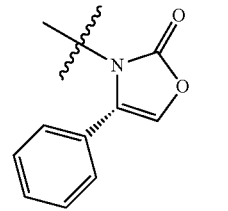 | 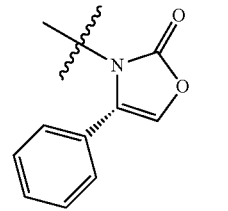 | 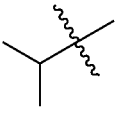 |
| 4.68 | 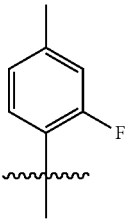 | 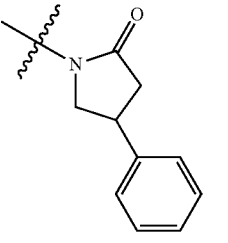 | 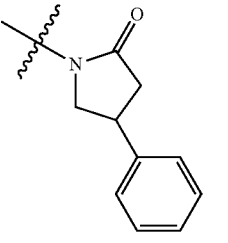 |
| 4.69 | 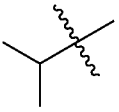 | 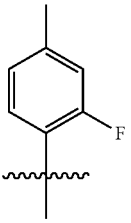 | 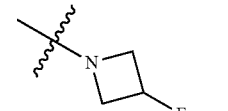 |
| 4.70 | 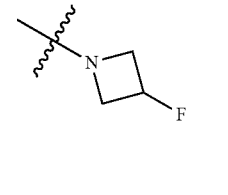 | 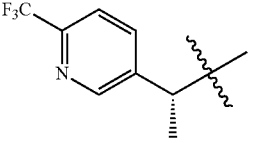 | 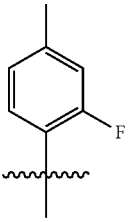 |

TABLE 4-continued
| Example | R¹ | R² | R³ |
|---|---|---|---|
| 4.71 | 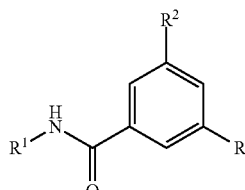 | 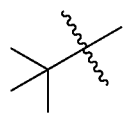 | 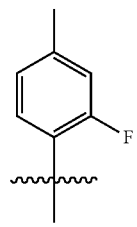 |
| 4.72 | 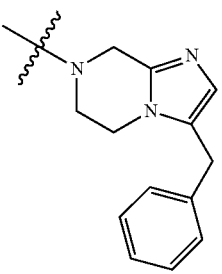 | 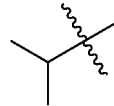 | 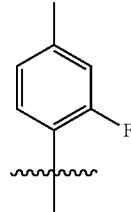 |
| 4.73 | 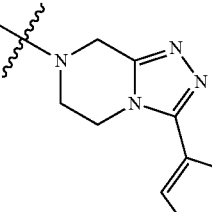 | 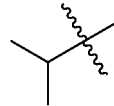 | 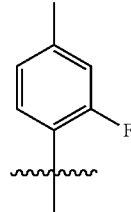 |
| 4.74 | 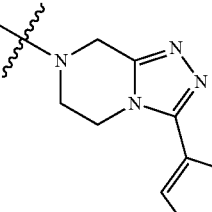 | 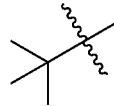 | 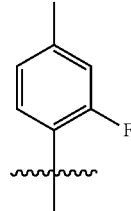 |
| 4.75 | 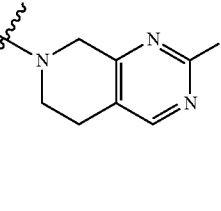 | 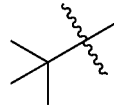 | 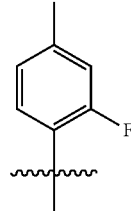 |

TABLE 4-continued
| Example | R¹ | R² | R³ |
|---|---|---|---|
| 4.76 | 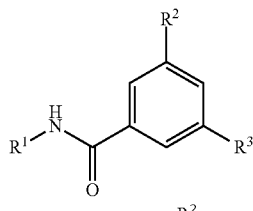 | 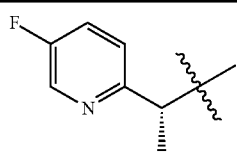 | 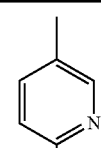 |
| 4.77 | 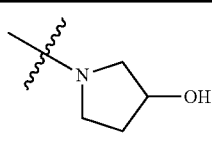 | 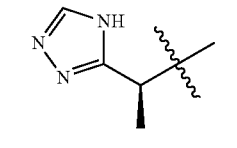 | 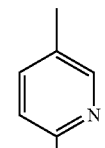 |
| 4.78 | 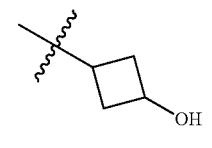 | 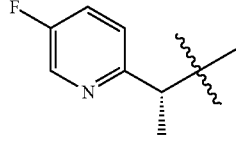 | 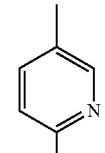 |
| 4.79 | 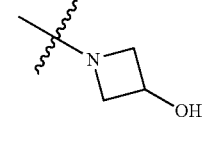 | 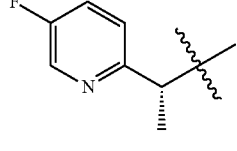 | 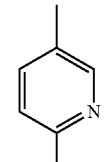 |
| 4.80 | 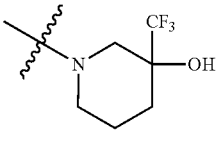 | 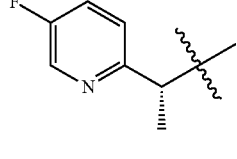 | 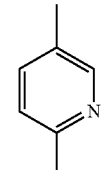 |
| 4.81 | 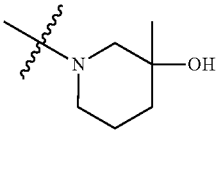 | 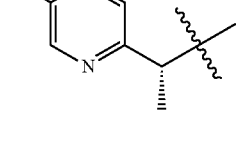 | 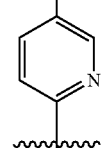 |

TABLE 4-continued
| Example | R¹ | R² | R³ |
|---|---|---|---|
| 4.82 | 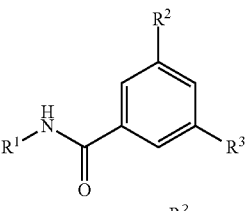 | 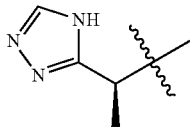 | 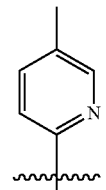 |
| 4.83 | 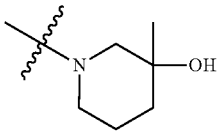 | 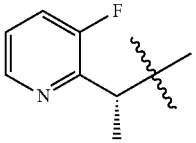 | 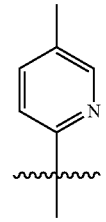 |
| 4.84 | 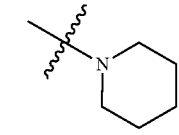 | 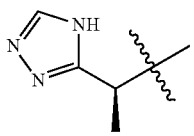 | 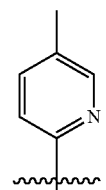 |
| 4.85 | 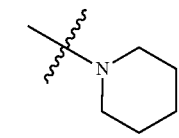 | 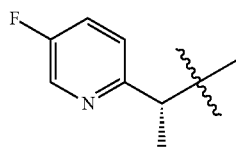 | 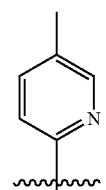 |
| 4.86 | 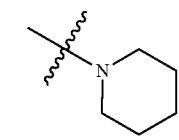 | 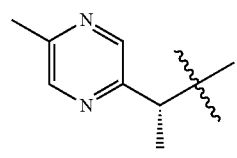 | 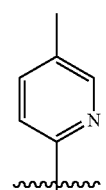 |
| 4.87 | 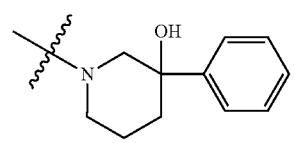 | 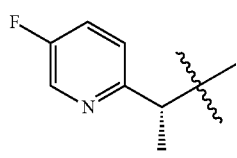 | 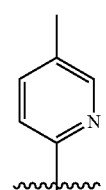 |

TABLE 4-continued
| Example | R¹ | R² | R³ |
|---------|----|----|----|
| 4.88 | 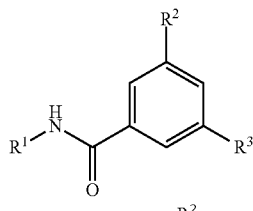 | 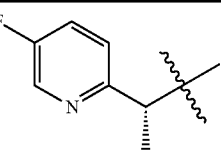 | 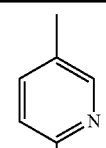 |
| 4.89 | 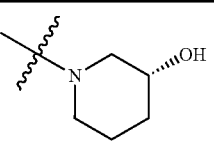 | 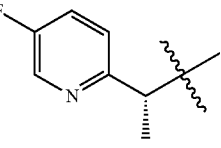 | 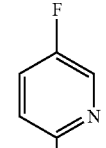 |
| 4.90 | 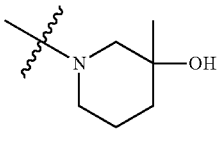 | 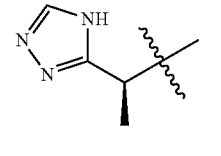 | 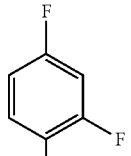 |
| 4.91 | 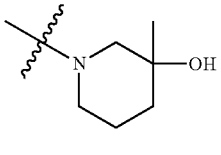 | 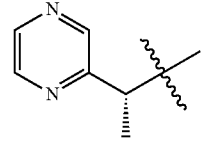 | 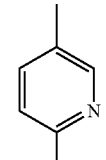 |
| 4.92 | 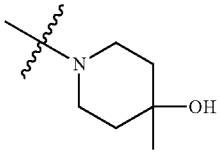 | 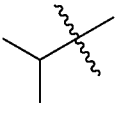 | 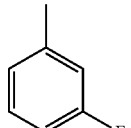 |
| 4.93 | 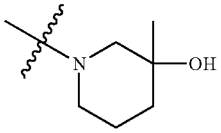 | 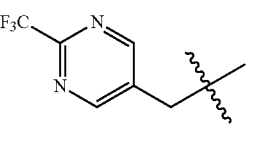 | 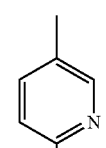 |

TABLE 4-continued

| Example | R¹ | R² | R³ |
|---|---|---|---|
| 4.94 | 3,5-difluoropyridin-2-yl (R)-ethyl | pyridin-2-yl (5-position) | piperazin-1-yl |
| 4.95 | 4H-1,2,4-triazol-3-yl (R)-ethyl | pyridin-2-yl (5-position) | piperazin-1-yl |
| 4.96 | 3-methyl-1,2,4-oxadiazol-5-yl (R)-ethyl | pyridin-2-yl (5-position) | piperazin-1-yl |
| 4.97 | 5-oxo-4,5-dihydro-1H-1,2,4-triazol-3-yl isopropyl | pyridin-2-yl (5-position) | 3,3-dimethylpiperazin-1-yl |
| 4.98 | 5-(trifluoromethyl)pyrazin-2-yl (R)-ethyl | pyridin-2-yl (5-position) | 3,3-dimethylpiperazin-1-yl |
| 4.99 | 2-(trifluoromethyl)pyrimidin-5-yl (R)-ethyl | pyridin-2-yl (5-position) | 3,3-dimethylpiperazin-1-yl |

TABLE 4-continued
| Example | R¹ | R² | R³ |
|---|---|---|---|
| 4.100 | 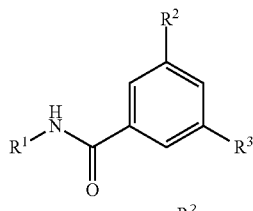 | 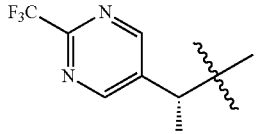 | 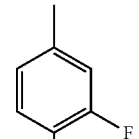 |
| 4.101 | 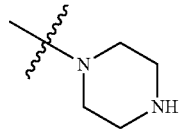 | 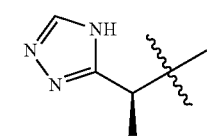 | 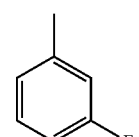 |
| 4.102 | 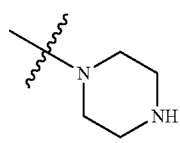 | 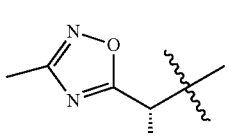 | 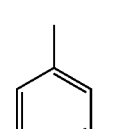 |
| 4.103 | 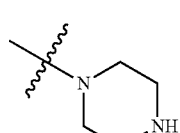 | 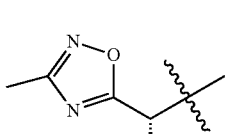 | 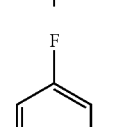 |
| 4.104 | 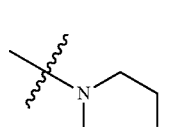 | 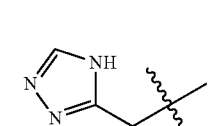 | 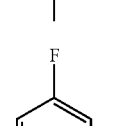 |
| 4.105 | 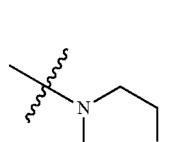 | 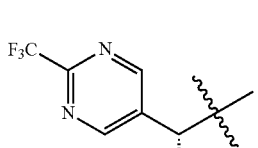 | 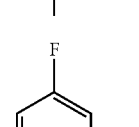 |

TABLE 4-continued
| Example | R¹ | R² | R³ |
|---|---|---|---|
| 4.106 | 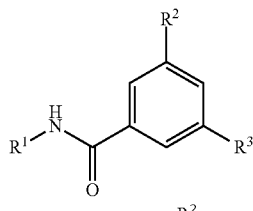 | 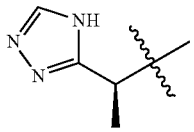 | 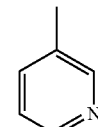 |
| 4.107 | 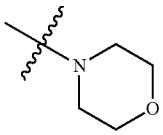 | 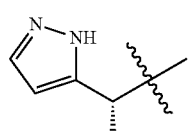 | 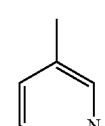 |
| 4.108 | 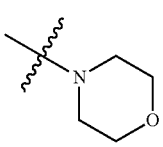 | 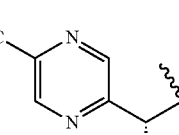 | 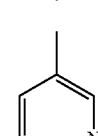 |
| 4.109 | 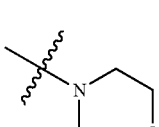 | 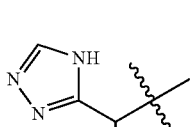 | 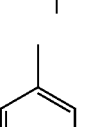 |
| 4.110 | 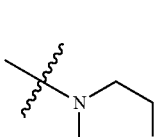 | 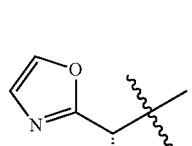 | 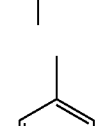 |
| 4.111 | 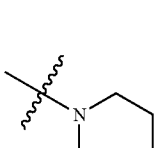 | 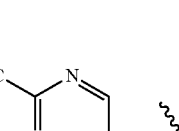 |  |

TABLE 4-continued

| Example | R¹ | R² | R³ |
|---|---|---|---|
| 4.112 | 5-fluoropyridin-2-yl with chiral methyl | pyridin-2-yl (5-linked) | morpholin-4-yl |
| 4.113 | 3-fluoropyridin-2-yl with chiral methyl | pyridin-2-yl (5-linked) | morpholin-4-yl |
| 4.114 | 4H-1,2,4-triazol-3-yl with chiral methyl | pyridin-2-yl (5-linked) | 2,2-dimethylmorpholin-4-yl |
| 4.115 | 5-fluoropyridin-2-yl with chiral methyl | pyridin-2-yl (5-linked) | 1-oxa-4-azaspiro[4.5]... (oxa-azaspiro) |
| 4.116 | 1H-imidazol-5-yl with chiral methyl | pyridin-2-yl (5-linked) | 2-phenylmorpholin-4-yl |
| 4.117 | 5-(trifluoromethyl)pyridin-2-yl with chiral methyl | pyridin-2-yl (5-linked) | 2-phenylmorpholin-4-yl |

TABLE 4-continued
| Example | R¹ | R² | R³ |
|---|---|---|---|
| 4.118 | 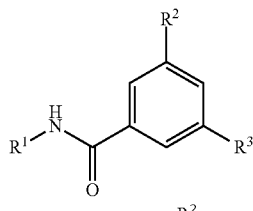 | 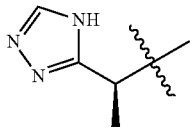 | 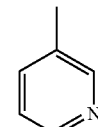 |
| 4.119 | 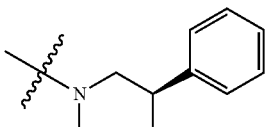 | 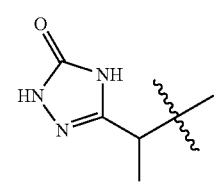 | 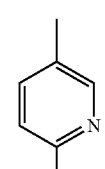 |
| 4.120 | 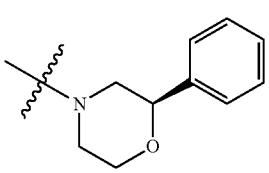 |  | 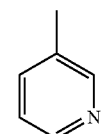 |
| 4.121 | 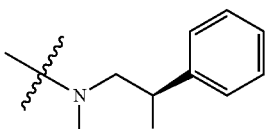 | 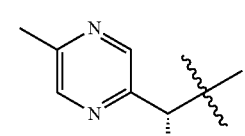 | 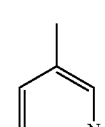 |
| 4.122 | 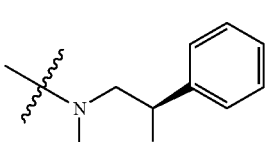 | 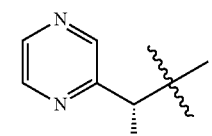 | 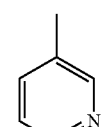 |
| 4.123 | 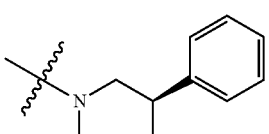 | 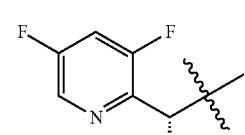 | 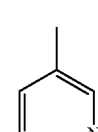 |

TABLE 4-continued

| Example | R¹ | R² | R³ |
|---|---|---|---|
| 4.124 | 1-(2-(trifluoromethyl)pyrimidin-5-yl)ethyl | pyridin-2,5-diyl | 2-phenylmorpholin-4-yl |
| 4.125 | 2-(pyridin-3-yl)ethyl | pyridin-2,5-diyl | 2-phenylmorpholin-4-yl |
| 4.126 | (1-ethyl-5-oxopyrrolidin-3-yl)methyl | pyridin-2,5-diyl | 2-phenylmorpholin-4-yl |
| 4.127 | 2-methyl-2-(pyridin-2-yl)ethyl (via CH₂) | pyridin-2,5-diyl | 2-phenylmorpholin-4-yl |
| 4.128 | cyclopropylmethyl | pyridin-2,5-diyl | 2-phenylmorpholin-4-yl |
| 4.129 | (furan-2-yl)methyl | pyridin-2,5-diyl | 2-phenylmorpholin-4-yl |

TABLE 4-continued
| Example | R¹ | R² | R³ |
|---|---|---|---|
| 4.130 | 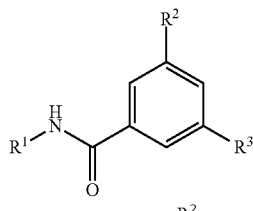 | 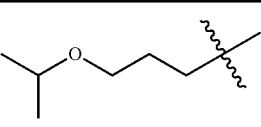 | 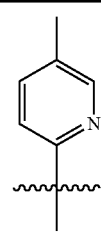 |
| 4.131 | 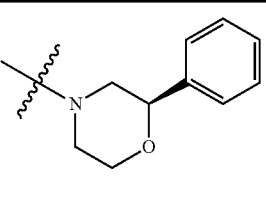 | 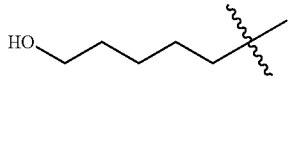 | 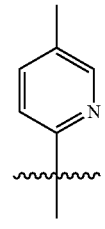 |
| 4.132 | 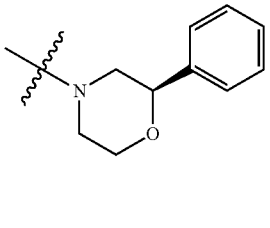 | 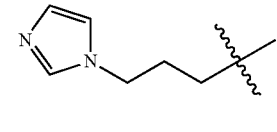 | 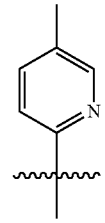 |
| 4.133 | 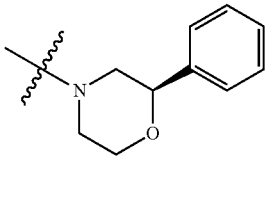 | 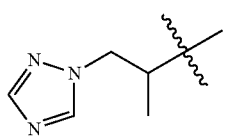 | 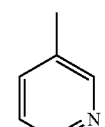 |
| 4.134 | 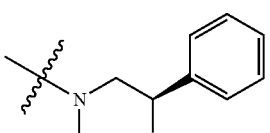 | 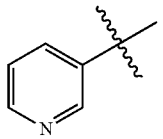 | 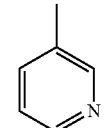 |
| 4.135 | 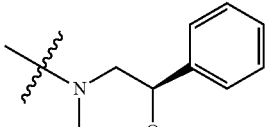 | 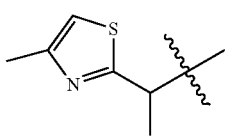 | 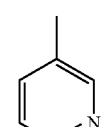 |

TABLE 4-continued
| Example | R¹ | R² | R³ |
|---|---|---|---|
| 4.136 | 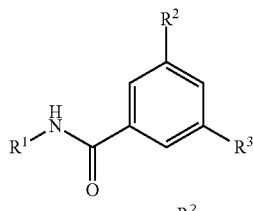 | 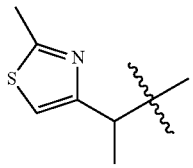 | 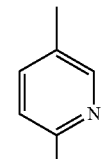 |
| 4.137 | 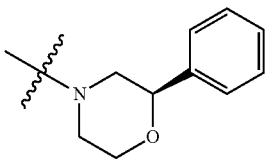 | 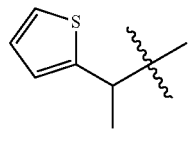 | 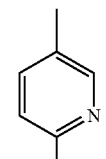 |
| 4.138 | 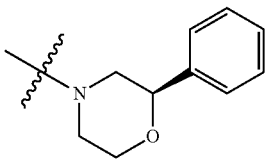 | 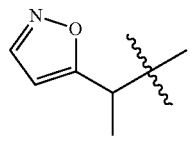 | 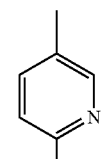 |
| 4.139 | 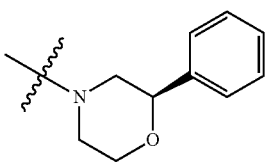 | 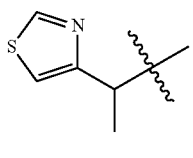 | 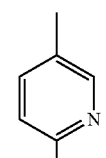 |
| 4.140 | 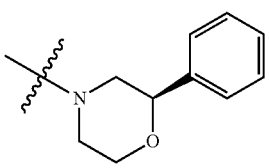 | 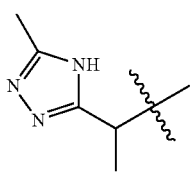 | 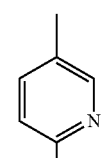 |
| 4.141 | 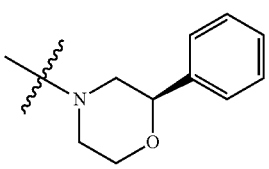 | 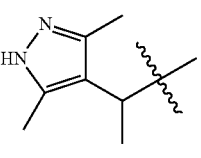 | 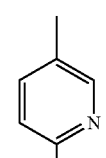 |

TABLE 4-continued

| Example | R¹ | R² | R³ |
|---|---|---|---|
| 4.142 | 2H-triazol-4-yl-methyl | pyridin-2,5-diyl | 2-phenylmorpholin-4-yl |
| 4.143 | (5-cyclopropyl-1H-pyrazol-3-yl)methyl | pyridin-2,5-diyl | 2-phenylmorpholin-4-yl |
| 4.144 | cyclohexyl | pyridin-2,5-diyl | 2-phenylmorpholin-4-yl |
| 4.145 | (1,1-dioxidotetrahydrothiophen-3-yl)methyl | pyridin-2,5-diyl | 2-phenylmorpholin-4-yl |
| 4.146 | 2,3-dihydro-1H-inden-1-yl | pyridin-2,5-diyl | 2-phenylmorpholin-4-yl |
| 4.147 | tetrahydro-2H-pyran-4-yl | pyridin-2,5-diyl | 2-phenylmorpholin-4-yl |

TABLE 4-continued
| Example | R¹ | R² | R³ |
|---|---|---|---|
| 4.148 | 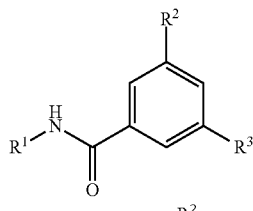 | 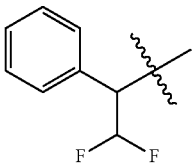 | 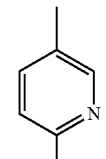 |
| 4.149 | 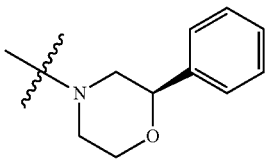 | 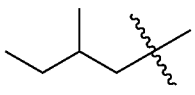 | 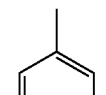 |
| 4.150 | 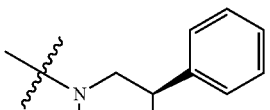 | 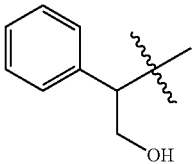 | 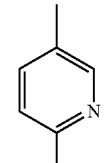 |
| 4.151 | 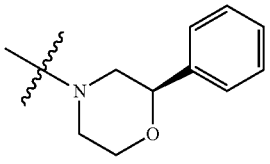 | 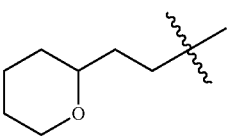 | 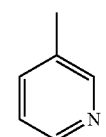 |
| 4.152 | 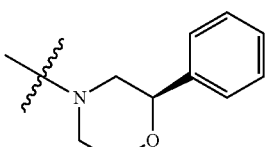 | 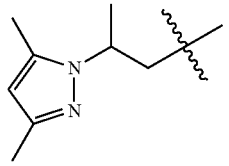 | 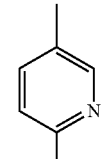 |
| 4.153 | 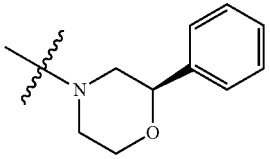 | 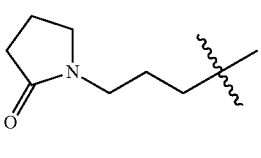 | 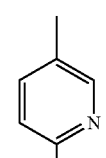 |

TABLE 4-continued
| Example | R[1] | R[2] | R[3] |
|---|---|---|---|
| 4.154 | 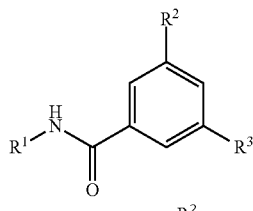 | 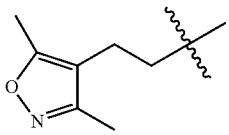 | 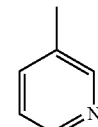 |
| 4.155 | 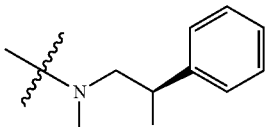 | 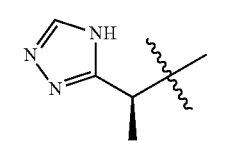 | 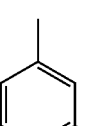 |
| 4.156 | 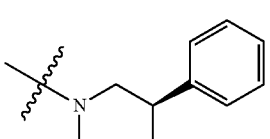 | 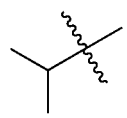 | 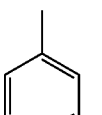 |
| 4.157 | 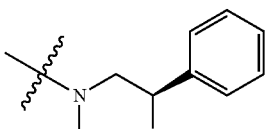 | 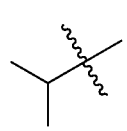 | 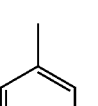 |
| 4.158 | 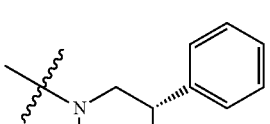 | 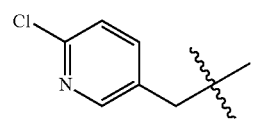 | 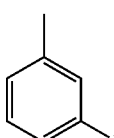 |
| 4.159 | 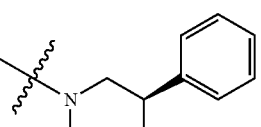 | 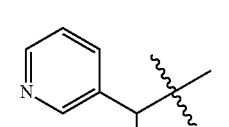 | 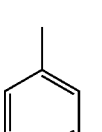 |

TABLE 4-continued
| Example | R¹ | R² | R³ |
|---|---|---|---|
| 4.160 | 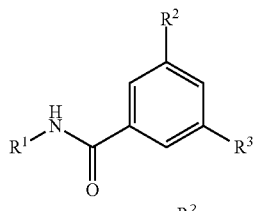 | 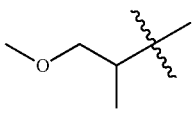 | 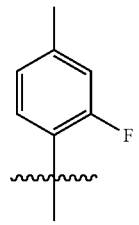 |
| 4.161 | 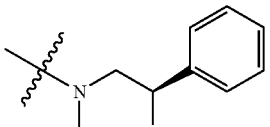 | 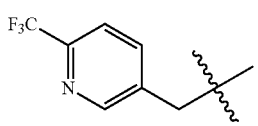 | 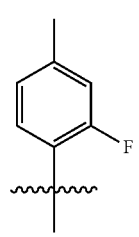 |
| 4.162 | 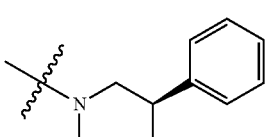 | 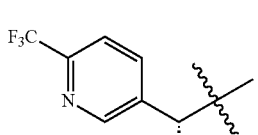 | 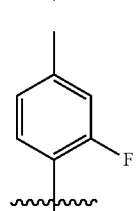 |
| 4.163 | 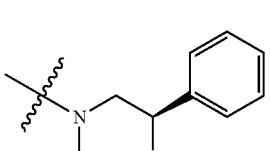 | 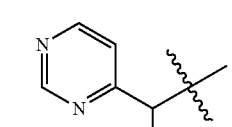 | 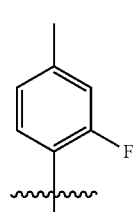 |
| 4.164 | 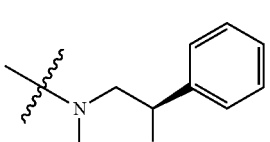 | 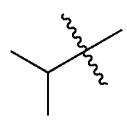 | 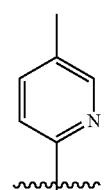 |
| 4.165 | 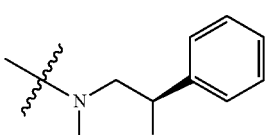 | 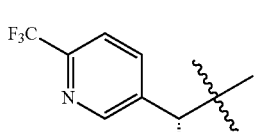 | 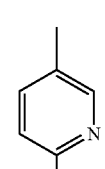 |

TABLE 4-continued

| Example | R¹ | R² | R³ |
|---|---|---|---|
| 4.166 | pyrimidinyl-CH(CH₃)- | pyridinyl | 2-phenylmorpholinyl |
| 4.167 | pyrimidinyl-CH(CH₃)- | pyridinyl | 3-phenylpiperidinyl |
| 4.168 | isobutyl | pyridinyl | 3-phenylpiperidinyl |
| 4.169 | isobutyl | pyridinyl | cyclohexylamino |
| 4.170 | isobutyl | pyridinyl | 3-phenylpiperazinyl |
| 4.171 | isobutyl | 2-fluorophenyl | 3-phenylpiperazinyl |

TABLE 4-continued
| Example | R¹ | R² | R³ |
|---|---|---|---|
| 4.172 | 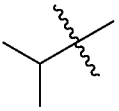 | 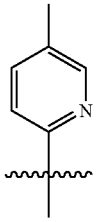 | 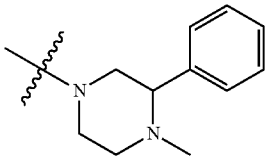 |
| 4.173 | 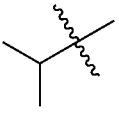 | 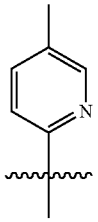 | 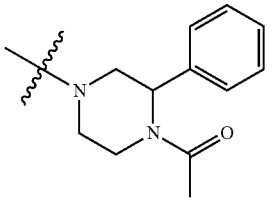 |
| 4.174 | 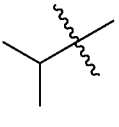 | 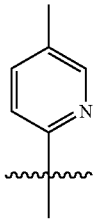 | 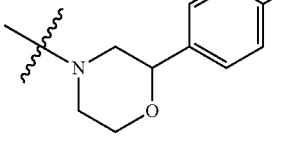 |
| 4.175 | 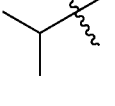 | 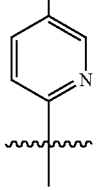 | 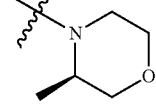 |
| 4.176 | 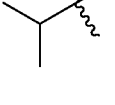 | 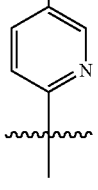 | 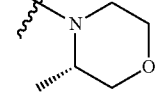 |
| 4.177 | 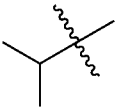 | 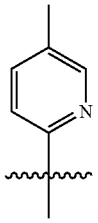 | 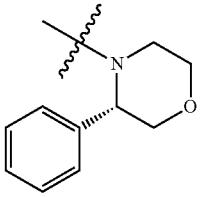 |

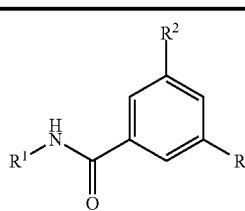

TABLE 4-continued
| Example | R¹ | R² | R³ |
|---|---|---|---|
| 4.184 | 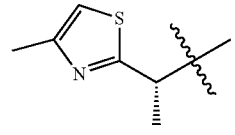 | 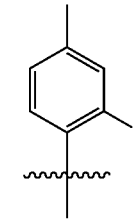 | 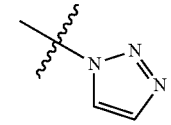 |
| 4.185 | 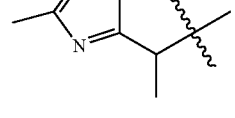 | 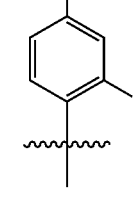 | 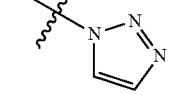 |
| 4.186 | 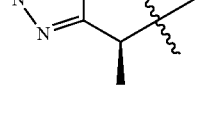 | 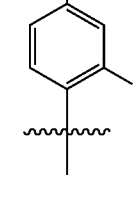 | 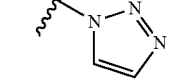 |
| 4.187 | 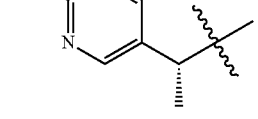 | 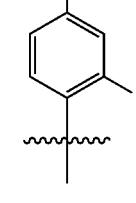 | 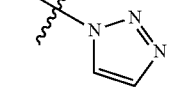 |
| 4.188 | 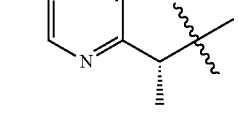 | 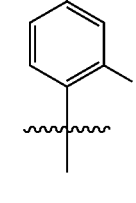 | 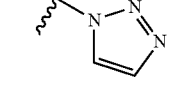 |
| 4.189 | 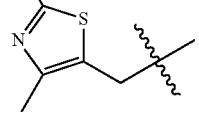 | 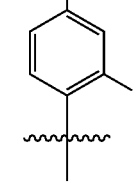 | 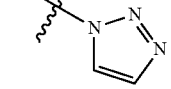 |

TABLE 4-continued

| Example | R¹ | R² | R³ |
|---|---|---|---|
| 4.190 | isopropyl-methyl | 2-fluorophenyl | 1H-1,2,3-triazol-1-yl |
| 4.191 | 1-(5-fluoropyridin-2-yl)ethyl (S) | 5-methylpyridin-2-yl | 1H-1,2,3-triazol-1-yl |
| 4.192 | 1-(5-fluoropyridin-2-yl)ethyl (S) | 5-fluoropyridin-2-yl | 1H-1,2,3-triazol-1-yl |
| 4.193 | isopropyl-methyl | 2-fluorophenyl | 2H-1,2,3-triazol-2-yl |
| 4.194 | 1-(3-methyl-4H-1,2,4-triazol-5-yl)ethyl | 2-fluorophenyl | 2H-1,2,3-triazol-2-yl |
| 4.195 | 2-hydroxy-1-phenylethyl | 2-fluorophenyl | 2H-1,2,3-triazol-2-yl |

TABLE 4-continued

| Example | R¹ | R² | R³ |
|---|---|---|---|
| 4.196 | 1,2,5-thiadiazol-3-ylmethyl | 2-fluorophenyl | 2H-1,2,3-triazol-2-yl |
| 4.197 | 1-(4H-1,2,4-triazol-3-yl)ethyl | 2-fluorophenyl | 2H-1,2,3-triazol-2-yl |
| 4.198 | 1-(4-methylthiazol-2-yl)ethyl | 2-fluorophenyl | 2H-1,2,3-triazol-2-yl |
| 4.199 | (2,4-dimethylthiazol-5-yl)methyl | 2-fluorophenyl | 2H-1,2,3-triazol-2-yl |
| 4.200 | 1-(5-fluoropyridin-2-yl)ethyl | 2-fluorophenyl | 2H-1,2,3-triazol-2-yl |
| 4.201 | 1-(6-(trifluoromethyl)pyridin-3-yl)ethyl | 2-fluorophenyl | 2H-1,2,3-triazol-2-yl |

TABLE 4-continued
| Example | R¹ | R² | R³ |
|---|---|---|---|
| 4.202 | 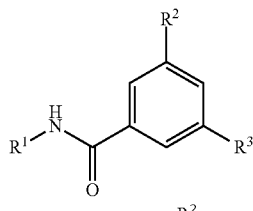 | 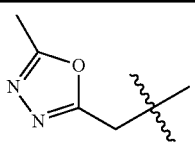 | 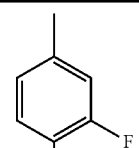 |
| 4.203 | 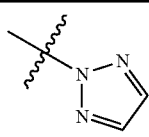 | 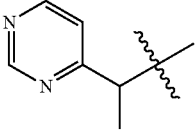 | 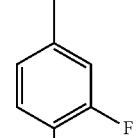 |
| 4.204 | 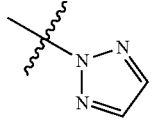 | 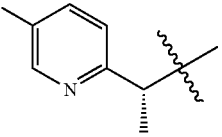 | 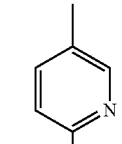 |
| 4.205 | 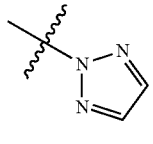 | 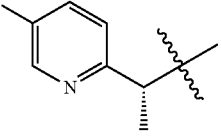 | 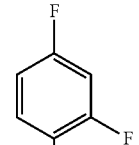 |
| 4.206 | 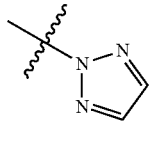 | 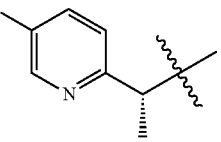 | 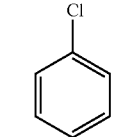 |
| 4.207 | 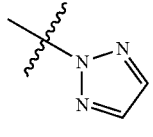 | 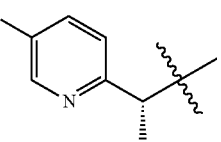 | 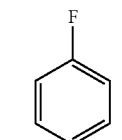 |

TABLE 4-continued
| Example | R¹ | R² | R³ |
|---|---|---|---|
| 4.208 | 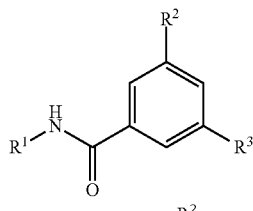 |  | 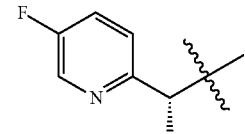 |
| 4.209 | 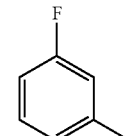 | 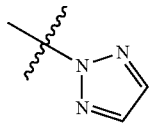 | 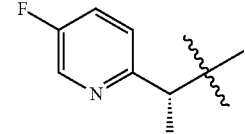 |
| 4.210 | 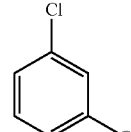 | 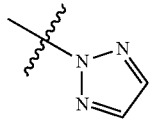 | 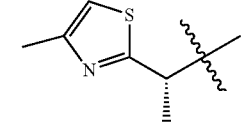 |
| 4.211 | 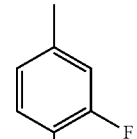 | 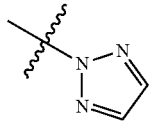 | 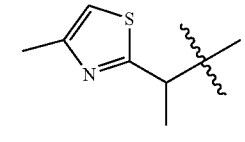 |
| 4.212 | 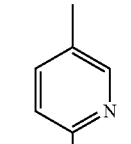 | 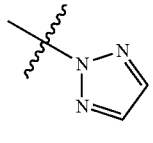 | 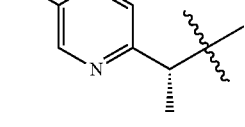 |
| 4.213 | 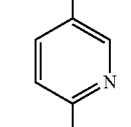 | 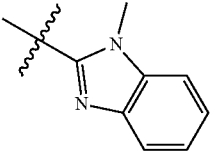 | 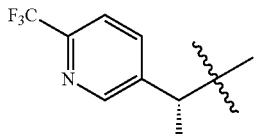 |

TABLE 4-continued
| Example | R¹ | R² | R³ |
|---|---|---|---|
| 4.214 | 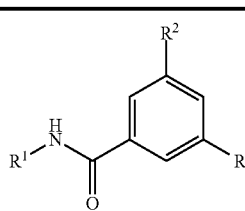 | 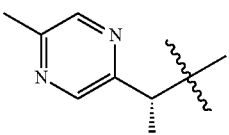 | 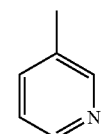 |
| 4.215 | 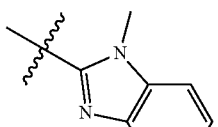 | 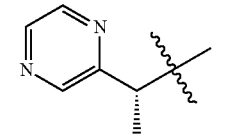 | 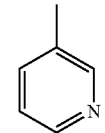 |
| 4.216 | 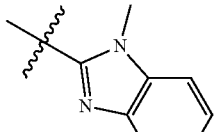 | 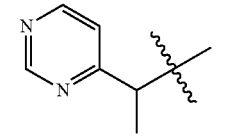 | 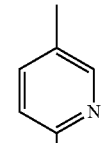 |
| 4.217 | 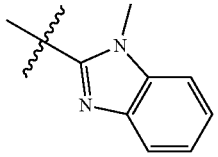 | 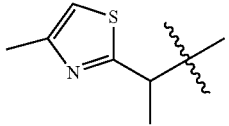 | 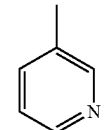 |
| 4.218 | 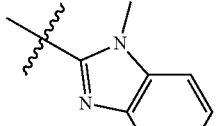 | 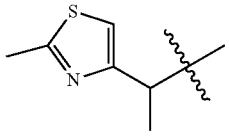 | 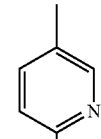 |
| 4.219 | 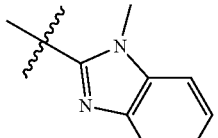 | 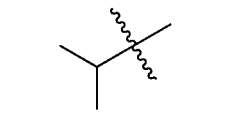 | 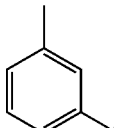 |

TABLE 4-continued
| Example | R¹ | R² | R³ |
|---|---|---|---|
| 4.220 | 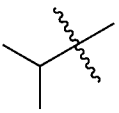 | 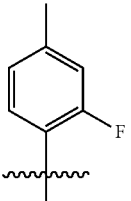 | 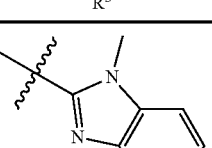 |
| 4.221 | 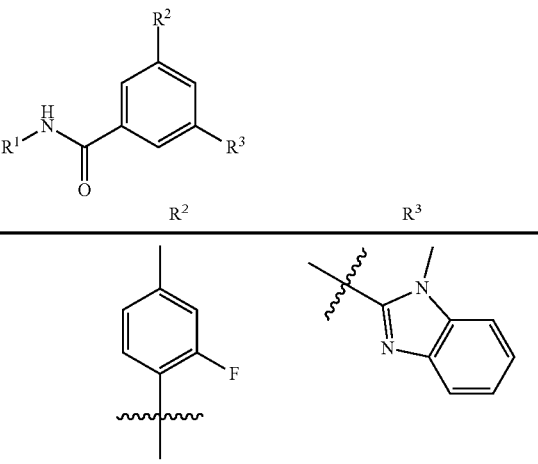 | 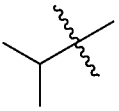 | 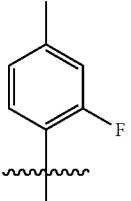 |
| 4.222 | 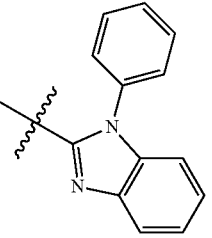 | 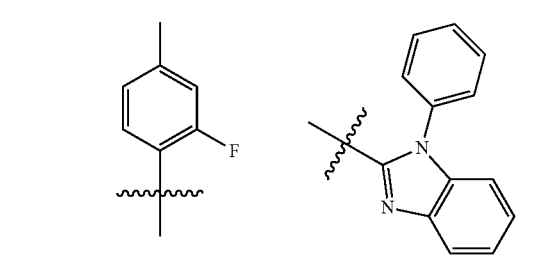 | 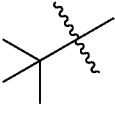 |
| 4.223 | 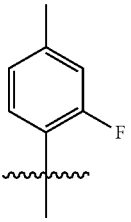 | 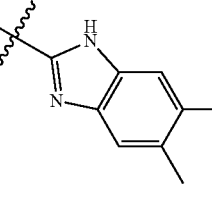 | 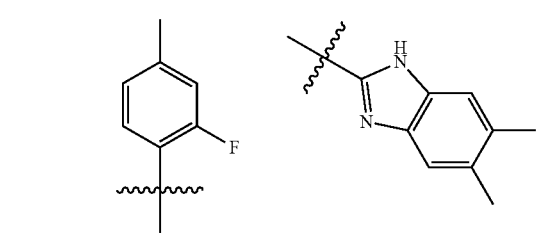 |
| 4.224 | 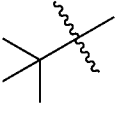 | 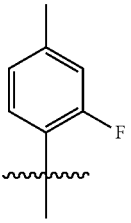 | 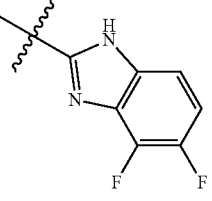 |
| 4.225 | 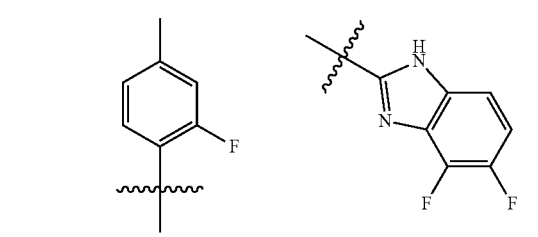 | 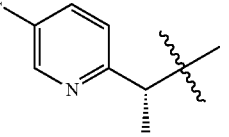 | 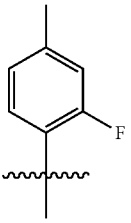 |

TABLE 4-continued
| Example | R¹ | R² | R³ |
|---|---|---|---|
| 4.226 | 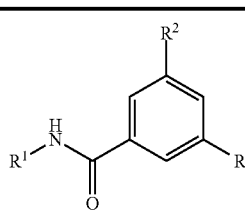 | 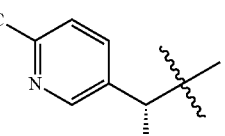 | 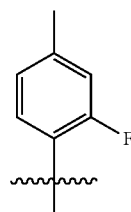 |
| 4.227 | 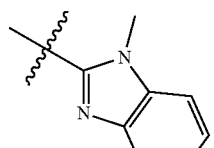 | 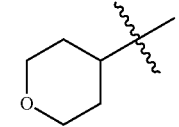 | 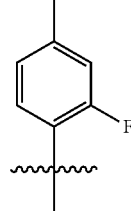 |
| 4.228 | 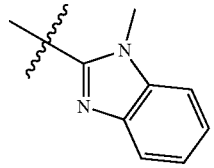 | 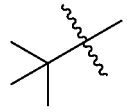 | 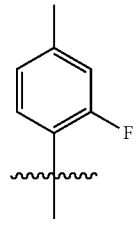 |
| 4.229 | 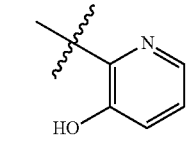 |  | 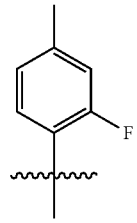 |
| 4.230 | 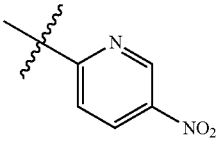 | 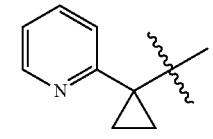 | 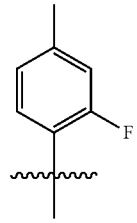 |
| 4.231 | 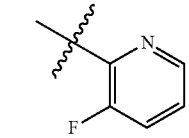 | 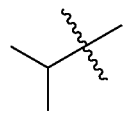 | 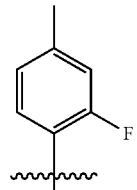 |

TABLE 4-continued
| Example | R¹ | R² | R³ |
|---|---|---|---|
| 4.232 | 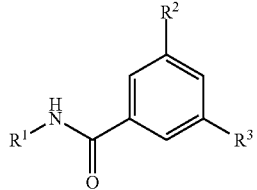 | 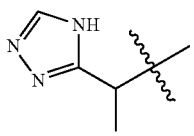 | 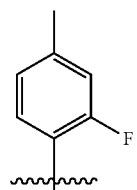 |
| 4.233 | 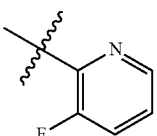 | 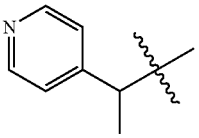 | 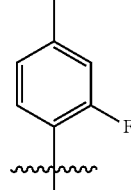 |
| 4.234 | 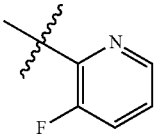 | 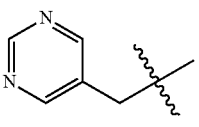 | 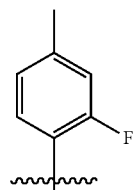 |
| 4.235 | 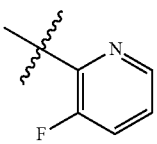 | 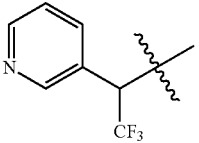 | 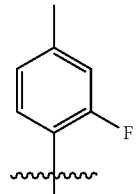 |
| 4.236 | 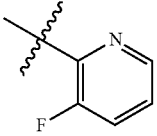 | 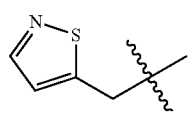 | 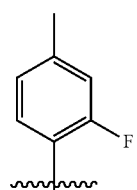 |
| 4.237 | 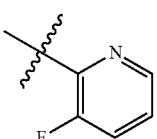 | 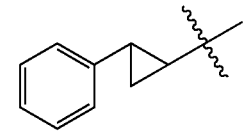 | 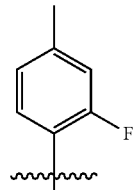 |

TABLE 4-continued

| Example | R¹ | R² | R³ |
|---|---|---|---|
| 4.238 | cyclopropyl-CH(CH₃)- | 4-(3-fluorophenyl) | 3-fluoropyridin-2-yl |
| 4.239 | CF₃CH₂C(CH₃)- | 4-(3-fluorophenyl) | 3-fluoropyridin-2-yl |
| 4.240 | (4-methylthiazol-2-yl)CH(CH₃)- | 4-(3-fluorophenyl) | 3-fluoropyridin-2-yl |
| 4.241 | (2-methylthiazol-4-yl)CH(CH₃)- | 4-(3-fluorophenyl) | 3-fluoropyridin-2-yl |
| 4.242 | (5-fluoropyridin-2-yl)CH(CH₃)- | 4-(3-fluorophenyl) | 3-fluoropyridin-2-yl |
| 4.243 | (pyrimidin-4-yl)CH(CH₃)- | 4-(3-fluorophenyl) | 3-fluoropyridin-2-yl |

TABLE 4-continued
| Example | R¹ | R² | R³ |
|---|---|---|---|
| 4.244 | 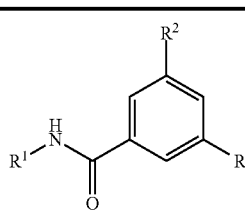 | 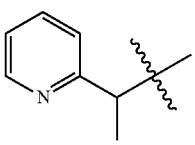 | 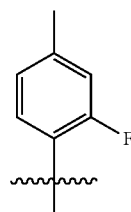 |
| 4.245 | 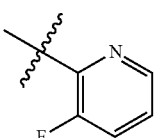 | 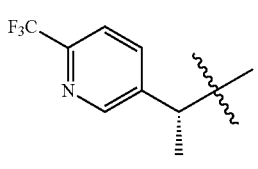 | 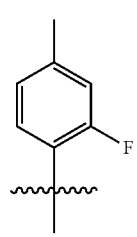 |
| 4.246 | 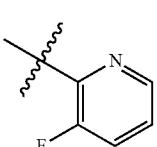 | 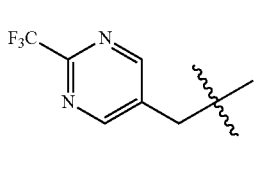 | 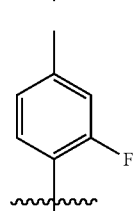 |
| 4.247 | 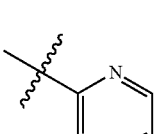 | 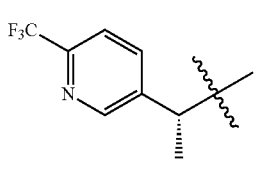 | 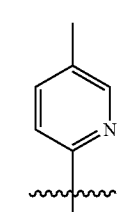 |
| 4.248 | 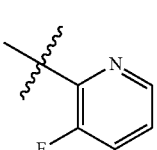 | 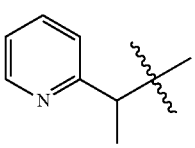 | 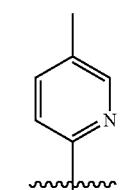 |
| 4.249 | 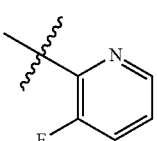 | 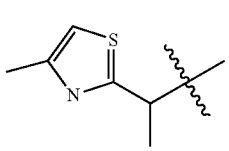 | 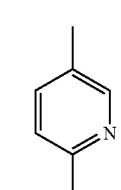 |

TABLE 4-continued

| Example | R¹ | R² | R³ |
|---|---|---|---|
| 4.250 | 4H-1,2,4-triazol-3-yl-CH(CH₃)- | pyridin-2,5-diyl | 3-fluoropyridin-2-yl |
| 4.251 | (2-trifluoromethylpyrimidin-5-yl)-CH₂- | pyridin-2,5-diyl | 3-fluoropyridin-2-yl |
| 4.252 | (5-fluoropyridin-2-yl)-CH(CH₃)- | pyridin-2,5-diyl | 3-fluoropyridin-2-yl |
| 4.253 | (pyrimidin-5-yl)-CH₂- | pyridin-2,5-diyl | 3-fluoropyridin-2-yl |
| 4.254 | (2-methylthiazol-4-yl)-CH(CH₃)- | pyridin-2,5-diyl | 3-fluoropyridin-2-yl |
| 4.255 | (pyrimidin-4-yl)-CH(CH₃)- | pyridin-2,5-diyl | 3-fluoropyridin-2-yl |

TABLE 4-continued

| Example | R¹ | R² | R³ |
|---|---|---|---|
| 4.256 | cyclopropyl-CH(CH₃)- | pyridin-2-yl (attached at 5-position) | 3-fluoropyridin-2-yl |
| 4.257 | (2-trifluoromethylpyrimidin-5-yl)-CH(CH₃)- | pyridin-2-yl (attached at 5-position) | 3-fluoropyridin-2-yl |
| 4.258 | (4H-1,2,4-triazol-3-yl)-CH(CH₃)- | pyridin-2-yl (attached at 5-position) | 3-fluoropyridin-2-yl |
| 4.259 | (4H-1,2,4-triazol-3-yl)-CH(CH₃)- (stereo) | pyridin-2-yl (attached at 5-position) | 3-fluoropyridin-2-yl |
| 4.260 | (2-trifluoromethylpyrimidin-5-yl)-CH(CH₃)- (stereo) | pyridin-2-yl (attached at 5-position) | 3-fluoropyridin-2-yl |
| 4.261 | (5-trifluoromethylpyridin-2-yl)-CH(CH₃)- (stereo) | pyridin-2-yl (attached at 5-position) | 3-fluoropyridin-2-yl |

TABLE 4-continued
| Example | R¹ | R² | R³ |
|---|---|---|---|
| 4.262 | 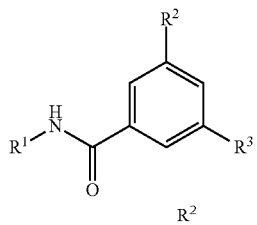 | 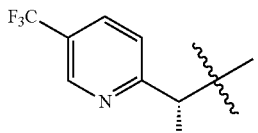 | 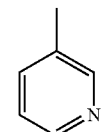 |
| 4.263 | 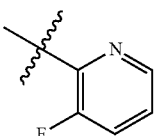 | 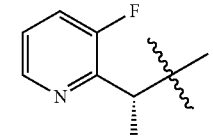 | 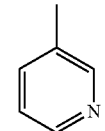 |
| 4.264 | 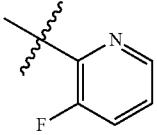 | 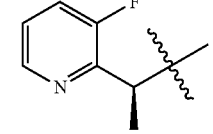 | 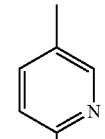 |
| 4.265 | 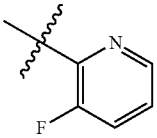 | 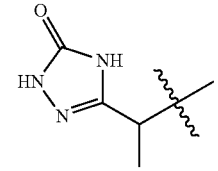 | 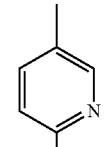 |
| 4.266 | 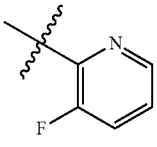 | 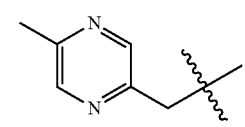 | 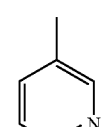 |
| 4.267 | 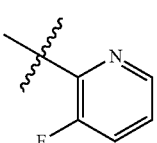 | 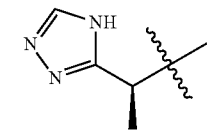 | 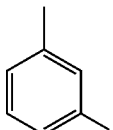 |

TABLE 4-continued

| Example | R¹ | R² | R³ |
|---|---|---|---|
| 4.268 | (S)-1-(pyrazin-2-yl)ethyl | pyridin-2,5-diyl | 3-fluoropyridin-2-yl |
| 4.269 | (R)-1-(pyrazin-2-yl)ethyl | pyridin-2,5-diyl | 3-fluoropyridin-2-yl |
| 4.270 | (S)-1-(5-chloropyridin-2-yl)ethyl | pyridin-2,5-diyl | 3-fluoropyridin-2-yl |
| 4.271 | (R)-1-(5-chloropyridin-2-yl)ethyl | pyridin-2,5-diyl | 3-fluoropyridin-2-yl |
| 4.272 | (pyrazin-2-yl)methyl | pyridin-2,5-diyl | 3-fluoropyridin-2-yl |
| 4.273 | (S)-1-(5-fluoro-1-oxidopyridin-2-yl)ethyl | pyridin-2,5-diyl | 3-fluoropyridin-2-yl |

TABLE 4-continued

| Example | R¹ | R² | R³ |
|---|---|---|---|
| 4.274 | 2-CF₃-pyrimidin-5-yl N-oxide, CH(CH₃)- | pyridin-2-yl | 3-fluoropyridin-2-yl |
| 4.275 | 3,5-difluoropyridin-2-yl-CH₂- | pyridin-2-yl | 3-fluoropyridin-2-yl |
| 4.276 | 5-methylpyrazin-2-yl, CH(CH₃)- (S) | 5-methylpyridin-2-yl | 3-fluoropyridin-2-yl |
| 4.277 | 5-methylpyrazin-2-yl, CH(CH₃)- (R) | pyridin-2-yl | 3-fluoropyridin-2-yl |
| 4.278 | 3,5-difluoropyridin-2-yl, CH(CH₃)- | methyl (pyridin-2-yl) | 3-fluoropyridin-2-yl |
| 4.279 | 3-fluoro-5-trifluoromethylpyridin-2-yl-CH₂- | pyridin-2-yl | 3-fluoropyridin-2-yl |

TABLE 4-continued

| Example | R¹ | R² | R³ |
|---|---|---|---|
| 4.280 | (S)-1-(oxazol-5-yl)ethyl | 5-pyridyl | 3-fluoro-2-pyridyl |
| 4.281 | (R)-1-(oxazol-5-yl)ethyl | 5-pyridyl | 3-fluoro-2-pyridyl |
| 4.282 | 2-(pyrazin-2-yl)propan-2-yl | 5-pyridyl | 3-fluoro-2-pyridyl |
| 4.283 | (5-methyl-1,3,4-oxadiazol-2-yl)methyl | 5-pyridyl | 3-fluoro-2-pyridyl |
| 4.284 | 2-(pyridin-2-yl)propan-2-yl | 5-pyridyl | 3-fluoro-2-pyridyl |
| 4.285 | 2-(4-methylthiazol-2-yl)propan-2-yl | 5-pyridyl | 3-fluoro-2-pyridyl |

TABLE 4-continued

| Example | R¹ | R² | R³ |
|---|---|---|---|
| 4.286 | 5-fluoro-2-(1-methylethyl)pyridine N-oxide | 3-fluoro-4-yl phenyl with methyl | 3-fluoro-2-pyridinyl with methyl |
| 4.287 | oxazol-2-yl(methyl)methyl | 5-methylpyridin-2-yl | 3-fluoro-2-pyridinyl with methyl |
| 4.288 | oxazol-2-yl(methyl)methyl (stereo) | 5-methylpyridin-2-yl | 3-fluoro-2-pyridinyl with methyl |
| 4.289 | 6-(trifluoromethyl)pyridine N-oxide with methyl | 3-fluoro-4-yl phenyl with methyl | 3-fluoro-2-pyridinyl with methyl |
| 4.290 | 2-amino-6-fluorobenzyl | 5-methylpyridin-2-yl | 3-fluoro-2-pyridinyl with methyl |
| 4.291 | (2-hydroxypyridin-3-yl)methyl | 5-methylpyridin-2-yl | 3-fluoro-2-pyridinyl with methyl |

TABLE 4-continued
| Example | R¹ | R² | R³ |
|---|---|---|---|
| 4.292 | 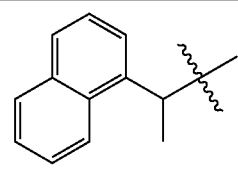 | 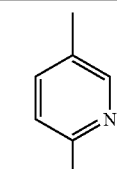 | 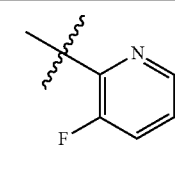 |
| 4.293 | 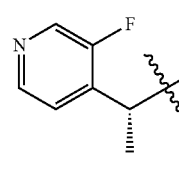 | 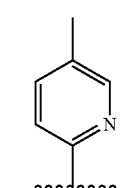 | 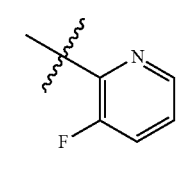 |
| 4.294 | 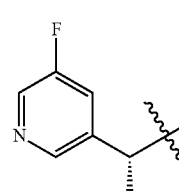 | 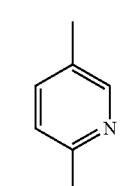 | 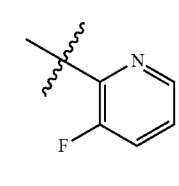 |
| 4.295 | 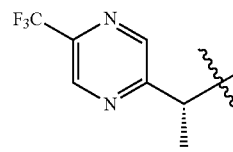 | 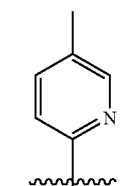 | 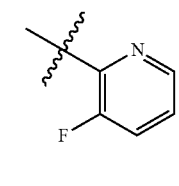 |
| 4.296 | 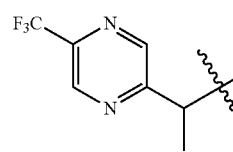 | 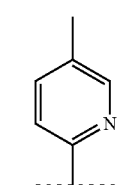 | 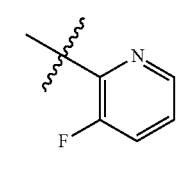 |
| 4.297 | 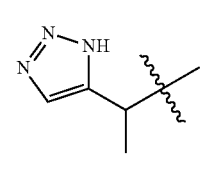 | 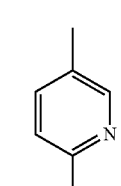 | 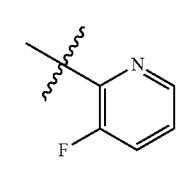 |

TABLE 4-continued
| Example | R¹ | R² | R³ |
|---|---|---|---|
| 4.298 | 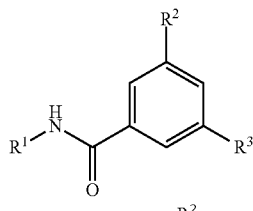 | 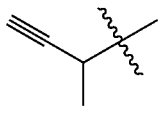 | 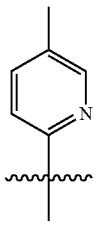 |
| 4.299 | 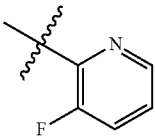 | 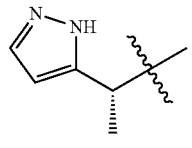 | 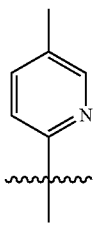 |
| 4.300 | 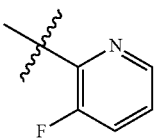 | 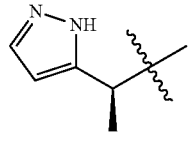 | 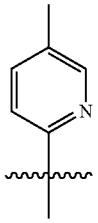 |
| 4.301 | 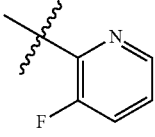 | 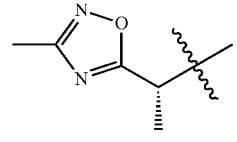 | 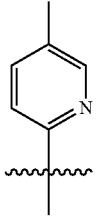 |
| 4.302 | 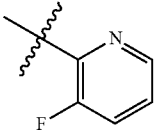 | 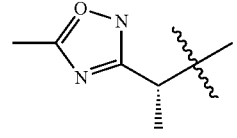 | 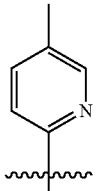 |
| 4.303 | 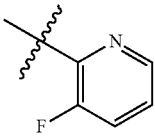 | 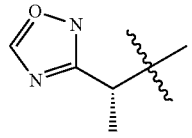 | 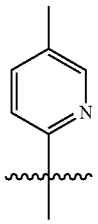 |

TABLE 4-continued

| Example | R¹ | R² | R³ |
|---|---|---|---|
| 4.304 | 1-(1H-imidazol-4-yl)ethyl | pyridin-2-yl (via 5-position) | 3-fluoropyridin-2-yl |
| 4.305 | (3-isopropyl-1,2,4-oxadiazol-5-yl)methyl | pyridin-2-yl (via 5-position) | 3-fluoropyridin-2-yl |
| 4.306 | 1-(3-isopropyl-1,2,4-oxadiazol-5-yl)ethyl | pyridin-2-yl (via 5-position) | 3-fluoropyridin-2-yl |
| 4.307 | (3-ethyl-1,2,4-oxadiazol-5-yl)methyl | pyridin-2-yl (via 5-position) | 3-fluoropyridin-2-yl |
| 4.308 | (1,2,4-oxadiazol-3-yl)methyl | pyridin-2-yl (via 5-position) | 3-fluoropyridin-2-yl |
| 4.309 | (5-ethyl-1,2,4-oxadiazol-3-yl)methyl | pyridin-2-yl (via 5-position) | 3-fluoropyridin-2-yl |

TABLE 4-continued
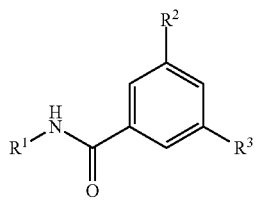

TABLE 4-continued

| Example | R¹ | R² | R³ |
|---|---|---|---|
| 4.316 | 2-CF₃-pyridin-5-yl-CH(CH₃)– | 4-(cyclopropyl)phenyl | 3-F-pyridin-2-yl |
| 4.317 | 2-CF₃-pyridin-5-yl-CH(CH₃)– | pyridin-2-yl | 3-F-pyridin-2-yl |
| 4.318 | 2-CF₃-pyridin-5-yl-CH(CH₃)– | 4-(C(CH₃)(OH))phenyl | 3-F-pyridin-2-yl |
| 4.319 | 2-CF₃-pyridin-5-yl-CH(CH₃)– | 5-F-pyridin-2-yl | 3-F-pyridin-2-yl |
| 4.320 | 2-CF₃-pyridin-5-yl-CH(CH₃)– | 3-F-pyridin-2-yl | 3-F-pyridin-2-yl |
| 4.321 | 2-CF₃-pyridin-5-yl-CH(CH₃)– | 5-Cl-pyridin-2-yl | 3-F-pyridin-2-yl |

TABLE 4-continued

| Example | R¹ | R² | R³ |
|---|---|---|---|
| 4.322 | 6-(trifluoromethyl)pyridin-3-yl, α-methyl | 5-(trifluoromethyl)pyridin-2-yl | 3-fluoropyridin-2-yl |
| 4.323 | pyrazin-2-yl, α-methyl | 3-fluorophenyl (para-attached) | 3-fluoropyridin-2-yl |
| 4.324 | tert-butyl (isopropyl-methyl) | 3-fluorophenyl (para-attached) | pyridin-2-yl |
| 4.325 | tert-butyl (isopropyl-methyl) | 3-fluorophenyl (para-attached) | 3-chloropyridin-2-yl |
| 4.326 | tert-butyl (isopropyl-methyl) | 3-fluorophenyl (para-attached) | 6-cyanopyridin-2-yl |
| 4.327 | tert-butyl (isopropyl-methyl) | 3-fluorophenyl (para-attached) | 3-cyanopyridin-2-yl |

TABLE 4-continued
| Example | R¹ | R² | R³ |
|---|---|---|---|
| 4.328 | 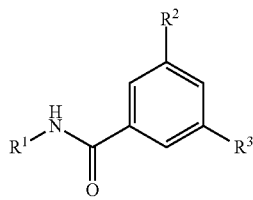 | 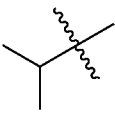 3-F phenyl | 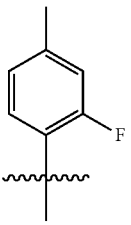 5-F pyridin-2-yl |
| 4.329 | 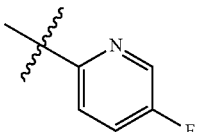 | 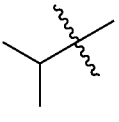 3-F phenyl | 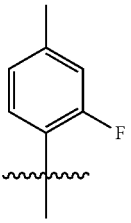 5-Cl pyridin-2-yl |
| 4.330 | 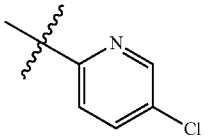 | 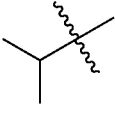 3-F phenyl | 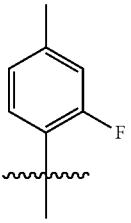 5-Me pyridin-2-yl |
| 4.331 | 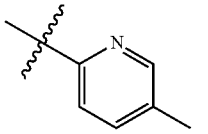 | 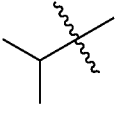 3-F phenyl | 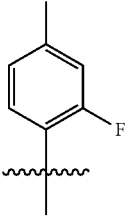 5-CF₃ pyridin-2-yl |
| 4.332 | 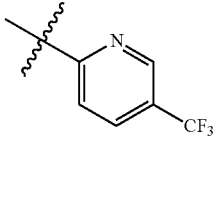 | 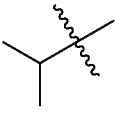 3-F phenyl | 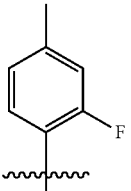 3-CF₃ pyridin-2-yl |
| 4.333 | 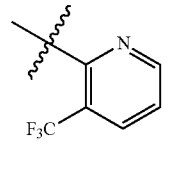 | 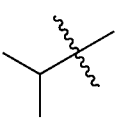 3-F phenyl | 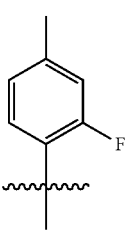 1,8-naphthyridin-2-yl |

TABLE 4-continued

| Example | R¹ | R² | R³ |
|---|---|---|---|
| 4.334 | isobutyl | 3-fluorophenyl | 5-amino-pyridin-2-yl |
| 4.335 | isobutyl | 3-fluorophenyl | 4-methoxy-pyridin-2-yl |
| 4.336 | isobutyl | 3-fluorophenyl | 6-amino-pyridin-2-yl |
| 4.337 | isobutyl | 3-fluorophenyl | 3-amino-pyridin-2-yl |
| 4.338 | isobutyl | 3-fluorophenyl | 6-oxo-5,6-dihydro-1,5-naphthyridin-2-yl |
| 4.339 | isobutyl | 3-fluorophenyl | 6-(methoxycarbonyl)-pyridin-2-yl |

TABLE 4-continued
| Example | R¹ | R² | R³ |
|---|---|---|---|
| 4.340 | 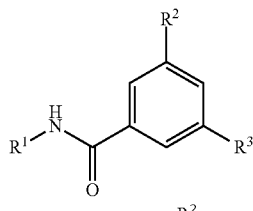 | 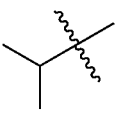 | 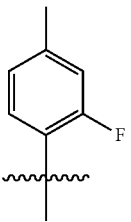 |
| 4.341 | 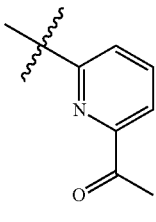 | 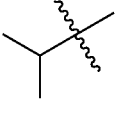 | 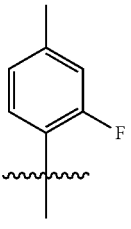 |
| 4.342 | 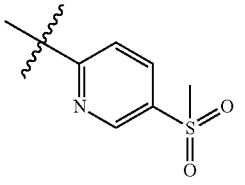 | 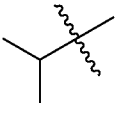 | 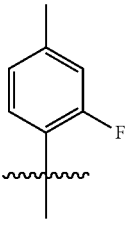 |
| 4.343 | 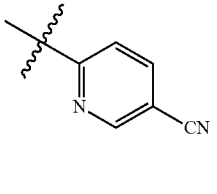 | 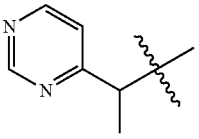 | 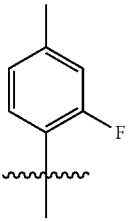 |
| 4.344 | 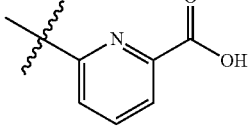 | 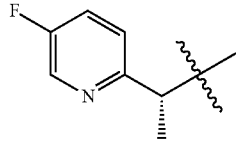 | 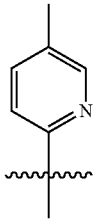 |
| 4.345 | 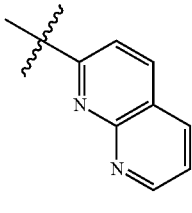 | 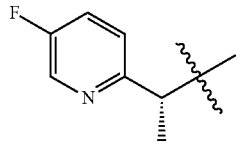 | 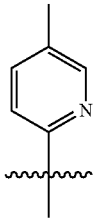 |

TABLE 4-continued

TABLE 4-continued
| Example | R¹ | R² | R³ |
|---|---|---|---|
| 4.352 | 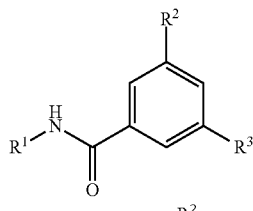 | 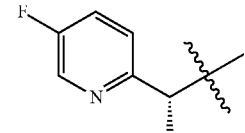 | 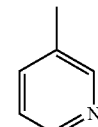 |
| 4.353 | 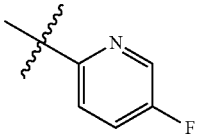 | 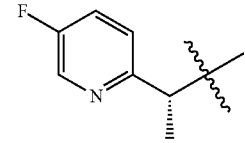 | 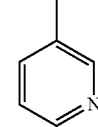 |
| 4.354 | 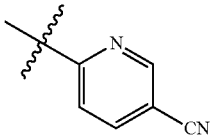 | 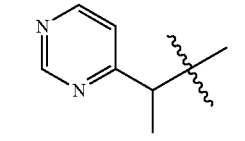 | 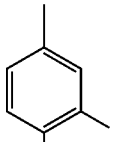 |
| 4.355 | 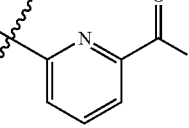 | 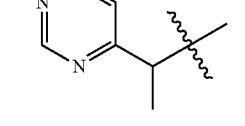 | 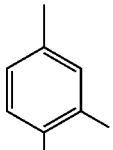 |
| 4.356 | 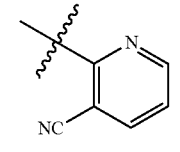 | 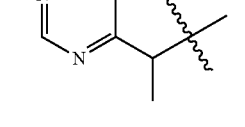 | 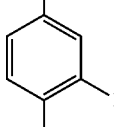 |
| 4.357 | 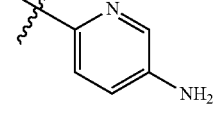 | 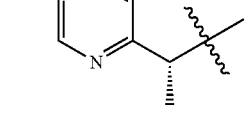 | 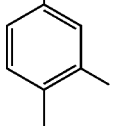 |

TABLE 4-continued

| Example | R¹ | R² | R³ |
|---|---|---|---|
| 4.358 | 5-F-pyridin-2-yl with (R)-CH(CH₃)– | 5-methylpyridin-2-yl | 3-F-5-methylpyridin-2-yl |
| 4.359 | 2-(CF₃)pyrimidin-5-yl with (R)-CH(CH₃)– | 5-methylpyridin-2-yl | 3-F-5-methylpyridin-2-yl |
| 4.360 | 3-F-pyridin-2-yl with (R)-CH(CH₃)– | 5-methylpyridin-2-yl | 3-F-5-methylpyridin-2-yl |
| 4.361 | 5-(CF₃)pyridin-2-yl with (R)-CH(CH₃)– | 5-methylpyridin-2-yl | 3-F-5-methylpyridin-2-yl |
| 4.362 | 4H-1,2,4-triazol-3-yl with (R)-CH(CH₃)– | 5-methylpyridin-2-yl | 3-F-5-methylpyridin-2-yl |
| 4.363 | 6-(CF₃)pyridin-3-yl with (R)-CH(CH₃)– | 5-methylpyridin-2-yl | 3-F-5-methylpyridin-2-yl |

TABLE 4-continued
| Example | R¹ | R² | R³ |
|---|---|---|---|
| 4.364 | 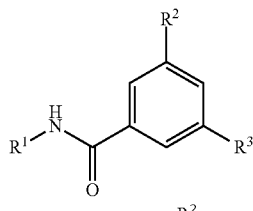 | 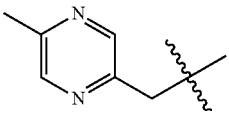 | 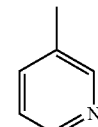 |
| 4.365 | 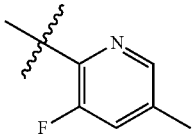 | 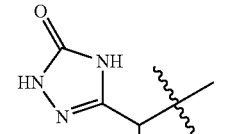 | 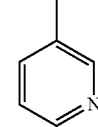 |
| 4.366 | 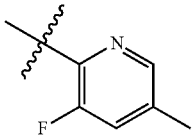 | 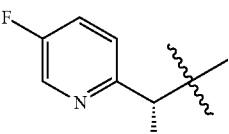 | 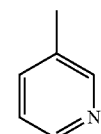 |
| 4.367 | 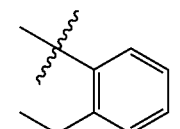 | 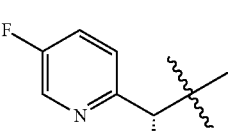 | 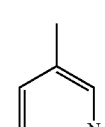 |
| 4.368 | 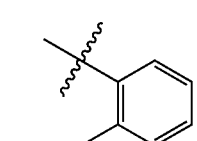 | 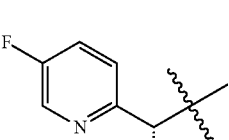 | 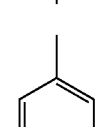 |
| 4.369 | 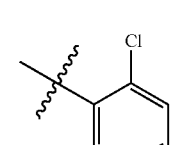 | 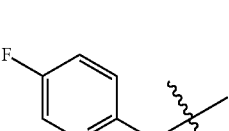 | 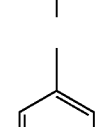 |

TABLE 4-continued
| Example | R¹ | R² | R³ |
|---|---|---|---|
| 4.370 | 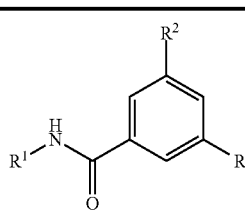 | 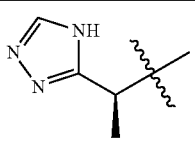 | 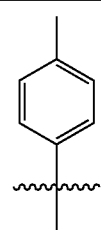 |
| 4.371 | 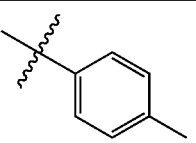 | 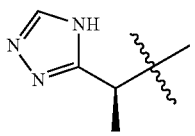 | 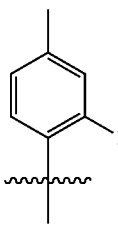 |
| 4.372 | 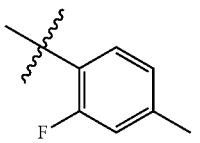 | 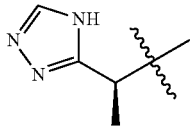 | 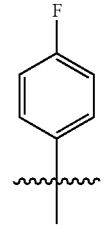 |
| 4.373 | 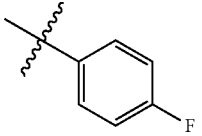 | 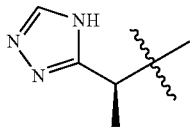 | 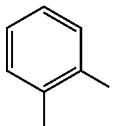 |
| 4.374 | 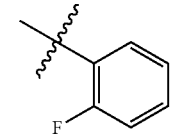 | 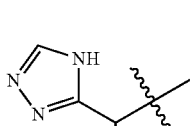 | 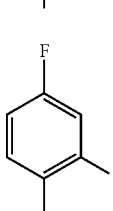 |
| 4.375 | 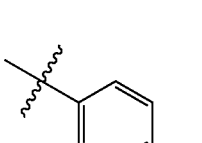 | 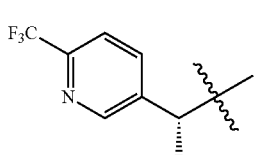 | 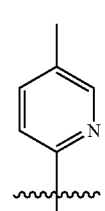 |

TABLE 4-continued
| Example | R¹ | R² | R³ |
|---|---|---|---|
| 4.376 | 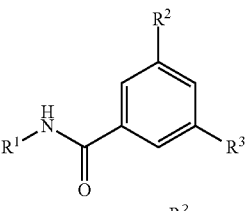 | 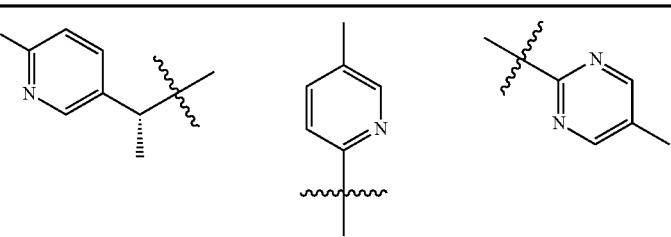 | 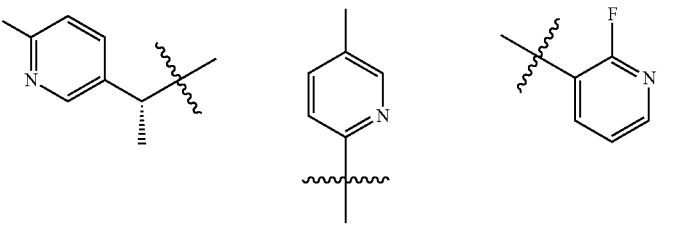 |
| 4.377 | 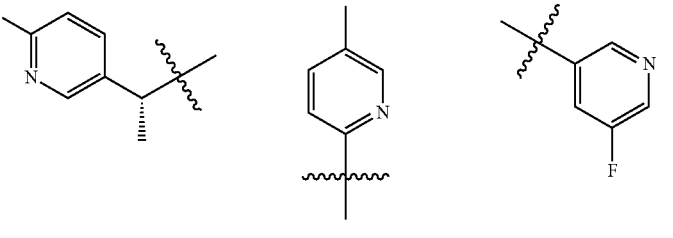 | 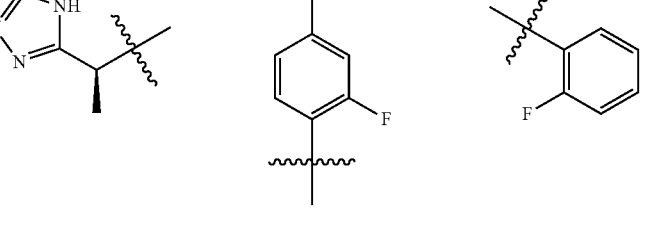 | 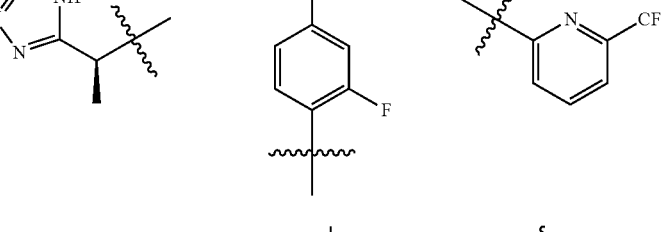 |
| 4.378 | 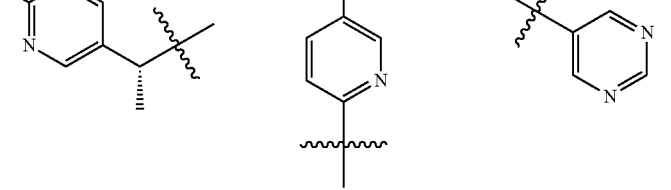 | 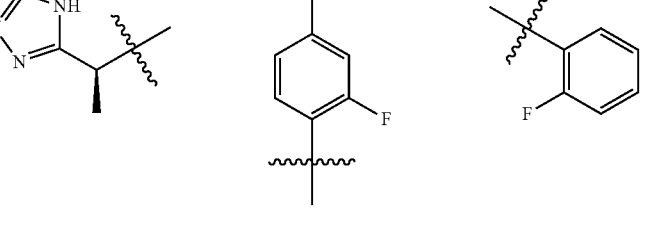 | 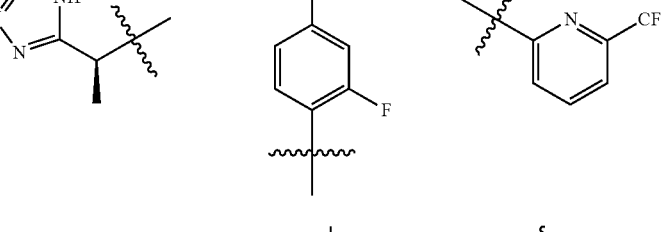 |
| 4.379 | 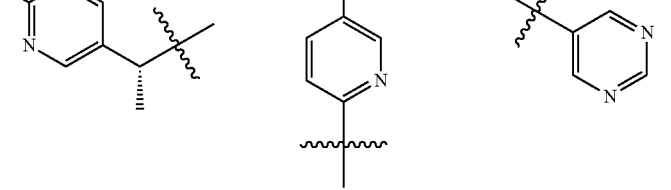 | 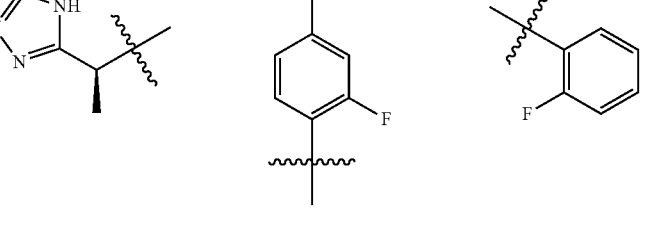 | 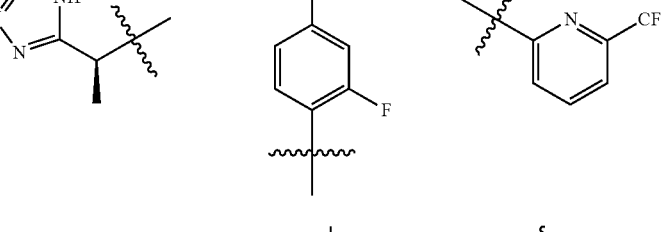 |
| 4.380 | 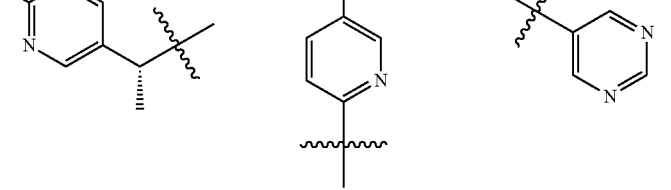 | 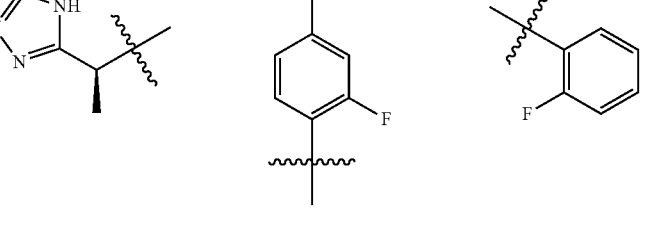 | 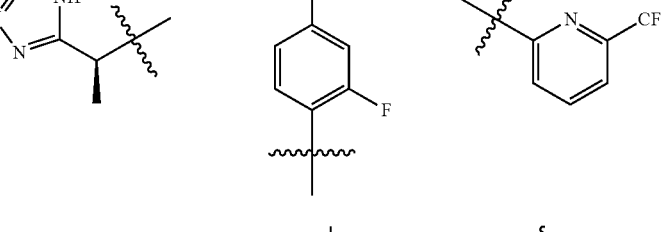 |
| 4.381 | 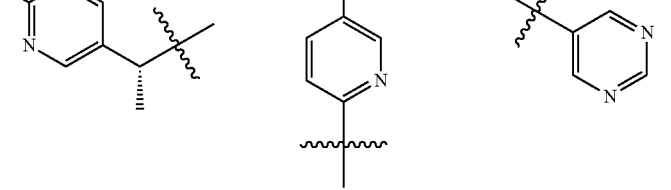 | 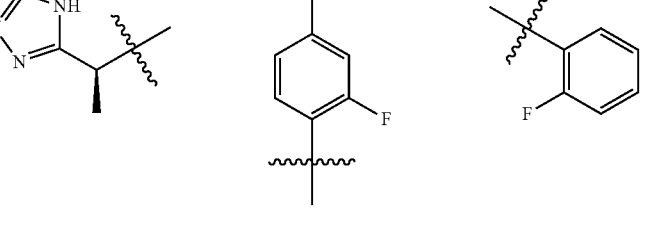 | 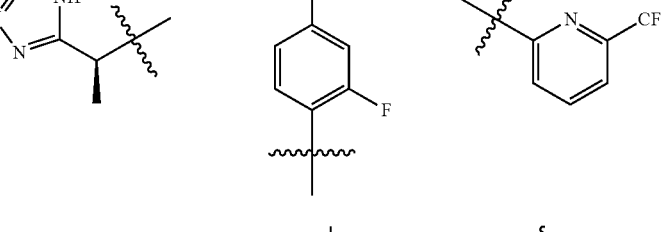 |

TABLE 4-continued
| Example | R¹ | R² | R³ |
|---|---|---|---|
| 4.382 | 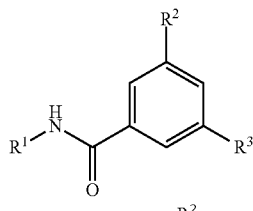 | 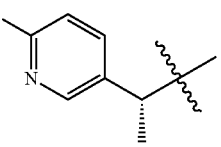 | 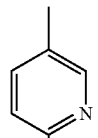 |
| 4.383 | 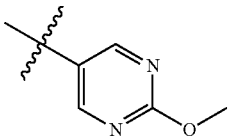 | 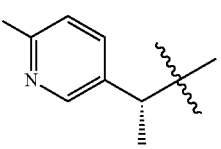 | 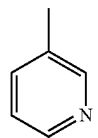 |
| 4.384 | 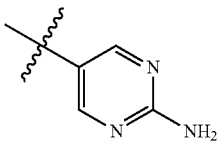 | 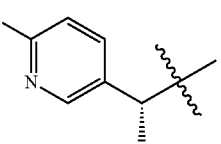 | 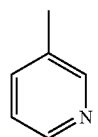 |
| 4.385 | 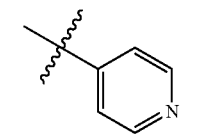 | 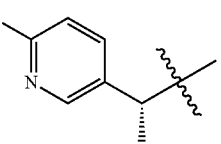 | 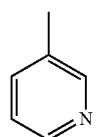 |
| 4.386 | 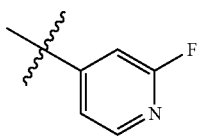 | 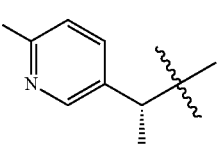 | 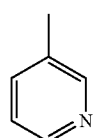 |
| 4.387 | 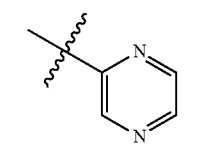 | 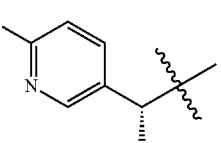 | 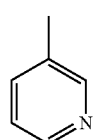 |

TABLE 4-continued
| Example | R¹ | R² | R³ |
|---|---|---|---|
| 4.388 | 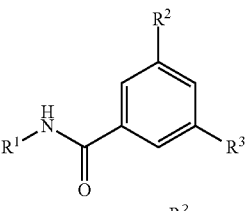 | 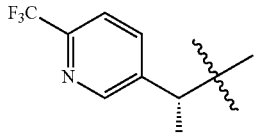 | 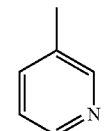 |
| 4.389 | 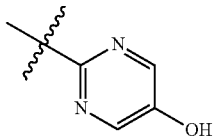 | 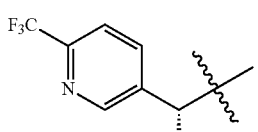 | 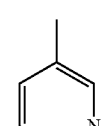 |
| 4.390 | 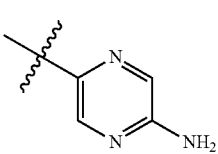 | 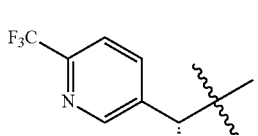 | 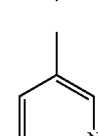 |
| 4.391 | 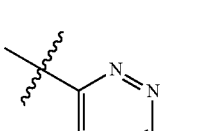 | 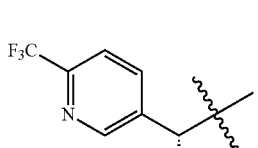 | 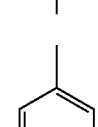 |
| 4.392 | 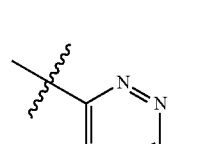 | 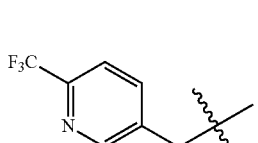 | 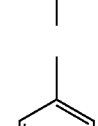 |
| 4.393 | 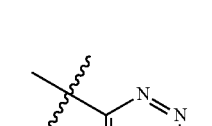 | 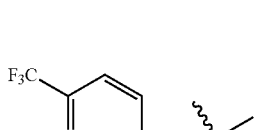 |  |

TABLE 4-continued

| Example | R¹ | R² | R³ |
|---|---|---|---|
| 4.394 | F₃C-pyridyl-CH(CH₃)- | pyridyl | 3,5-difluoropyridin-1-oxide-2-yl |
| 4.395 | F₃C-pyridyl-CH(CH₃)- | pyridyl | pyrimidin-2-yl |
| 4.396 | F₃C-pyridyl-CH(CH₃)- | pyridyl | 6-methylpyridazin-3-yl |
| 4.397 | F₃C-pyridyl-CH(CH₃)- | pyridyl | 2-hydroxypyridin-4-yl |
| 4.398 | F₃C-pyridyl-CH(CH₃)- | pyridyl | 2-hydroxypyrimidin-5-yl |
| 4.399 | F₃C-pyridyl-CH(CH₃)- | pyridyl | 6-hydroxypyridazin-3-yl |

TABLE 4-continued
| Example | R¹ | R² | R³ |
|---|---|---|---|
| 4.400 | 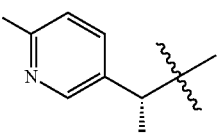 | 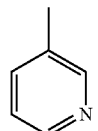 | 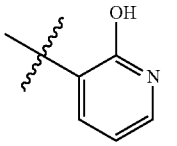 |
| 4.401 | 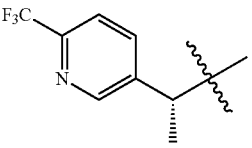 | 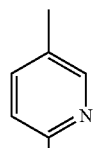 | 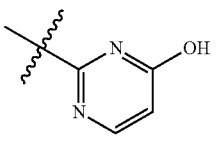 |
| 4.402 | 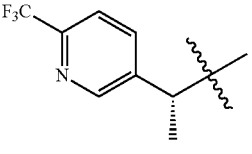 | 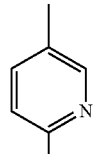 | 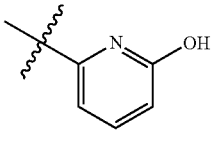 |
| 4.403 | 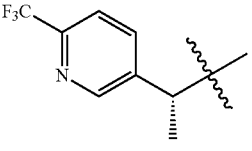 | 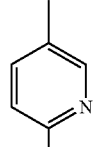 | 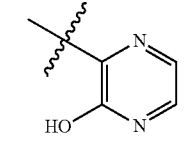 |
| 4.404 | 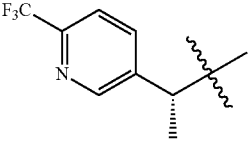 | 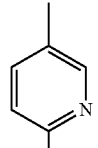 | 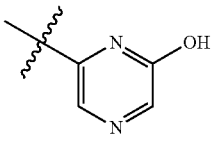 |
| 4.405 | 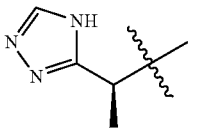 | 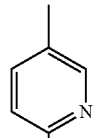 | 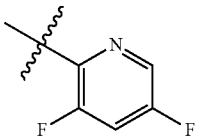 |

TABLE 4-continued
| Example | R¹ | R² | R³ |
|---|---|---|---|
| 4.406 | 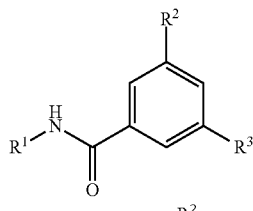 | 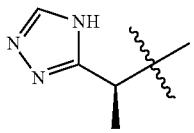 | 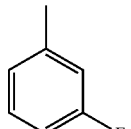 |
| 4.407 | 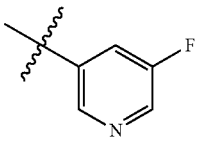 | 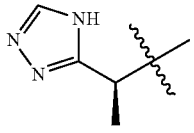 | 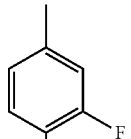 |
| 4.408 | 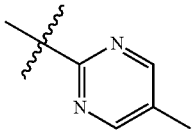 | 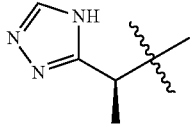 | 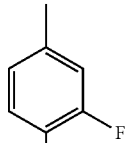 |
| 4.409 | 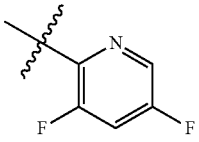 | 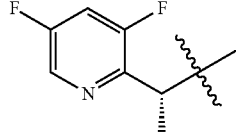 | 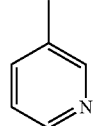 |
| 4.410 | 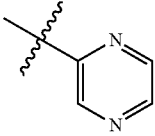 | 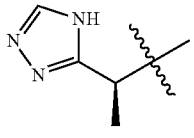 | 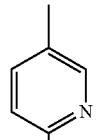 |
| 4.411 | 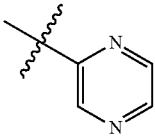 | 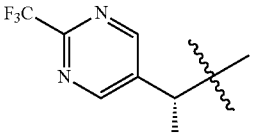 | 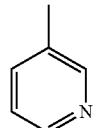 |

TABLE 4-continued
| Example | R¹ | R² | R³ |
|---|---|---|---|
| 4.412 | 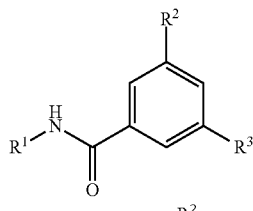 | 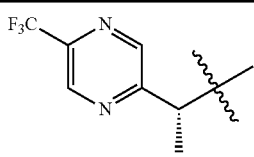 | 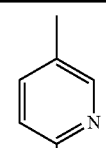 |
| 4.413 | 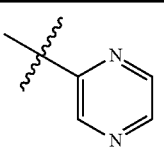 | 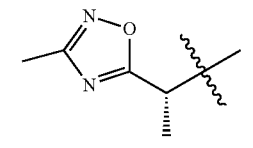 | 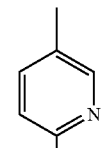 |
| 4.414 | 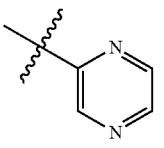 | 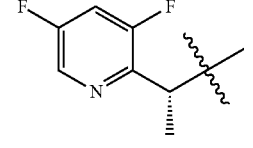 | 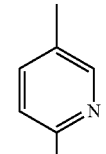 |
| 4.415 | 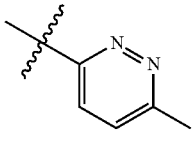 | 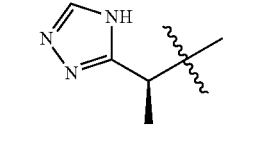 | 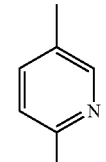 |
| 4.416 | 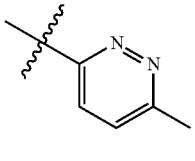 | 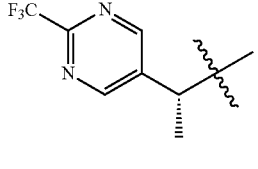 | 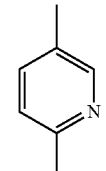 |
| 4.417 | 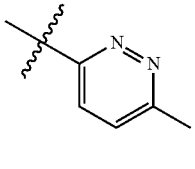 | 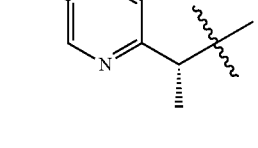 | 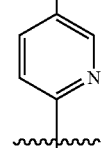 |

TABLE 4-continued

| Example | R¹ | R² | R³ |
|---|---|---|---|
| 4.418 | 3-methyl-1,2,4-oxadiazol-5-yl CH(CH3) | pyridin-2-yl (5-position) | 6-methylpyridazin-3-yl |
| 4.419 | 3,5-difluoropyridin-2-yl CH(CH3) | pyridin-2-yl (5-position) | 2-aminopyrimidin-5-yl |
| 4.420 | 4H-1,2,4-triazol-3-yl CH(CH3) | pyridin-2-yl (5-position) | 2-aminopyrimidin-5-yl |
| 4.421 | 2-(trifluoromethyl)pyrimidin-5-yl CH(CH3) | pyridin-2-yl (5-position) | 2-aminopyrimidin-5-yl |
| 4.422 | 5-(trifluoromethyl)pyrazin-2-yl CH(CH3) | pyridin-2-yl (5-position) | 2-aminopyrimidin-5-yl |
| 4.423 | 3-methyl-1,2,4-oxadiazol-5-yl CH(CH3) | pyridin-2-yl (5-position) | 2-aminopyrimidin-5-yl |

TABLE 4-continued

| Example | R¹ | R² | R³ |
|---|---|---|---|
| 4.424 | 6-(trifluoromethyl)pyridin-3-yl-CH(CH₃)- | pyridin-2-yl | 2-methylpyrimidin-5-yl |
| 4.425 | (4H-1,2,4-triazol-3-yl)-CH(CH₃)- | pyridin-2-yl | 2-methylpyrimidin-5-yl |
| 4.426 | (3-methyl-1,2,4-oxadiazol-5-yl)-CH(CH₃)- | pyridin-2-yl | 2-methylpyrimidin-5-yl |
| 4.427 | 6-(trifluoromethyl)pyridin-3-yl-CH(CH₃)- | pyridin-2-yl | 2-(trifluoromethyl)pyrimidin-5-yl |
| 4.428 | 5-fluoropyridin-2-yl-CH(CH₃)- | pyridin-2-yl | 2-(trifluoromethyl)pyrimidin-5-yl |
| 4.429 | (4H-1,2,4-triazol-3-yl)-CH(CH₃)- | pyridin-2-yl | 2-(trifluoromethyl)pyrimidin-5-yl |

TABLE 4-continued
| Example | R¹ | R² | R³ |
|---|---|---|---|
| 4.430 | 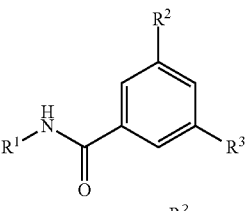 | 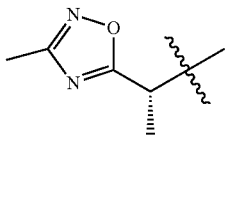 | 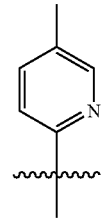 |
| 4.431 | 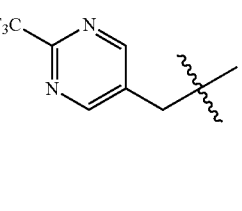 | 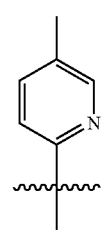 | 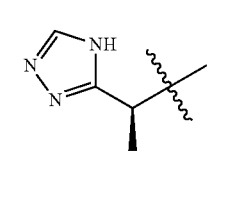 |
| 4.432 | 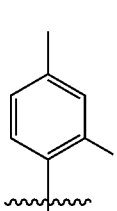 | 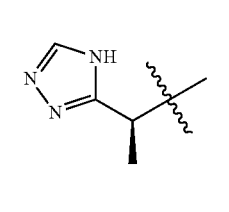 | |
| 4.433 | 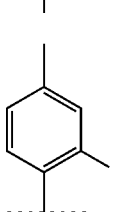 | 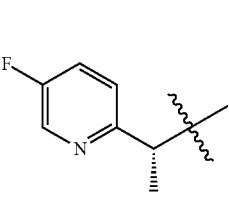 | |
| 4.434 | 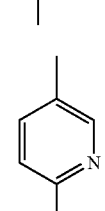 | 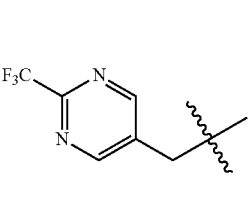 | |
| 4.435 | 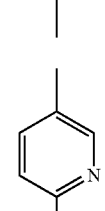 | | |

TABLE 4-continued

| Example | R¹ | R² | R³ |
|---|---|---|---|
| 4.436 | (S)-1-(4H-1,2,4-triazol-3-yl)ethyl | 3-fluoro-4-yl-phenyl | tert-butyl |
| 4.437 | (S)-1-(4H-1,2,4-triazol-3-yl)ethyl | 3-fluoro-4-yl-phenyl | 1-methylcyclopropyl |
| 4.438 | (S)-1-(4H-1,2,4-triazol-3-yl)ethyl | 5-methylpyridin-2-yl | isopropyl |
| 4.439 | (S)-1-(5-fluoropyridin-2-yl)ethyl | 5-methylpyridin-2-yl | sec-butyl |
| 4.440 | (S)-1-(5-fluoropyridin-2-yl)ethyl | 5-methylpyridin-2-yl | tert-pentyl |
| 4.441 | (S)-1-(5-fluoropyridin-2-yl)ethyl | 5-methylpyridin-2-yl | 1-methylcyclopropyl |

TABLE 4-continued

| Example | R¹ | R² | R³ |
|---|---|---|---|
| 4.442 | 5-fluoropyridin-2-yl with CH(CH₃) linker | pyridin-2,5-diyl | C(CH₃)₂OH |
| 4.443 | 3,5-difluoropyridin-2-yl with CH(CH₃) linker | pyridin-2,5-diyl | C(CH₃)₂CF₃ |
| 4.444 | 3-methyl-1,2,4-oxadiazol-5-yl with CH(CH₃) linker | pyridin-2,5-diyl | C(CH₃)₂CF₃ |
| 4.445 | 4H-1,2,4-triazol-3-yl with CH(CH₃) linker | pyridin-2,5-diyl | C(CH₃)₂CF₃ |
| 4.446 | 5-fluoropyridin-2-yl with CH(CH₃) linker | pyridin-2,5-diyl | C(CH₃)₂CF₃ |
| 4.447 | 4H-1,2,4-triazol-3-yl with CH(CH₃) linker | pyridin-2,5-diyl | C(CH₃)₂OH |

TABLE 4-continued

| Example | R¹ | R² | R³ |
|---|---|---|---|
| 4.448 | 5-fluoropyridin-2-yl with (S)-methyl linker | 5-pyridyl (N at 2-position) | C(CH₃)₂OH |
| 4.449 | 3-methyl-1,2,4-oxadiazol-5-yl with (S)-methyl linker | 5-pyridyl (N at 2-position) | C(CH₃)₂OH |
| 4.450 | 3,5-difluoropyridin-2-yl with (S)-methyl linker | 5-pyridyl (N at 2-position) | C(CH₃)₂OH |
| 4.451 | 5-methyl-1,2,4-oxadiazol-3-yl with (S)-methyl linker | 5-pyridyl (N at 2-position) | C(CH₃)₂OH |
| 4.452 | 2-(trifluoromethyl)pyrimidin-5-yl with (S)-methyl linker | 5-pyridyl (N at 2-position) | C(CH₃)₂OH |
| 4.453 | 4H-1,2,4-triazol-3-yl with (S)-methyl linker | 2-fluoro-4-phenyl | C(CH₃)₂OH |

TABLE 4-continued

| Example | R¹ | R² | R³ |
|---------|----|----|----|
| 4.454 | 3-methyl-1,2,4-oxadiazol-5-yl-CH(CH₃)- | 2-fluorophenyl | -C(CH₃)₂OH |
| 4.455 | 2-(trifluoromethyl)pyrimidin-5-yl-CH(CH₃)- | 2-fluorophenyl | -C(CH₃)₂OH |
| 4.456 | 2-(trifluoromethyl)pyrimidin-5-yl-CH(CH₃)- | 2,4-difluorophenyl | -C(CH₃)₂OH |
| 4.457 | 3-methyl-1,2,4-oxadiazol-5-yl-CH(CH₃)- | 2,4-difluorophenyl | -C(CH₃)₂OH |
| 4.458 | 4H-1,2,4-triazol-3-yl-CH(CH₃)- | 2,4-difluorophenyl | -C(CH₃)₂OH |
| 4.459 | 2-(trifluoromethyl)pyridin-5-yl N-oxide-CH(CH₃)- | 2,4-difluorophenyl | -C(CH₃)₂OH |

TABLE 4-continued

| Example | R¹ | R² | R³ |
|---|---|---|---|
| 4.460 | 3-methyl-1,2,4-oxadiazol-5-yl, CH(CH₃)- with methyl | 5-pyridyl (attached at 2) | C(CH₃)₂OMe |
| 4.461 | 5-fluoropyridin-2-yl, CH(CH₃)- | 2,4-difluorophenyl | piperazin-1-yl (NH) |
| 4.462 | 5-fluoropyridin-2-yl, CH(CH₃)- | 3-fluoro-4-methylphenyl | piperazin-1-yl (NH) |
| 4.463 | 5-fluoropyridin-2-yl, CH(CH₃)- | 5-fluoropyridin-2-yl | piperazin-1-yl (NH) |
| 4.464 | 3-methyl-1,2,4-oxadiazol-5-yl, CH(CH₃)- | 5-fluoropyridin-2-yl | piperazin-1-yl (NH) |

TABLE 4-continued
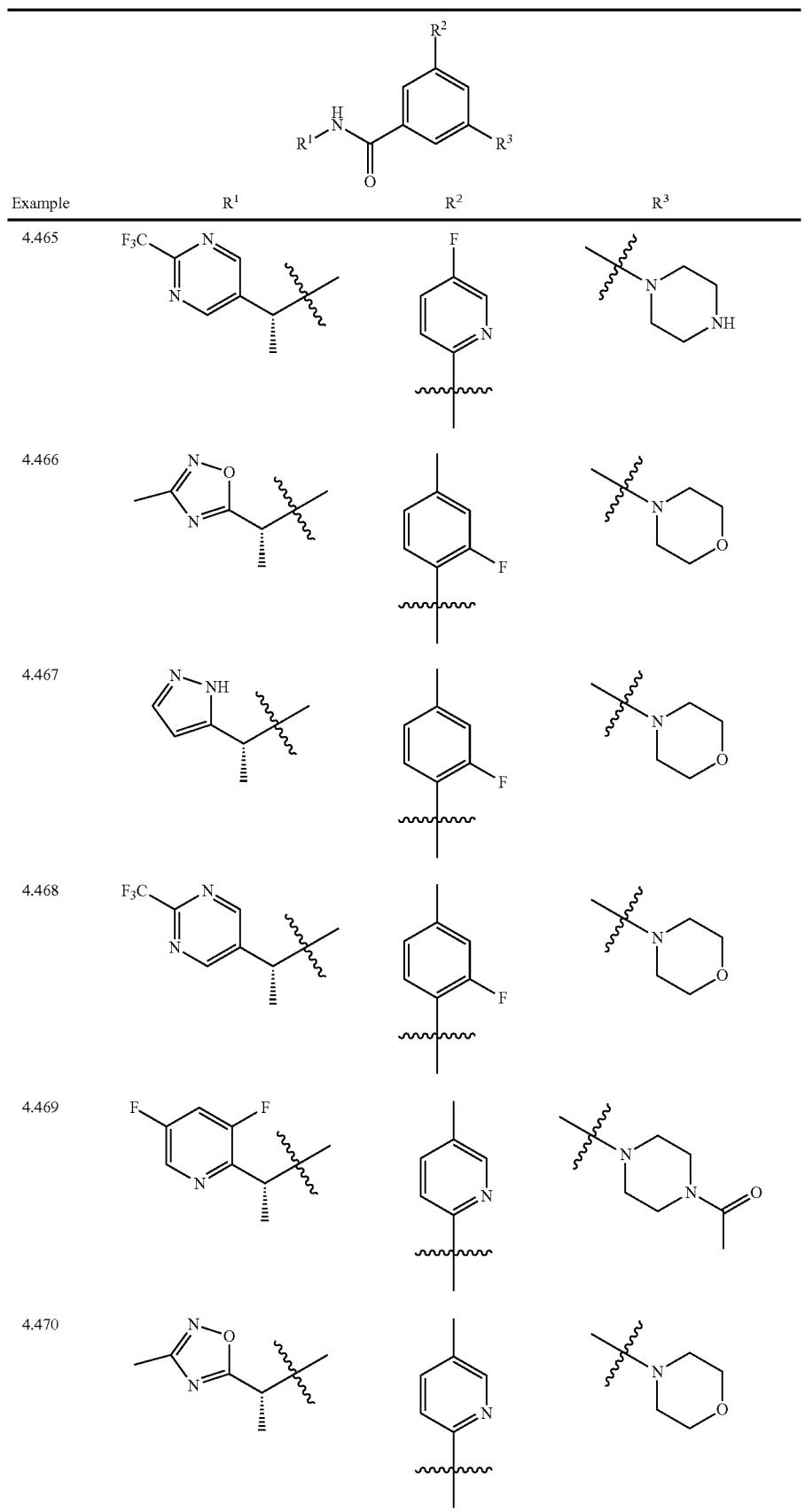

TABLE 4-continued
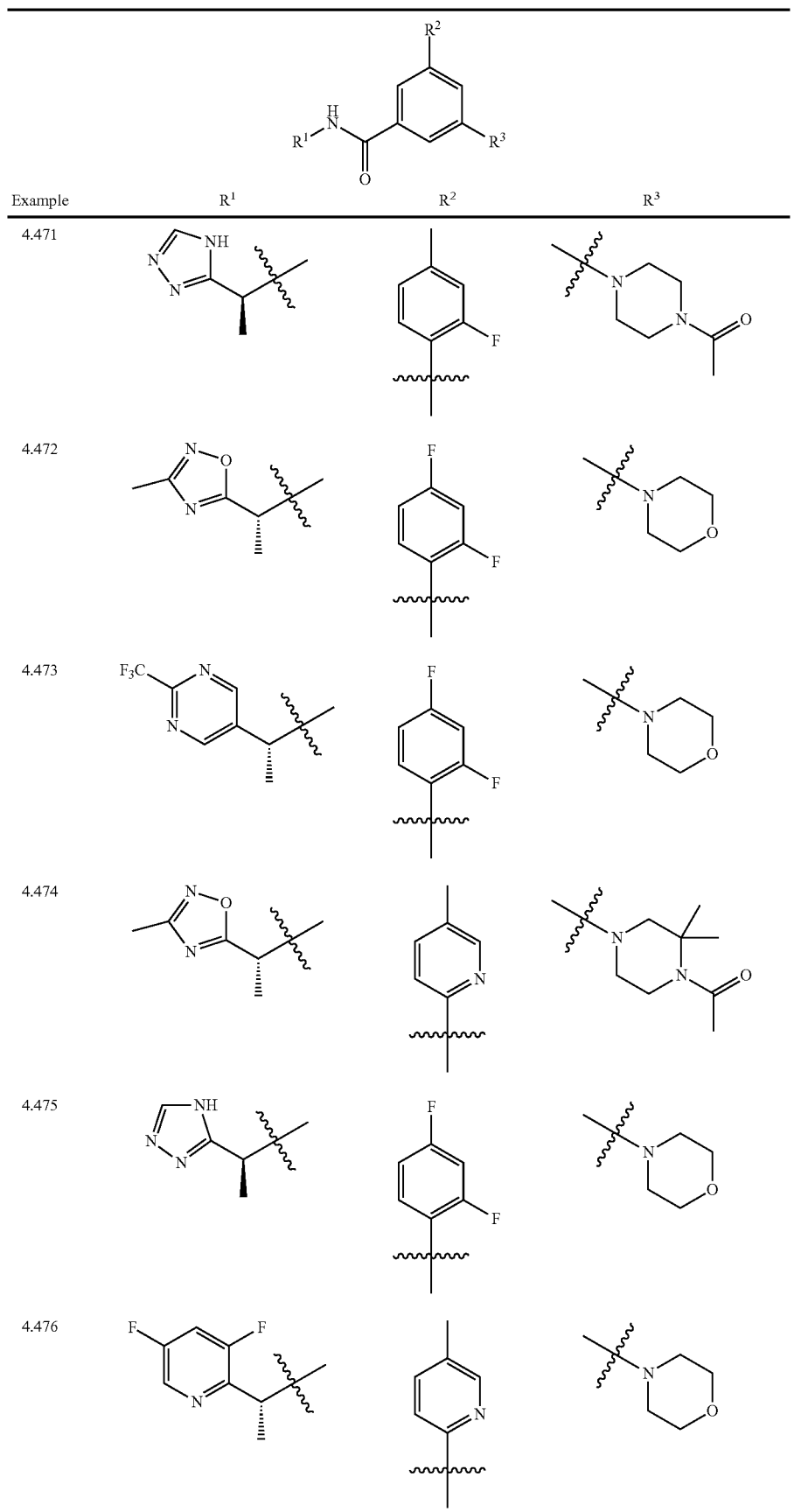

TABLE 4-continued

| Example | R¹ | R² | R³ |
|---|---|---|---|
| 4.477 | 5-(trifluoromethyl)pyridin-2-yl with chiral methyl | pyridin-2-yl | morpholin-4-yl |
| 4.478 | 3-methyl-1,2,4-oxadiazol-5-yl with chiral methyl | pyridin-2-yl | 2-(trifluoromethyl)morpholin-4-yl |
| 4.479 | 3-methyl-1,2,4-oxadiazol-5-yl with chiral methyl | pyridin-2-yl | 3,3-dimethyl-4-(methylsulfonyl)piperazin-1-yl |
| 4.480 | 3,5-difluoropyridin-2-yl with chiral methyl | pyridin-2-yl | 2-(trifluoromethyl)morpholin-4-yl |
| 4.481 | 5-(trifluoromethyl)pyridin-2-yl with chiral methyl | pyridin-2-yl | 2-(trifluoromethyl)morpholin-4-yl |
| 4.482 | 3,5-difluoropyridin-2-yl with chiral methyl | 2,4-difluorophenyl | 3,3-dimethylpiperazin-1-yl |

TABLE 4-continued
| Example | R¹ | R² | R³ |
|---|---|---|---|
| 4.483 | 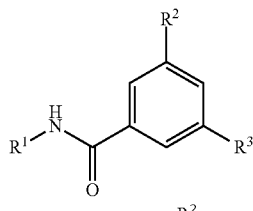 | 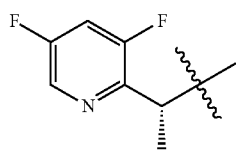 | 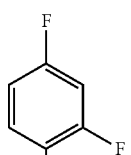 |
| 4.484 | 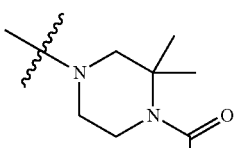 | 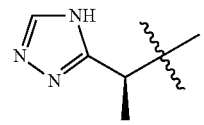 | 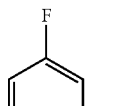 |
| 4.485 | 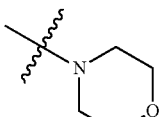 | 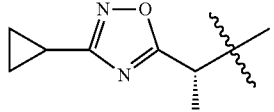 | 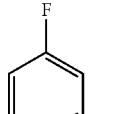 |
| 4.486 | 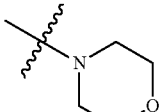 | 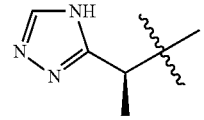 | 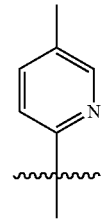 |
| 4.487 | 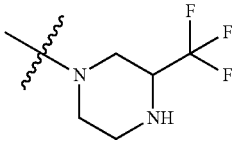 | 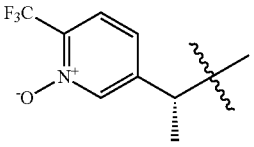 | 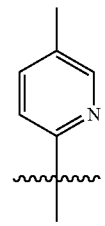 |
| 4.488 | 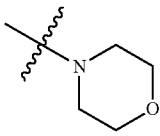 | 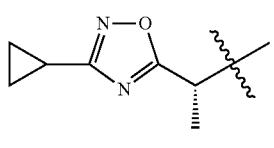 | 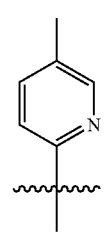 |

TABLE 4-continued
| Example | R¹ | R² | R³ |
|---|---|---|---|
| 4.489 | 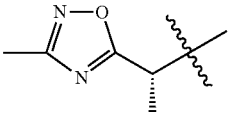 | 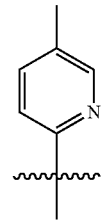 | 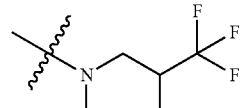 |
| 4.490 | 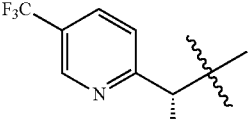 | 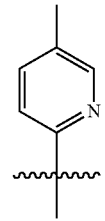 | 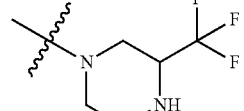 |
| 4.491 | 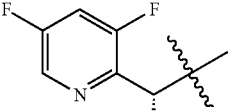 | 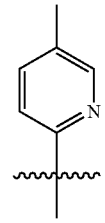 | 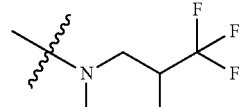 |
| 4.492 | 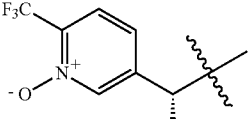 | 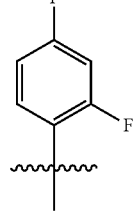 | 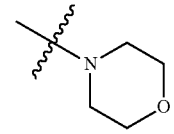 |
| 4.493 | 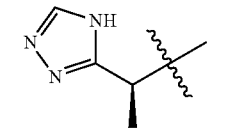 | 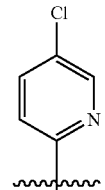 | 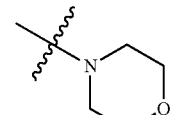 |
| 4.494 | 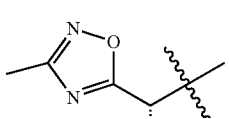 | 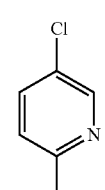 | 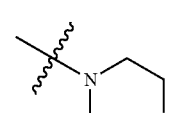 |

TABLE 4-continued

| Example | R¹ | R² | R³ |
|---|---|---|---|
| 4.495 | 2-(trifluoromethyl)pyridin-5-yl N-oxide, α-methyl | 5-chloropyridin-2-yl | morpholin-4-yl |
| 4.496 | 4H-1,2,4-triazol-3-yl, α-methyl | pyridin-2-yl (5-linked) | 2-(trifluoromethyl)morpholin-4-yl |
| 4.497 | 1H-pyrazol-5-yl, α-methyl | pyridin-2-yl (5-linked) | 2-hydroxy-2-methylpropyl (tert-hydroxy) |
| 4.498 | 3-methyl-1,2,4-oxadiazol-5-yl, α-methyl | 5-fluoropyridin-2-yl | 2-hydroxy-2-methylpropyl |
| 4.499 | 2-(trifluoromethyl)pyrimidin-5-yl, α-methyl | 5-fluoropyridin-2-yl | 2-hydroxy-2-methylpropyl |
| 4.500 | 5-(trifluoromethyl)pyridin-2-yl, α-methyl | pyridin-2-yl (5-linked) | 2-hydroxy-2-methylpropyl |

TABLE 4-continued

| Example | R¹ | R² | R³ |
|---|---|---|---|
| 4.501 | 1-(2-(trifluoromethyl)pyrimidin-5-yl)ethyl | pyridin-2-yl (via 5-position) | 2-hydroxypropan-2-yl |
| 4.502 | 1-(2-(trifluoromethyl)pyrimidin-5-yl)ethyl | pyridin-2-yl (via 5-position) | 2-methoxypropan-2-yl |
| 4.503 | 1-(2-(trifluoromethyl)pyrimidin-5-yl)ethyl | pyridin-2-yl (via 5-position) | 2-aminopropan-2-yl |
| 4.504 | 1-(5-methyl-1,2,4-oxadiazol-3-yl)ethyl | pyridin-2-yl (via 5-position) | 2-aminopyrimidin-5-yl |
| 4.505 | 1-(4H-1,2,4-triazol-3-yl)ethyl | pyridin-2-yl (via 5-position) | 2-methoxypropan-2-yl |
| 4.506 | 1-(2-(trifluoromethyl)pyrimidin-5-yl)ethyl | pyridin-2-yl (via 5-position) | 2-methylpyrimidin-5-yl |

TABLE 4-continued

| Example | R¹ | R² | R³ |
|---|---|---|---|
| 4.507 | 5-methyl-1,2,4-oxadiazol-3-yl-CH(CH₃)- | pyridin-2-yl (5-) | 2-methylpyrimidin-5-yl |
| 4.508 | 4H-1,2,4-triazol-3-yl-CH(CH₃)- | pyridin-2-yl (5-) | -C(CH₃)₂NH₂ |
| 4.509 | 3-methyl-1,2,4-oxadiazol-5-yl-CH(CH₃)- | pyridin-2-yl (5-) | -C(CH₃)₂NH₂ |
| 4.510 | 5-fluoropyridin-2-yl 1-oxide-CH(CH₃)- | 2,4-difluorophenyl | -C(CH₃)₂OH |
| 4.511 | 4H-1,2,4-triazol-3-yl-CH(CH₃)- | 2,4-difluorophenyl | -C(CH₃)₂NH₂ |
| 4.512 | 2-trifluoromethylpyrimidin-5-yl-CH(CH₃)- | 2,4-difluorophenyl | -C(CH₃)₂NH₂ |

TABLE 4-continued
| Example | R¹ | R² | R³ |
|---|---|---|---|
| 4.513 | 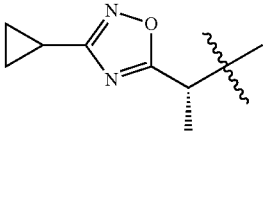 | 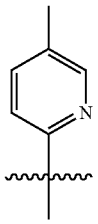 | 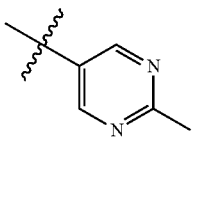 |
| 4.514 | 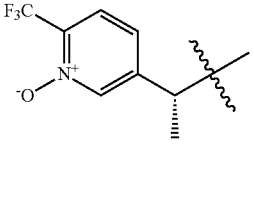 | 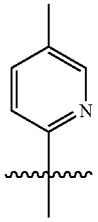 | 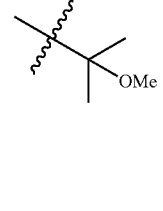 |
| 4.515 | 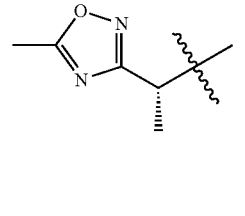 | 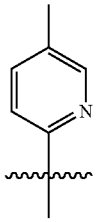 | 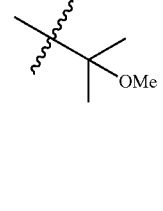 |
| 4.516 | 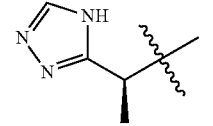 | 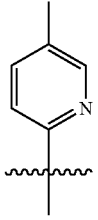 | 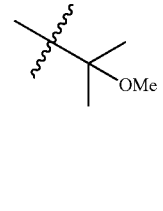 |
| 4.517 | 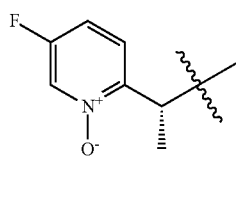 | 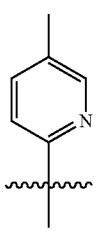 | 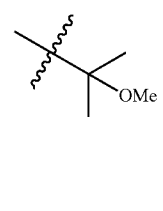 |
| 4.518 | 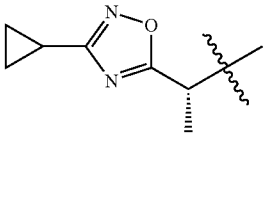 | 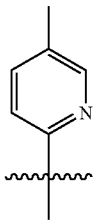 | 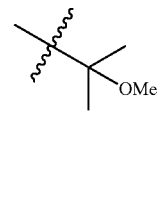 |

TABLE 4-continued
| Example | R¹ | R² | R³ |
|---|---|---|---|
| 4.519 | 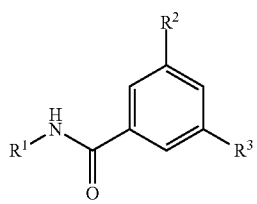 | 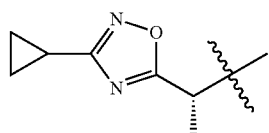 | 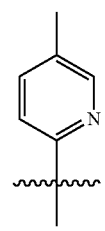 |
| 4.520 |  | 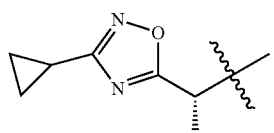 | 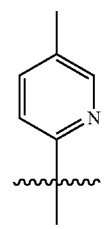 |
| 4.521 | 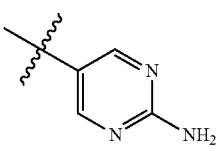 | 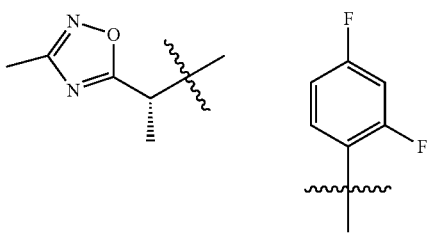 | 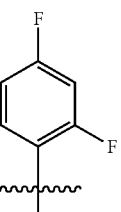 |
| 4.522 | 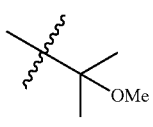 | 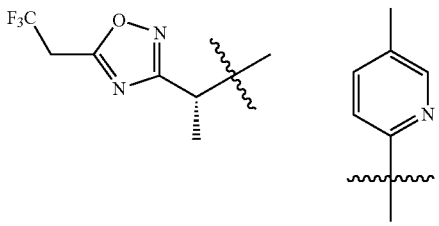 | 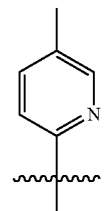 |
| 4.523 | 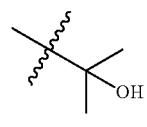 | 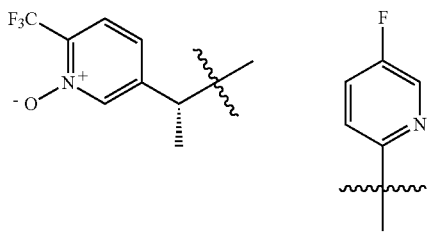 | 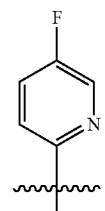 |

TABLE 4-continued

| Example | R¹ | R² | R³ |
|---|---|---|---|
| 4.524 | (S)-1-(4H-1,2,4-triazol-3-yl)ethyl | 5-fluoropyridin-2-yl | 2-hydroxyprop-2-yl |
| 4.525 | (S)-1-(5-methyl-1,2,4-oxadiazol-3-yl)ethyl | 5-fluoropyridin-2-yl | 2-hydroxyprop-2-yl |
| 4.526 | (S)-1-(5-methyl-1,2,4-oxadiazol-3-yl)ethyl | 2,4-difluorophenyl | 2-hydroxyprop-2-yl |
| 4.527 | (S)-1-(6-(trifluoromethyl)pyridin-1-oxide-3-yl)ethyl | phenyl | 2-hydroxyprop-2-yl |
| 4.528 | (S)-1-(4H-1,2,4-triazol-3-yl)ethyl | 4-chlorophenyl | 2-hydroxyprop-2-yl |
| 4.529 | (S)-1-(6-(trifluoromethyl)pyridin-1-oxide-3-yl)ethyl | 4-chlorophenyl | 2-hydroxyprop-2-yl |

TABLE 4-continued
| Example | R¹ | R² | R³ |
|---|---|---|---|
| 4.530 | 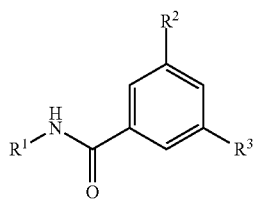 | 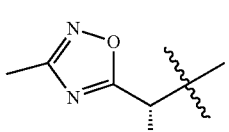 | 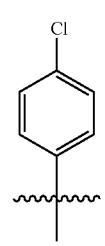 |
| 4.531 | 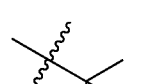 | 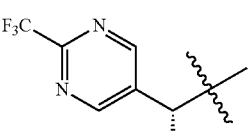 | 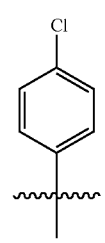 |
| 4.532 | 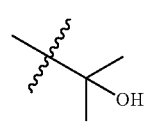 | 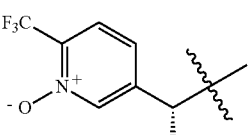 | 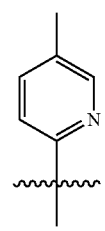 |
| 4.533 | 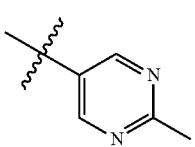 | 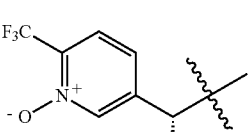 | 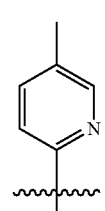 |
| 4.534 | 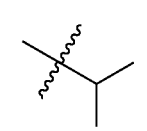 | 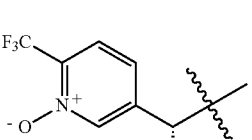 | 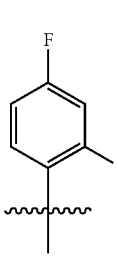 |

TABLE 4-continued

| Example | R¹ | R² | R³ |
|---|---|---|---|
| 4.535 | 3-methyl-1,2,4-oxadiazol-5-yl-CH(CH₃)- | 2,4-difluorophenyl | 2-methylpyrimidin-5-yl |
| 4.536 | 2-(trifluoromethyl)pyridin-5-yl N-oxide-CH(CH₃)- | 5-fluoropyridin-2-yl | 2-methylpyrimidin-5-yl |
| 4.537 | 2-(trifluoromethyl)pyridin-5-yl N-oxide-CH(CH₃)- | 5-fluoropyridin-2-yl | isopropyl |
| 4.538 | 4H-1,2,4-triazol-3-yl-CH(CH₃)- | 5-chloropyridin-2-yl | 2-hydroxypropan-2-yl |
| 4.539 | 2-(trifluoromethyl)pyridin-5-yl N-oxide-CH(CH₃)- | 5-chloropyridin-2-yl | 2-hydroxypropan-2-yl |
| 4.540 | 3-methyl-1,2,4-oxadiazol-5-yl-CH(CH₃)- | 5-chloropyridin-2-yl | 2-hydroxypropan-2-yl |

TABLE 4-continued

TABLE 4-continued

| Example | R¹ | R² | R³ |
|---|---|---|---|
| 4.547 | 2-(trifluoromethyl)pyrimidin-5-yl with methyl stereocenter | pyridin-2-yl (5-substituted) | 1-methyl-1H-1,2,3-triazol-5-yl |
| 4.548 | 4H-1,2,4-triazol-3-yl with methyl stereocenter | pyridin-2-yl (5-substituted) | 1-methyl-1H-1,2,3-triazol-5-yl |
| 4.549 | pyrazin-2-yl with methyl stereocenter | pyridin-2-yl (5-substituted) | 1-methyl-1H-1,2,3-triazol-5-yl |
| 4.550 | 3-methyl-1,2,4-oxadiazol-5-yl with methyl stereocenter | pyridin-2-yl (5-substituted) | 1-methyl-1H-1,2,3-triazol-5-yl |
| 4.551 | 5-fluoropyridin-2-yl with methyl stereocenter | 2,4-difluorophenyl | 4-methyl-4H-1,2,4-triazol-3-yl |
| 4.552 | 6-(trifluoromethyl)pyridin-3-yl with methyl stereocenter | 2,4-difluorophenyl | 4-methyl-4H-1,2,4-triazol-3-yl |

TABLE 4-continued

| Example | R¹ | R² | R³ |
|---|---|---|---|
| 4.553 | | | |
| 4.554 | | | |
| 4.555 | | | |
| 4.556 | | | |
| 4.557 | | | |

TABLE 4-continued

| Example | R¹ | R² | R³ |
|---|---|---|---|
| 4.558 | 5-fluoropyridin-2-yl with (S)-methyl linker | 2,4-difluorophenyl | 4-methyl-5-cyclopropyl-4H-1,2,4-triazol-3-yl |
| 4.559 | 4H-1,2,4-triazol-3-yl with (S)-methyl linker | 2,4-difluorophenyl | 4-methyl-5-cyclopropyl-4H-1,2,4-triazol-3-yl |
| 4.560 | 2-(trifluoromethyl)pyrimidin-5-yl with (S)-methyl linker | 2,4-difluorophenyl | 4-methyl-5-cyclopropyl-4H-1,2,4-triazol-3-yl |
| 4.561 | 3-methyl-1,2,4-oxadiazol-5-yl with (S)-methyl linker | 2,4-difluorophenyl | 4-methyl-5-cyclopropyl-4H-1,2,4-triazol-3-yl |
| 4.562 | 5-methyl-1,2,4-oxadiazol-3-yl with (S)-methyl linker | 2,4-difluorophenyl | 4-methyl-5-cyclopropyl-4H-1,2,4-triazol-3-yl |
| 4.563 | 5-fluoropyridin-2-yl N-oxide with (S)-methyl linker | 2,4-difluorophenyl | 4-methyl-4H-1,2,4-triazol-3-yl |

TABLE 4-continued

| Example | R¹ | R² | R³ |
|---|---|---|---|
| 4.564 | 5-fluoro-2-(1-methylethyl)pyridine N-oxide | 2,4-difluorophenyl | 4-methyl-5-cyclopropyl-4H-1,2,4-triazol-3-yl |
| 4.565 | 5-fluoro-2-(1-methylethyl)pyridin-2-yl | 5-fluoropyridin-2-yl | 4-methyl-4H-1,2,4-triazol-3-yl |
| 4.566 | 6-(trifluoromethyl)pyridin-3-yl with methylethyl | 5-fluoropyridin-2-yl | 4-methyl-4H-1,2,4-triazol-3-yl |
| 4.567 | 4H-1,2,4-triazol-3-yl with methylethyl | 5-fluoropyridin-2-yl | 4-methyl-4H-1,2,4-triazol-3-yl |
| 4.568 | 2-(trifluoromethyl)pyrimidin-5-yl with methylethyl | 5-fluoropyridin-2-yl | 4-methyl-4H-1,2,4-triazol-3-yl |
| 4.569 | 3,5-difluoropyridin-2-yl with methylethyl | 5-fluoropyridin-2-yl | 4-methyl-4H-1,2,4-triazol-3-yl |

TABLE 4-continued

| Example | R¹ | R² | R³ |
|---|---|---|---|
| 4.570 | 3-methyl-1,2,4-oxadiazol-5-yl with α-methyl linker | 5-fluoropyridin-2-yl | 4-methyl-4H-1,2,4-triazol-3-yl |
| 4.571 | 5-methyl-1,2,4-oxadiazol-3-yl with α-methyl linker | 5-fluoropyridin-2-yl | 4-methyl-4H-1,2,4-triazol-3-yl |
| 4.572 | 5-fluoropyridin-2-yl with α-methyl linker | 5-fluoropyridin-2-yl | 5-cyclopropyl-4-methyl-4H-1,2,4-triazol-3-yl |
| 4.573 | 4H-1,2,4-triazol-3-yl with α-methyl linker | 5-fluoropyridin-2-yl | 5-cyclopropyl-4-methyl-4H-1,2,4-triazol-3-yl |
| 4.574 | 2-(trifluoromethyl)pyrimidin-5-yl with α-methyl linker | 5-fluoropyridin-2-yl | 5-cyclopropyl-4-methyl-4H-1,2,4-triazol-3-yl |
| 4.575 | 5-methyl-1,2,4-oxadiazol-3-yl with α-methyl linker | 5-fluoropyridin-2-yl | 5-cyclopropyl-4-methyl-4H-1,2,4-triazol-3-yl |

TABLE 4-continued

| Example | R¹ | R² | R³ |
|---|---|---|---|
| 4.576 | (5-methyl-1,2,4-oxadiazol-3-yl)(methyl)methyl | 5-fluoropyridin-2-yl | 5-cyclopropyl-4-methyl-4H-1,2,4-triazol-3-yl |
| 4.577 | 1-(5-fluoro-1-oxidopyridin-2-yl)ethyl | 5-fluoropyridin-2-yl | 5-cyclopropyl-4-methyl-4H-1,2,4-triazol-3-yl |
| 4.578 | 1-(1-oxido-6-(trifluoromethyl)pyridin-3-yl)ethyl | 5-fluoropyridin-2-yl | 5-cyclopropyl-4-methyl-4H-1,2,4-triazol-3-yl |
| 4.579 | 1-(6-(trifluoromethyl)pyridin-3-yl)ethyl | 5-methylpyridin-2-yl | 4-methyl-5-(2,2,2-trifluoroethyl)-4H-1,2,4-triazol-3-yl |
| 4.580 | 1-(5-fluoro-1-oxidopyridin-2-yl)ethyl | 5-methylpyridin-2-yl | 1-methyl-1H-1,2,3-triazol-5-yl |
| 4.581 | 1-(1-oxido-6-(trifluoromethyl)pyridin-3-yl)ethyl | 5-methylpyridin-2-yl | 1-methyl-1H-1,2,3-triazol-5-yl |

TABLE 4-continued

| Example | R¹ | R² | R³ |
|---|---|---|---|
| 4.582 | 6-(trifluoromethyl)pyridin-3-yl N-oxide, CH(CH₃) | 2,4-difluorophenyl | 4-methyl-4H-1,2,4-triazol-3-yl |
| 4.583 | 6-(trifluoromethyl)pyridin-3-yl N-oxide, CH(CH₃) | 2,4-difluorophenyl | 5-cyclopropyl-4-methyl-4H-1,2,4-triazol-3-yl |
| 4.584 | 6-(trifluoromethyl)pyridin-3-yl N-oxide, CH(CH₃) | 5-fluoropyridin-2-yl | 4-methyl-4H-1,2,4-triazol-3-yl |
| 4.585 | 6-(trifluoromethyl)pyridin-3-yl N-oxide, CH(CH₃) | pyridin-2-yl | 5-cyclopropyl-4-methyl-4H-1,2,4-triazol-3-yl |
| 4.586 | 6-(trifluoromethyl)pyridin-3-yl N-oxide, CH(CH₃) | pyridin-2-yl | 1-methyl-1H-imidazol-2-yl |
| 4.587 | 6-(trifluoromethyl)pyridin-3-yl N-oxide, CH(CH₃) | pyridin-2-yl | oxazol-2-yl |

TABLE 4-continued
| Example | R¹ | R² | R³ |
|---|---|---|---|
| 4.588 | 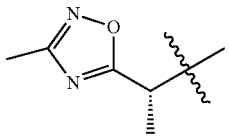 | 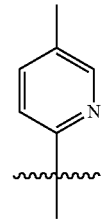 | 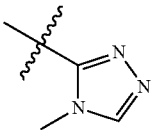 |
| 4.589 | 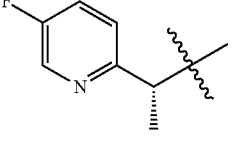 | 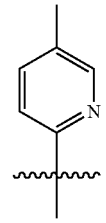 | 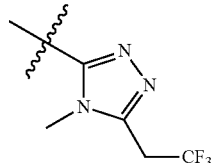 |
| 4.590 | 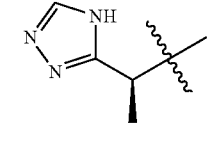 | 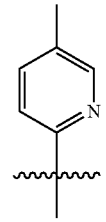 | 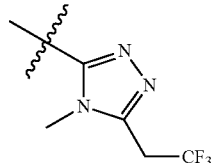 |
| 4.591 | 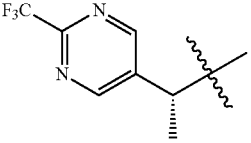 | 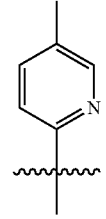 | 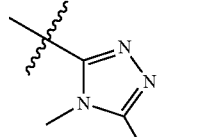 |
| 4.592 | 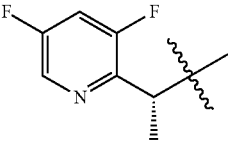 | 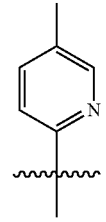 | 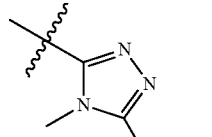 |
| 4.593 | 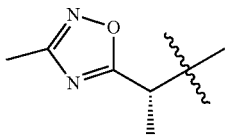 | 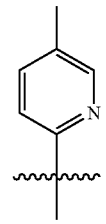 | 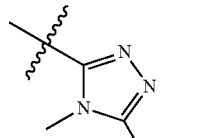 |

TABLE 4-continued

| Example | R¹ | R² | R³ |
|---|---|---|---|
| 4.594 | 5-methyl-1,2,4-oxadiazol-3-yl with (S)-CH(CH₃)– linker | pyridin-2-yl (5-linked) | 4-methyl-5-(2,2,2-trifluoroethyl)-4H-1,2,4-triazol-3-yl |
| 4.595 | 5-(trifluoromethyl)pyridin-2-yl with (S)-CH(CH₃)– linker | pyridin-2-yl (5-linked) | 4-methyl-5-(2,2,2-trifluoroethyl)-4H-1,2,4-triazol-3-yl |
| 4.596 | 5-fluoropyridin-2-yl N-oxide with (S)-CH(CH₃)– linker | pyridin-2-yl (5-linked) | 4-methyl-5-(2,2,2-trifluoroethyl)-4H-1,2,4-triazol-3-yl |
| 4.597 | 5-(trifluoromethyl)pyrazin-2-yl with (S)-CH(CH₃)– linker | pyridin-2-yl (5-linked) | 4-methyl-5-(2,2,2-trifluoroethyl)-4H-1,2,4-triazol-3-yl |
| 4.598 | 6-(trifluoromethyl)pyridin-3-yl N-oxide with (S)-CH(CH₃)– linker | pyridin-2-yl (5-linked) | 4-methyl-5-(2,2,2-trifluoroethyl)-4H-1,2,4-triazol-3-yl |
| 4.599 | 5-methyl-1,2,4-oxadiazol-3-yl with (S)-CH(CH₃)– linker | pyridin-2-yl (5-linked) | 4-methyl-4H-1,2,4-triazol-3-yl |

TABLE 4-continued
| Example | R¹ | R² | R³ |
|---|---|---|---|
| 4.600 | 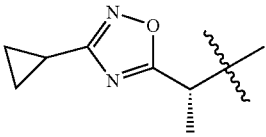 | 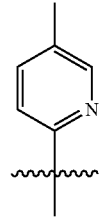 | 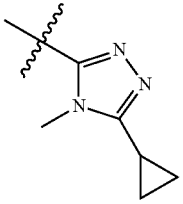 |
| 4.601 | 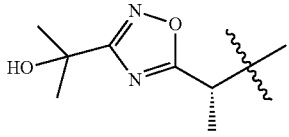 | 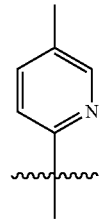 | 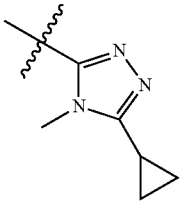 |
| 4.602 | 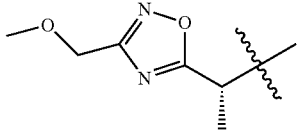 | 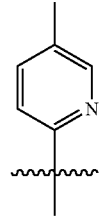 | 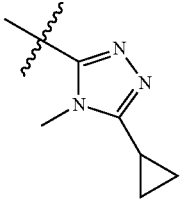 |
| 4.603 | 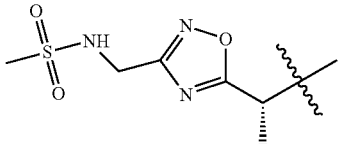 | 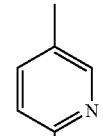 | 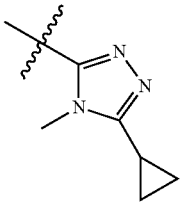 |
| 4.604 | 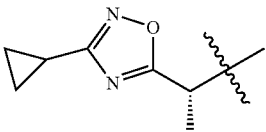 | 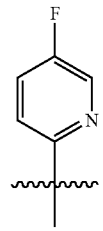 | 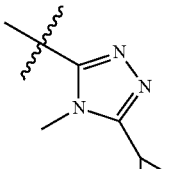 |
| 4.605 | 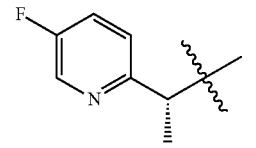 | 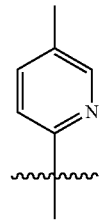 | 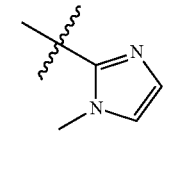 |

TABLE 4-continued

| Example | R¹ | R² | R³ |
|---|---|---|---|
| 4.606 | (S)-1-(4H-1,2,4-triazol-3-yl)ethyl | 5-pyridin-2-yl | 1-methyl-1H-imidazol-2-yl |
| 4.607 | (S)-1-(2-(trifluoromethyl)pyrimidin-5-yl)ethyl | 5-pyridin-2-yl | 1-methyl-1H-imidazol-2-yl |
| 4.608 | (S)-1-(3,5-difluoropyridin-2-yl)ethyl | 5-pyridin-2-yl | 1-methyl-1H-imidazol-2-yl |
| 4.609 | (S)-1-(5-methyl-1,2,4-oxadiazol-3-yl)ethyl | 5-pyridin-2-yl | 1-methyl-1H-imidazol-2-yl |
| 4.610 | (S)-1-(5-methyl-1,2,4-oxadiazol-3-yl)ethyl | 5-pyridin-2-yl | 1-methyl-1H-imidazol-2-yl |
| 4.611 | (S)-1-(5-(trifluoromethyl)pyridin-2-yl)ethyl | 5-pyridin-2-yl | 1-methyl-1H-imidazol-2-yl |

TABLE 4-continued

| Example | R¹ | R² | R³ |
|---|---|---|---|
| 4.612 | pyrazolyl-CH(CH₃)- | 5-pyridyl (2-linked) | 1-methylimidazol-2-yl |
| 4.613 | 5-fluoropyridine N-oxide-2-yl-CH(CH₃)- | 5-pyridyl (2-linked) | 1-methylimidazol-2-yl |
| 4.614 | oxazol-2-yl-CH(CH₃)- | 5-pyridyl (2-linked) | 1-methylimidazol-2-yl |
| 4.615 | 3-cyclopropyl-1,2,4-oxadiazol-5-yl-CH(CH₃)- | 2,4-difluorophenyl | 4-methyl-5-cyclopropyl-1,2,4-triazol-3-yl |
| 4.616 | 3-methyl-1,2,4-oxadiazol-5-yl-CH(CH₃)- | 5-pyridyl (2-linked) | 3-fluoropyridin-2-yl |
| 4.617 | 3-methyl-1,2,4-oxadiazol-5-yl-CH(CH₂OH)- | 5-pyridyl (2-linked) | 3-fluoropyridin-2-yl |

TABLE 4-continued
| Example | R¹ | R² | R³ |
|---|---|---|---|
| 4.618 | 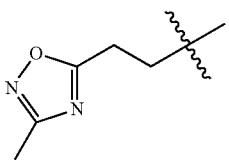 | 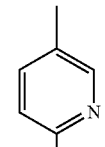 | 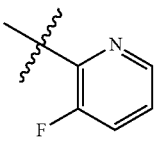 |
| 4.619 | 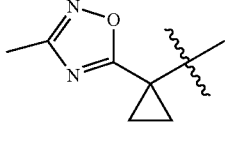 | 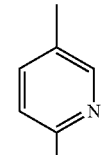 | 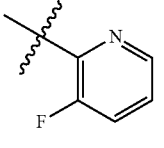 |
| 4.620 | 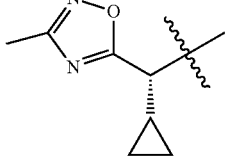 | 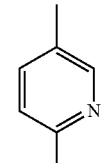 | 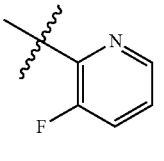 |
| 4.621 | 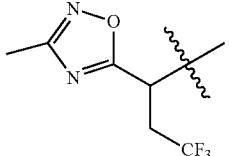 | 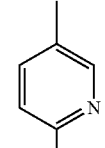 | 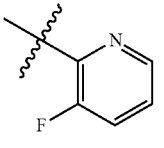 |
| 4.622 | 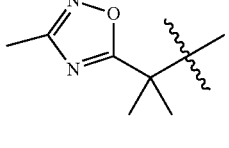 | 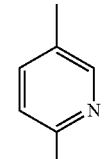 | 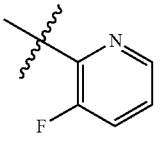 |
| 4.623 | 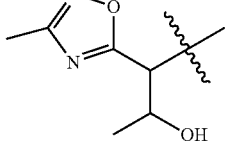 | 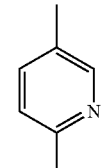 | 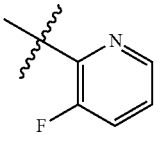 |

TABLE 4-continued
| Example | R¹ | R² | R³ |
|---|---|---|---|
| 4.624 | 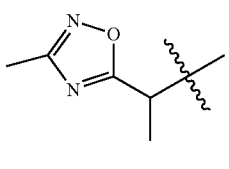 | 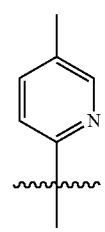 | 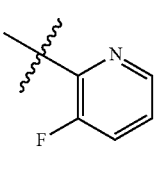 |
| 4.625 | 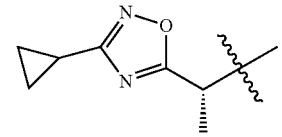 | 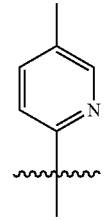 | 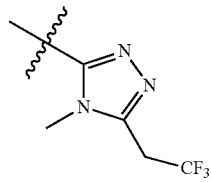 |
| 4.626 | 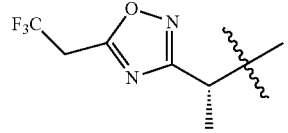 | 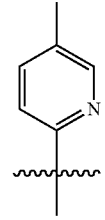 |  |
| 4.627 | 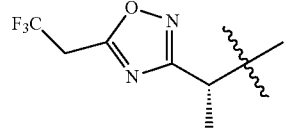 | 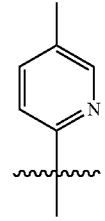 | 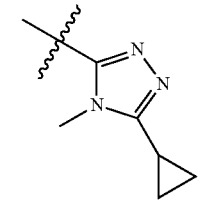 |
| 4.628 | 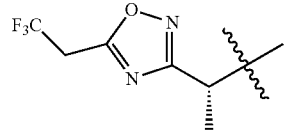 | 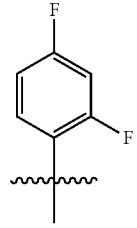 | 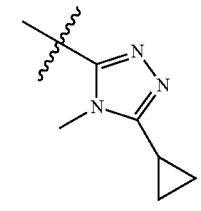 |
| 4.629 | 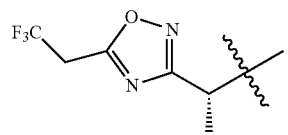 | 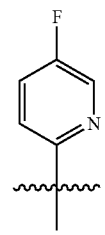 | 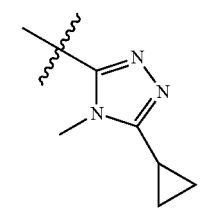 |

TABLE 4-continued

| Example | R¹ | R² | R³ |
|---|---|---|---|
| 4.630 | | | |
| 4.631 | | | |
| 4.632 | | | |
| 4.633 | | | |
| 4.634 | | | |

TABLE 4-continued

| Example | R¹ | R² | R³ |
|---|---|---|---|
| 4.635 | 5-methyl-1,2,4-oxadiazol-3-yl-CH(CH₃)- | 2,4-difluorophenyl | 1-methyl-1,2,3-triazol-5-yl |
| 4.636 | 5-fluoropyridin-2-yl N-oxide-CH(CH₃)- | 2,4-difluorophenyl | 1-methyl-1,2,3-triazol-5-yl |
| 4.637 | 6-(trifluoromethyl)pyridin-3-yl N-oxide-CH(CH₃)- | 2,4-difluorophenyl | 1-methyl-1,2,3-triazol-5-yl |
| 4.638 | 4H-1,2,4-triazol-3-yl-CH(CH₃)- | 4-methylphenyl | 1-methyl-1,2,3-triazol-5-yl |
| 4.639 | 2-methylpyrimidin-5-yl-CH(CH₃)- | 2,4-difluorophenyl | 5-cyclopropyl-4-methyl-4H-1,2,4-triazol-3-yl |
| 4.640 | 4H-1,2,4-triazol-3-yl-CH(CH₃)- | pyridin-2-yl | -C(CH₃)₂CH₂CF₃ |

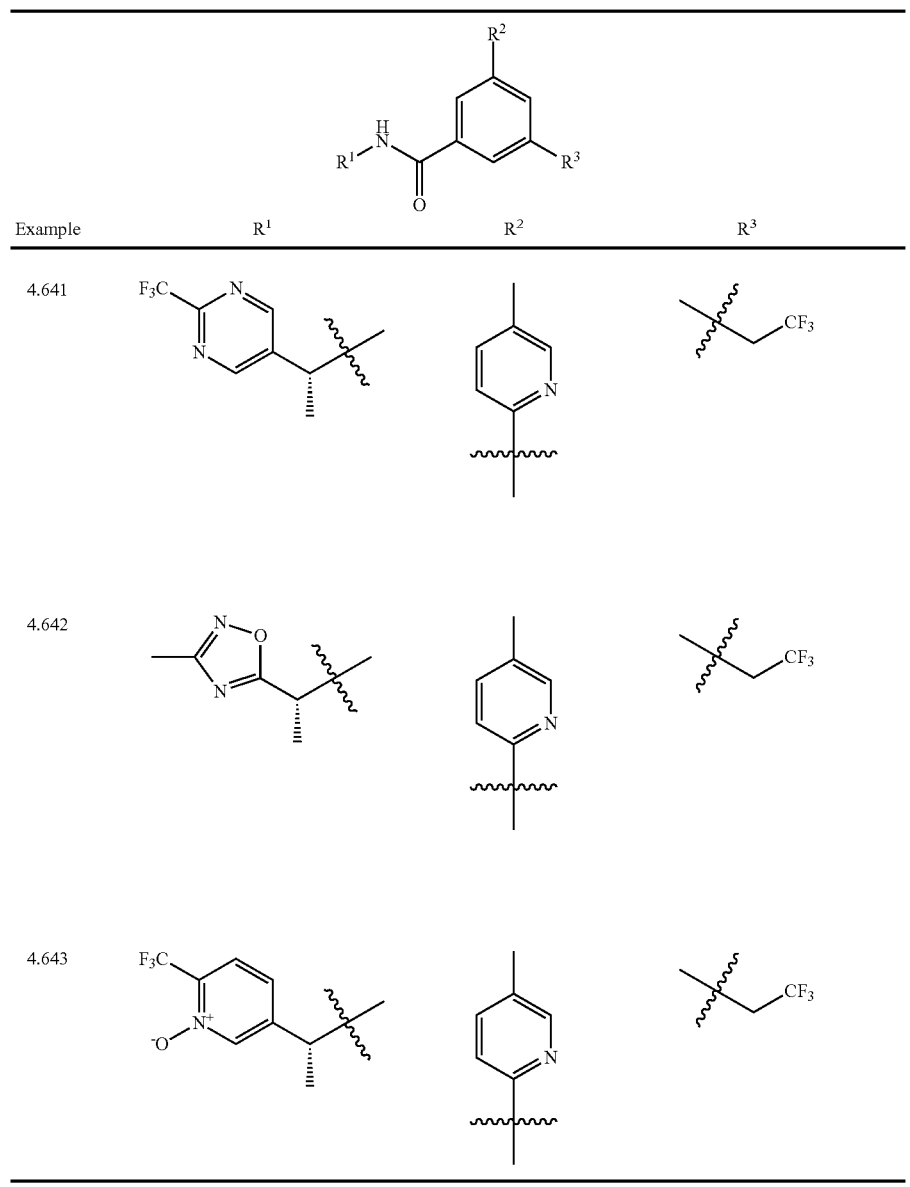

TABLE 5-continued
| EX | Structure |
|---|---|
| 5.3 | 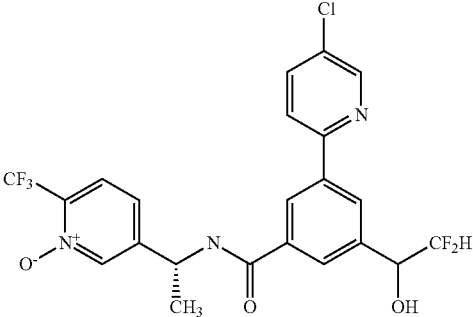 |
| 5.4 | 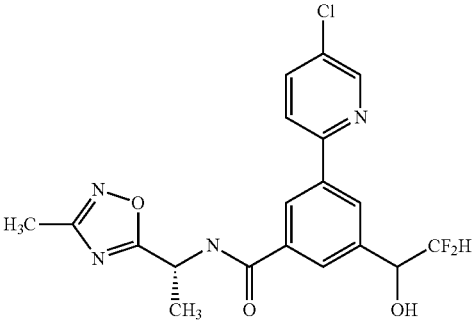 |
| 5.5 | 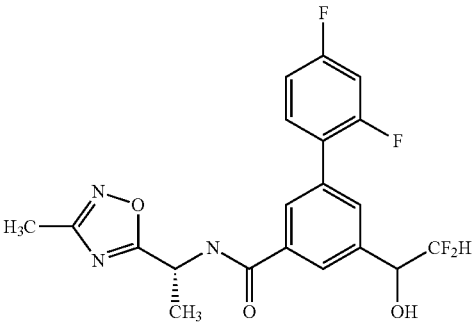 |
| 5.6 | 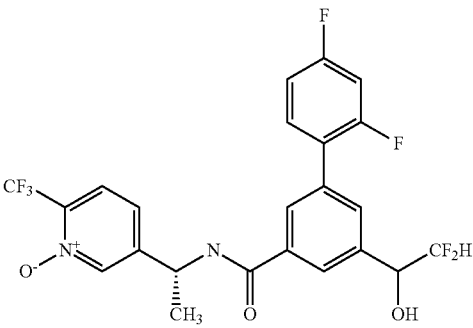 |
| 5.7 | 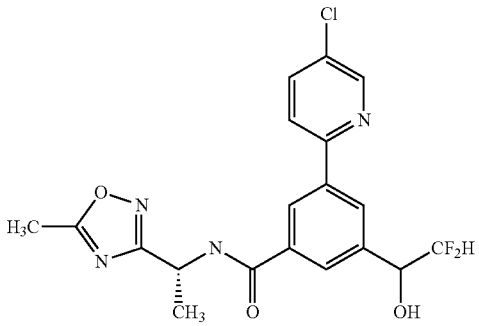 |
| 5.8 | 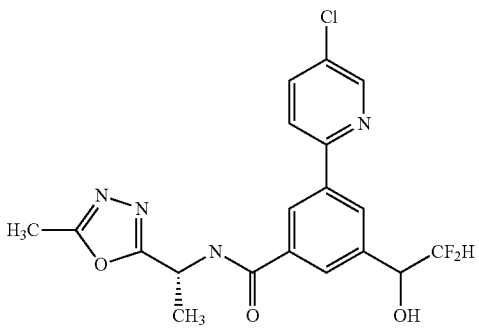 |
| 5.9 | 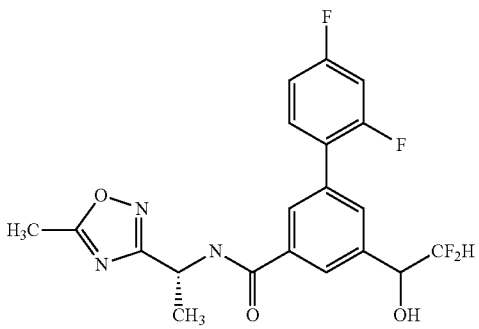 |
| 5.10 | 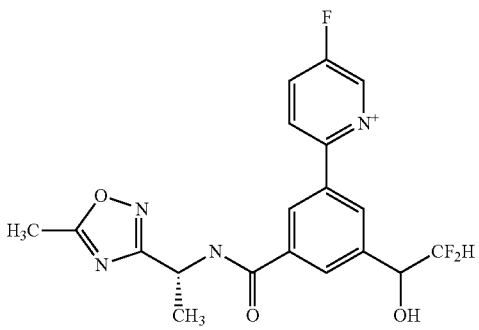 |

TABLE 6
| EX | Structure |
|---|---|
| 6.1 | 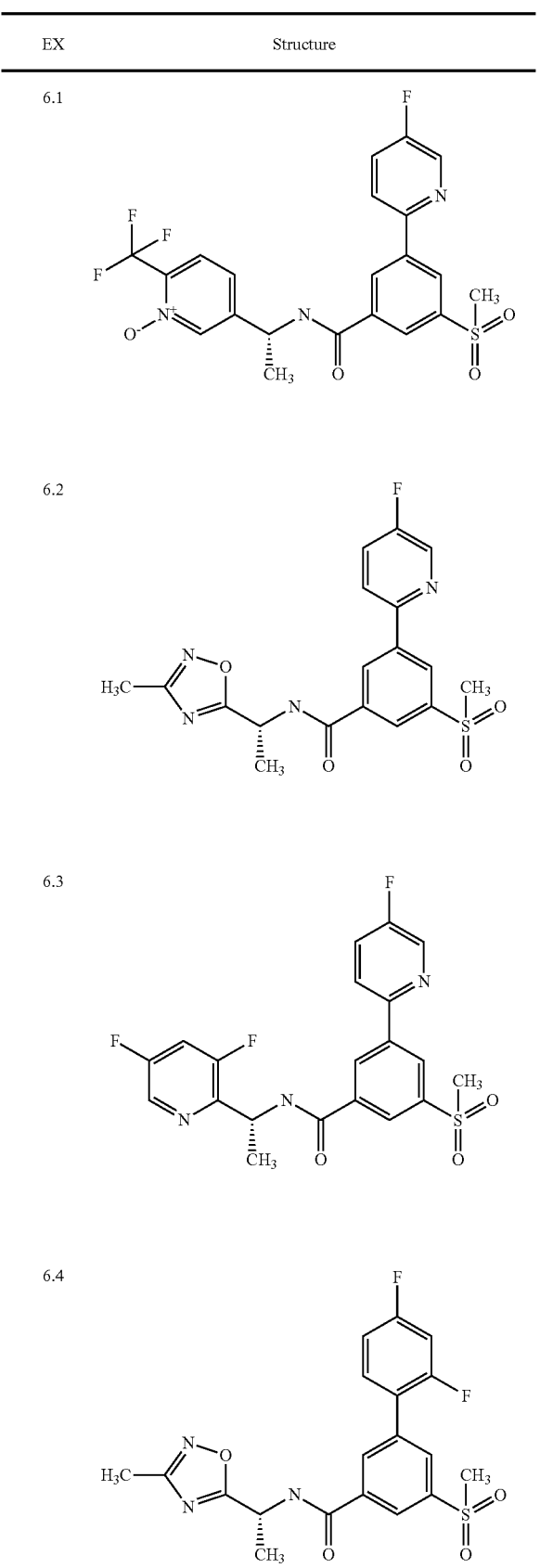 |
| 6.2 | 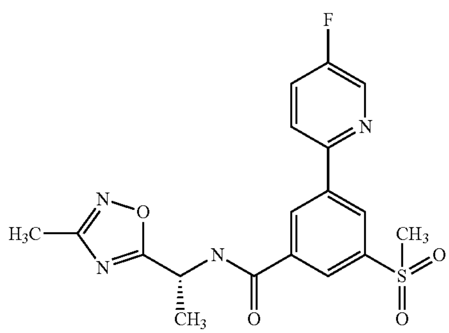 |
| 6.3 | 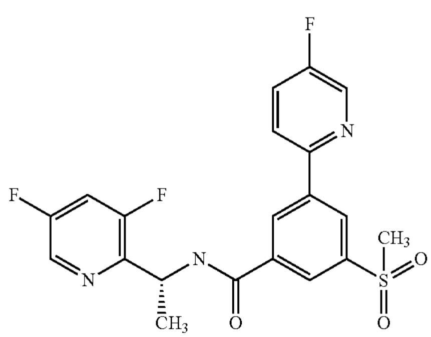 |
| 6.4 | 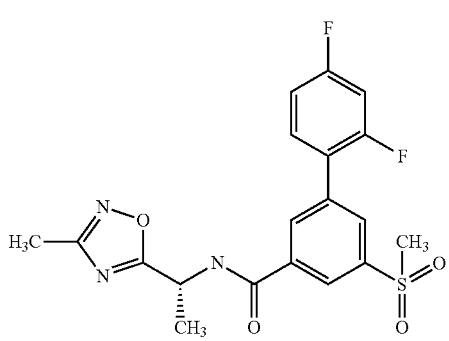 |
TABLE 6-continued
| EX | Structure |
|---|---|
| 6.5 | 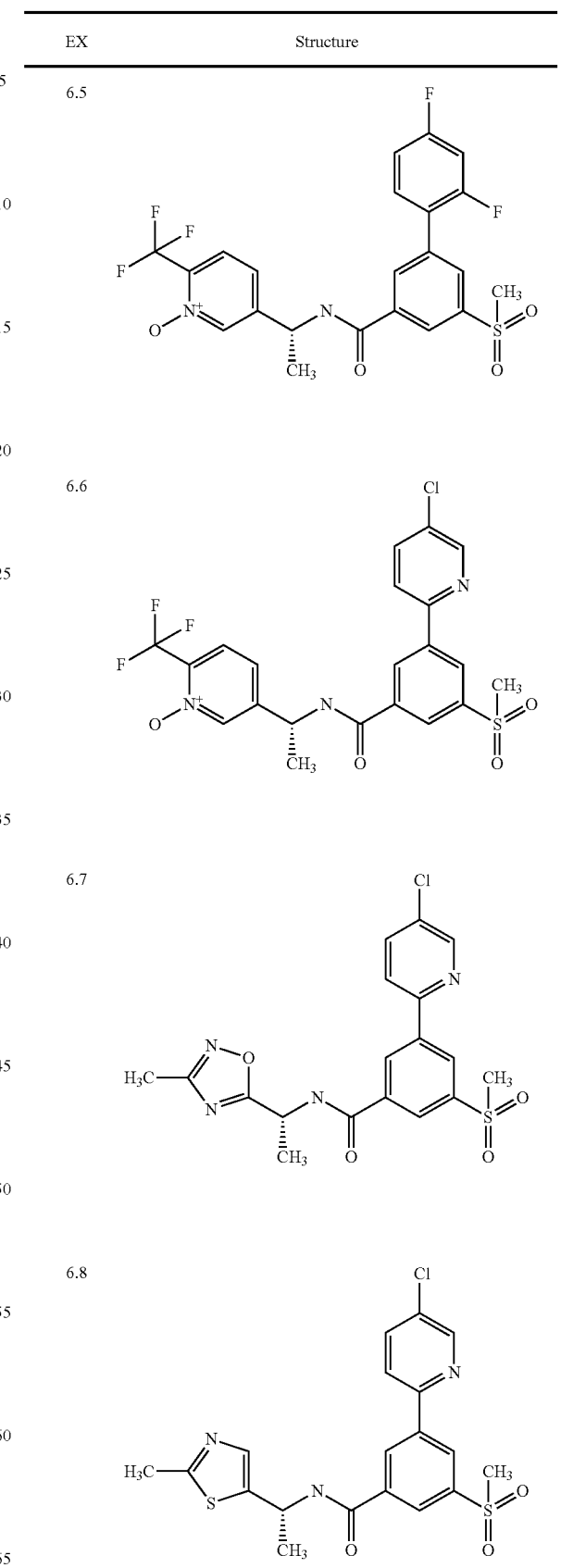 |
| 6.6 | 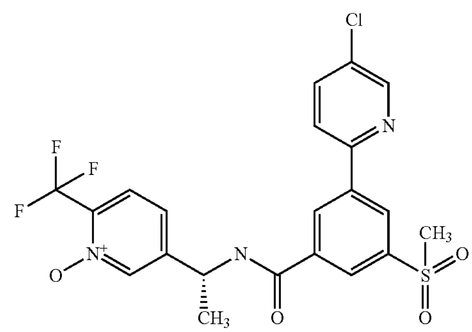 |
| 6.7 | 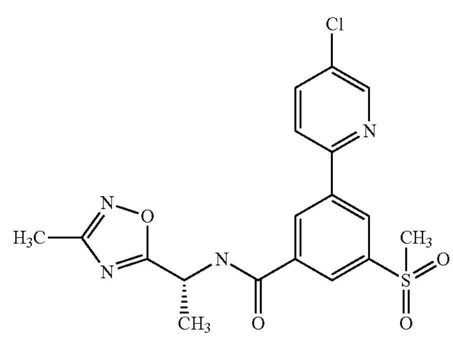 |
| 6.8 | 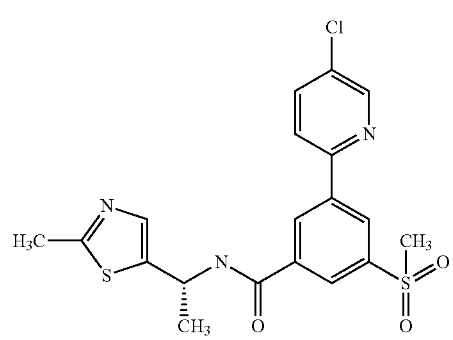 |

TABLE 6-continued

| EX | Structure |
|---|---|
| 6.9 | (chemical structure) |

TABLE 7

| EX | Structure |
|---|---|
| 7.1 | (chemical structure) |
| 7.2 | (chemical structure) |
| 7.3 | (chemical structure) |

TABLE 7-continued

| EX | Structure |
|---|---|
| 7.4 | (chemical structure) |
| 7.5 | (chemical structure) |
| 7.6 | (chemical structure) |
| 7.7 | (chemical structure) |

TABLE 7-continued

| EX | Structure |
|---|---|
| 7.8 | 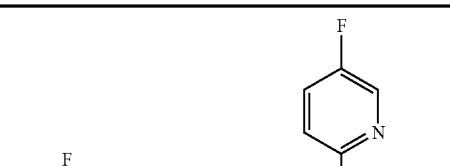 |

17. A compound according to claim 16 which is:
N-[(1R)-1-(5-Fluoropyridin-2-yl)ethyl]-3-(5-methylpyridin-2-yl)-5-[(R/S)-2,2,2-trifluoro-1-hydroxyethyl]benzamide;
4'-Methyl-N-(2,2,2-trifluoroethyl)-5-(2,2,2-trifluoro-1-hydroxyethyl)biphenyl-3-carboxamide;
3-(5-Fluoropyridin-2-yl)-N-{(1R)-1-[1-oxido-6-(trifluoromethyl)pyridin-3-yl]ethyl}-5-[(R/S)-2,2,2-trifluoro-1-hydroxyethyl]benzamide;
4'-Methyl-5-[2,2,2-trifluoro-1-hydroxy-(trifluoromethyl)ethyl]-N-{(1R)-1-[2-(trifluoromethyl)-pyrimidine-5-yl]ethyl}biphenyl-3-carboxamide
4'-Methyl-N-{(1R)-1-[1-oxido-6-(trifluoromethyl)pyridyn-3-yl]ethyl}-5-[2,2,2-trifluoro-1-hydroxy-1-(trifluoromethyl)ethyl]biphenyl-3-carboxamide;
N-[(1R)-1-(4-Fluorophenyl)ethyl]-3-(5-methylpyridin-2-yl)-5-[2,2,2-trifluoro-1-hydroxy-1(trifluoromethyl)ethyl]benzamide;
2'-Fluoro-5-[hydroxy(phenyl)methyl]-N-isopropyl-4'-methylbiphenyl-3-carboxamide;
3-(5-Cyclopropyl-4-methyl-4H-1,2,4-triazol-3-yl)-N-[(1R)-1-(5-fluoropyridin-2-yl)ethyl]-5-(5-methylpyridin-2-yl)benzamide;
3-(5-Cyclopropyl-4-methyl-4H-1,2,4-triazol-3-yl)-N-[(1R)-1-(3,5-difluoropyridin-2-yl)ethyl]-5-(5-methylpyridin-2-yl)benzamide;
3-(5-Methylpyridin-2-yl)-5-(4-methyl-4H-1,2,4-triazol-3-yl)-N-{(1R)-1-[5-(trifluoromethyl)pyridin-2-yl]ethyl}benzamide;
N-[(1R)-1-(3,5-Difluoropyridin-2-yl)ethyl]-3-(5-methylpyridin-2-yl)-5-(1-methyl-1H-1,2,3-triazol-5-yl)benzamide;
2',4'-Difluoro-5-piperazin-1-yl-N-{(1R)-1-[2-(trifluoromethyl)pyrimidin-5-yl]ethyl}biphenyl-3-carboxamide;
2'-Fluoro-4'-methyl-5-morpholin-4-yl-N-[(1R)-1-(1H-1,2,4-triazol-3-yl)ethyl]biphenyl-3-carboxamide;
3-(3-Fluoropyridin-2-yl)-N-[(1R)-1-(5-fluoropyridin-2-yl)ethyl]-5-(5-methylpyridin-2-yl)benzamide;
3-(3-Fluoropyridin-2-yl)-N-[(1R)-1-(5-methyl-1,2,4-oxadiazol-3-yl)ethyl]-5-(5-methylpyridin-2-yl)benzamide;
3-(5-Chloropyridin-2-yl)-5-(1-hydroxy-1-methylethyl)-N-{(1R)-1-[1-oxido-6-(trifluoromethyl)pyridin-3-yl]ethyl}benzamide;
N-[(1R)-1-(3-Methyl-1,2,4-oxadiazol-5-yl)ethyl]-3-(5-methylpyridin-2-yl)-5-(2-methylpyrimidin-5-yl)benzamide;
3-Isopropyl-5-(5-methylpyridin-2-yl)-N-[(1S)-1-(4H-1,2,4-triazole-3-yl)ethyl]benzamide;
3-(1-Hydroxy-1-methylethyl)-5-(5-methylpyridin-2-yl)-N-{(1R)-1-[2-(trifluoromethyl)pyrimidin-5-yl]ethyl}benzamide; or
2',4'-Difluoro-5-(1-hydroxy-1-methylethyl)-N-[(1R)-1-(3-methyl-1,2,4-oxadiazol-5-yl)ethyl]biphenyl-3-carboxamide;
or pharmaceutically acceptable salts and individual enantiomers and diastereomers thereof.

18. A compound according to claim 17 which is 3-(5-Chloropyridin-2-yl)-5-(1-hydroxy-1-methylethyl)-N-{(1R)-1-[1-oxido-6-(trifluoromethyl)pyridin-3-yl]ethyl}benzamide or pharmaceutically acceptable salts and individual enantiomers and diastereomers thereof.

19. A pharmaceutical composition comprising an inert carrier and an effective amount of a compound according to claim 1.

* * * * *